US012214023B2

(12) United States Patent
Finn et al.

(10) Patent No.: US 12,214,023 B2
(45) Date of Patent: Feb. 4, 2025

(54) COMPOSITIONS AND METHODS FOR EXPRESSING FACTOR IX

(71) Applicants: Intellia Therapeutics, Inc., Cambridge, MA (US); Regeneron Pharmaceuticals, Inc., Tarrytown, NY (US)

(72) Inventors: Jonathan Douglas Finn, Cambridge, MA (US); Hon-Ren Huang, Cambridge, MA (US); Moitri Roy, Cambridge, MA (US); KehDih Lai, Tarrytown, NY (US); Rachel Sattler, Tarrytown, NY (US); Christos Kyratsous, Tarrytown, NY (US); Cheng Wang, Tarrytown, NY (US)

(73) Assignees: Intellia Therapeutics, Inc., Cambridge, MA (US); Regeneron Pharmaceuticals, Inc., Tarrytown, NY (US)

( * ) Notice: Subject to any disclaimer, the term of this patent is extended or adjusted under 35 U.S.C. 154(b) by 1231 days.

(21) Appl. No.: 16/657,961

(22) Filed: Oct. 18, 2019

(65) Prior Publication Data

US 2020/0289628 A1 Sep. 17, 2020

Related U.S. Application Data

(60) Provisional application No. 62/829,621, filed on Apr. 4, 2019, provisional application No. 62/840,352, filed on Apr. 29, 2019, provisional application No. 62/747,509, filed on Oct. 18, 2018, provisional application No. 62/829,009, filed on Apr. 3, 2019.

(51) Int. Cl.

| | |
|---|---|
| ***A61K 38/48*** | (2006.01) |
| ***A61K 38/46*** | (2006.01) |
| ***A61K 48/00*** | (2006.01) |
| ***A61P 7/00*** | (2006.01) |
| ***C12N 15/113*** | (2010.01) |
| ***C12N 15/86*** | (2006.01) |
| ***C12N 15/90*** | (2006.01) |

(52) U.S. Cl.

CPC ........ *A61K 38/4846* (2013.01); *A61K 38/465* (2013.01); *A61K 48/005* (2013.01); *A61P 7/00* (2018.01); *C12N 15/113* (2013.01); *C12N 15/86* (2013.01); *C12N 15/90* (2013.01); *C12Y 304/21022* (2013.01)

(58) Field of Classification Search

CPC .............. A61K 38/4846; A61K 38/465; A61K 48/005; A61P 7/00; C12N 15/113; C12N 15/86; C12N 15/90; C12Y 304/21022

USPC .................... 514/44 R; 435/320.1, 455, 199; 530/384; 536/24.31

See application file for complete search history.

(56) References Cited

U.S. PATENT DOCUMENTS

| | | | |
|---|---|---|---|
| 4,797,368 | A | 1/1989 | Carter et al. |
| 4,897,355 | A | 1/1990 | Eppstein et al. |
| 4,946,787 | A | 8/1990 | Eppstein et al. |
| 4,994,371 | A | 2/1991 | Davie et al. |
| 5,049,386 | A | 9/1991 | Eppstein et al. |
| 5,173,414 | A | 12/1992 | Lebkowski et al. |
| 5,378,825 | A | 1/1995 | Cook et al. |
| 5,585,481 | A | 12/1996 | Arnold, Jr. et al. |
| 6,008,336 | A | 12/1999 | Hanson et al. |
| 6,046,380 | A | 4/2000 | Clark |
| 6,531,298 | B2 | 3/2003 | Stafford et al. |
| 7,282,199 | B2 | 10/2007 | Gao et al. |
| 7,465,583 | B2 | 12/2008 | Samulski et al. |
| 7,790,154 | B2 | 9/2010 | Samulski et al. |
| 7,790,449 | B2 | 9/2010 | Gao et al. |
| 7,951,925 | B2 | 5/2011 | Ando et al. |
| 7,998,734 | B2 | 8/2011 | High et al. |
| 8,030,065 | B2 | 10/2011 | Gray |
| 8,110,379 | B2 | 2/2012 | DeKelver et al. |
| 8,168,425 | B2 | 5/2012 | Gray |
| 8,198,421 | B2 | 6/2012 | Samulski |
| 8,318,480 | B2 | 11/2012 | Gao et al. |
| 8,361,457 | B2 | 1/2013 | Samulski et al. |
| 8,383,388 | B2 | 2/2013 | Oyhenart et al. |
| 8,632,765 | B2 | 1/2014 | Samulski |
| 8,697,359 | B1 | 4/2014 | Zhang |
| 8,784,799 | B2 | 7/2014 | Samulski et al. |
| 8,865,406 | B2 | 10/2014 | Zhang et al. |
| 8,889,356 | B2 | 11/2014 | Zhang |
| 8,962,330 | B2 | 2/2015 | Gao et al. |
| 8,962,332 | B2 | 2/2015 | Gao et al. |
| 9,150,847 | B2 | 10/2015 | Rebar |

(Continued)

FOREIGN PATENT DOCUMENTS

| | | | |
|---|---|---|---|
| CN | 105950626 | A | 9/2016 |
| EP | 0107278 | A1 | 5/1984 |

(Continued)

OTHER PUBLICATIONS

Merriam-Webster, (n.d.), "Promotor", In: Merriam-Webster.com dictionary, retrieved Sep. 15, 2022, from https://www .merriam-webster.com/dictionary/promotor. (Year: 2022).

(Continued)

*Primary Examiner* — Anne Marie S Wehbe
(74) *Attorney, Agent, or Firm* — Foley Hoag LLP; Brendan T. Jones; David E. Shore

(57) ABSTRACT

Compositions and methods for expressing Factor IX in a host cell or a population of host cells are provided. Also provided are engineered host cells expressing Factor IX.

16 Claims, 36 Drawing Sheets

Specification includes a Sequence Listing.

(56) References Cited

U.S. PATENT DOCUMENTS

| | | | | |
|---|---|---|---|---|
| 9,175,280 | B2 | 11/2015 | Gregory et al. | |
| 9,222,105 | B2 | 12/2015 | Cost et al. | |
| 9,249,405 | B2 | 2/2016 | Simioni | |
| 9,255,250 | B2 | 2/2016 | Gregory et al. | |
| 9,394,545 | B2 | 7/2016 | Rebar | |
| 9,447,431 | B2 | 9/2016 | Thess et al. | |
| 9,493,788 | B2 | 11/2016 | Gao et al. | |
| 9,506,052 | B2 | 11/2016 | Samulski | |
| 9,587,250 | B2 | 3/2017 | Gao et al. | |
| 9,616,090 | B2 | 4/2017 | Conway et al. | |
| 9,629,930 | B2 | 4/2017 | Gregory et al. | |
| 9,677,089 | B2 | 6/2017 | Gao et al. | |
| 9,771,403 | B2 | 9/2017 | Miller et al. | |
| 9,777,281 | B2 | 10/2017 | Rebar | |
| 9,790,490 | B2 | 10/2017 | Zhang et al. | |
| 9,873,894 | B2 † | 1/2018 | Conway | |
| 9,877,988 | B2 | 1/2018 | Rebar | |
| 9,902,974 | B2 | 2/2018 | Conway et al. | |
| 9,909,142 | B2 | 3/2018 | Yazicioglu et al. | |
| 9,956,247 | B2 | 5/2018 | Rebar | |
| 9,982,248 | B2 | 5/2018 | Simioni | |
| 10,081,661 | B2 | 9/2018 | Miller et al. | |
| 10,111,968 | B2 | 10/2018 | Thess et al. | |
| 10,196,651 | B2 | 2/2019 | Conway et al. | |
| 10,196,652 | B2 | 2/2019 | Conway et al. | |
| 10,266,846 | B2 | 4/2019 | Gao et al. | |
| 10,293,000 | B2 | 5/2019 | Rebar | |
| 10,407,476 | B2 | 9/2019 | Miller et al. | |
| 10,639,383 | B2 | 5/2020 | Holmes et al. | |
| 11,091,756 | B2 * | 8/2021 | Baltes | C12N 15/902 |
| 11,254,930 | B2 | 2/2022 | Baltes | |
| 11,479,767 | B2 | 10/2022 | Smith et al. | |
| 11,549,107 | B2 | 1/2023 | Odate et al. | |
| 2003/0108524 | A1 | 6/2003 | Diagana et al. | |
| 2003/0143740 | A1 | 7/2003 | Wooddell et al. | |
| 2003/0192066 | A1 | 10/2003 | Zhang et al. | |
| 2006/0191038 | A1 | 8/2006 | Flasinski | |
| 2008/0159996 | A1 | 7/2008 | Ando et al. | |
| 2010/0047805 | A1 | 2/2010 | Wang | |
| 2010/0218264 | A1 | 8/2010 | Cui et al. | |
| 2011/0207221 | A1 | 8/2011 | Cost et al. | |
| 2011/0265198 | A1 | 10/2011 | Gregory et al. | |
| 2011/0281361 | A1 | 11/2011 | DeKelver et al. | |
| 2012/0017290 | A1 | 1/2012 | Cui et al. | |
| 2012/0164130 | A1 | 6/2012 | Brooks et al. | |
| 2013/0122591 | A1 | 5/2013 | Cost et al. | |
| 2013/0137104 | A1 | 5/2013 | Cost et al. | |
| 2013/0177960 | A1 | 7/2013 | Rebar | |
| 2013/0177983 | A1 | 7/2013 | Rebar | |
| 2013/0243855 | A1 | 9/2013 | Oyhenart et al. | |
| 2014/0017212 | A1 | 1/2014 | Rebar | |
| 2014/0037585 | A1 | 2/2014 | Wright et al. | |
| 2014/0112896 | A1 | 4/2014 | Rebar | |
| 2014/0155468 | A1 | 6/2014 | Gregory et al. | |
| 2014/0242702 | A1 | 8/2014 | Chen et al. | |
| 2014/0335063 | A1 | 11/2014 | Cannon et al. | |
| 2015/0056705 | A1 * | 2/2015 | Conway | C12N 15/90 435/468 |
| 2015/0159172 | A1 | 6/2015 | Miller et al. | |
| 2015/0166618 | A1 | 6/2015 | Miller et al. | |
| 2015/0203872 | A1 | 7/2015 | Zhang | |
| 2015/0240263 | A1 | 8/2015 | Holmes et al. | |
| 2015/0344893 | A1 | 12/2015 | Rebar | |
| 2016/0060656 | A1 | 3/2016 | Rebar | |
| 2016/0090607 | A1 | 3/2016 | Conway et al. | |
| 2016/0122740 | A1 | 5/2016 | Simioni | |
| 2016/0143953 | A1 | 5/2016 | Gregory et al. | |
| 2016/0153006 | A1 | 6/2016 | Zhang et al. | |
| 2016/0168593 | A1 | 6/2016 | Cost et al. | |
| 2016/0298134 | A1 | 10/2016 | Chen et al. | |
| 2016/0312198 | A1 | 10/2016 | Joung et al. | |
| 2016/0312199 | A1 | 10/2016 | Joung et al. | |
| 2016/0375110 | A1 | 12/2016 | High et al. | |
| 2017/0016027 | A1 | 1/2017 | Lee et al. | |
| 2017/0114334 | A1 | 4/2017 | May et al. | |
| 2017/0119906 | A1 | 5/2017 | Riley | |
| 2017/0165862 | A1 | 6/2017 | Slama et al. | |
| 2017/0196992 | A1 | 7/2017 | Holmes et al. | |
| 2017/0198302 | A1 | 7/2017 | Feng et al. | |
| 2017/0202931 | A1 | 7/2017 | DeKelver et al. | |
| 2017/0306354 | A1 | 10/2017 | Gao et al. | |
| 2017/0342118 | A1 | 11/2017 | Miller et al. | |
| 2017/0355999 | A1 | 12/2017 | Rebar | |
| 2018/0064827 | A1 | 3/2018 | Conway et al. | |
| 2018/0110808 | A1 | 4/2018 | Rebar | |
| 2018/0110877 | A1 | 4/2018 | Wilson et al. | |
| 2018/0117181 | A1 | 5/2018 | Huston | |
| 2018/0119182 | A1 | 5/2018 | Herrema et al. | |
| 2018/0127786 | A1 | 5/2018 | Bouchon et al. | |
| 2018/0177894 | A1 | 6/2018 | Thess et al. | |
| 2018/0185516 | A1 | 7/2018 | Ansell et al. | |
| 2018/0185517 | A1 | 7/2018 | Thess et al. | |
| 2018/0187186 | A1 | 7/2018 | Yin et al. | |
| 2018/0214490 | A1 | 8/2018 | Rebar | |
| 2018/0245098 | A1 | 8/2018 | Yazicioglu et al. | |
| 2018/0258413 | A1 | 9/2018 | Simioni | |
| 2018/0339026 | A1 | 11/2018 | Horling et al. | |
| 2018/0362601 | A1 | 12/2018 | Miller et al. | |
| 2019/0017068 | A1 | 1/2019 | Gao et al. | |
| 2019/0048338 | A1 | 2/2019 | Yin et al. | |
| 2019/0075770 | A1 | 3/2019 | Shindo et al. | |
| 2019/0153441 | A1 * | 5/2019 | Kantardzhieva | A61K 31/7088 |
| 2019/0225991 | A1 | 7/2019 | Izpisua Belmonte et al. | |
| 2019/0247517 | A1 | 8/2019 | Brooks | |
| 2019/0316121 | A1 | 10/2019 | Smith et al. | |
| 2019/0345208 | A1 | 11/2019 | Miller et al. | |
| 2019/0351073 | A1 | 11/2019 | Laterza et al. | |
| 2019/0352671 | A1 | 11/2019 | Holmes et al. | |
| 2019/0365924 | A1 | 12/2019 | Conway et al. | |
| 2019/0382798 | A1 * | 12/2019 | Cowan | C12N 15/11 |
| 2019/0390195 | A1 | 12/2019 | Tondera et al. | |
| 2020/0040362 | A1 | 2/2020 | Carlo et al. | |
| 2020/0115700 | A1 † | 4/2020 | Baltes | |
| 2020/0268906 | A1 | 8/2020 | Finn et al. | |
| 2020/0270617 | A1 | 8/2020 | Finn et al. | |
| 2020/0270618 | A1 | 8/2020 | Finn et al. | |
| 2020/0289628 | A1 | 9/2020 | Finn et al. | |
| 2021/0180053 | A1 | 6/2021 | Beverly et al. | |
| 2021/0187125 | A1 | 6/2021 | Brooks | |
| 2021/0198696 | A1 | 7/2021 | Kong et al. | |
| 2021/0316014 | A1 | 10/2021 | Finn et al. | |
| 2022/0218843 | A1 * | 7/2022 | Venditti | A61K 48/005 |
| 2022/0354967 | A1 | 11/2022 | Finn et al. | |

FOREIGN PATENT DOCUMENTS

| | | | |
|---|---|---|---|
| EP | 1626091 | A2 | 2/2006 |
| EP | 1290205 | B1 | 3/2006 |
| EP | 1453547 | B1 | 9/2006 |
| EP | 2359869 | A2 | 8/2011 |
| EP | 2423305 | A1 | 2/2012 |
| EP | 2423306 | A1 | 2/2012 |
| EP | 2423307 | A1 | 2/2012 |
| EP | 1804839 | B1 | 3/2012 |
| EP | 2438931 | A1 | 4/2012 |
| EP | 2037892 | B1 | 3/2015 |
| EP | 2848253 | A1 | 3/2015 |
| EP | 2627665 | B1 | 12/2015 |
| EP | 2872625 | B1 | 11/2016 |
| EP | 3138910 | A1 | 3/2017 |
| EP | 3138911 | A1 | 3/2017 |
| EP | 3196301 | A1 | 7/2017 |
| EP | 3252157 | A1 | 12/2017 |
| EP | 2675484 | B1 | 5/2018 |
| EP | 2337849 | B1 | 6/2018 |
| EP | 3080143 | B1 | 2/2019 |
| EP | 3444342 | A1 | 2/2019 |
| EP | 2758529 | B1 | 3/2019 |
| EP | 3011032 | B1 | 10/2019 |
| EP | 3569708 | A1 | 11/2019 |
| EP | 3867376 | A1 | 8/2021 |
| EP | 3867378 | A1 | 8/2021 |
| WO | WO-9313121 | A1 | 7/1993 |
| WO | WO-9324641 | A2 | 12/1993 |

(56) References Cited

FOREIGN PATENT DOCUMENTS

| | | | |
|---|---|---|---|
| WO | WO-1994026877 | A1 | 11/1994 |
| WO | WO-9532305 | A1 | 11/1995 |
| WO | WO-01092551 | A2 | 12/2001 |
| WO | WO-03052051 | A2 | 6/2003 |
| WO | WO-2006036502 | A2 | 4/2006 |
| WO | WO-2007149406 | A2 | 12/2007 |
| WO | WO-2007149852 | A2 | 12/2007 |
| WO | WO-2010029178 | A1 | 3/2010 |
| WO | WO-2010117464 | A1 | 10/2010 |
| WO | WO-2011011767 | A1 | 1/2011 |
| WO | WO-2011014890 | A1 | 2/2011 |
| WO | WO-2011097036 | A1 | 8/2011 |
| WO | WO-2011100058 | A1 | 8/2011 |
| WO | WO-2011146885 | A2 | 11/2011 |
| WO | WO-2012015938 | A2 | 2/2012 |
| WO | WO-2012051343 | A1 | 4/2012 |
| WO | WO-2012112578 | A2 | 8/2012 |
| WO | WO-2013044008 | A2 | 3/2013 |
| WO | WO-2013063315 | A2 | 5/2013 |
| WO | WO-2013120629 | A1 | 8/2013 |
| WO | WO-2013158309 | A2 | 10/2013 |
| WO | WO-2013158879 | A1 | 10/2013 |
| WO | WO-2013176772 | A1 | 11/2013 |
| WO | WO-2014011237 | A1 | 1/2014 |
| WO | WO-2014065596 | A1 | 5/2014 |
| WO | WO-2014089212 | A1 | 6/2014 |
| WO | WO-2014130955 | A1 | 8/2014 |
| WO | WO-2014136086 | A1 | 9/2014 |
| WO | WO-2014186585 | A2 | 11/2014 |
| WO | WO-2014204728 | A1 | 12/2014 |
| WO | WO-2015089046 | A1 | 6/2015 |
| WO | WO-2015089077 | A2 | 6/2015 |
| WO | WO-2015095340 | A1 | 6/2015 |
| WO | WO-2015127439 | A1 | 8/2015 |
| WO | WO-2016/011080 | A2 | 1/2016 |
| WO | WO-2016010840 | A1 | 1/2016 |
| WO | WO-2016106121 | A1 | 6/2016 |
| WO | WO-2016205749 | A1 | 12/2016 |
| WO | WO-2016210170 | A1 | 12/2016 |
| WO | WO-2017004279 | A2 | 1/2017 |
| WO | WO-2017011519 | A1 | 1/2017 |
| WO | WO-2017/077386 | A1 | 5/2017 |
| WO | WO-2017074526 | A1 | 5/2017 |
| WO | WO-2017091512 | A1 | 6/2017 |
| WO | WO-2017093804 | A2 | 6/2017 |
| WO | WO-2017106657 | A1 | 6/2017 |
| WO | WO-2017136794 | A1 | 8/2017 |
| WO | WO-2017/158422 | A1 | 9/2017 |
| WO | WO-2017173054 | A1 | 10/2017 |
| WO | WO-2017184786 | A1 | 10/2017 |
| WO | WO-2017189308 | A1 | 11/2017 |
| WO | WO-2018013932 | A1 | 1/2018 |
| WO | WO-2018035387 | A1 | 2/2018 |
| WO | WO-2018075736 | A1 | 4/2018 |
| WO | WO-2018/119182 | A1 | 6/2018 |
| WO | WO-2018107026 | A1 | 6/2018 |
| WO | WO-2018107028 | A1 | 6/2018 |
| WO | WO-2018126087 | A1 | 7/2018 |
| WO | WO-2018129586 | A1 | 7/2018 |
| WO | WO-2018140573 | A1 | 8/2018 |
| WO | WO-2018154459 | A1 | 8/2018 |
| WO | WO-2018208973 | A1 | 11/2018 |
| WO | WO-2018217731 | A1 | 11/2018 |
| WO | WO-2018231018 | A2 | 12/2018 |
| WO | WO-2018232382 | A1 | 12/2018 |
| WO | WO-2019067910 | A1 | 4/2019 |
| WO | WO-2019067992 | A1 | 4/2019 |
| WO | WO-2019079527 | A1 | 4/2019 |
| WO | WO-2019122302 | A1 | 6/2019 |
| WO | WO-2019212973 | A1 | 11/2019 |
| WO | WO-2019237069 | A1 | 12/2019 |
| WO | WO-2019239361 | A1 | 12/2019 |
| WO | WO-2019246203 | A1 | 12/2019 |
| WO | WO-2020/081438 | A1 | 4/2020 |

OTHER PUBLICATIONS

Finn et al., "A single administration of CRISPR/Cas9 lipid nanoparticles achieves robust and persistent in vivo genome editing," Cell Rep, 22: 2227-2235 (2018).

International Search Report and Written Opinion for International Application No. PCT/US2019/057086 dated Jun. 24, 2020.

International Search Report and Written Opinion for International Application No. PCT/US2019/057090 dated Jul. 10, 2020.

International Search Report and Written Opinion for International Application No. PCT/US2019/057092 dated Apr. 23, 2020.

International Search Report and Written Opinion for PCT/US2019/057084 dated Apr. 1, 2020.

Jiang et al., "A non-viral CRISPR/Cas9 delivery system for therapeutically targeting HBV DNA and pcsk9 in vivo," Cell Res, 27: 440-443 (2017).

Lino et al., "Delivering CRISPR: a review of the challenges and approaches," Drug Delivery, 25(1): 1234-1257 (2018).

Miyaoka et al., "Systematic quantification of HDR and NHEJ reveals effects of locus, nuclease, and cell type on genome-editing," Scientific Reports, 6: 23549 pp. 1-12 (2016).

Nishio et al., "Complete structure of the human alpha-albumin gene, a new member of the serum albumin multigene family," PNAS, 93: 7557-7561 (1996).

Shen et al., "Amelioration of Alpha-1 Antitrypsin Deficiency Diseases with Genome Editing in Transgenic Mice," Human Gene Therapy, 29(8): 861-873 (2018).

Zuris et al., "Cationic lipid-mediated delivery of proteins enables efficient protein-based genome editing in vitro and in vivo," Nat Biotech, 33: 73-81 (2015).

Abbas, Yazan M et al., "Structure of human IFIT1 with capped RNA reveals adaptable mRNA binding and mechanisms for sensing N1 and N2 ribose 2'-O methylations." Proceedings of the National Academy of Sciences of the United States of America vol. 114,11 (2017): E2106-E2115.

Adams et al., "The Biochemistry of the Nucleic Acids", ed., 11th ed., 1992.

Adcock et al., "Coagulation Handbook", Esoterix Laboratory Services, 2006.

Alvarez et al., "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients. University of Alabama Comprehensive Cancer Center, Birmingham, AL", Hum. Gene Ther. 5:597-613 (1997).

Amiral et al., "Application of enzyme immunoassays to coagulation testing", Clinical Chemistry, 1984, 30(9), 1512-16.

Anguela et al., "In Vivo Genome Editing of Liver Albumin for Therapeutic Gene Expression: Rescue of Hemophilic Mice via Integration of Factor 9," Blood 120(21):751, (2012).

Attallah et al., "A highly efficient modified human serum albumin signal peptide to secrete proteins in cells derived from different mammalian species," Protein Expression and Purification, 132:27-33, (2017).

Barzel et al., "Promoterless gene targeting without nucleases ameliorates haemophilia Bin mice", Nature, vol. 517, No. 7534, Oct. 29, 2014 (Oct. 29, 2014), pp. 360-364.

Bruni et al., "Update on Treatment of Lysosomal Storage Diseases," Acta Myol., 26(1):87-92, (2007).

Buchschacher, G L Jr, and A T Panganiban, "Human immunodeficiency virus vectors for inducible expression of foreign genes." Journal of virology vol. 66,5 (1992): 2731-9.

Burset, M et al., "SpliceDB: database of canonical and non-canonical mammalian splice sites." Nucleic acids research vol. 29,1 (2001): 255-9.

Cameron et al., "Mapping the genomic landscape of CRISPR-Cas9 cleavage", Nature Methods. 6, 600-606; 2017.

Chang and Wilson, "Modification of DNA Ends can Decrease end Joining Relative to Homologous Recombination in Mammalian Cells", (1987), Proc. Natl. Acad. Sci. USA 84:4959-4963.

Choong-Hwan Ryu et al., "Generation of T-DNA Tagging Lines with a Bidirectional Gene Trap Vector and the Establishment of an

(56) References Cited

OTHER PUBLICATIONS

Insertion-Site Database" , Plant Molecular Biology, vol. 54, No. 4, Mar. 2004 (Mar. 2004), pp. 489-502.
Deng Sheng et al., "Bidirectional promoter trapping T-DNA for insertional mutagenesis in Verticillium dahliae", Canadian Journal of Microbiology, NRC Research Press, CA, vol. 60, No. 7, Jun. 3, 2014 (Jun. 3, 2014), pp. 445-45.
Dreyer Timothy et al., "Improved antiviral efficacy using TALEN-mediated homology directed recombination to introduce artificial primary miRNAs into DNA of hepatitis B virus", Biochemical and Biophysical Research Communications, Elsevier, Amsterdam, NL, vol. 478, No. 4, Aug. 30, 2016 (Aug. 30, 2016), pp. 1563-1568.
Feng, Bo, "High-efficiency CRISPR-based technology for hemophilia B gene therapy," A-Biotech (Hong Kong) Co. Ltd. (2018).
Fischer et al., "The effects of postponing prophylactic treatment on long-term outcome in patients with severe hemophilia", (2002), Blood 99 (7):2337.
Follenzi et al., "Targeting lentiviral vector expression to hepatocytes limits transgene-specific immune response and establishes long-term expression of human antihemophilic factor IX in mice," Blood, 103(10):3700-3709, (2004).
George, et al., "Hemophilia B Gene Therapy with a High-Specific-Activity Factor IX Variant", New England Journal of Medicine (2017) 377(23), 2215-27.
Guo, P X, and B Moss, "Interaction and mutual stabilization of the two subunits of vaccinia virus mRNA capping enzyme coexpressed in *Escherichia coli*." Proceedings of the National Academy of Sciences of the United States of America vol. 87,11 (1990): 4023-7.
Hajj et al., "Tools For translation: non-viral materials for therapeutic mRNA delivery", Nature Reviews Materials, vol. 2, No. 10, Sep. 12, 2017 (Sep. 12, 2017).
He et al., "Knock-in of large reporter genes in human cells via CRISPR/Cas9-induced homology-dependent and independent DNA repair," Nucleic Acids Research, 44(9):e85, pp. 1-14, (2016).
Hermonat, P L and N Muzyczka, "Use of adeno-associated virus as a mammalian DNA cloning vector: transduction of neomycin resistance into mammalian tissue culture cells." Proceedings of the National Academy of Sciences of the United States of America vol. 81,20 (1984): 6466-70.
Hsin et al., "Hepatocyte death in liver inflammation, fibrosis, and tumorigenesis," Cellular Injury in Liver Diseases, (2017), 219-235.
Iyama, Teruaki, and David M Wilson, 3rd. "DNA repair mechanisms in dividing and non-dividing cells." DNA repair vol. 12,8 (2013): 620-36.
Johann et al., "GLVR1, a receptor for gibbon ape leukemia virus, is homologous to a phosphate permease of Neurospora crassa and is expressed at high levels in the brain and thymus", Journal of Virology (1992) 66:1635-1640.
Katibah, George E et al., "Broad and adaptable RNA structure recognition by the human interferon-induced tetratricopeptide repeat protein IFIT5." Proceedings of the National Academy of Sciences of the United States of America vol. 111,33 (2014): 12025-30.
Kellendonk et al., "Hepatocyte-Specific Expression of Cre Recombinase," Genesis, 26(2):151-153, (2000).
Kolb A F et al., "Genomic Targeting of a Bicistronic DNA Fragment by Cre-Mediated Site-Specific Recombination", Gene, Elsevier, Amsterdam, NL, vol. 203, Dec. 24, 1997 (Dec. 24, 1997), pp. 209-216.
Kotin, "Prospects for the Use of Adeno-Associated Virus as a Vector for Human Gene Therapy", Human Gene Therapy, 5:793-801 (1994).
Laoharawee et al., "Dose-Dependent Prevention of Metabolic and Neurologic Disease in Murine MPS II by ZFN-Mediated In Vivo Genome Editing," Molecular Therapy, 26(4):1127-1136, (2018).
Li et al., "In vivo genome editing restores haemostasis in a mouse model of haemophilia," Nature, 475(7355):217-221, (2011).
Lock, Martin et al., "Rapid, simple, and versatile manufacturing of recombinant adeno-associated viral vectors at scale." Human gene therapy vol. 21,10 (2010): 1259-71.
Mao, X. and Shuman, S., "Intrinsic RNA (Guanine-7) Methyltransferase Activity of the Vaccinia Virus Capping Enzyme D1 Subunit is Stimulated by the D12 Subunit", Journal of Biological Chemistry, 1994, 269, 24472-24479.
Makarova, Kira S, et al., "An updated evolutionary classification of CRISPR-Cas systems." Nature reviews. Microbiology vol. 13,11 (2015): 722-36.
Matissek et al., "Choosing Targets for Gene Therapy," Targets in Gene Therapy, Yongping You (Ed.), InTechOpen, pp. 3-28, (2011).
McIntosh, Jenny et al., "Therapeutic levels of FVIII following a single peripheral vein administration of rAAV vector encoding a novel human factor VIII variant." Blood vol. 121,17 (2013): 3335-44.
Mefferd et al., "Expression of CRISPR/Cas single guide RNAs using small tRNA promoters", RNA, (2015), 21:1683-9.
Miller, A D et al., "Construction and properties of retrovirus packaging cells based on gibbon ape leukemia virus." Journal of virology vol. 65,5 (1991): 2220-4.
Muzyczka, N., "Adeno-associated virus (AAV) vectors: will they work?." The Journal of clinical investigation vol. 94,4 (1994): 1351.
Nehls et al., "Two Genetically Separable Steps in the Differentiation of Thymic Epithelium", (1996) Science 272:886-889.
Nguyen et al., "Liver gene therapy: advances and hurdles," Gene Ther., 11 Suppl 1:S76-S84, (2004).
Ohmori et al., "CRISPR/Cas9-mediated genome editing via post-natal administration of AAV vector cures haemophilia B mice", Scientific Reports, vol. 7, No. 1, Jun. 23, 2017 (Jun. 23, 2017).
Osterud et al., "Human blood coagulation factor IX. Purification, properties, and mechanism of activation by activated factor XI.", J Biol Chem. Sep. 10, 1978;253(17):5946-51.
Papapetrou et al., "Gene Insertion Into Genomic Safe Harbors for Human Gene Therapy," Molecular Therapy, 24 (4):678-684, (2016).
Pelletier et al., "RNA Based Gene Therapy for Dominantly Inherited Diseases," Curr. Gene Ther., 6(1):131-146, (2006).
Petrini, "What factors should influence the dosage and interval of prophylactic treatment in patients with severe Hemophilia A and B?", Haemophilia, (Jan. 2001);7(1):99-102.
Porro et al., "Promoterless gene targeting without nucleases rescues lethality of a Crigler-Najjar syndrome mouse model," EMBO Molecular Medicine, 9(10):1346-1355, (2017).
Porteus et al., "A Look to Future Directions in Gene Therapy Research for Monogenic Diseases," PLoS Genet., 2 (9):e133, 8 pages, (2006).
Proudfoot, Nick J., "Ending the message: poly(A) signals then and now." Genes & development vol. 25, 17 (2011): 1770-82.
Richard, I., "The genetic and molecular bases of monogenic disorders affecting proteolytic systems," J. Med. Genet., 42(7):529-539, (2005).
Rosenecker et al., "Adenovirus infection in cystic fibrosis patients: Implications for the use of adenoviral vectors for gene transfer", Infection, 24:1 5-10 (1996).
Ross et al., "Huntington's disease: from molecular pathogenesis to clinical treatment," Lancet Neurol., 10(1):83-98, (2011).
Sadelain et al., "Safe harbours for the integration of new DNA in the human genome," Nat. Rev. Cancer, 12 (1):51-58, (2012).
Samulski, R J et al., "Helper-free stocks of recombinant adeno-associated viruses: normal integration does not require viral gene expression." Journal of virology vol. 63,9 (1989): 3822-8.
Sands et al., "Gene Therapy for Lysosomal Storage Diseases," Mol. Ther., 13(5):839-849, (2006).
Scherer, Lisa J et al., "Optimization and characterization of tRNA-shRNA expression constructs." Nucleic acids research vol. 35,8 (2007): 2620-8.
Senis et al., "TALEN/CRISPR-mediated engineering of a promoterless anti-viral RNAi hairpin into an endogenous miRNA locus", Nucleic Acids Research Advance Access, vol. 45, No. 1, Sep. 9, 2016 (Sep. 9, 2016), p. e3.
Shapiro, M B, and P Senapathy, "RNA splice junctions of different classes of eukaryotes: sequence statistics and functional implications in gene expression." Nucleic acids research vol. 15, 17 (1987): 7155-74.

(56) References Cited

OTHER PUBLICATIONS

Sharma et al., "Correction of Hemophilia B Phenotype Following ZFN Mediated Genome Editing in Adult Mice," Molecular Therapy, 20(Suppl 1):S24, (2012).
R. Sharma et al., "In vivo genome editing of the albumin locus as a platform for protein replacement therapy", Blood, vol. 126, No. 15, Oct. 8, 2015 (Oct. 8, 2015), pp. 1777-1784.
Shmakov, Sergey et al., "Discovery and Functional Characterization of Diverse Class 2 CRISPR-Cas Systems." Molecular cell vol. 60,3 (2015): 385-97.
Simioni et al., "X-Linked Thrombophilia with a Mutant Factor IX (Factor IX Padua)" New England Journal of Medicine 361(17), 1671-75, 2009.
Sommerfelt and Weiss, "Receptor Interference Groups of 20 Retroviruses Plating on Human Cells", J. Virol. 176:58-59 (1990).
Stepinski et al., "Synthesis and Properties of mRNAs Containing the Novel (anti-reverse) Cap Analogs 7-methyl(3'-O-methyl)GpppG and 7-methyl(3'-deoxy)GpppG", RNA, (2001) 7:1486-1495.
Sterman et al., "Adenovirus-Mediated Herpes Simplex Virus Thymidine Kinase/Ganciclovir Gene Therapy in Patients with Localized Malignancy: Results of a Phase I Clinical Trial in Malignant Mesothelioma", Hum. Gene Ther. 9:7 1083-1089 (1998).
Suzuki et al., "In vivo genome editing via CRISPR/Cas9 mediated homology-independent targeted integration," Nature, 540:144-149, (2016).
Swarts, Daan C et al., "DNA-guided DNA interference by a prokaryotic Argonaute." Nature vol. 507, 7491 (2014): 258-261.
Topf et al., "Regional 'pro-drug' gene therapy: intravenous administration of an adenoviral vector expressing the *E. coli* cytosine deaminase gene and systemic administration of 5-fluorocytosine suppresses growth of hepatic metastasis of colon carcinoma", Gene Ther. (1998) 5:507-513.
Tratschin et al., "Adeno-associated virus vector for high-frequency integration, expression, and rescue of genes in mammalian cells", Mol. Cell. Biol. 5:3251-3260 (1985).
Tratschin, et al., "A human parvovirus, adeno-associated virus, as a eucaryotic vector: transient expression and encapsidation of the procaryotic gene for chloramphenicol acetyltransferase", Mol. Cell. Biol. 4:2072-2081 (1984).
Tripathi P et al., "An adenoviral vector for probing promoter activity in primary immune cells", Journal of Immunological Methods, Elsevier Science Publishers B.V.,Amsterdam, NL, vol. 311, No. 1-2, Feb. 20, 2006 (Feb. 20, 2006), pp. 19-30.
Vester and Wengel, "LNA (locked nucleic acid): high-affinity targeting of complementary RNA and DNA", Biochemistry, (2004), 43(42):13233-41.
Wechsler et al., "ZFN-Mediated Gene Targeting at the Albumin Locus in Liver Results in Therapeutic Levels of Human FIX in Mice and Non-Human Primates," Blood, 126(23):200, (2015).
Welsh et al., "Adenovirus-Mediated Gene Transfer for Cystic Fibrosis: Part A. Safety of Dose and Repeat Administration in the Nasal Epithelium. Part B. Clinical Efficacy in the Maxillary Sinus. Howard Hughes Medical Institute, Iowa City, Iowa", Hum. Gene Ther. 2:205-18 (1995).
West et al., "Gene expression in adeno-associated virus vectors: The effects of chimeric mRNA structure, helper virus, and adenovirus VA, RNA", Virology 160:38-47 (1987).
Wilson, C et al., "Formation of infectious hybrid virions with gibbon ape leukemia virus and human T-cell leukemia virus retroviral envelope glycoproteins and the gag and pol proteins of Moloney murine leukemia virus." Journal of virology vol. 63, 5 (1989): 2374-8.
Wooddell et al., "Sustained liver-specific transgene expression from the albumin promoter in mice following hydrodynamic plasmid DNA delivery," J. Gene Med., 10(5):551-563, (2008).
Yang M et al., "The DNA element controlling expression of the varicella-zoster virus open reading frame 28 and 29 genes consists of two divergent unidirectional promoters which have a common USF site", Journal of Virology, the American Society for Microbiology, US, vol. 78, No. 20, Sep. 27, 2004 (Sep. 27, 2004), pp. 10939-10952.
Yin et al., "Structure-guided chemical modification of guide RNA enables potent non-viral in vivo genome editing," Nature Biotechnology, 35(12):1179-1187, (2017).
Zetsche et al., "Cpf1 is a Single RNA-Guided Endonuclease of a Class 2 CRISPR-Cas System," Cell, (2015) 163, 3:759-771.
Mahpour et al., "A methyl-sensitive element induces bidirectional transcription in TATA-less CpG island-associated promoters", PLoS One. 13(10): pp. e0205608 (2018).
Stiles et al., "Intrapleural Gene Therapy for Alpha-1 Antitrypsin Deficiency-Related Lung Disease", Chronic Obstr Pulm Dis. 5(4): pp. 244-257 (2018).
U.S. Appl. No. 62/746,497, entitled Methods for Targeted Insertion of DNA in Genes, pdf pp. 1-43, by Nicholas Baltes, filed Oct. 16, 2018, and published on Apr. 16, 2020, when U.S. Patent Publication No. 2020/0115700 A1 was published.†

* cited by examiner
† cited by third party

COMPOSITIONS AND METHODS FOR EXPRESSING FACTOR IX

This application claims the benefit of priority from U.S. Provisional Application No. 62/747,509, filed on Oct. 18, 2018, U.S. Provisional Application No. 62/829,009, filed on Apr. 3, 2019, U.S. Provisional Application No. 62/829,621, filed on Apr. 4, 2019 and U.S. Provisional Application No. 62/840,352, filed on Apr. 29, 2019. The specifications of each of the foregoing applications are incorporated herein by reference in their entirety.

SEQUENCE LISTING

The instant application contains a Sequence Listing which has been filed electronically in ASCII format and is hereby incorporated by reference in its entirety. Said ASCII copy, created on Nov. 21, 2019, is named 1861884-0002-004-101_SL.txt and is 194,154 bytes in size.

Bleeding disorders are caused by inadequate blood clotting. This deficiency may be caused by congenital coagulation disorders, acquired coagulation disorders, or hemorrhagic conditions induced by trauma. Bleeding is one of the most serious and significant manifestations of disease, and may occur from a local site or be generalized. Localized bleeding may be associated with lesions and may be further complicated by a defective haemostatic mechanism. Congenital or acquired deficiencies of any of the coagulation factors may be associated with a hemorrhagic tendency. Classic examples of bleeding disorders include hemophilia, such as hemophilia A, which results from a deficiency in factor VIII, or hemophilia B (Christmas Disease), which results from a deficiency in factor IX. Hemophilia occurs in all racial and ethnic groups, and affects many people in the United States and worldwide.

Traditional therapy for bleeding disorders includes parenteral replacement of deficient clotting factors, such as factor VII, factor VIII or factor IX. For example, current treatments for Hemophilia B rely on chronic, repeated intravenous infusions of purified recombinant Factor IX. However, those treatments suffer from a number of drawbacks including the need for repeated intravenous infusions, being associated with inhibitor formation, and generally being more prophylactic rather than curative. See, e.g., Petrini 2001, *Hemophilia* 7:99; Fischer et al. 2002, *Blood* 99 (7):2337.

Gene therapy, which involves introducing a copy of a missing or defective gene into a patient, provide one possible method of introducing Factor IX to patients for a longer duration. However, there exists a need for additional compositions and methods that offer improved, long term expression of Factor IX.

The present disclosure provides compositions and methods useful for expressing Factor IX in a host cell or a population of host cells (in vitro or in vivo), and for treating hemophilia (e.g., hemophilia B). Provided herein are guide RNAs for use in targeted insertion of a sequence encoding Factor IX into a human genomic locus, e.g., a safe harbor site, such as an albumin safe harbor site. Also provided are donor constructs (e.g., bidirectional constructs), comprising a sequence encoding Factor IX, for use in targeted insertion into a safe harbor site, such as intron 1 of the albumin safe harbor site. In some embodiments, the guide RNA disclosed herein can be used in combination with an RNA-guided DNA binding agent (e.g., Cas nuclease) and a donor construct (e.g., bidirectional construct) comprising a Factor IX transgene. In some embodiments, the donor construct (e.g., bidirectional construct) can be used with a gene editing system (e.g., CRISPR/Cas system; zinc finger nuclease (ZFN) system; transcription activator-like effector nuclease (TALEN) system). In some embodiments, the guide RNA disclosed herein can be used in combination with an RNA-guided DNA binding agent (e.g., Cas nuclease) and a donor construct (e.g., bidirectional construct) that comprises a Factor IX transgene. The following embodiments are provided.

In some aspects, provided herein is a method of introducing a Factor IX nucleic acid to a cell or a population of cells, comprising administering: i) a nucleic acid construct comprising a Factor IX protein coding sequence; ii) an RNA-guided DNA binding agent; and iii) a guide RNA (gRNA) comprising a sequence. In some embodiments, the guide RNA comprises a sequence that is at least 95%, 90%, 85%, 80%, or 75% identical to a sequence selected from the group consisting of SEQ ID Nos: 2, 8, 13, 19, 28, 29, 31, 32, 33. In some embodiments, the guide RNA comprises a sequence that is at least 17, 18, 19, or 20 contiguous nucleotides of a sequence selected from the group consisting of SEQ ID NOs: 2, 8, 13, 19, 28, 29, 31, 32, 33. In some embodiments, the guide RNA comprises a sequence that is a sequence selected from the group consisting of SEQ ID NOs: 34, 40, 45, 51, 60, 61, 63, 64, 65, 66, 72, 77, 83, 92, 93, 95, 96, and 97. In some embodiments, the guide RNA comprises a sequence that is a sequence that is at least 95%, 90%, 85%, 80%, or 75% identical to a sequence selected from the group consisting of SEQ ID NOs: 2-33. In some embodiments, the guide RNA comprises a sequence that is at least 17, 18, 19, or 20 contiguous nucleotides of a sequence selected from the group consisting of SEQ ID NOs: 2-33. In some embodiments, the guide RNA comprises a sequence that is selected from the group consisting of SEQ ID NOs: 34-97. In some embodiments, the guide RNA comprises a sequence that is at least 95%, 90%, 85%, 80%, or 75% identical to a sequence selected from the group consisting of SEQ ID NOs: 98-119. In some embodiments, the guide RNA comprises a sequence that is at least 17, 18, 19, or 20 contiguous nucleotides of a sequence selected from the group consisting of SEQ ID NOs: 98-119. In some embodiments, the guide RNA comprises a sequence that is a sequence selected from the group consisting of SEQ ID NOs: 120-163.

In some aspects, provided herein is a method of expressing Factor IX in a cell or population of cells, comprising administering: i) a nucleic acid construct comprising a Factor IX protein coding sequence; ii) an RNA-guided DNA binding agent; and iii) a guide RNA (gRNA) comprising a sequence. In some embodiments, the guide RNA comprises a sequence that is at least 95%, 90%, 85%, 80%, or 75% identical to a sequence selected from the group consisting of SEQ ID Nos: 2, 8, 13, 19, 28, 29, 31, 32, 33. In some embodiments, the guide RNA comprises a sequence that is at least 17, 18, 19, or 20 contiguous nucleotides of a sequence selected from the group consisting of SEQ ID NOs: 2, 8, 13, 19, 28, 29, 31, 32, 33. In some embodiments, the guide RNA comprises a sequence that is selected from the group consisting of SEQ ID NOs: 34, 40, 45, 51, 60, 61, 63, 64, 65, 66, 72, 77, 83, 92, 93, 95, 96, and 97. In some embodiments, the guide RNA comprises a sequence that is at least 95%, 90%, 85%, 80%, or 75% identical to a sequence selected from the group consisting of SEQ ID NOs: 2-33. In some embodiments, the guide RNA comprises a sequence that is least 17, 18, 19, or 20 contiguous nucleotides of a sequence selected from the group consisting of SEQ ID NOs: 2-33. In some embodiments, the guide RNA comprises a sequence selected from the group consisting of SEQ ID NOs: 34-97. In some embodiments, the guide RNA comprises a sequence that is at least 95%, 90%, 85%, 80%, or 75% identical to a sequence selected from the group consisting of SEQ ID NOs: 98-119. In some embodiments, the guide RNA comprises a sequence that is at least 17, 18, 19, or 20 contiguous nucleotides of a sequence selected from the group consisting of SEQ ID NOs: 98-119. In some embodiments, the guide RNA comprises a sequence that is selected from the group consisting of SEQ ID NOs: 120-163.

In some aspects, provided herein is a method of introducing or expressing Factor IX in a cell or population of cells, comprising administering: i) a nucleic acid construct comprising a Factor IX protein coding sequence; ii) an RNA-guided DNA binding agent; and iii) a guide RNA (gRNA) comprising a sequence wherein the administration is in vitro.

In some embodiments, the guide RNA comprises a sequence that is at least 95%, 90%, 85%, 80%, or 75% identical to a sequence selected from the group consisting of SEQ ID Nos: 2, 8, 13, 19, 28, 29, 31, 32, 33. In some embodiments, the guide RNA comprises at least 17, 18, 19, or 20 contiguous nucleotides of a sequence selected from the group consisting of SEQ ID NOs: 2, 8, 13, 19, 28, 29, 31, 32, 33. In some embodiments, the guide RNA comprises a sequence selected from the group consisting of SEQ ID NOs: 34, 40, 45, 51, 60, 61, 63, 64, 65, 66, 72, 77, 83, 92, 93, 95, 96, and 97. In some embodiments, the guide RNA comprises a sequence that is at least 95%, 90%, 85%, 80%, or 75% identical to a sequence selected from the group consisting of SEQ ID NOs: 2-33. In some embodiments, the guide RNA comprises at least 17, 18, 19, or 20 contiguous nucleotides of a sequence selected from the group consisting of SEQ ID NOs: 2-33. In some embodiments, the guide RNA comprises a sequence selected from the group consisting of SEQ ID NOs: 34-97.

In some embodiments, the nucleic acid construct is administered in a nucleic acid vector and/or a lipid nanoparticle. In some embodiments, the RNA-guided DNA binding agent and/or gRNA is administered in a nucleic acid vector and/or lipid nanoparticle. In some embodiments, the nucleic acid vector is a viral vector. In some embodiments, the viral vector is selected from the group consisting of an adeno associate viral (AAV) vector, adenovirus vector, retrovirus vector, and lentivirus vector. In some embodiments, the AAV vector is selected from the group consisting of AAV1, AAV3, AAV4, AAV5, AAV6, AAV8, AAV-DJ, and AAV2/8.

In some embodiments, the nucleic acid construct, RNA-guided DNA binding agent, and gRNA are administered sequentially, in any order and/or in any combination. In some embodiments, wherein the nucleic acid construct, RNA-guided DNA binding agent, and gRNA, individually or in any combination, are administered simultaneously. In some embodiments, the RNA-guided DNA binding agent, or RNA-guided DNA binding agent and gRNA in combination, is administered prior to administering the nucleic acid construct. In some embodiments, the nucleic acid construct is administered prior to administering the gRNA and/or RNA-guided DNA binding agent.

In some embodiments, the RNA-guided DNA binding agent is a Cas nuclease. In some embodiments, the Cas nuclease is a class 2 Cas nuclease. In some embodiments the Cas nuclease is Cas9. In some embodiments, the Cas nuclease is an *S. pyogenes* Cas9 nuclease. In some embodiments, the Cas nuclease is a nickase.

In some embodiments, the nucleic acid construct is a bidirectional nucleic acid construct. In some embodiments, the nucleic acid construct is single-stranded or double-stranded. In some embodiments, the nucleic acid construct is a single-stranded DNA or a double-stranded DNA. In some embodiments, the bidirectional construct does not comprise a promoter that drives the expression of the Factor IX protein. In some embodiments, the cell or population of cells expresses Factor IX with a heterologous peptide, such as an albumin signal peptide.

In some embodiments, the cell or population of cells includes a liver cell. In some embodiments, the liver cell is a hepatocyte.

In some embodiments, the nucleic acid encodes a wild-type Factor IX protein. In some embodiments, the nucleic acid encodes a mutant Factor IX protein. In some embodiments, the nucleic acid encodes a Factor IX protein having a mutation R338L.

In some aspects, provided herein is a method of introducing a Factor IX nucleic acid to a cell or population of cells, comprising administering to the cell or population of cells a bidirectional nucleic acid construct comprising a Factor IX protein coding sequence, thereby expressing Factor IX in the cell or population of cells. Provided herein is a method of expressing Factor IX in a cell or population of cells, comprising administering to the cell or population of cells a bidirectional nucleic acid construct comprising a Factor IX protein coding sequence, thereby expressing Factor IX expression in the cell or population of cells.

In some embodiments, the bidirectional nucleic acid construct comprises: a) a first segment comprising a coding sequence for Factor IX; and b) a second segment comprising a reverse complement of a coding sequence of Factor IX, wherein the construct does not comprise a promoter that drives the expression of Factor IX. In some embodiments, the bidirectional nucleic acid construct comprises: a) a first segment comprising a coding sequence for Factor IX; and b) a second segment comprising a reverse complement of a coding sequence of a second polypeptide, wherein the construct does not comprise a promoter that drives the expression of the polypeptide.

In some embodiments, the method of introducing a Factor IX nucleic acid to a cell or population of cells further comprises administering an RNA-guided DNA binding agent. In some embodiments, the method further comprises administering a gRNA. In some embodiments, the bidirectional nucleic acid construct is administered in a nucleic acid vector and/or a lipid nanoparticle. In some embodiments, the RNA-guided DNA binding agent is administered in a nucleic acid vector and/or lipid nanoparticle. In some embodiments, the gRNA is administered in a nucleic acid vector and/or lipid nanoparticle. In some embodiments, the nucleic acid vector is a viral vector. In some embodiments, the viral vector is selected from the group consisting of an adeno associate viral (AAV) vector, adenovirus vector, retrovirus vector, and lentivirus vector. In some embodiments, the AAV vector is selected from the group consisting of AAV1, AAV3, AAV4, AAV5, AAV6, AAV8, AAV-DJ, and AAV2/8.

In some embodiments, the bidirectional nucleic acid construct, RNA-guided DNA binding agent, and gRNA are administered sequentially, in any order and/or in any combination. In some embodiments, the bidirectional nucleic acid construct, RNA-guided DNA binding agent, and gRNA, in any combination, are administered simultaneously. In some embodiments, the RNA-guided DNA binding agent, or RNA-guided DNA binding agent and gRNA in combination, is administered prior to administering the bidirectional nucleic acid construct. In some embodiments, the bidirectional nucleic acid construct is administered prior to administering the gRNA and/or RNA-guided DNA binding agent.

In some embodiments, the RNA-guided DNA binding agent is a Cas nuclease. In some embodiments, the Cas nuclease is a class 2 Cas nuclease. In some embodiments, the Cas nuclease is selected from the group consisting of *S. pyogenes* nuclease, *S. aureus* nuclease, *C. jejuni* nuclease, *S. thermophilus* nuclease, *N. meningitidis* nuclease, and variants thereof. In some embodiments, the Cas nuclease is Cas9. In some embodiments, the Cas nuclease is a nickase.

In some embodiments, the bidirectional construct does not comprise a promoter that drives the expression of the Factor IX protein. In some embodiments, the bidirectional construct is single-stranded or double-stranded. In some embodiments, the nucleic acid construct is a single-stranded DNA or a double-stranded DNA. In some embodiments, the gRNA comprises at least 17, 18, 19, or 20 contiguous nucleotides of a sequence selected from the group consisting of SEQ ID NOs: 2-33 or a sequence that is at least 95%, 90%, 85%, 80%, or 75% identical to a sequence selected from the group consisting of SEQ ID NOs: 2-33.

In some aspects, provided herein is a composition for use in expressing Factor IX in a cell, wherein the composition comprises: i) a nucleic acid construct comprising a Factor IX protein coding sequence; ii) an RNA-guided DNA binding agent; and iii) a guide RNA (gRNA) comprising a guide sequence selected from the group consisting of SEQ ID NOs: 2-33 or a sequence that is at least 95%, 90%, 85%, 80%, or 75% identical to a sequence selected from the group consisting of SEQ ID NOs: 2-33. Provided herein is a composition for use in expressing Factor IX in a cell or population of cells, wherein the composition comprises a bidirectional nucleic acid construct comprising a Factor IX protein coding sequence. In some embodiments, a host cell is made by the method of any preceding embodiment.

In some embodiments, the host cell is a liver cell. In some embodiments, the host cell is a non-dividing cell type. In some embodiments, the host cell expresses the Factor IX polypeptide encoded by the bidirectional construct. In some embodiments, the host cell is a hepatocyte.

In some embodiments of the method, construct, or host cell of any above method, the gRNA comprises SEQ ID NO: 401.

BRIEF DESCRIPTION OF THE DRAWINGS

FIG. 3A shows liver editing levels as measured by indel formation of ~60% were detected in each group of animals treated with LNPs comprising CRISPR/Cas9 components. FIG. 3B shows animals receiving the ssAAV vectors without homology arms (derived from P00147) in combination with LNP treatment resulted in the highest level of hFIX expression in serum.

FIG. 4A compares targeted insertion with vectors derived from plasmids P00350, P00356, P00362 (having asymmetrical homology arms as shown), and P00147 (bidirectional construct as shown in FIG. 4B). FIG. 4B compares insertion into a second site targeted with vectors derived from plasmids P00353, P00354 (having symmetrical homology arms as shown), and P00147.

FIG. 5A shows the schematics of each of the vectors tested. FIG. 5B shows editing as measured by indel formation for each of the treatment groups across each combination tested. FIG. 5C and FIG. 5D show that significant levels of editing (as indel formation at a specific target site) did not necessarily result in more efficient insertion or expression of the transgenes. hSA=human F9 splice acceptor; mSA=mouse albumin splice acceptor; HiBit=tag for luciferase based detection; pA=polyA signal sequence; Nluc=nanoluciferase reporter; GFP=green fluorescent reporter.

FIG. 7A shows varied levels of editing as measured by indel formation were detected for each of the treatment groups across each LNP/vector combination tested. FIG. 7B provides corresponding targeted insertion data. The results show poor correlation between indel formation and insertion or expression of the bidirectional constructs (FIG. 7B and FIG. 7D), and a positive correlation between in vitro and in vivo results (FIG. 7C).

FIG. 13A shows varied levels of editing as measured by indel formation detected for each of the samples. FIG. 13B and FIG. 13C show that significant levels of indel formation was not predictive for insertion or expression of the bidirectional constructs into intron 1 of albumin.

FIG. 14A shows editing as measured by indel formation detected for each of the samples. FIG. 14B, FIG. 14C, and 14D show that significant levels of indel formation was not predictive for insertion or expression of the bidirectional constructs into intron 1 of the albumin gene.

DETAILED DESCRIPTION

Figure 1:
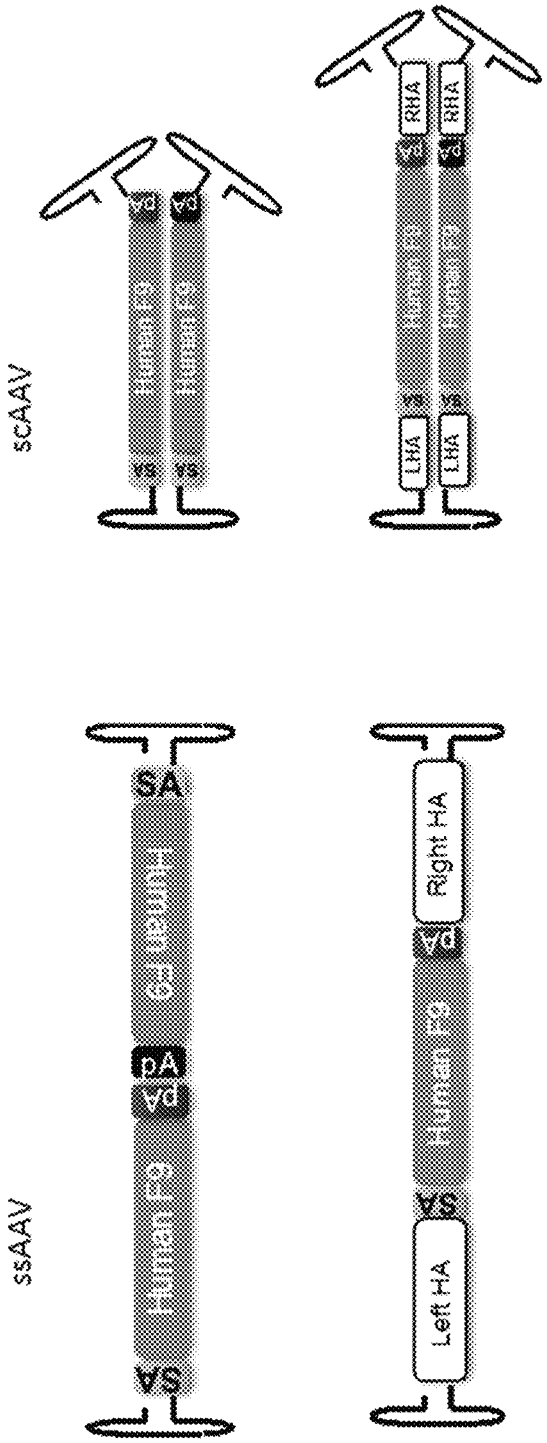
FIG. 1 shows construct formats as represented in AAV genomes. SA=splice acceptor; pA=polyA signal sequence; HA=homology arm; LHA=left homology arm; RHA=right homology arm

Reference will now be made in detail to certain embodiments of the invention, examples of which are illustrated in the accompanying drawings. While the invention is described in conjunction with the illustrated embodiments, it will be understood that they are not intended to limit the invention to those embodiments. On the contrary, the invention is intended to cover all alternatives, modifications, and equivalents, which may be included within the invention as defined by the appended embodiments.

Before describing the present teachings in detail, it is to be understood that the disclosure is not limited to specific compositions or process steps, as such may vary. It should be noted that, as used in this specification and the appended embodiments, the singular form "a", "an" and "the" include plural references unless the context clearly dictates otherwise. Thus, for example, reference to "a conjugate" includes a plurality of conjugates and reference to "a cell" includes a plurality or population of cells and the like. As used herein, the term "include" and its grammatical variants are intended to be non-limiting, such that recitation of items in a list is not to the exclusion of other like items that can be substituted or added to the listed items.

Numeric ranges are inclusive of the numbers defining the range. Measured and measureable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). The term "or" is used in an inclusive sense, i.e., equivalent to "and/or," unless the context clearly indicates otherwise. The term "about", when used before a list, modifies each member of the list. The term "about" or "approximately" means an acceptable error for a particular value as determined by one of ordinary skill in the art, which depends in part on how the value is measured or determined.

The term "about", when used before a list, modifies each member of the list. The term "about" or "approximately" means an acceptable error for a particular value as determined by one of ordinary skill in the art, which depends in part on how the value is measured or determined.

The section headings used herein are for organizational purposes only and are not to be construed as limiting the desired subject matter in any way. In the event that any material incorporated by reference contradicts any term defined in this specification or any other express content of this specification, this specification controls.

I. Definitions

Unless stated otherwise, the following terms and phrases as used herein are intended to have the following meanings:

"Polynucleotide" and "nucleic acid" are used herein to refer to a multimeric compound comprising nucleosides or nucleoside analogs which have nitrogenous heterocyclic bases or base analogs linked together along a backbone, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., modified uridines such as 5-methoxyuridine, pseudouridine, or N1-methylpseudouridine, or others); inosine; derivatives of purines or pyrimidines (e.g., N4-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methylaminopurine, O-methylguanine, 4-thio-pyrimidines, 4-amino-pyrimidines, 4-dimethylhydrazine-pyrimidines, and $0^4$-alkyl-pyrimidines; U.S. Pat. No. 5,378,825 and PCT No. WO 93/13121). For general discussion see *The Biochemistry of the Nucleic Acids* 5-36, Adams et al., ed., $11^{th}$ ed., 1992). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42): 13233-41). RNA and DNA have different sugar moieties and can differ by the presence of uracil or analogs thereof in RNA and thymine or analogs thereof in DNA.

"Guide RNA", "gRNA", and simply "guide" are used herein interchangeably to refer to either a guide that comprises a guide sequence, e.g., crRNA (also known as CRISPR RNA), or the combination of a crRNA and a trRNA (also known as tracrRNA). The crRNA and trRNA may be associated as a single RNA molecule (single guide RNA, sgRNA) or, for example, in two separate RNA molecules (dual guide RNA, dgRNA). "Guide RNA" or "gRNA" refers to each type. The trRNA may be a naturally-occurring sequence, or a trRNA sequence with modifications or variations compared to naturally-occurring sequences. Guide RNAs, such as sgRNAs or dgRNAs, can include modified RNAs as described herein.

As used herein, a "guide sequence" refers to a sequence within a guide RNA that is complementary to a target sequence and functions to direct a guide RNA to a target sequence for binding or modification (e.g., cleavage) by an RNA-guided DNA binding agent. A "guide sequence" may also be referred to as a "targeting sequence," or a "spacer sequence." A guide sequence can be 20 base pairs in length, e.g., in the case of *Streptococcus pyogenes* (i.e., Spy Cas9) and related Cas9 homologs/orthologs. Shorter or longer sequences can also be used as guides, e.g., 15-, 16-, 17-, 18-, 19-, 21-, 22-, 23-, 24-, or 25-nucleotides in length. For example, in some embodiments, the guide sequence comprises at least 15, 16, 17, 18, 19, or 20 contiguous nucleotides of a sequence selected from SEQ ID NOs:2-33. In some embodiments, the target sequence is in a gene or on a chromosome, for example, and is complementary to the guide sequence. In some embodiments, the degree of complementarity or identity between a guide sequence and its corresponding target sequence may be about 75%, 80%, 85%, 90%, 95%, 96%, 97%, 98%, 99%, or 100%. For example, in some embodiments, the guide sequence comprises a sequence with about 75%, 80%, 85%, 90%, 95%, 96%, 97%, 98%, 99%, or 100% identity to at least 15, 16, 17, 18, 19, or 20 contiguous nucleotides of a sequence selected from SEQ ID NOs: 2-33. In some embodiments, the guide sequence and the target region may be 100% complementary or identical. In other embodiments, the guide sequence and the target region may contain at least one mismatch. For example, the guide sequence and the target sequence may contain 1, 2, 3, or 4 mismatches, where the total length of the target sequence is at least 15, 16, 17, 18, 19, 20 or more base pairs. In some embodiments, the guide sequence and the target region may contain 1-4 mismatches where the guide sequence comprises at least 15, 16, 17, 18, 19, 20 or more nucleotides. In some embodiments, the guide sequence and the target region may contain 1, 2, 3, or 4 mismatches where the guide sequence comprises 20 nucleotides.

Target sequences for RNA-guided DNA binding agents include both the positive and negative strands of genomic DNA (i.e., the sequence given and the sequence's reverse complement), as a nucleic acid substrate for an RNA-guided DNA binding agent is a double stranded nucleic acid. Accordingly, where a guide sequence is said to be "complementary to a target sequence", it is to be understood that the guide sequence may direct a guide RNA to bind to the reverse complement of a target sequence. Thus, in some embodiments, where the guide sequence binds the reverse complement of a target sequence, the guide sequence is identical to certain nucleotides of the target sequence (e.g., the target sequence not including the PAM) except for the substitution of U for T in the guide sequence.

As used herein, an "RNA-guided DNA-binding agent" means a polypeptide or complex of polypeptides having RNA and DNA binding activity, or a DNA-binding subunit of such a complex, wherein the DNA binding activity is sequence-specific and depends on the sequence of the RNA. The term RNA-guided DNA binding-agent also includes nucleic acids encoding such polypeptides. Exemplary RNA-guided DNA-binding agents include Cas cleavases/nickases. Exemplary RNA-guided DNA-binding agents may include inactivated forms thereof ("dCas DNA-binding agents"), e.g. if those agents are modified to permit DNA cleavage, e.g. via fusion with a FokI cleavase domain. "Cas nuclease", as used herein, encompasses Cas cleavases and Cas nickases. Cas cleavases and Cas nickases include a Csm or Cmr complex of a type III CRISPR system, the Cas10, Csm1, or Cmr2 subunit thereof, a Cascade complex of a type I CRISPR system, the Cas3 subunit thereof, and Class 2 Cas nucleases. As used herein, a "Class 2 Cas nuclease" is a single-chain polypeptide with RNA-guided DNA binding activity. Class 2 Cas nucleases include Class 2 Cas cleavases/nickases (e.g., H840A, D10A, or N863A variants), which further have RNA-guided DNA cleavases or nickase activity, and Class 2 dCas DNA-binding agents, in which cleavase/nickase activity is inactivated"), if those agents are modified to permit DNA cleavage. Class 2 Cas nucleases include, for example, Cas9, Cpf1, C2c1, C2c2, C2c3, HF Cas9 (e.g., N497A, R661A, Q695A, Q926A variants), HypaCas9 (e.g., N692A, M694A, Q695A, H698A variants), eSPCas9(1.0) (e.g, K810A, K1003A, R1060A variants), and eSPCas9(1.1) (e.g., K848A, K1003A, R1060A variants) proteins and modifications thereof. Cpf1 protein, Zetsche et al., *Cell,* 163: 1-13 (2015), also contains a RuvC-like nuclease domain. Cpf1 sequences of Zetsche are incorporated by reference in their entirety. See, e.g., Zetsche, Tables S1 and S3. See, e.g., Makarova et al., *Nat Rev Microbiol,* 13(11): 722-36 (2015); Shmakov et al., *Molecular Cell,* 60:385-397 (2015). As used herein, delivery of an RNA-guided DNA-binding agent (e.g. a Cas nuclease, a Cas9 nuclease, or an *S. pyogenes* Cas9 nuclease) includes delivery of the polypeptide or mRNA.

As used herein, "ribonucleoprotein" (RNP) or "RNP complex" refers to a guide RNA together with an RNA-guided DNA binding agent, such as a Cas nuclease, e.g., a Cas cleavase, Cas nickase, or dCas DNA binding agent (e.g., Cas9). In some embodiments, the guide RNA guides the RNA-guided DNA binding agent such as Cas9 to a target sequence, and the guide RNA hybridizes with and the agent binds to the target sequence; in cases where the agent is a cleavase or nickase, binding can be followed by cleaving or nicking.

As used herein, a first sequence is considered to "comprise a sequence with at least X % identity to" a second sequence if an alignment of the first sequence to the second sequence shows that X % or more of the positions of the second sequence in its entirety are matched by the first sequence. For example, the sequence AAGA comprises a sequence with 100% identity to the sequence AAG because an alignment would give 100% identity in that there are matches to all three positions of the second sequence. The differences between RNA and DNA (generally the exchange of uridine for thymidine or vice versa) and the presence of nucleoside analogs such as modified uridines do not contribute to differences in identity or complementarity among polynucleotides as long as the relevant nucleotides (such as thymidine, uridine, or modified uridine) have the same complement (e.g., adenosine for all of thymidine, uridine, or modified uridine; another example is cytosine and 5-methylcytosine, both of which have guanosine or modified guanosine as a complement). Thus, for example, the sequence 5'-AXG where X is any modified uridine, such as pseudouridine, N1-methyl pseudouridine, or 5-methoxyuridine, is considered 100% identical to AUG in that both are perfectly complementary to the same sequence (5'-CAU). Exemplary alignment algorithms are the Smith-Waterman and Needleman-Wunsch algorithms, which are well-known in the art. One skilled in the art will understand what choice of algorithm and parameter settings are appropriate for a given pair of sequences to be aligned; for sequences of generally similar length and expected identity>50% for amino acids or >75% for nucleotides, the Needleman-Wunsch algorithm with default settings of the Needleman-Wunsch algorithm interface provided by the EBI at the www.ebi.ac.uk web server is generally appropriate.

As used herein, a first sequence is considered to be "X % complementary to" a second sequence if X % of the bases of the first sequence base pairs with the second sequence. For example, a first sequence 5'AAGA3' is 100% complementary to a second sequence 3'TTCT5', and the second sequence is 100% complementary to the first sequence. In some embodiments, a first sequence 5'AAGA3' is 100% complementary to a second sequence 3'TTCTGTGA5', whereas the second sequence is 50% complementary to the first sequence.

As used herein, "mRNA" is used herein to refer to a polynucleotide that is entirely or predominantly RNA or modified RNA and comprises an open reading frame that can be translated into a polypeptide (i.e., can serve as a substrate for translation by a ribosome and amino-acylated tRNAs). mRNA can comprise a phosphate-sugar backbone including ribose residues or analogs thereof, e.g., 2'-methoxy ribose residues. In some embodiments, the sugars of an mRNA phosphate-sugar backbone consist essentially of ribose residues, 2'-methoxy ribose residues, or a combination thereof.

Guide sequences useful in the guide RNA compositions and methods described herein are shown in Table 1 throughout the application.

As used herein, "indels" refer to insertion/deletion mutations consisting of a number of nucleotides that are either inserted or deleted at the site of double-stranded breaks (DSBs) in a target nucleic acid.

As used herein, "Factor IX" is used interchangeably with "FIX" or "F9", and is also known as Christmas Factor. The human wild-type Factor IX protein sequence is available at NCBI NP_000124; gene sequence is available at NCBI NM_000133. Examples of the Factor IX protein sequence are described herein (e.g. SEQ ID NO: 700, SEQ ID NO: 701, and/or SEQ ID NO: 702). As used herein, Factor IX also encompasses a variant of Factor IX, e.g., a variant that possesses increased coagulation activity as compared to wild type Factor IX. A hyperactive variant of Factor IX may comprise a substitution of R338. An example of such a variant Factor IX comprises the mutation R338L relative to SEQ ID NO: 701. The terms hyperactive and hyperfunctional are being used interchangeably herein. Further examples of variant Factor IX comprise an amino acid at residue 338 chosen from alanine, leucine, valine, isoleucine, phenylalanine, tryptophan, methionine, serine, and threonine. Further Factor IX variants comprise an amino acid at residue 338 chosen from leucine, cysteine, aspartic acid, glutamic acid, histidine, lysine, asparagine, glutamine, or tyrosine. As used herein, Factor IX also encompasses a variant that is 80%, 85%, 90%, 93%, 95%, 97%, 99% identical to SEQ ID NO: 700, having at least 60%, 70%, 80%, 85%, 90%, 92%, 94%, 96%, 98%, 99%, 100%, or more, activity as compared to wild-type Factor IX. As used herein, Factor IX also encompasses a variant that is 80%, 85%, 90%, 93%, 95%, 97%, 99% identical to SEQ ID NO: 700, having at least 60%, 70%, 80%, 85%, 90%, 92%, 94%, 96%, 98%, 99%, 100%, or more, activity as compared to SEQ ID NO: 701 or SEQ ID NO: 702. As used herein, Factor IX also encompasses a fragment that possesses at least 80%, 85%, 90%, 92%, 94%, 96%, 98%, 99%, 100%, or more, activity as compared to wild type Factor IX. In some embodiments, a Factor IX variant may be a hyperactive Factor IX variant. In certain instances, the Factor IX variant possesses between about 80% and about 100%, 120%, 140%, 160%, 180%, or 200% of the activity as compared to the wild-type Factor IX. The specific activity of the Factor IX variant can be used to calculate its functionally normalized activity, for example as described in Example 13. The specific activities of Factor IX variants, e.g. R338L, are known in the literature and can be calculated using known methods. A hyperfunctional Factor IX variant may have about 1.2, 1.5, 2, 3, 4, 5, 6, 8, 10, 12, or 15 times the specific activity of a corresponding wild type Factor IX protein. In one embodiment, the hyperfunctional Factor IX may have about 8-12 times the specific activity of a corresponding wild type Factor IX protein. In another embodiment, the hyperfunctional Factor IX may have 1.2-5 times the specific activity of a corresponding wild type Factor IX protein. Exemplary sequences are known in the art, and include sequences in U.S. Pat. Nos. 4,770,999, 4,994,371, 5,521,070, 6,046,380, 6,531,298, and 8,383,388, for example.

As used herein, a "target sequence" refers to a sequence of nucleic acid in a target gene that has complementarity to the guide sequence of the gRNA. The interaction of the target sequence and the guide sequence directs an RNA-guided DNA binding agent to bind, and potentially nick or cleave (depending on the activity of the agent), within the target sequence.

As used herein, "hemophilia" refers to a disorder caused by a missing or defective Factor IX gene or polypeptide. The disorder includes conditions that are inherited and/or acquired (e.g., caused by a spontaneous mutation in the gene), and includes hemophilia B. In some embodiments, the defective Factor IX gene or polypeptide results in reduced Factor IX level in the plasma and/or a reduced coagulation activity of Factor IX. As used herein, hemophilia includes mild, moderate, and severe hemophilia. For example, individuals with less than about 1% active factor are classified as having severe haemophilia, those with about 1-5% active factor have moderate haemophilia, and those with mild haemophilia have between about 5-40% of normal levels of active clotting factor.

As used herein, "normal" or "healthy" individuals include those having between 50 and 160% of normal pooled plasma level of Factor IX activity and antigen levels. Based on its purification from human plasma, the concentration of Factor IX in the normal adult (normal pooled plasma level of Factor IX) is about 300-400 μg/ml of plasma. In some embodiments, the level of Factor IX, e.g., circulating Factor IX, can be measured by a coagulation and/or an immunologic assay, e.g., an sandwich immunoassay, ELISA (see, e.g., Example 13), MSD (see, e.g., Example 14). Factor IX procoagulant activity is determined by the ability of the patient's plasma to correct the clotting time of Factor IX-deficient plasma.

As used herein, "treatment" refers to any administration or application of a therapeutic for disease or disorder in a subject, and includes inhibiting the disease, arresting its development, relieving one or more symptoms of the disease, curing the disease, or preventing reoccurrence of one or more symptoms of the disease. For example, treatment of hemophilia may comprise alleviating symptoms of hemophilia.

As used herein, a "bidirectional nucleic acid construct" (interchangeably referred to herein as a "bidirectional construct") comprises at least two nucleic acid segments, wherein one segment (the first segment) comprises a coding sequence that encodes a polypeptide of interest (the coding sequence may be referred to herein as "transgene" or a first transgene), while the other segment (the second segment) comprises a sequence wherein the complement of the sequence encodes a polypeptide of interest, or a second transgene. That is, the at least two segments can encode identical or different polypeptides. When the two segments encode the identical polypeptide, the coding sequence of the first segment need not be identical to the complement of the sequence of the second segment. In some embodiments, the sequence of the second segment is a reverse complement of the coding sequence of the first segment. A bidirectional construct can be single-stranded or double-stranded. The bidirectional construct disclosed herein encompasses a construct that is capable of expressing any polypeptide of interest.

In some embodiments, a bidirectional nucleic acid construct comprises a first segment that comprises a coding sequence that encodes a first polypeptide (a first transgene), and a second segment that comprises a sequence wherein the complement of the sequence encodes a second polypeptide (a second transgene). In some embodiments, the first and the second polypeptides are at least 50%, 55%, 60%, 65%, 70%, 75%, 80%, 85%, 90%, 91%, 92%, 93%, 94%, 95%, 96%, 97%, 98%, 99%, or 100% identical. In some embodiments, the first and the second polypeptides comprise an amino acid sequence that is at least 80%, 85%, 90%, 91%, 92%, 93%, 94%, 95%, 96%, 97%, 98%, 99%, or 100% identical, e.g. across 50, 100, 200, 500, 1000 or more amino acid residues.

As used herein, a "reverse complement" refers to a sequence that is a complement sequence of a reference sequence, wherein the complement sequence is written in the reverse orientation. For example, for a hypothetical sequence 5'CTGGACCGA3' (SEQ ID NO: 500), the "perfect" complement sequence is 3'GACCTGGCT5' (SEQ ID NO: 501), and the "perfect" reverse complement is written 5'TCGGTCCAG3' (SEQ ID NO: 502). A reverse complement sequence need not be "perfect" and may still encode the same polypeptide or a similar polypeptide as the reference sequence. Due to codon usage redundancy, a reverse complement can diverge from a reference sequence that encodes the same polypeptide. As used herein, "reverse complement" also includes sequences that are, e.g., 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical to the reverse complement sequence of a reference sequence.

As used herein, "polypeptide" refers to a wild-type or variant protein (e.g., mutant, fragment, fusion, or combinations thereof). A variant polypeptide may possess at least or about 5%, 10%, 15%, 20%, 30%, 35%, 40%, 45%, 50%, 55%, 60%, 65%, 70%, 75%, 80%, 85%, 90%, 95%, or 100% functional activity of the wild-type polypeptide. In some embodiments, the variant is at least 70%, 75%, 80%, 85%, 90%, 92%, 93%, 94%, 95%, 96%, 97%, 98%, or 99% identical to the sequence of the wild-type polypeptide. In some embodiments, a variant polypeptide may be a hyperactive variant. In certain instances, the variant possesses between about 80% and about 120%, 140%, 160%, 180%, 200%, 300%, 400%, 500%, or more of a functional activity of the wild-type polypeptide.

As used herein, a "heterologous gene" refers to a gene that has been introduced as an exogenous source to a site within a host cell genome (e.g., at a genomic locus such as a safe harbor locus including an albumin intron 1 site). That is, the introduced gene is heterologous with respect to its insertion site. A polypeptide expressed from such heterologous gene is referred to as a "heterologous polypeptide." The heterologous gene can be naturally-occurring or engineered, and can be wild type or a variant. The heterologous gene may include nucleotide sequences other than the sequence that encodes the heterologous polypeptide (e.g., an internal ribosomal entry site). The heterologous gene can be a gene that occurs naturally in the host genome, as a wild type or a variant (e.g., mutant). For example, although the host cell contains the gene of interest (as a wild type or as a variant), the same gene or variant thereof can be introduced as an exogenous source for, e.g., expression at a locus that is highly expressed. The heterologous gene can also be a gene that is not naturally occurring in the host genome, or that expresses a heterologous polypeptide that does not naturally occur in the host genome. "Heterologous gene", "exogenous gene", and "transgene" are used interchangeably. In some embodiments, the heterologous gene or transgene includes an exogenous nucleic acid sequence, e.g. a nucleic acid sequence is not endogenous to the recipient cell. In some embodiments, the heterologous gene or transgene includes an exogenous nucleic acid sequence, e.g. a nucleic acid sequence that does not naturally occur in the recipient cell. For example, a heterologous gene may be heterologous with respect to its insertion site and with respect to its recipient cell.

A "safe harbor" locus is a locus within the genome wherein a gene may be inserted without significant deleterious effects on the host cell, e.g. hepatocyte, e.g., without causing apoptosis, necrosis, and/or senescence, or without causing more than 5%, 10%, 15%, 20%, 25%, 30%, or 40% apoptosis, necrosis, and/or senescence as compared to a control cell. See, e.g., Hsin et al., "Hepatocyte death in liver inflammation, fibrosis, and tumorigenesis," 2017. In some embodiments, a safe harbor locus allows overexpression of an exogenous gene without significant deleterious effects on the host cell, e.g. hepatocyte, e.g., without causing apoptosis, necrosis, and/or senescence, or without causing more than 5%, 10%, 15%, 20%, 25%, 30%, or 40% apoptosis, necrosis, and/or senescence as compared to a control cell. In some embodiments, a desirable safe harbor locus may be one in which expression of the inserted gene sequence is not perturbed by read-through expression from neighboring genes. The safe harbor may be within an albumin gene, such as a human albumin gene. The safe harbor may be within an albumin intron 1 region, e.g., human albumin intron 1. The safe harbor may be a human safe harbor, e.g., for a liver tissue or hepatocyte host cell. In some embodiments, a safe harbor allows overexpression of an exogenous gene without significant deleterious effects on the host cell or cell population, such as hepatocytes or liver cells, e.g. without causing apoptosis, necrosis, and/or senescence, or without causing more than 5%, 10%, 15%, 20%, 25%, 30%, or 40% apoptosis, necrosis, and/or senescence as compared to a control cell or cell population.

II. Compositions

A. Compositions Comprising Guide RNA (gRNAs)

Provided herein are guide RNA compositions and methods useful for inserting and expressing a Factor IX gene within a genomic locus, e.g., a safe harbor site of a host cell or a population of host cells. In particular, as exemplified herein, targeting and inserting an exogenous gene at the albumin locus (e.g., at intron 1) allows the use of albumin's endogenous promoter to drive robust expression of the exogenous gene. The present disclosure is based, in part, on the identification of guide RNAs that specifically target sites within intron 1 of the albumin gene, and which provide efficient insertion and expression of the Factor IX gene. As shown in the Examples and further described herein, the ability of identified gRNAs to mediate high levels of editing as measured through indel forming activity, unexpectedly does not necessarily correlate with use of the same gRNAs to mediate efficient insertion of transgenes as measured through, e.g., expression of the transgene. That is, certain gRNAs that are able to achieve a high level of indel formation are not necessarily able to mediate efficient insertion, and conversely, some gRNAs shown to achieve low levels of indel formation may mediate efficient insertion and expression of a transgene.

In some embodiments, provided herein are compositions and methods useful for inserting and expressing a Factor IX gene within a region of an albumin locus (e.g., intron 1) of a host cell. In some embodiments, disclosed herein are compositions useful for introducing or inserting a heterologous Factor IX nucleic acid within an albumin locus of a host cell, e.g., using a guide RNA disclosed herein with an RNA-guided DNA binding agent, and a construct (e.g., donor construct or template) comprising a heterologous Factor IX nucleic acid ("Factor IX transgene"). In some embodiments, disclosed herein are compositions useful for expressing a heterologous Factor IX from an albumin locus of a host cell, e.g., using a guide RNA disclosed herein with an RNA-guided DNA binding agent and a construct (e.g., donor) comprising a heterologous Factor IX nucleic acid. In some embodiments, disclosed herein are compositions useful for expressing a heterologous Factor IX from an albumin locus of a host cell, e.g., using a guide RNA disclosed herein with an RNA-guided DNA binding agent and a bidirectional construct comprising a heterologous Factor IX nucleic acid. In some embodiments, disclosed herein are compositions useful for inducing a break (e.g., double-stranded break (DSB) or single-stranded break (nick)) within the serum albumin gene of a host cell, e.g., using a guide RNA disclosed herein with an RNA-guided DNA binding agent (e.g., a CRISPR/Cas system). The compositions may be used in vitro or in vivo for, e.g., treating hemophilia.

In some embodiments, the guide RNAs disclosed herein comprise a guide sequence that binds, or is capable of binding, within an intron of an albumin locus. In some embodiments, the guide RNAs disclosed herein bind within a region of intron 1 of the human albumin gene (SEQ ID NO: 1). It will be appreciated that not every base of the guide sequence must bind within the recited regions. For example, in some embodiments, 15, 16, 17, 18, 19, 20, or more bases of the guide RNA sequence bind with the recited regions. For example, in some embodiments, 15, 16, 17, 18, 19, 20, or more contiguous bases of the guide RNA sequence bind with the recited regions.

In some embodiments, the guide RNAs disclosed herein mediate a target-specific cutting by an RNA-guided DNA binding agent (e.g., Cas nuclease) at a site within human albumin intron 1 (SEQ ID NO: 1). It will be appreciated that, in some embodiments, the guide RNAs comprise guide sequences that bind to, or are capable of binding to, said regions.

In some embodiments, the guide RNAs disclosed herein comprise a guide sequence that is at least 95%, 90%, 85%, 80%, or 75% identical to a sequence selected from the group consisting of SEQ ID NOs: 2-33._In some embodiments, the guide RNAs disclosed herein comprise a guide sequence that is at least 95%, 90%, 85%, 80%, or 75% identical to a sequence selected from the group consisting of SEQ ID NOs: 2-5, 10-17, 21-27, and 29-33.

In some embodiments, the guide RNAs disclosed herein comprise a guide sequence having at least 15, 16, 17, 18, 19, or 20 contiguous nucleotides of a sequence selected from the group consisting of a sequence that is at least 95%, 90%, 85%, 80%, or 75% identical to a sequence selected from the group consisting of SEQ ID Nos: 2-33. In some embodiments, the guide RNAs disclosed herein comprise a guide sequence selected from the group consisting of SEQ ID NO: 2, 8, 13, 19, 28, 29, 31, 32, 33. In some embodiments, the guide RNAs disclosed herein comprise a guide sequence at least 17, 18, 19, or 20 contiguous nucleotides of a sequence selected from the group consisting of SEQ ID NOs: 2, 8, 13, 19, 28, 29, 31, 32, 33. In some embodiments, the guide RNAs disclosed herein comprise a guide sequence selected from the group consisting of SEQ ID NOs: 34, 40, 45, 51, 60, 61, 63, 64, 65, 66, 72, 77, 83, 92, 93, 95, 96, and 97. In some embodiments, the guide RNAs disclosed herein comprise a guide sequence that is at least 95%, 90%, 85%, 80%, or 75% identical to a sequence selected from the group consisting of SEQ ID NOs: 2-33. In some embodiments, the guide RNAs disclosed herein comprise a guide sequence that is at least 17, 18, 19, or 20 contiguous nucleotides of a sequence selected from the group consisting of SEQ ID NOs: 2-33. In some embodiments, the guide RNAs disclosed herein comprise a guide sequence that is selected from the group consisting of SEQ ID NOs: 34-97.

In some embodiments, the guide RNAs disclosed herein comprise a guide sequence having at least 15, 16, 17, 18, 19, or 20 contiguous nucleotides of a sequence selected from the group consisting of a sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 2-5, 10-17, 21-27, and 29-33. In some embodiments, the guide RNAs disclosed herein comprise a guide sequence at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 34-37, 42-49, 53-59, 61-69, 74-81, 85-91, and 93-97. In some embodiments, the guide RNAs disclosed herein comprise a guide sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence that is at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence that is selected from the group consisting of SEQ ID NOs: 34-37, 42-49, 53-59, 61-69, 74-81, 85-91, and 93-97.

In some embodiments, the guide RNAs disclosed herein mediate a target-specific cutting resulting in a double-stranded break (DSB). In some embodiments, the guide RNAs disclosed herein mediate a target-specific cutting resulting in a single-stranded break (nick).

In some embodiments, the guide RNAs disclosed herein bind to a region upstream of a propospacer adjacent motif (PAM). As would be understood by those of skill in the art, the PAM sequence occurs on the strand opposite to the strand that contains the target sequence. That is, the PAM sequence is on the complement strand of the target strand (the strand that contains the target sequence to which the guide RNA binds). In some embodiments, the PAM is selected from the group consisting of NGG, NNGRRT, NNGRR(N), NNAGAAW, NNNNG(A/C)TT, and NNNN-RYAC.

In some embodiments, the guide RNA sequences provided herein are complementary to a sequence adjacent to a PAM sequence.

In some embodiments, the guide RNA sequence comprises a sequence that is complementary to a sequence within a genomic region selected from the tables herein according to coordinates in human reference genome hg38. In some embodiments, the guide RNA sequence comprises a sequence that is complementary to a sequence that comprises 5, 6, 7, 8, 9, 10, 11, 12, 13, 14, 15, 16, 17, 18, 19, 20, 21, 22, 23, 24, or 25 consecutive nucleotides from within a genomic region selected from the tables herein. In some embodiments, the guide RNA sequence comprises a sequence that is complementary to a sequence that comprises 5, 6, 7, 8, 9, 10, 11, 12, 13, 14, 15, 16, 17, 18, 19, 20, 21, 22, 23, 24, or 25 consecutive nucleotides spanning a genomic region selected from the tables herein.

The guide RNAs disclosed herein mediate a target-specific cutting resulting in a double-stranded break (DSB). The guide RNAs disclosed herein mediate a target-specific cutting resulting in a single-stranded break (SSB or nick).

In some embodiments, the guide RNAs disclosed herein mediates target-specific cutting by an RNA-guided DNA binding agent (e.g., a Cas nuclease, as disclosed herein), resulting in insertion of a heterologous Factor IX nucleic acid within intron 1 of an albumin gene. In some embodiments, the guide RNA and/or cutting results in a rate of between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% insertion of a heterologous Factor IX gene. In some embodiments, the guide RNA and/or cutting results in a rate of at least 20%, at least 30%, at least 40%, at least 50%, at least 60%, at least 70%, at least 80%, at least 90% insertion of a heterologous Factor IX nucleic acid. Insertion rates can be measured in vitro or in vivo. For example, in some embodiments, rate of insertion can be determined by detecting and measuring the inserted Factor IX nucleic acid within a population of cells, and calculating a percentage of the population that contains the inserted Factor IX nucleic acid. Methods of measuring insertion rates are known and available in the art. In some embodiments, the guide RNA allows between 5 and 10%, 10 and 15%, 15 and 20%, 20 and 25%, 25 and 30%, 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, 95 and 99% or more increased expression of a heterologous Factor IX gene. Increased expression of a heterologous Factor IX gene can be measured in vitro or in vivo. For example, in some embodiments, increased expression can be determined by detecting and measuring the Factor IX polypeptide level and comparing the level against the Factor IX polypeptide level before, e.g., treating the cells or administration to a subject. In some embodiments, the guide RNA allows between 5 and 10%, 10 and 15%, 15 and 20%, 20 and 25%, 25 and 30%, 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, 95 and 99% or more increased activity that results from expression of a heterologous Factor IX gene. For example, increased activity can be determined by detecting and measuring the coagulation activity and comparing the activity against the the coagulation activity before, e.g., treating the cells or administration to a subject. In some embodiments, increased activity can be determined using by assessing clotting function in an aPTT assay and/or thrombin generation in an TGA-EA assay. Such methods are available and known in the art (e.g. Simioni et al, NEJM 2009).

Each of the guide sequences shown in Table 1 at SEQ ID NOs:2-33 may further comprise additional nucleotides to form a crRNA and/or guide RNA, e.g., with the following exemplary nucleotide sequence following the guide sequence at its 3' end: GUUUUAGAGCUAUGCU-GUUUUG (SEQ ID NO: 400) in 5' to 3' orientation. Genomic coordinates are according to human reference genome hg38. In the case of a sgRNA, the above guide sequences may further comprise additional nucleotides to form a sgRNA, e.g., with the following exemplary nucleotide sequence following the 3' end of the guide sequence:

(SEQ ID NO: 401)
GUUUUAGAGCUAGAAAUAGCAAGUUAAAAUAAGGCUAGUCCGUUAUC

AACUUGAAAAAGUGGCACCGAGUCGGUGCUUUU or (SEQ ID NO: 402)
GUUUUAGAGCUAGAAAUAGCAAGUUAAAAUAAGGCUAGUCCGUUAUC

AACUUGAAAAAGUGGCACCGAGUCGGUGC in

5' to 3' orientation.

Each of the guide sequences in Table 1 at SEQ ID NOs: 2-5, 10-17, 21-27, and 29-33 may further comprise additional nucleotides to form a crRNA, e.g., with the following exemplary nucleotide sequence following the guide sequence at its 3' end: GUUUUAGAGCUAUGCU-GUUUUG (SEQ ID NO: 400) in 5' to 3' orientation. In the case of a sgRNA, the above guide sequences may further comprise additional nucleotides to form a sgRNA, e.g., with the following exemplary nucleotide sequence following the 3' end of the guide sequence:

(SEQ ID NO: 401)
GUUUUAGAGCUAGAAAUAGCAAGUUAAAAUAAGGCUAGUCCGUUAUC

AACUUGAAAAAGUGGCACCGAGUCGGUGCUUUU or (SEQ ID NO: 402)
GUUUUAGAGCUAGAAAUAGCAAGUUAAAAUAAGGCUAGUCCGUUAUC

AACUUGAAAAAGUGGCACCGAGUCGGUGC in

5' to 3' orientation.

TABLE 1

| Human guide RNA sequences and chromosomal coordinates | | | |
|---|---|---|---|
| Guide ID | Guide Sequence | Human Genomic Coordinates (hg38) | SEQ ID NO: |
| G009844 | GAGCAACCUC ACUCUUGUCU | chr4: 73405113-73405133 | 2 |
| G009851 | AUGCAUUUGU UUCAAAAUAU | chr4: 73405000-73405020 | 3 |
| G009852 | UGCAUUUGUU UCAAAAUAUU | chr4: 73404999-73405019 | 4 |
| G009857 | AUUUAUGAGA UCAACAGCAC | chr4: 73404761-73404781 | 5 |
| G009858 | GAUCAACAGC ACAGGUUUUG | chr4: 73404753-73404773 | 6 |
| G009859 | UUAAAUAAAG CAUAGUGCAA | chr4: 73404727-73404747 | 7 |
| G009860 | UAAAGCAUAG UGCAAUGGAU | chr4: 73404722-73404742 | 8 |
| G009861 | UAGUGCAAUG GAUAGGUCUU | chr4: 73404715-73404735 | 9 |
| G009866 | UACUAAAACU UUAUUUUACU | chr4: 73404452-73404472 | 10 |
| G009867 | AAAGUUGAAC AAUAGAAAAA | chr4: 73404418-73404438 | 11 |
| G009868 | AAUGCAUAAU CUAAGUCAAA | chr4: 73405013-73405033 | 12 |
| G009874 | UAAUAAAAUU CAAACAUCCU | chr4: 73404561-73404581 | 13 |
| G012747 | GCAUCUUUAA AGAAUUAUUU | chr4: 73404478-73404498 | 14 |
| G012748 | UUUGGCAUUU AUUUCUAAAA | chr4: 73404496-73404516 | 15 |
| G012749 | UGUAUUUGUG AAGUCUUACA | chr4: 73404529-73404549 | 16 |
| G012750 | UCCUAGGUAA AAAAAAAAAA | chr4: 73404577-73404597 | 17 |
| G012751 | UAAUUUUCUU UUGCGCACUA | chr4: 73404620-73404640 | 18 |
| G012752 | UGACUGAAAC UUCACAGAAU | chr4: 73404664-73404684 | 19 |
| G012753 | GACUGAAACU UCACAGAAUA | chr4: 73404665-73404685 | 20 |
| G012754 | UUCAUUUUAG UCUGUCUUCU | chr4: 73404803-73404823 | 21 |
| G012755 | AUUAUCUAAG UUUGAAUAUA | chr4: 73404859-73404879 | 22 |
| G012756 | AAUUUUUAAA AUAGUAUUCU | chr4: 73404897-73404917 | 23 |
| G012757 | UGAAUUAUUC UUCUGUUUAA | chr4: 73404924-73404944 | 24 |
| G012758 | AUCAUCCUGA GUUUUUCUGU | chr4: 73404965-73404985 | 25 |

TABLE 1-continued

| Human guide RNA sequences and chromosomal coordinates | | | |
|---|---|---|---|
| Guide ID | Guide Sequence | Human Genomic Coordinates (hg38) | SEQ ID NO: |
| G012759 | UUACUAAAAC UUUAUUUUAC | chr4: 73404453-73404473 | 26 |
| G012760 | ACCUUUUUUU UUUUUUACCU | chr4: 73404581-73404601 | 27 |
| G012761 | AGUGCAAUGG AUAGGUCUUU | chr4: 73404714-73404734 | 28 |
| G012762 | UGAUUCCUAC AGAAAAACUC | chr4: 73404973-73404993 | 29 |
| G012763 | UGGGCAAGGG AAGAAAAAAA | chr4: 73405094-73405114 | 30 |
| G012764 | CCUCACUCUU GUCUGGGCAA | chr4: 73405107-73405127 | 31 |
| G012765 | ACCUCACUCU UGUCUGGGCA | chr4: 73405108-73405128 | 32 |
| G012766 | UGAGCAACCU CACUCUUGUC | chr4: 73405114-73405134 | 33 |

The guide RNA may further comprise a trRNA. In each composition and method embodiment described herein, the crRNA and trRNA may be associated as a single RNA (sgRNA) or may be on separate RNAs (dgRNA). In the context of sgRNAs, the crRNA and trRNA components may be covalently linked, e.g., via a phosphodiester bond or other covalent bond. In some embodiments, the sgRNA comprises one or more linkages between nucleotides that is not a phosphodiester linkage.

In each of the composition, use, and method embodiments described herein, the guide RNA may comprise two RNA molecules as a "dual guide RNA" or "dgRNA". The dgRNA comprises a first RNA molecule comprising a crRNA comprising, e.g., a guide sequence shown in Table 1, and a second RNA molecule comprising a trRNA. The first and second RNA molecules may not be covalently linked, but may form a RNA duplex via the base pairing between portions of the crRNA and the trRNA.

In each of the composition, use, and method embodiments described herein, the guide RNA may comprise a single RNA molecule as a "single guide RNA" or "sgRNA". The sgRNA may comprise a crRNA (or a portion thereof) comprising a guide sequence shown in Table 1 covalently linked to a trRNA. The sgRNA may comprise 15, 16, 17, 18, 19, or 20 contiguous nucleotides of a guide sequence shown in Table 1. In some embodiments, the crRNA and the trRNA are covalently linked via a linker. In some embodiments, the sgRNA forms a stem-loop structure via the base pairing between portions of the crRNA and the trRNA. In some embodiments, the crRNA and the trRNA are covalently linked via one or more bonds that are not a phosphodiester bond.

In some embodiments, the trRNA may comprise all or a portion of a trRNA sequence derived from a naturally-occurring CRISPR/Cas system. In some embodiments, the trRNA comprises a truncated or modified wild type trRNA. The length of the trRNA depends on the CRISPR/Cas system used. In some embodiments, the trRNA comprises or consists of 5, 6, 7, 8, 9, 10, 11, 12, 13, 14, 15, 16, 17, 18, 19, 20, 25, 30, 40, 50, 60, 70, 80, 90, 100, or more than 100 nucleotides. In some embodiments, the trRNA may comprise certain secondary structures, such as, for example, one or more hairpin or stem-loop structures, or one or more bulge structures.

In some embodiments, the target sequence or region within intron 1 of a human albumin locus (SEQ ID NO: 1) may be complementary to the guide sequence of the guide RNA. In some embodiments, the degree of complementarity or identity between a guide sequence of a guide RNA and its corresponding target sequence may be at least 75%, 80%, 85%, 90%, 95%, 96%, 97%, 98%, 99%, or 100%. In some embodiments, the target sequence and the guide sequence of the gRNA may be 100% complementary or identical. In other embodiments, the target sequence and the guide sequence of the gRNA may contain at least one mismatch. For example, the target sequence and the guide sequence of the gRNA may contain 1, 2, 3, 4, or 5 mismatches, where the total length of the guide sequence is about 20, or 20. In some embodiments, the target sequence and the guide sequence of the gRNA may contain 1-4 mismatches where the guide sequence is about 20, or 20 nucleotides.

In some embodiments, a composition or formulation disclosed herein comprises an mRNA comprising an open reading frame (ORF) encoding an RNA-guided DNA binding agent, such as a Cas nuclease as described herein. In some embodiments, an mRNA comprising an ORF encoding an RNA-guided DNA binding agent, such as a Cas nuclease, is provided, used, or administered.

B. Modified gRNAs and mRNAs

In some embodiments, the gRNA is chemically modified. A gRNA comprising one or more modified nucleosides or nucleotides is called a "modified" gRNA or "chemically modified" gRNA, to describe the presence of one or more non-naturally and/or naturally occurring components or configurations that are used instead of or in addition to the canonical A, G, C, and U residues. In some embodiments, a modified gRNA is synthesized with a non-canonical nucleoside or nucleotide, is here called "modified." Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii) modification or replacement of the sugar (an exemplary sugar modification).

Chemical modifications such as those listed above can be combined to provide modified gRNAs and/or mRNAs comprising nucleosides and nucleotides (collectively "residues") that can have two, three, four, or more modifications. For example, a modified residue can have a modified sugar and a modified nucleobase. In some embodiments, every base of a gRNA is modified, e.g., all bases have a modified phosphate group, such as a phosphorothioate group. In certain embodiments, all, or substantially all, of the phosphate groups of an gRNA molecule are replaced with phosphorothioate groups. In some embodiments, modified gRNAs comprise at least one modified residue at or near the 5' end of the RNA. In some embodiments, modified gRNAs comprise at least one modified residue at or near the 3' end of the RNA. Certain gRNAs comprise at least one modified residue at or near the 5' end and 3' end of the RNA.

In some embodiments, the gRNA comprises one, two, three or more modified residues. In some embodiments, at least 5% (e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%) of the positions in a modified gRNA are modified nucleosides or nucleotides.

Unmodified nucleic acids can be prone to degradation by, e.g., intracellular nucleases or those found in serum. For example, nucleases can hydrolyze nucleic acid phosphodiester bonds. Accordingly, in one aspect the gRNAs described herein can contain one or more modified nucleosides or nucleotides, e.g., to introduce stability toward intracellular or serum-based nucleases. In some embodiments, the modified gRNA molecules described herein can exhibit a reduced innate immune response when introduced into a population of cells, both in vivo and ex vivo. The term "innate immune response" includes a cellular response to exogenous nucleic acids, including single stranded nucleic acids, which involves the induction of cytokine expression and release, particularly the interferons, and cell death.

In some embodiments of a backbone modification, the phosphate group of a modified residue can be modified by replacing one or more of the oxygens with a different substituent. Further, the modified residue, e.g., modified residue present in a modified nucleic acid, can include the wholesale replacement of an unmodified phosphate moiety with a modified phosphate group as described herein. In some embodiments, the backbone modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. The phosphorous atom in an unmodified phosphate group is achiral. However, replacement of one of the non-bridging oxygens with one of the above atoms or groups of atoms can render the phosphorous atom chiral. The stereogenic phosphorous atom can possess either the "R" configuration (herein Rp) or the "S" configuration (herein Sp). The backbone can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

The phosphate group can be replaced by non-phosphorus containing connectors in certain backbone modifications. In some embodiments, the charged phosphate group can be replaced by a neutral moiety. Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Scaffolds that can mimic nucleic acids can also be constructed wherein the phosphate linker and ribose sugar are replaced by nuclease resistant nucleoside or nucleotide surrogates. Such modifications may comprise backbone and sugar modifications. In some embodiments, the nucleobases can be tethered by a surrogate backbone. Examples can include, without limitation, the morpholino, cyclobutyl, pyrrolidine and peptide nucleic acid (PNA) nucleoside surrogates.

The modified nucleosides and modified nucleotides can include one or more modifications to the sugar group, i.e. at sugar modification. For example, the 2' hydroxyl group (OH) can be modified, e.g. replaced with a number of different "oxy" or "deoxy" substituents. In some embodiments, modifications to the 2' hydroxyl group can enhance the stability of the nucleic acid since the hydroxyl can no longer be deprotonated to form a 2'-alkoxide ion.

Examples of 2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In some embodiments, the 2' hydroxyl group modification can be 2'-O-Me. In some embodiments, the 2' hydroxyl group modification can be a 2'-fluoro modification, which replaces the 2' hydroxyl group with a fluoride. In some embodiments, the 2' hydroxyl group modification can be a 2'-H, which replaces the 2' hydroxyl group with a hydrogen. In some embodiments, the 2' hydroxyl group modification can include "locked" nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In some embodiments, the 2' hydroxyl group modification can include "unlocked" nucleic acids (UNA) in which the ribose ring lacks the C2'-C3' bond. In some embodiments, the 2' hydroxyl group modification can include the methoxyethyl group (MOE), ($OCH_2CH_2OCH_3$, e.g., a PEG derivative).

"Deoxy" 2' modifications can include hydrogen (i.e. deoxyribose sugars, e.g., at the overhang portions of partially dsRNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH_2CH_2$— amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar modification can comprise a sugar group which may also contain one or more carbons that possess the opposite stereochemical configuration than that of the corresponding carbon in ribose. Thus, a modified nucleic acid can include nucleotides containing e.g., arabinose, as the sugar. The modified nucleic acids can also include abasic sugars. These abasic sugars can also be further modified at one or more of the constituent sugar atoms. The modified nucleic acids can also include one or more sugars that are in the L form, e.g. L-nucleosides.

The modified nucleosides and modified nucleotides described herein, which can be incorporated into a modified nucleic acid, can include a modified base, also called a nucleobase. Examples of nucleobases include, but are not limited to, adenine (A), guanine (G), cytosine (C), and uracil (U). These nucleobases can be modified or wholly replaced to provide modified residues that can be incorporated into modified nucleic acids. The nucleobase of the nucleotide can be independently selected from a purine, a pyrimidine, a purine analog, or pyrimidine analog. In some embodiments, the nucleobase can include, for example, naturally-occurring and synthetic derivatives of a base.

In embodiments employing a dual guide RNA, each of the crRNA and the tracr RNA can contain modifications. Such modifications may be at one or both ends of the crRNA and/or tracr RNA. In embodiments comprising an sgRNA, one or more residues at one or both ends of the sgRNA may be chemically modified, and/or internal nucleosides may be modified, and/or the entire sgRNA may be chemically modified. Certain embodiments comprise a 5 end modification. Certain embodiments comprise a 3' end modification.

In some embodiments, the guide RNAs disclosed herein comprise one of the modification patterns disclosed in WO2018/107028 A1, filed Dec. 8, 2017, titled "Chemically Modified Guide RNAs," the contents of which are hereby incorporated by reference in their entirety. In some embodiments, the guide RNAs disclosed herein comprise one of the structures/modification patterns disclosed in US20170114334, the contents of which are hereby incorporated by reference in their entirety. In some embodiments, the guide RNAs disclosed herein comprise one of the structures/modification patterns disclosed in WO2017/136794, WO2017004279, US2018187186, US2019048338, the contents of which are hereby incorporated by reference in their entirety.

In some embodiments, the sgRNA of the present disclosure comprises the modification patterns shown below in Table 2. "Full Sequence" in Table 2 refers to an sgRNA sequence for each of the guides listed in Table 1. "Full Sequence Modified" shows a modification pattern for each sgRNA.

TABLE 2 sgRNA and modification patterns to sgRNA of human albumin guide sequences

| Guide ID | Full Sequence | SEQ ID NO: | Full Sequence Modified | SEQ ID NO: |
|---|---|---|---|---|
| G009844 | GAGCAACCUCACUCUUGUCUGUUUUAGAGCUAGAAAUAGCAAGUUAAAAUAAGGCUAGUCCGUUAUCAACUUGAAAAAGUGGCACCGAGUCGGUGCUUUU | 34 | mG*mA*mG*CAACCUCACUCUUGUCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 66 |

TABLE 2-continued sgRNA and modification patterns to sgRNA of human albumin guide sequences

| Guide ID | Full Sequence | SEQ ID NO: | Full Sequence Modified | SEQ ID NO: |
|---|---|---|---|---|
| G009851 | AUGCAUUUGUUUCAAAAUAUGUUUU AGAGCUAGAAAUAGCAAGUUAAAAU AAGGCUAGUCCGUUAUCAACUUGAA AAAGUGGCACCGAGUCGGUGCUUUU | 35 | mA*mU*mG*CAUUUGUUUCAAAAUAUG UUUUAGAmGmCmUmAmGmAmAmAmUm AmGmCAAGUUAAAAUAAGGCUAGUCCG UUAUCAmAmCmUmUmGmAmAmAmAmAm GmUmGmGmCmAmCmCmGmAmGmUmCm GmGmUmGmCmU*mU*mU*mU | 67 |
| G009852 | UGCAUUUGUUUCAAAAUAUUGUUUU AGAGCUAGAAAUAGCAAGUUAAAAU AAGGCUAGUCCGUUAUCAACUUGAA AAAGUGGCACCGAGUCGGUGCUUUU | 36 | mU*mG*mC*AUUUGUUUCAAAAUAUUGU UUUAGAmGmCmUmAmGmAmAmAmUmAm GmCAAGUUAAAAUAAGGCUAGUCCGUUA UCAmAmCmUmUmGmAmAmAmAmAmGmUm GmGmCmAmCmCmGmAmGmUmCmGmGmUm GmCmU*mU*mU*mU | 68 |
| G009857 | AUUUAUGAGAUCAACAGCACGUUUU AGAGCUAGAAAUAGCAAGUUAAAAU AAGGCUAGUCCGUUAUCAACUUGAA AAAGUGGCACCGAGUCGGUGCUUUU | 37 | mA*mU*mU*UAUGAGAUCAACAGCACGU UUUAGAmGmCmUmAmGmAmAmAmUmAm GmCAAGUUAAAAUAAGGCUAGUCCGUUA UCAmAmCmUmUmGmAmAmAmAmAmGm UmGmGmCmAmCmCmGmAmGmUmCmGmGm UmGmCmU*mU*mU*mU | 69 |
| G009858 | GAUCAACAGCACAGGUUUUGGUUUU AGAGCUAGAAAUAGCAAGUUAAAAU AAGGCUAGUCCGUUAUCAACUUGAA AAAGUGGCACCGAGUCGGUGCUUUU | 38 | mG*mA*mU*CAACAGCACAGGUUUUGGU UUUAGAmGmCmUmAmGmAmAmAmUmAm GmCAAGUUAAAAUAAGGCUAGUCCGUUA UCAmAmCmUmUmGmAmAmAmAmAmGm UmGmGmCmAmCmCmGmAmGmUmCmGm GmUmGmCmU*mU*mU*mU | 70 |
| G009859 | UUAAAUAAAGCAUAGUGCAAGUUUU AGAGCUAGAAAUAGCAAGUUAAAAU AAGGCUAGUCCGUUAUCAACUUGAA AAAGUGGCACCGAGUCGGUGCUUUU | 39 | mU*mU*mA*AAUAAAGCAUAGUGCAAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 71 |
| G009860 | UAAAGCAUAGUGCAAUGGAUGUUUU AGAGCUAGAAAUAGCAAGUUAAAAU AAGGCUAGUCCGUUAUCAACUUGAA AAAGUGGCACCGAGUCGGUGCUUUU | 40 | mU*mA*mA*AGCAUAGUGCAAUGGAUGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 72 |
| G009861 | UAGUGCAAUGGAUAGGUCUUGUUUU AGAGCUAGAAAUAGCAAGUUAAAAU AAGGCUAGUCCGUUAUCAACUUGAA AAAGUGGCACCGAGUCGGUGCUUUU | 41 | mU*mA*mG*UGCAAUGGAUAGGUCUUGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 73 |
| G009866 | UACUAAAACUUUAUUUUACUGUUUU AGAGCUAGAAAUAGCAAGUUAAAAU AAGGCUAGUCCGUUAUCAACUUGAA AAAGUGGCACCGAGUCGGUGCUUUU | 42 | mU*mA*mC*UAAAACUUUAUUUUACUGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 74 |
| G009867 | AAAGUUGAACAAUAGAAAAAGUUUU AGAGCUAGAAAUAGCAAGUUAAAAU AAGGCUAGUCCGUUAUCAACUUGAA AAAGUGGCACCGAGUCGGUGCUUUU | 43 | mA*mA*mA*GUUGAACAAUAGAAAAAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 75 |
| G009868 | AAUGCAUAAUCUAAGUCAAAGUUUU AGAGCUAGAAAUAGCAAGUUAAAAU AAGGCUAGUCCGUUAUCAACUUGAA AAAGUGGCACCGAGUCGGUGCUUUU | 44 | mA*mA*mU*GCAUAAUCUAAGUCAAAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 76 |
| G009874 | UAAUAAAAUUCAAACAUCCUGUUUU AGAGCUAGAAAUAGCAAGUUAAAAU | 45 | mU*mA*mA*UAAAAUUCAAACAUCCUGUUU UAGAmGmCmUmAmGmAmAmAmUmAmGmC | 77 |

TABLE 2-continued sgRNA and modification patterns to sgRNA of human albumin guide sequences

| Guide ID | Full Sequence | SEQ ID NO: | Full Sequence Modified | SEQ ID NO: |
|---|---|---|---|---|
| | AAGGCUAGUCCGUUAUCAACUUGAA AAAGUGGCACCGAGUCGGUGCUUUU | | AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | |
| G012747 | GCAUCUUUAAAGAAUUAUUUGUUUU AGAGCUAGAAAUAGCAAGUUAAAAU AAGGCUAGUCCGUUAUCAACUUGAA AAAGUGGCACCGAGUCGGUGCUUUU | 46 | mG*mC*mA*UCUUUAAAGAAUUAUUUGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 78 |
| G012748 | UUUGGCAUUUAUUUCUAAAAGUUUU AGAGCUAGAAAUAGCAAGUUAAAAU AAGGCUAGUCCGUUAUCAACUUGAA AAAGUGGCACCGAGUCGGUGCUUUU | 47 | mU*mU*mU*GGCAUUUAUUUCUAAAAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 79 |
| G012749 | UGUAUUUGUGAAGUCUUACAGUUUU AGAGCUAGAAAUAGCAAGUUAAAAU AAGGCUAGUCCGUUAUCAACUUGAA AAAGUGGCACCGAGUCGGUGCUUUU | 48 | mU*mG*mU*AUUUGUGAAGUCUUACAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 80 |
| G012750 | UCCUAGGUAAAAAAAAAAAAGUUUU AGAGCUAGAAAUAGCAAGUUAAAAU AAGGCUAGUCCGUUAUCAACUUGAA AAAGUGGCACCGAGUCGGUGCUUUU | 49 | mU*mC*mC*UAGGUAAAAAAAAAAAAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 81 |
| G012751 | UAAUUUUCUUUUGCGCACUAGUUUU AGAGCUAGAAAUAGCAAGUUAAAAU AAGGCUAGUCCGUUAUCAACUUGAA AAAGUGGCACCGAGUCGGUGCUUUU | 50 | mU*mA*mA*UUUUCUUUUGCGCACUAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 82 |
| G012752 | UGACUGAAACUUCACAGAAUGUUUU AGAGCUAGAAAUAGCAAGUUAAAAU AAGGCUAGUCCGUUAUCAACUUGAA AAAGUGGCACCGAGUCGGUGCUUUU | 51 | mU*mG*mA*CUGAAACUUCACAGAAUGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 83 |
| G012753 | GACUGAAACUUCACAGAAUAGUUUU AGAGCUAGAAAUAGCAAGUUAAAAU AAGGCUAGUCCGUUAUCAACUUGAA AAAGUGGCACCGAGUCGGUGCUUUU | 52 | mG*mA*mC*UGAAACUUCACAGAAUAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 84 |
| G012754 | UUCAUUUUAGUCUGUCUUCUGUUUU AGAGCUAGAAAUAGCAAGUUAAAAU AAGGCUAGUCCGUUAUCAACUUGAA AAAGUGGCACCGAGUCGGUGCUUUU | 53 | mU*mU*mC*AUUUUAGUCUGUCUUCUGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 85 |
| G012755 | AUUAUCUAAGUUUGAAUAUAGUUUU AGAGCUAGAAAUAGCAAGUUAAAAU AAGGCUAGUCCGUUAUCAACUUGAA AAAGUGGCACCGAGUCGGUGCUUUU | 54 | mA*mU*mU*AUCUAAGUUUGAAUAUAGUUU UAGAmGmCmUmAmGmAmAmAmUmAmGmC AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | 86 |

TABLE 2-continued sgRNA and modification patterns to sgRNA of human albumin guide sequences

| Guide ID | Full Sequence | SEQ ID NO: | Full Sequence Modified | SEQ ID NO: |
|---|---|---|---|---|
| G012756 | AAUUUUUAAAAUAGUAUUCUGUUUUAGAGCUAGAAAUAGCAAGUUAAAAUAAGGCUAGUCCGUUAUCAACUUGAAAAAGUGGCACCGAGUCGGUGCUUUU | 55 | mA*mA*mU*UUUUAAAAUAGUAUUCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 87 |
| G012757 | UGAAUUAUUCUUCUGUUUAAGUUUUAGAGCUAGAAAUAGCAAGUUAAAAUAAGGCUAGUCCGUUAUCAACUUGAAAAAGUGGCACCGAGUCGGUGCUUUU | 56 | mU*mG*mA*AUUAUUCUUCUGUUUAAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 88 |
| G012758 | AUCAUCCUGAGUUUUUCUGUGUUUUAGAGCUAGAAAUAGCAAGUUAAAAUAAGGCUAGUCCGUUAUCAACUUGAAAAAGUGGCACCGAGUCGGUGCUUUU | 57 | mA*mU*mC*AUCCUGAGUUUUUCUGUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 89 |
| G012759 | UUACUAAAACUUUAUUUUACGUUUUAGAGCUAGAAAUAGCAAGUUAAAAUAAGGCUAGUCCGUUAUCAACUUGAAAAAGUGGCACCGAGUCGGUGCUUUU | 58 | mU*mU*mA*CUAAAACUUUAUUUUACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 90 |
| G012760 | ACCUUUUUUUUUUUUUACCUGUUUUAGAGCUAGAAAUAGCAAGUUAAAAUAAGGCUAGUCCGUUAUCAACUUGAAAAAGUGGCACCGAGUCGGUGCUUUU | 59 | mA*mC*mC*UUUUUUUUUUUUUACCUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 91 |
| G012761 | AGUGCAAUGGAUAGGUCUUUGUUUUAGAGCUAGAAAUAGCAAGUUAAAAUAAGGCUAGUCCGUUAUCAACUUGAAAAAGUGGCACCGAGUCGGUGCUUUU | 60 | mA*mG*mU*GCAAUGGAUAGGUCUUUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 92 |
| G012762 | UGAUUCCUACAGAAAAACUCGUUUUAGAGCUAGAAAUAGCAAGUUAAAAUAAGGCUAGUCCGUUAUCAACUUGAAAAAGUGGCACCGAGUCGGUGCUUUU | 61 | mU*mG*mA*UUCCUACAGAAAAACUCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 93 |
| G012763 | UGGGCAAGGGAAGAAAAAAAGUUUUAGAGCUAGAAAUAGCAAGUUAAAAUAAGGCUAGUCCGUUAUCAACUUGAAAAAGUGGCACCGAGUCGGUGCUUUU | 62 | mU*mG*mG*GCAAGGGAAGAAAAAAAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 94 |
| G012764 | CCUCACUCUUGUCUGGGCAAGUUUUAGAGCUAGAAAUAGCAAGUUAAAAUAAGGCUAGUCCGUUAUCAACUUGAAAAAGUGGCACCGAGUCGGUGCUUUU | 63 | mC*mC*mU*CACUCUUGUCUGGGCAAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 95 |
| G012765 | ACCUCACUCUUGUCUGGGCAGUUUUAGAGCUAGAAAUAGCAAGUUAAAAUAAGGCUAGUCCGUUAUCAACUUGAAAAAGUGGCACCGAGUCGGUGCUUUU | 64 | mA*mC*mC*UCACUCUUGUCUGGGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 96 |
| G012766 | UGAGCAACCUCACUCUUGUCGUUUUAGAGCUAGAAAUAGCAAGUUAAAAU | 65 | mU*mG*mA*GCAACCUCACUCUUGUCGUUUUAGAmGmCmUmAmGmAmAmAmUmAmGmC | 97 |

TABLE 2-continued sgRNA and modification patterns to sgRNA of human albumin guide sequences

| Guide ID | Full Sequence | SEQ ID NO: | Full Sequence Modified | SEQ ID NO: |
|---|---|---|---|---|
| | AAGGCUAGUCCGUUAUCAACUUGAA AAAGUGGCACCGAGUCGGUGCUUUU | | AAGUUAAAAUAAGGCUAGUCCGUUAUCAm AmCmUmUmGmAmAmAmAmAmGmUmGmGm CmAmCmCmGmAmGmUmCmGmGmUmGmCm U*mU*mU*mU | |

In some embodiments, the modified sgRNA comprises the following sequence: mGmCAAGUUAAAAUAAGGCUA-GUCCGUUAUCAmAmCmUmUmGAmnAAm GmUmGmGmCmAmCmCmGmAmGmUmCmGmGmUm GmCmU*mU*mU*mU (SEQ ID NO: 300), where "N" may be any natural or non-natural nucleotide, and wherein the totality of N's comprise an albumin intron 1 guide sequence as described in Table 1. For example, encompassed herein is SEQ ID NO: 300, where the N's are replaced with any of the guide sequences disclosed herein in Table 1 (SEQ ID Nos: 2-33).

For example, encompassed herein is SEQ ID NO: 300, where the N's are replaced with any of the guide sequences disclosed herein in Table 1 (SEQ ID NOs: 2-5, 10-17, 21-27, and 29-33).

Any of the modifications described below may be present in the gRNAs and mRNAs described herein.

The terms "mA," "mC," "mU," or "mG" may be used to denote a nucleotide that has been modified with 2'-O-Me.

Modification of 2'-O-methyl can be depicted as follows:

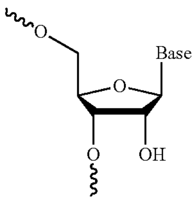

RNA

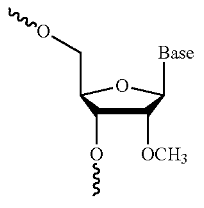

2'-O-Me

Another chemical modification that has been shown to influence nucleotide sugar rings is halogen substitution. For example, 2'-fluoro (2'-F) substitution on nucleotide sugar rings can increase oligonucleotide binding affinity and nuclease stability.

In this application, the terms "fA," "fC," "fU," or "fG" may be used to denote a nucleotide that has been substituted with 2'-F.

Substitution of 2'-F can be depicted as follows:

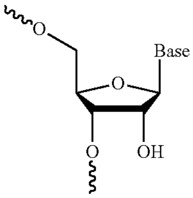

RNA
Natural composition of RNA

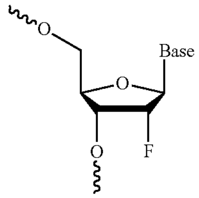

2'F-RNA
2'F substitution

Phosphorothioate (PS) linkage or bond refers to a bond where a sulfur is substituted for one nonbridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond.

The diagram below shows the substitution of S— into a nonbridging phosphate oxygen, generating a PS bond in lieu of a phosphodiester bond:

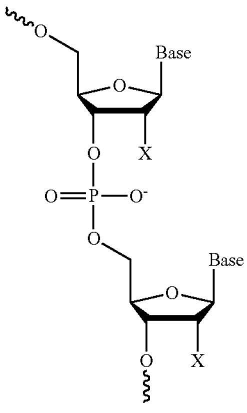

Phosphodiester
Natural phosphodiester linkage of RNA

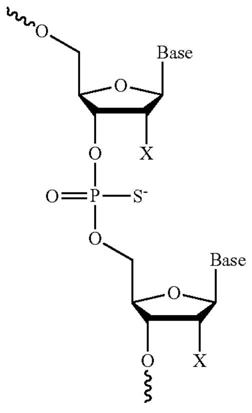

Phosphorothioate (PS)
Modified Phosphorothioate (PS) bond

Abasic nucleotides refer to those which lack nitrogenous bases. The figure below depicts an oligonucleotide with an abasic (also known as apurinic) site that lacks a base:

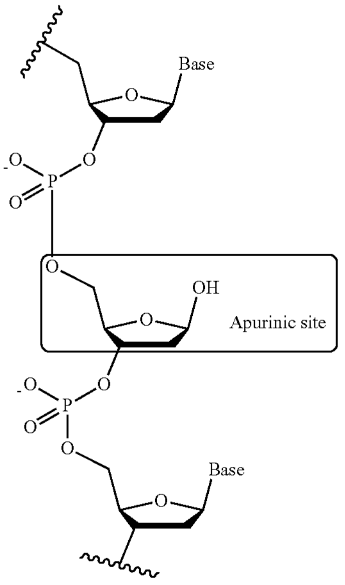

Inverted bases refer to those with linkages that are inverted from the normal 5' to 3' linkage (i.e., either a 5' to 5' linkage or a 3' to 3' linkage). For example:

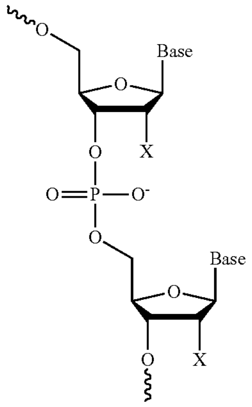

Normal oligonucleotide linkage

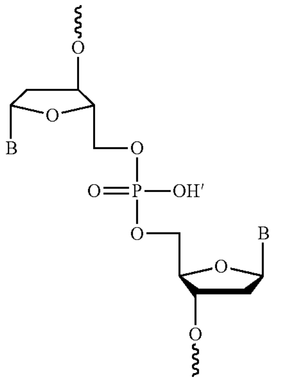

Inverted oligonucleotide linkage

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3' nucleotide may also be called an inverted abasic end cap.

In some embodiments, one or more of the first three, four, or five nucleotides at the 5' terminus, and one or more of the last three, four, or five nucleotides at the 3' terminus are modified. In some embodiments, the modification is a 2'-O-Me, 2'-F, inverted abasic nucleotide, PS bond, or other nucleotide modification well known in the art to increase stability and/or performance.

In some embodiments, the first four nucleotides at the 5' terminus, and the last four nucleotides at the 3' terminus are linked with phosphorothioate (PS) bonds.

In some embodiments, the first three nucleotides at the 5' terminus, and the last three nucleotides at the 3' terminus comprise a 2'-O-methyl (2'-O-Me) modified nucleotide. In some embodiments, the first three nucleotides at the 5' terminus, and the last three nucleotides at the 3' terminus comprise a 2'-fluoro (2'-F) modified nucleotide. In some embodiments, the first three nucleotides at the 5' terminus, and the last three nucleotides at the 3' terminus comprise an inverted abasic nucleotide.

In some embodiments, the guide RNA comprises a modified sgRNA. In some embodiments, the sgRNA comprises the modification pattern shown in SEQ ID No: 300, where N is any natural or non-natural nucleotide, and where the totality of the N's comprise a guide sequence that directs a nuclease to a target sequence in human albumin intron 1, e.g., as shown in Table 1.

In some embodiments, the guide RNA comprises a sgRNA shown in any one of SEQ ID No: 34-97. In some embodiments, the guide RNA comprises a sgRNA comprising any one of the guide sequences of SEQ ID No: 2-33 and the nucleotides of SEQ ID No: 300 wherein the nucleotides of SEQ ID No: 300 are on the 3' end of the guide sequence, and wherein the sgRNA may be modified, e.g., as shown in SEQ ID NO: 300.

In some embodiments, the guide RNA comprises a sgRNA shown in any one of SEQ ID NOs: 34-37,42-49, 53-59, 61-69, 74-81, 85-91, and 93-97. In some embodiments, the guide RNA comprises a sgRNA comprising any one of the guide sequences of SEQ ID NOs: 2-5, 10-17, 21-27, and 29-33 and the nucleotides of SEQ ID No: 300 wherein the nucleotides of SEQ ID NO: 300 are on the 3' end of the guide sequence, and wherein the sgRNA may be modified, e.g., as shown in SEQ ID NO: 300.

As noted above, in some embodiments, a composition or formulation disclosed herein comprises an mRNA comprising an open reading frame (ORF) encoding an RNA-guided DNA binding agent, such as a Cas nuclease as described herein. In some embodiments, an mRNA comprising an ORF encoding an RNA-guided DNA binding agent, such as a Cas nuclease, is provided, used, or administered. As described below, the mRNA comprising a Cas nuclease may comprise a Cas9 nuclease, such as an *S. pyogenes* Cas9 nuclease having cleavase, nickase, and/or site-specific DNA binding activity. In some embodiments, the ORF encoding an RNA-guided DNA nuclease is a "modified RNA-guided DNA binding agent ORF" or simply a "modified ORF," which is used as shorthand to indicate that the ORF is modified.

Cas9 ORFs, including modified Cas9 ORFs, are provided herein and are known in the art. As one example, the Cas9 ORF can be codon optimized, such that coding sequence includes one or more alternative codons for one or more amino acids. An "alternative codon" as used herein refers to variations in codon usage for a given amino acid, and may or may not be a preferred or optimized codon (codon optimized) for a given expression system. Preferred codon usage, or codons that are well-tolerated in a given system of expression, is known in the art. The Cas9 coding sequences, Cas9 mRNAs, and Cas9 protein sequences of WO2013/176772, WO2014/065596, WO2016/106121, and WO2019/067910 are hereby incorporated by reference. In particular, the ORFs and Cas9 amino acid sequences of the table at paragraph [0449] WO2019/067910, and the Cas9 mRNAs and ORFs of paragraphs [0214]-[0234] of WO2019/067910 are hereby incorporated by reference.

In some embodiments, the modified ORF may comprise a modified uridine at least at one, a plurality of, or all uridine positions. In some embodiments, the modified uridine is a uridine modified at the 5 position, e.g., with a halogen, methyl, or ethyl. In some embodiments, the modified uridine is a pseudouridine modified at the 1 position, e.g., with a halogen, methyl, or ethyl. The modified uridine can be, for example, pseudouridine, N1-methyl-pseudouridine, 5-methoxyuridine, 5-iodouridine, or a combination thereof. In some embodiments, the modified uridine is 5-methoxyuridine. In some embodiments, the modified uridine is 5-iodouridine. In some embodiments, the modified uridine is pseudouridine. In some embodiments, the modified uridine is N1-methyl-pseudouridine. In some embodiments, the modified uridine is a combination of pseudouridine and N1-methyl-pseudouridine. In some embodiments, the modified uridine is a combination of pseudouridine and 5-methoxyuridine. In some embodiments, the modified uridine is a combination of N1-methyl pseudouridine and 5-methoxyuridine. In some embodiments, the modified uridine is a combination of 5-iodouridine and N1-methyl-pseudouridine. In some embodiments, the modified uridine is a combination of pseudouridine and 5-iodouridine. In some embodiments, the modified uridine is a combination of 5-iodouridine and 5-methoxyuridine.

In some embodiments, an mRNA disclosed herein comprises a 5' cap, such as a Cap0, Cap1, or Cap2. A 5' cap is generally a 7-methylguanine ribonucleotide (which may be further modified, as discussed below e.g. with respect to ARCA) linked through a 5'-triphosphate to the 5' position of the first nucleotide of the 5'-to-3' chain of the mRNA, i.e., the first cap-proximal nucleotide. In Cap0, the riboses of the first and second cap-proximal nucleotides of the mRNA both comprise a 2'-hydroxyl. In Cap1, the riboses of the first and second transcribed nucleotides of the mRNA comprise a 2'-methoxy and a 2'-hydroxyl, respectively. In Cap2, the riboses of the first and second cap-proximal nucleotides of the mRNA both comprise a 2'-methoxy. See, e.g., Katibah et al. (2014) *Proc Natl Acad Sci USA* 111(33):12025-30; Abbas et al. (2017) *Proc Natl Acad Sci USA* 114(11):E2106-E2115. Most endogenous higher eukaryotic mRNAs, including mammalian mRNAs such as human mRNAs, comprise Cap1 or Cap2. Cap0 and other cap structures differing from Cap1 and Cap2 may be immunogenic in mammals, such as humans, due to recognition as "non-self" by components of the innate immune system such as IFIT-1 and IFIT-5, which can result in elevated cytokine levels including type I interferon. Components of the innate immune system such as IFIT-1 and FIT-5 may also compete with eIF4E for binding of an mRNA with a cap other than Cap1 or Cap2, potentially inhibiting translation of the mRNA.

A cap can be included co-transcriptionally. For example, ARCA (anti-reverse cap analog; Thermo Fisher Scientific Cat. No. AM8045) is a cap analog comprising a 7-methylguanine 3'-methoxy-5'-triphosphate linked to the 5' position of a guanine ribonucleotide which can be incorporated in vitro into a transcript at initiation. ARCA results in a Cap0 cap in which the 2' position of the first cap-proximal nucleotide is hydroxyl. See, e.g., Stepinski et al., (2001) "Synthesis and properties of mRNAs containing the novel 'anti-reverse' cap analogs 7-methyl(3'-O-methyl)GpppG and 7-methyl(3'deoxy)GpppG," RNA 7: 1486-1495. The ARCA structure is shown below.

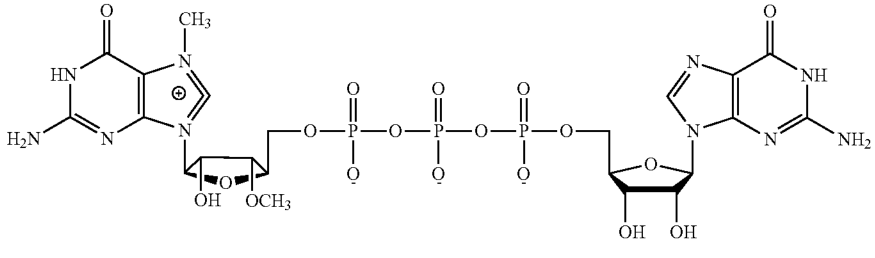

CleanCap™ AG (m7G(5')ppp(5')(2'OMeA)pG; TriLink Biotechnologies Cat. No. N-7113) or CleanCap™ GG (m7G (5')ppp(5')(2'OMeG)pG; TriLink Biotechnologies Cat. No. N-7133) can be used to provide a Cap1 structure co-transcriptionally. 3'-O-methylated versions of CleanCap™ AG and CleanCap™ GG are also available from TriLink Biotechnologies as Cat. Nos. N-7413 and N-7433, respectively. The CleanCap™ AG structure is shown below.

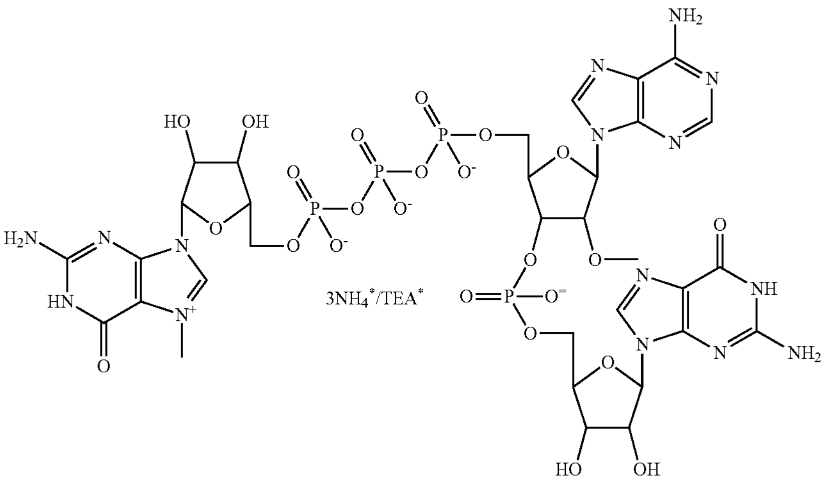

Alternatively, a cap can be added to an RNA post-transcriptionally. For example, Vaccinia capping enzyme is commercially available (New England Biolabs Cat. No. M2080S) and has RNA triphosphatase and guanylyltransferase activities, provided by its D1 subunit, and guanine methyltransferase, provided by its D12 subunit. As such, it can add a 7-methylguanine to an RNA, so as to give Cap0, in the presence of S-adenosyl methionine and GTP. See, e.g., Guo, P. and Moss, B. (1990) *Proc. Natl. Acad. Sci. USA* 87, 4023-4027; Mao, X. and Shuman, S. (1994) *J. Biol. Chem.* 269, 24472-24479.

In some embodiments, the mRNA further comprises a poly-adenylated (poly-A) tail. In some embodiments, the poly-A tail comprises at least 20, 30, 40, 50, 60, 70, 80, 90, or 100 adenines, optionally up to 300 adenines. In some embodiments, the poly-A tail comprises 95, 96, 97, 98, 99, or 100 adenine nucleotides.

C. Donor Constructs

The compositions and methods described herein include the use of a nucleic acid construct that comprises a sequence encoding a heterologous Factor IX gene to be inserted into a cut site created by a guide RNA of the present disclosure and an RNA-guided DNA binding agent. As used herein, such a construct is sometimes referred to as a "donor construct/template". In some embodiments, the construct is a DNA construct. Methods of designing and making various functional/structural modifications to donor constructs are known in the art. In some embodiments, the construct may comprise any one or more of a polyadenylation tail sequence, a polyadenylation signal sequence, splice acceptor site, or selectable marker. In some embodiments, the polyadenylation tail sequence is encoded, e.g., as a "poly-A" stretch, at the 3' end of the coding sequence. Methods of designing a suitable polyadenylation tail sequence and/or polyadenylation signal sequence are well known in the art. For example, the polyadenylation signal sequence AAUAAA (SEQ ID NO: 800) is commonly used in mammalian systems, although variants such as UAUAAA (SEQ ID NO: 801) or AU/GUAAA (SEQ ID NO: 802) have been identified. See, e.g., NJ Proudfoot, Genes & Dev. 25(17): 1770-82, 2011.

In some embodiments, the donor construct comprises a sequence encoding Factor IX, wherein the Factor IX sequence is wild type Factor IX, e.g., SEQ ID NO: 700. In some embodiments, the donor construct comprises a sequence encoding Factor IX, wherein the Factor IX sequence is wild type Factor IX, e.g., SEQ ID NO: 701. In some embodiments, the sequence encodes a variant of Factor IX. For example, the variant can possess increased coagulation activity than wild type Factor IX. For example, the variant Factor IX can comprise one or mutations, such as an amino acid substitution in position R338 (e.g., R338L), relative to SEQ ID NO: 701. In some embodiments, the sequence encodes a Factor IX variant that is 80%, 85%, 90%, 93%, 95%, 97%, 99% identical to SEQ ID NO: 700, SEQ ID NO: 701, or SEQ ID NO: 702, having at least 80%, 85%, 90%, 92%, 94%, 96%, 98%, 99%, 100%, or more, activity as compared to wild type Factor IX. In some embodiments, the sequence encodes a fragment of Factor IX, wherein the fragment possesses at least 80%, 85%, 90%, 92%, 94%, 96%, 98%, 99%, 100%, or more, activity as compared to wild type Factor IX.

In some embodiments, the donor construct comprises a sequence encoding a Factor IX variant, wherein the Factor IX variant activates coagulation in the absence of its cofactor, Factor VIII. Such Factor IX variants can further maintain the activity of wild type Factor IX. Such Factor IX variants can be used to treat hemophilia, such as hemophilia B. For example, such a Factor IX variant can comprise an amino acid substation at position L6, V181, K265, 1383, E185, or a combination thereof relative to wild type Factor IX (e.g., relative to SEQ ID NO: 701). For example, such a Factor IX variant can comprise an L6F mutation, a V181I mutation, a K265A mutation, an I383V mutation, an E185D mutation, or a combination thereof relative to wild type Factor IX (e.g., relative to SEQ ID NO: 701).

In one example, the Factor IX protein can comprise amino acid substitutions at positions L6 and V181. In another example, the Factor IX protein can comprise amino acid substitutions at positions L6 and K265. In another example, the Factor IX protein can comprise amino acid substitutions at positions L6 and 1383. In another example, the Factor IX protein can comprise amino acid substitutions at positions L6 and E185. In another example, the Factor IX protein can comprise amino acid substitutions at positions V181 and K265. In another example, the Factor IX protein can comprise amino acid substitutions at positions V181 and an 1383. In another example, the Factor IX protein can comprise amino acid substitutions at positions V181 and E185. In another example, the Factor IX protein can comprise amino acid substitutions at positions K265 and 1383. In another example, the Factor IX protein can comprise amino acid substitutions at positions K265 and E185. In another example, the Factor IX protein can comprise amino acid substitutions at positions 1383 and E185. In another example, the Factor IX protein can comprise amino acid substitutions at positions L6, V181, and K265. In another example, the Factor IX protein can comprise amino acid substitutions at positions L6, V181, and 1383. In another example, the Factor IX protein can comprise amino acid substitutions at positions L6, V181, and E185. In another example, the Factor IX protein can comprise amino acid substitutions at positions L6, K265, and 1383. In another example, the Factor IX protein can comprise amino acid substitutions at positions L6, K265, and E185. In another example, the Factor IX protein can comprise amino acid substitutions at positions L6, 1383, and E186. In another example, the Factor IX protein can comprise amino acid substitutions at positions V181, K265, and 1383. In another example, the Factor IX protein can comprise amino acid substitutions at positions V181, K265, and E185. In another example, the Factor IX protein can comprise amino acid substitutions at positions V181, 1383, and E186. In another example, the Factor IX protein can comprise amino acid substitutions at positions K265, 1383, and E185. In another example, the Factor IX protein can comprise amino acid substitutions at positions L6, V181, K265, and 1383. In another example, the Factor IX protein can comprise amino acid substitutions at positions L6, V181, 1383, and E185. In another example, the Factor IX protein can comprise amino acid substitutions at positions L6, K265, 1383, and E185. In another example, the Factor IX protein can comprise amino acid substitutions at positions V181, K265, 1383, and E185.

In a specific example, the Factor IX protein can comprise amino acid substitutions at positions V181, K265, and 1383. In another specific example, the Factor IX protein can comprise amino acid substitutions at positions V181, K265, 1383, and E185. In another specific example, the Factor IX protein can comprise amino acid substitutions at positions L6, V181, K265, and 1383.

In one example, the Factor IX protein can comprise an L6F mutation and a V181I mutation. In another example, the Factor IX protein can comprise an L6F mutation and a K265A mutation. In another example, the Factor IX protein can comprise an L6F mutation and an I383V mutation. In another example, the Factor IX protein can comprise an L6F mutation and an E185D mutation. In another example, the Factor IX protein can comprise a V181I mutation and a K265A mutation. In another example, the Factor IX protein can comprise a V181I mutation and an 1383V mutation. In another example, the Factor IX protein can comprise a V181I mutation and an E185D mutation. In another example, the Factor IX protein can comprise a K265A mutation and an I383V mutation. In another example, the Factor IX protein can comprise a K265A mutation and an E185D mutation. In another example, the Factor IX protein can comprise an I383V mutation and an E185D mutation. In another example, the Factor IX protein can comprise an L6F mutation, a V181I mutation, and a K265A mutation. In another example, the Factor IX protein can comprise an L6F mutation, a V181I mutation, and an I383V mutation. In another example, the Factor IX protein can comprise an L6F mutation, a V181I mutation and an E185D mutation. In another example, the Factor IX protein can comprise an L6F mutation, a K265A mutation, and an I383V mutation. In another example, the Factor IX protein can comprise an L6F mutation, a K265A mutation, and an E185D mutation. In another example, the Factor IX protein can comprise an L6F mutation, an I383V mutation, and an E186D mutation. In another example, the Factor IX protein can comprise a V181I mutation, a K265A mutation, and an I383V mutation. In another example, the Factor IX protein can comprise a V181I mutation, a K265A mutation, and an E185D mutation. In another example, the Factor IX protein can comprise a V181I mutation, an I383V mutation, and an E186D mutation. In another example, the Factor IX protein can comprise a K265A mutation, an I383V mutation, and an E185D mutation. In another example, the Factor IX protein can comprise an L6F mutation, a V181I mutation, a K265A mutation, and an I383V mutation. In another example, the Factor IX protein can comprise an L6F mutation, a V181I mutation, an I383V mutation, and an E185D mutation. In another example, the Factor IX protein can comprise an L6F mutation, a K265A mutation, an I383V mutation, and an E185D mutation. In another example, the Factor IX protein can comprise a V181I mutation, a K265A mutation, an I383V mutation, and an E185D mutation.

In a specific example, the Factor IX protein can comprise a V181I mutation, an K265A mutation, and an 1383V mutation. In another specific example, the Factor IX protein can comprise a V181I mutation, a K265A mutation, an I383V mutation, and an E185D mutation. In some embodiments, the Factor IX variant is at least 80%, 85%, 90%, 93%, 95%, 97%, 99% identical to SEQ ID NO: 700, having at least 80%, 85%, 90%, 92%, 94%, 96%, 98%, 99%, 100%, or more, activity as compared to wild type Factor IX. In certain embodiments, the Factor IX variant is at least 80%, 85%, 90%, 93%, 95%, 97%, 99% identical to SEQ ID NO: 700, having at least 80%, 85%, 90%, 92%, 94%, 96%, 98%, 99%, 100%, or more, activity as compared to wild type Factor IX and comprises a V181I mutation, a K265A mutation, an I383V mutation, and/or an E185D mutation. In another specific example, the Factor IX protein can comprise an L6F mutation, a V181I mutation, a K265A mutation, and an I383V mutation. In some embodiments, the Factor IX variant is at least 80%, 85%, 90%, 93%, 95%, 97%, 99% identical to SEQ ID NO: 700, having at least 80%, 85%, 90%, 92%, 94%, 96%, 98%, 99%, 100%, or more, activity as compared to wild type Factor IX and comprises an L6F mutation, a V181I mutation, a K265A mutation, and/or an I383V mutation.

The length of the construct can vary, depending on the size of the gene to be inserted, and can be, for example, from 200 base pairs (bp) to about 5000 bp, such as about 200 bp to about 2000 bp, such as about 500 bp to about 1500 bp. In some embodiments, the length of the DNAdonor template is about 200 bp, or is about 500 bp, or is about 800 bp, or is about 1000 base pairs, or is about 1500 base pairs. In other embodiments, the length of the donor template is at least 200 bp, or is at least 500 bp, or is at least 800 bp, or is at least 1000 bp, or is at least 1500 bp. In other embodiments, the length of the donor template is at least 200 bp, or is at least 500 bp, or is at least 800 bp, or is at least 1000 bp, or is at least 1500 bp, or at least 2000, or at least 2500, or at least 3000, or at least 3500, or at least 4000, or at least 4500, or at least 5000.

The construct can be DNA or RNA, single-stranded, double-stranded or partially single- and partially double-stranded and can be introduced into a host cell in linear or circular (e.g., minicircle) form. See, e.g., U.S. Patent Publication Nos. 2010/0047805, 2011/0281361, 2011/0207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4%3; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A construct can be introduced into a cell as part of a vector molecule having additional sequences such as, for example, replication origins, promoters and genes encoding antibiotic resistance. A construct may omit viral elements. Moreover, donor constructs can be introduced as naked nucleic acid, as nucleic acid complexed with an agent such as a liposome or poloxamer, or can be delivered by viruses (e.g., adenovirus, AAV, herpesvirus, retrovirus, lentivirus).

In some embodiments, the construct may be inserted so that its expression is driven by the endogenous promoter at the insertion site (e.g., the endogenous albumin promoter when the donor is integrated into the host cell's albumin locus). In such cases, the transgene may lack control elements (e.g., promoter and/or enhancer) that drive its expression (e.g., a promoterless construct). Nonetheless, it will be apparent that in other cases the construct may comprise a promoter and/or enhancer, for example a constitutive promoter or an inducible or tissue specific (e.g., liver- or platelet-specific) promoter that drives expression of the functional protein upon integration. The construct may comprise a sequence encoding a heterologous Factor IX protein downstream of and operably linked to a signal sequence encoding a signal peptide. In some embodiments, the nucleic acid construct works in homology-independent insertion of a nucleic acid that encodes a Factor IX protein. In some embodiments, the nucleic acid construct works in non-dividing cells, e.g., cells in which NHFJ, not HR, is the primary mechanism by which double-stranded DNA breaks are repaired. The nucleic acid may be a homology-independent donor construct.

Some donor constructs comprising a heterologous Factor IX nucleic acid (Factor IX transgene) are capable of insertion into a cut site in a target DNA sequence for a gene editing system (e.g., capable of insertion into a safe harbor gene, such as an albumin locus) by non-homologous end joining. In some cases, such constructs do not comprise homology arms. For example, such constructs can be inserted into a blunt end double-strand break following cleavage with a gene editing system (e.g., CRISPR/Cas system) as disclosed herein. In a specific example, the construct can be delivered via AAV and can be capable of insertion by non-homologous end joining (e.g., the construct can be one that does not comprise homology arms).

In a specific example, the construct can be inserted via homology-independent targeted integration. For example, the heterologous Factor IX nucleic acid in the construct can be flanked on each side by a target site for a gene editing system (e.g., the same target site as in the target DNA sequence for targeted insertion (e.g., in a safe harbor gene), and the same gene editing system being used to cleave the target DNA sequence for targeted insertion). The gene editing system can then cleave the target sites flanking the heterologous Factor IX nucleic acid. In a specific example, the construct is delivered AAV-mediated delivery, and cleavage of the target sites flanking the heterologous Factor IX nucleic acid can remove the inverted terminal repeats (ITRs) of the AAV. In some methods, the target DNA sequence for targeted insertion (e.g., target DNA sequence in a safe harbor locus, e.g., a gRNA target sequence including the flanking protospacer adjacent motif) is no longer present if the heterologous Factor IX nucleic acid is inserted into the cut site or target DNA sequence in the correct orientation but it is reformed if the heterologous Factor IX nucleic acid is inserted into the cut site or target DNA sequence in the opposite orientation. This can help ensure that the heterologous Factor IX nucleic acid is inserted in the correct orientation for expression.

Also described herein are bidirectional nucleic acid constructs that allow enhanced insertion and expression of a Factor IX gene. Briefly, various bidirectional constructs disclosed herein comprise at least two nucleic acid segments, wherein one segment (the first segment) comprises a coding sequence that encodes Factor IX (sometimes interchangeably referred to herein as "transgene"), while the other segment (the second segment) comprises a sequence wherein the complement of the sequence encodes Factor IX.

In one embodiment, a bidirectional construct comprise at least two nucleic acid segments in cis, wherein one segment (the first segment) comprises a coding sequence (sometimes interchangeably referred to herein as "transgene"), while the other segment (the second segment) comprises a sequence wherein the complement of the sequence encodes a transgene. The first transgene and the second transgene may be the same or different. The bidirectional constructs may comprise at least two nucleic acid segments in cis, wherein one segment (the first segment) comprises a coding sequence that encodes a heterologous gene in one orientation, while the other segment (the second segment) comprises a sequence wherein its complement encodes the heterologous gene in the other orientation. That is, the first segment is a complement of the second segment (not necessarily a perfect complement); the complement of the second segment is the reverse complement of the first segment (not necessarily a perfect reverse complement though both encode the same heterologous protein). A bidirectional construct may comprise a first coding sequence that encodes a heterologous gene linked to a splice acceptor and a second coding sequence wherein the complement encodes a heterologous gene in the other orientation, also linked to a splice acceptor.

When used in combination with a gene editing system (e.g., CRISPR/Cas system; zinc finger nuclease (ZFN) system; transcription activator-like effector nuclease (TALEN) system) as described herein, the bidirectionality of the nucleic acid constructs allows the construct to be inserted in either direction (is not limited to insertion in one direction) within a target insertion site, allowing the expression of Factor IX from either a) a coding sequence of one segment (e.g., the left segment encoding "Human F9" of FIG. 1 upper left ssAAV construct), or b) a complement of the other segment (e.g., the complement of the right segment encoding "Human F9" indicated upside down in the upper left ssAAV construct FIG. 1), thereby enhancing insertion and expression efficiency, as exemplified herein. Various known gene editing systems can be used in the practice of the present disclosure, including, e.g., CRISPR/Cas system; zinc finger nuclease (ZFN) system; transcription activator-like effector nuclease (TALEN) system.

The bidirectional constructs disclosed herein can be modified to include any suitable structural feature as needed for any particular use and/or that confers one or more desired function. In some embodiments, the bidirectional nucleic acid construct disclosed herein does not comprise a homology arm. In some embodiments, the bidirectional nucleic acid construct disclosed herein is a homology-independent donor construct. In some embodiments, owing in part to the bidirectional function of the nucleic acid construct, the bidirectional construct can be inserted into a genomic locus in either direction as described herein to allow for efficient insertion and/or expression of a polypeptide of interest (e.g., Factor IX).

In some embodiments, the bidirectional nucleic acid construct does not comprise a promoter that drives the expression of Factor IX. For example, the expression of Factor IX is driven by a promoter of the host cell (e.g., the endogenous albumin promoter when the transgene is integrated into a host cell's albumin locus).

In some embodiments, the bidirectional nucleic acid construct comprises a first segment comprising a coding sequence for Factor IX and a second segment comprising a reverse complement of a coding sequence of Factor IX. Thus, the coding sequence in the first segment is capable of expressing Factor IX, while the complement of the reverse complement in the second segment is also capable of expressing Factor IX. As used herein, "coding sequence" when referring to the second segment comprising a reverse complement sequence refers to the complementary (coding) strand of the second segment (i.e., the complement coding sequence of the reverse complement sequence in the second segment).

In some embodiments, the coding sequence that encodes Factor IX in the first segment is less than 100% complementary to the reverse complement of a coding sequence that also encodes Factor IX. That is, in some embodiments, the first segment comprises a coding sequence (1) for Factor IX, and the second segment is a reverse complement of a coding sequence (2) for Factor IX, wherein the coding sequence (1) is not identical to the coding sequence (2). For example, coding sequence (1) and/or coding sequence (2) that encodes for Factor IX can be codon optimized, such that coding sequence (1) and the reverse complement of coding sequence (2) possess less than 100% complementarity. In some embodiments, the coding sequence of the second segment encodes Factor IX using one or more alternative codons for one or more amino acids of the same (i.e., same amino acid sequence) Factor IX encoded by the coding sequence in the first segment. An "alternative codon" as used herein refers to variations in codon usage for a given amino acid, and may or may not be a preferred or optimized codon (codon optimized) for a given expression system. Preferred codon usage, or codons that are well-tolerated in a given system of expression is known in the art.

In some embodiments, the second segment comprises a reverse complement sequence that adopts different codon usage from that of the coding sequence of the first segment in order to reduce hairpin formation. Such a reverse complement forms base pairs with fewer than all nucleotides of the coding sequence in the first segment, yet it optionally encodes the same polypeptide. In such cases, the coding sequence, e.g. for Polypeptide A, of the first segment many be homologous to, but not identical to, the coding sequence, e.g. for Polypeptide A of the second half of the bidirectional construct. In some embodiments, the second segment comprises a reverse complement sequence that is not substantially complementary (e.g., not more than 70% complementary) to the coding sequence in the first segment. In some embodiments, the second segment comprises a reverse complement sequence that is highly complementary (e.g., at least 90% complementary) to the coding sequence in the first segment. In some embodiments, the second segment comprises a reverse complement sequence having at least about 30%, about 35%, about 40%, about 45%, about 50%, about 55%, about 60%, about 65%, about 70%, about 75%, about 80%, about 85%, about 90%, about 95%, about 97%, or about 99% complementarity to the coding sequence in the first segment.

In some embodiments, the second segment comprises a reverse complement sequence having 100% complementarity to the coding sequence in the first segment. That is, the sequence in the second segment is a perfect reverse complement of the coding sequence in the first segment. By way of example, the first segment comprises a hypothetical sequence 5' CTGGACCGA 3' (SEQ ID NO: 500) and the second segment comprises the reverse complement of SEQ ID NO: 1—i.e., 5' TCGGTCCAG 3' (SEQ ID NO: 502).

In some embodiments, the bidirectional nucleic acid construct comprises a first segment comprising a coding sequence for Factor IX (a first polypeptide) and a second segment comprising a reverse complement of a coding sequence of a (second) polypeptide. In some embodiments, the first and second segments each comprise a coding sequence that encodes the same polypeptide (e.g., Factor IX), as described above. In some embodiments, the first and second segments each comprise a coding sequence that encodes different polypeptides. For example, the first polypeptide is Factor IX and the second polypeptide is Polypeptide B. As a further example, the first polypeptide is Factor IX and the second polypeptide is a variant (e.g., a fragment, mutant, fusion) of Factor IX (e.g., having R338L mutation described herein). A coding sequence that encodes a polypeptide may optionally comprise one or more additional sequences, such as sequences encoding amino- or carboxy-terminal amino acid sequences such as a signal sequence, label sequence (e.g. HiBit), or heterologous functional sequence (e.g. nuclear localization sequence (NLS) or self-cleaving peptide) linked to the polypeptide. A coding sequence that encodes a polypeptide may optionally comprise sequences encoding one or more amino-terminal signal peptide sequences. Each of these additional sequences can be the same or different in the first segment and second segment of the construct.

In some embodiments, the bidirectional nucleic acid construct is linear. For example, the first and second segments are joined in a linear manner through a linker sequence. In some embodiments, the 5' end of the second segment that comprises a reverse complement sequence is linked to the 3' end of the first segment. In some embodiments, the 5' end of the first segment is linked to the 3' end of the second segment that comprises a reverse complement sequence. In some embodiments, the linker sequence is about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 500, 1000, 1500, 2000 or more nucleotides in length. As would be appreciate by those of skill in the art, other structural elements in addition to, or instead of a linker sequence, can be inserted between the first and second segments.

The bidirectional constructs disclosed herein can be modified to include any suitable structural feature as needed for any particular use and/or that confers one or more desired function. In some embodiments, the bidirectional nucleic acid construct disclosed herein does not comprise a homology arm. In some embodiments, owing in part to the bidirectional function of the nucleic acid construct, the bidirectional construct can be inserted into a genomic locus in either direction (orientation) as described herein to allow for efficient insertion and/or expression of a polypeptide of interest (e.g., a heterologous Factor IX).

In some embodiments, one or both of the first and second segment comprises a polyadenylation tail sequence. Methods of designing a suitable polyadenylation tail sequence are well known in the art.

In some embodiments, one or both of the first and second segment comprises a polyadenylation tail sequence and/or a polyadenylation signal sequence downstream of an open reading frame. In some embodiments, the polyadenylation tail sequence is encoded, e.g., as a "poly-A" stretch, at the 3' end of the first and/or second segment. In some embodiments, a polyadenylation tail sequence is provided co-transcriptionally as a result of a polyadenylation signal sequence that is encoded at or near the 3' end of the first and/or second segment. In some embodiments, a poly-A tail comprises at least 20, 30, 40, 50, 60, 70, 80, 90, or 100 adenines, optionally up to 300 adenines. In some embodiments, the poly-A tail comprises 95, 96, 97, 98, 99, or 100 adenine nucleotides. Methods of designing a suitable polyadenylation tail sequence and/or polyadenylation signal sequence are well known in the art. Suitable splice acceptor sequences are disclosed and exemplified herein, including mouse albumin and human FIX splice acceptor sites. In some embodiments, the polyadenylation signal sequence AAUAAA (SEQ ID NO: 800) is commonly used in mammalian systems, although variants such as UAUAAA (SEQ ID NO: 801) or AU/GUAAA (SEQ ID NO: 802) have been identified. See, e.g., NJ Proudfoot, Genes & Dev. 25(17): 1770-82, 2011. In some embodiments, a polyA tail sequence is included.

In some embodiments, the constructs disclosed herein can be DNA or RNA, single-stranded, double-stranded, or partially single- and partially double-stranded. For example, the constructs can be single- or double-stranded DNA. In some embodiments, the nucleic acid can be modified (e.g., using nucleoside analogs), as described herein.

In some embodiments, the constructs disclosed herein comprise a splice acceptor site on either or both ends of the construct, e.g., 5' of an open reading frame in the first and/or second segments, or 5' of one or both transgene sequences. In some embodiments, the splice acceptor site comprises NAG. In further embodiments, the splice acceptor site consists of NAG. In some embodiments, the splice acceptor is an albumin splice acceptor, e.g., an albumin splice acceptor used in the splicing together of exons 1 and 2 of albumin. In some embodiments, the splice acceptor is derived from the human albumin gene. In some embodiments, the splice acceptor is derived from the mouse albumin gene. In some embodiments, the splice acceptor is a F9 (or "FIX") splice acceptor, e.g., the F9 splice acceptor used in the splicing together of exons 1 and 2 of F9. In some embodiments, the splice acceptor is derived from the human F9 gene. In some embodiments, the splice acceptor is derived from the mouse F9 gene. Additional suitable splice acceptor sites useful in eukaryotes, including artificial splice acceptors are known and can be derived from the art. See, e.g., Shapiro, et al., 1987, Nucleic Acids Res., 15, 7155-7174, Burset, et al., 2001, Nucleic Acids Res., 29, 255-259.

In some embodiments, the bidirectional constructs disclosed herein can be modified on either or both ends to include one or more suitable structural features as needed, and/or to confer one or more functional benefit. For example, structural modifications can vary depending on the method(s) used to deliver the constructs disclosed herein to a host cell—e.g., use of viral vector delivery or packaging into lipid nanoparticles for delivery. Such modifications include, without limitation, e.g., terminal structures such as inverted terminal repeats (ITR), hairpin, loops, and other structures such as toroid. In some embodiments, the constructs disclosed herein comprise one, two, or three ITRs. In some embodiments, the constructs disclosed herein comprise no more than two ITRs. Various methods of structural modifications are known in the art.

In some embodiments, one or both ends of the construct can be protected (e.g., from exonucleolytic degradation) by methods known in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting the constructs from degradation include, but are not limited to, addition of terminal amino group(s) and the use of modified internucleotide linkages such as, for example, phosphorothioates, phosphoramidates, and O-methyl ribose or deoxyribose residues.

In some embodiments, the constructs disclosed herein can be introduced into a cell as part of a vector having additional sequences such as, for example, replication origins, promoters and genes encoding antibiotic resistance. In some embodiments, the constructs can be introduced as naked nucleic acid, as nucleic acid complexed with an agent such as a liposome, polymer, or poloxamer, or can be delivered by viral vectors (e.g., adenovirus, AAV, herpesvirus, retrovirus, lentivirus).

In some embodiments, although not required for expression, the constructs disclosed herein may also include transcriptional or translational regulatory sequences, for example, promoters, enhancers, insulators, internal ribosome entry sites, sequences encoding peptides, and/or polyadenylation signals.

In some embodiments, the constructs comprising a coding sequence for Factor IX may include one or more of the following modifications: codon optimization (e.g., to human codons) and/or addition of one or more glycosylation sites. See, e.g., McIntosh et al. (2013) *Blood* (17):3335-44.

D. Gene Editing System

Various known gene editing systems can be used for targeted insertion of the Factor IX gene in the practice of the present disclosure, including, e.g., CRISPR/Cas system; zinc finger nuclease (ZFN) system; transcription activator-like effector nuclease (TALEN) system. Generally, the gene editing systems involve the use of engineered cleavage systems to induce a double strand break (DSB) or a nick (e.g., a single strand break, or SSB) in a target DNA sequence. Cleavage or nicking can occur through the use of specific nucleases such as engineered ZFN, TALENs, or using the CRISPR/Cas system with an engineered guide RNA to guide specific cleavage or nicking of a target DNA sequence. Further, targeted nucleases are being developed based on the Argonaute system (e.g., from *T. thermophilus*, known as 'TtAgo', see Swarts et al (2014) Nature 507 (7491): 258-261), which also may have the potential for uses in genome editing and gene therapy.

It will be appreciated that for methods that use the guide RNAs disclosed herein, the methods include the use of the CRISPR/Cas system (and any of the donor construct disclosed herein that comprises a sequence encoding Factor IX). It will also be appreciated that the present disclosure contemplates methods of targeted insertion and expression of Factor IX using the bidirectional constructs disclosed herein, which can be performed with or without the guide RNAs disclosed herein (e.g., using a ZFN system to cause a break in a target DNA sequence, creating a site for insertion of the bidirectional construct).

In some embodiments, a CRISPR/Cas system (e.g., a guide RNA and RNA-guided DNA binding agent) can be used to create a site of insertion at a desired locus within a host genome, at which site a donor construct (e.g., bidirectional construct) comprising a sequence encoding Factor IX disclosed herein can be inserted to express Factor IX. The Factor IX may be heterologous with respect to its insertion site or locus, for example a safe harbor locus from which Factor IX is not normally expressed, as described herein. Alternatively, in some embodiments, Factor IX may be non-heterologous with respect to its insertion site, for example, insertion of a wild type Factor IX into the endogenous locus to correct a defective Factor IX gene. The safe harbor may be within an albumin gene, such as a human albumin gene. The safe harbor may be within an albumin intron 1 region, e.g., human albumin intron 1. The safe harbor may be a human safe harbor, e.g., for a liver tissue or hepatocyte host cell. In some embodiments, a guide RNA described herein can be used according to the present methods with an RNA-guided DNA binding agent (e.g., Cas nuclease) to create a site of insertion, at which site a donor construct (e.g., bidirectional construct) comprising a sequence encoding Factor IX can be inserted to express Factor IX. The guide RNAs useful for targeted insertion of Factor IX into intron 1 of the human albumin locus are exemplified and described herein (see, e.g., Table 1).

Methods of using various RNA-guided DNA-binding agents, e.g., a nuclease, such as a Cas nuclease, e.g., Cas9, are also well known in the art. While the use of a bidirectional nucleic acid with a CRISPR/Cas system is exemplified herein, it will be appreciated that suitable variations to the system can also be used. It will be appreciated that, depending on the context, the RNA-guided DNA-binding agent can be provided as a nucleic acid (e.g., DNA or mRNA) or as a protein. In some embodiments, the present method can be practiced in a host cell that already comprises and/or expresses an RNA-guided DNA-binding agent.

In some embodiments, the RNA-guided DNA-binding agent, such as a Cas9 nuclease, has cleavase activity, which can also be referred to as double-strand endonuclease activity. In some embodiments, the RNA-guided DNA-binding agent, such as a Cas9 nuclease, has nickase activity, which can also be referred to as single-strand endonuclease activity. In some embodiments, the RNA-guided DNA-binding agent comprises a Cas nuclease. Examples of Cas nucleases include those of the type II CRISPR systems of *S. pyogenes*, *S. aureus*, and other prokaryotes (see, e.g., the list in the next paragraph), and variant or mutant (e.g., engineered, non-naturally occurring, naturally occurring, or or other variant) versions thereof. See, e.g., US2016/0312198 A1; US 2016/0312199 A1.

Non-limiting exemplary species that the Cas nuclease can be derived from include *Streptococcus pyogenes*, *Streptococcus thermophilus*, *Streptococcus* sp., *Staphylococcus aureus*, *Listeria innocua*, *Lactobacillus gasseri*, *Francisella novicida*, *Wolinella succinogenes*, *Sutterella wadsworthensis*, *Gammaproteobacterium*, *Neisseria meningitidis*, *Campylobacter jejuni*, *Pasteurella multocida*, *Fibrobacter succinogene*, *Rhodospirillum rubrum*, *Nocardiopsis dassonvillei*, *Streptomyces pristinaespiralis*, *Streptomyces viridochromogenes*, *Streptomyces viridochromogenes*, *Streptosporangium roseum*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Lactobacillus buchneri*, *Treponema denticola*, *Microscilla marina*, *Burkholderiales bacterium*, *Polaromonas naphthalenivorans*, *Polaromonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*. *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, *Streptococcus pasteurianus*, *Neisseria cinerea*, *Campylobacter lari*, *Parvibaculum lavamentivorans*, *Corynebacterium diphtheria*, *Acidaminococcus* sp., *Lachnospiraceae bacterium* ND2006, and *Acaryochloris marina*.

In some embodiments, the Cas nuclease is the Cas9 nuclease from *Streptococcus pyogenes*. In some embodiments, the Cas nuclease is the Cas9 nuclease from *Streptococcus thermophilus*. In some embodiments, the Cas nuclease is the Cas9 nuclease from *Neisseria meningitidis*. In some embodiments, the Cas nuclease is the Cas9 nuclease is from *Staphylococcus aureus*. In some embodiments, the Cas nuclease is the Cpf1 nuclease from *Francisella novicida*. In some embodiments, the Cas nuclease is the Cpf1 nuclease from *Acidaminococcus* sp. In some embodiments, the Cas nuclease is the Cpf1 nuclease from *Lachnospiraceae bacterium* ND2006. In further embodiments, the Cas nuclease is the Cpf1 nuclease from *Francisella tularensis*, *Lachnospiraceae bacterium*, *Butyrivibrio proteoclasticus*, *Peregrinibacteria bacterium*, *Parcubacteria bacterium*, *Smithella*, *Acidaminococcus*, *Candidatus Methanoplasma termitum*, *Eubacterium eligens*, *Moraxella bovoculi*, *Leptospira inadai*, *Porphyromonas crevioricanis*, *Prevotella disiens*, or *Porphyromonas macacae*. In certain embodiments, the Cas nuclease is a Cpf1 nuclease from an *Acidaninococcus* or *Lachnospiraceae*.

In some embodiments, the gRNA together with an RNA-guided DNA-binding agent is called a ribonucleoprotein complex (RNP). In some embodiments, the RNA-guided DNA-binding agent is a Cas nuclease. In some embodiments, the gRNA together with a Cas nuclease is called a Cas RNP. In some embodiments, the RNP comprises Type-I, Type-II, or Type-III components. In some embodiments, the Cas nuclease is the Cas9 protein from the Type-II CRISPR/Cas system. In some embodiment, the gRNA together with Cas9 is called a Cas9 RNP.

Wild type Cas9 has two nuclease domains: RuvC and HNH. The RuvC domain cleaves the non-target DNA strand, and the HNH domain cleaves the target strand of DNA. In some embodiments, the Cas9 protein comprises more than one RuvC domain and/or more than one HNH domain. In some embodiments, the Cas9 protein is a wild type Cas9. In each of the composition, use, and method embodiments, the Cas induces a double strand break in target DNA.

In some embodiments, chimeric Cas nucleases are used, where one domain or region of the protein is replaced by a portion of a different protein. In some embodiments, a Cas nuclease domain may be replaced with a domain from a different nuclease such as Fok1. In some embodiments, a Cas nuclease may be a modified nuclease.

In other embodiments, the Cas nuclease may be from a Type-I CRISPR/Cas system. In some embodiments, the Cas nuclease may be a component of the Cascade complex of a Type-I CRISPR/Cas system. In some embodiments, the Cas nuclease may be a Cas3 protein. In some embodiments, the Cas nuclease may be from a Type-III CRISPR/Cas system. In some embodiments, the Cas nuclease may have an RNA cleavage activity.

In some embodiments, the RNA-guided DNA-binding agent has single-strand nickase activity, i.e., can cut one DNA strand to produce a single-strand break, also known as a "nick." In some embodiments, the RNA-guided DNA-binding agent comprises a Cas nickase. A nickase is an enzyme that creates a nick in dsDNA, i.e., cuts one strand but not the other of the DNA double helix. In some embodiments, a Cas nickase is a version of a Cas nuclease (e.g., a Cas nuclease discussed above) in which an endonucleolytic active site is inactivated, e.g., by one or more alterations (e.g., point mutations) in a catalytic domain. See, e.g., U.S. Pat. No. 8,889,356 for discussion of Cas nickases and exemplary catalytic domain alterations. In some embodiments, a Cas nickase such as a Cas9 nickase has an inactivated RuvC or HNH domain.

In some embodiments, the RNA-guided DNA-binding agent is modified to contain only one functional nuclease domain. For example, the agent protein may be modified such that one of the nuclease domains is mutated or fully or partially deleted to reduce its nucleic acid cleavage activity. In some embodiments, a nickase is used having a RuvC domain with reduced activity. In some embodiments, a nickase is used having an inactive RuvC domain. In some embodiments, a nickase is used having an HNH domain with reduced activity. In some embodiments, a nickase is used having an inactive HNH domain.

In some embodiments, a conserved amino acid within a Cas protein nuclease domain is substituted to reduce or alter nuclease activity. In some embodiments, a Cas nuclease may comprise an amino acid substitution in the RuvC or RuvC-like nuclease domain. Exemplary amino acid substitutions in the RuvC or RuvC-like nuclease domain include D10A (based on the *S. pyogenes* Cas9 protein). See, e.g., Zetsche et al. (2015) *Cell* October 22:163(3): 759-771. In some embodiments, the Cas nuclease may comprise an amino acid substitution in the HNH or HNH-like nuclease domain. Exemplary amino acid substitutions in the HNH or HNH-like nuclease domain include E762A, H840A, N863A, H983A, and D986A (based on the *S. pyogenes* Cas9 protein). See, e.g., Zetsche et al. (2015). Further exemplary amino acid substitutions include D917A, E1006A, and D1255A (based on the *Francisella novicida* U112 Cpf1 (FnCpf1) sequence (UniProtKB—AOQ7Q2 (CPF1_FRATN)).

In some embodiments, a nickase is provided in combination with a pair of guide RNAs that are complementary to the sense and antisense strands of the target sequence, respectively. In this embodiment, the guide RNAs direct the nickase to a target sequence and introduce a DSB by generating a nick on opposite strands of the target sequence (i.e., double nicking). In some embodiments, a nickase is used together with two separate guide RNAs targeting opposite strands of DNA to produce a double nick in the target DNA. In some embodiments, a nickase is used together with two separate guide RNAs that are selected to be in close proximity to produce a double nick in the target DNA.

In some embodiments, the RNA-guided DNA-binding agent comprises one or more heterologous functional domains (e.g., is or comprises a fusion polypeptide).

In some embodiments, the heterologous functional domain may facilitate transport of the RNA-guided DNA-binding agent into the nucleus of a cell. For example, the heterologous functional domain may be a nuclear localization signal (NLS). In some embodiments, the RNA-guided DNA-binding agent may be fused with 1-10 NLS(s). In some embodiments, the RNA-guided DNA-binding agent may be fused with 1-5 NLS(s). In some embodiments, the RNA-guided DNA-binding agent may be fused with one NLS. Where one NLS is used, the NLS may be linked at the N-terminus or the C-terminus of the RNA-guided DNA-binding agent sequence. It may also be inserted within the RNA-guided DNA-binding agent sequence. In other embodiments, the RNA-guided DNA-binding agent may be fused with more than one NLS. In some embodiments, the RNA-guided DNA-binding agent may be fused with 2, 3, 4, or 5 NLSs. In some embodiments, the RNA-guided DNA-binding agent may be fused with two NLSs. In certain circumstances, the two NLSs may be the same (e.g., two SV40 NLSs) or different. In some embodiments, the RNA-guided DNA-binding agent is fused to two SV40 NLS sequences linked at the carboxy terminus. In some embodiments, the RNA-guided DNA-binding agent may be fused with two NLSs, one linked at the N-terminus and one at the C-terminus. In some embodiments, the RNA-guided DNA-binding agent may be fused with 3 NLSs. In some embodiments, the RNA-guided DNA-binding agent may be fused with no NLS. In some embodiments, the NLS may be a monopartite sequence, such as, e.g., the SV40 NLS, PKKKRKV (SEQ ID NO: 600) or PKKKRRV (SEQ ID NO: 601). In some embodiments, the NLS may be a bipartite sequence, such as the NLS of nucleoplasmin, KRPAATKKAGQAKKKK (SEQ ID NO: 602). In a specific embodiment, a single PKKKRKV (SEQ ID NO: 600) NLS may be linked at the C-terminus of the RNA-guided DNA-binding agent. One or more linkers are optionally included at the fusion site.

III. Delivery Methods

The guide RNA, RNA-guided DNA binding agents (e.g., Cas nuclease), and nucleic acid constructs (e.g., bidirectional construct) disclosed herein can be delivered to a host cell or population of host cells or a subject, in vivo or ex vivo, using various known and suitable methods available in the art. The guide RNA, RNA-guided DNA binding agents, and nucleic acid constructs can be delivered individually or together in any combination, using the same or different delivery methods as appropriate.

Conventional viral and non-viral based gene delivery methods can be used to introduce the guide RNA disclosed herein as well as the RNA-guided DNA binding agent and donor construct in cells (e.g., mammalian cells) and target tissues. As further provided herein, non-viral vector delivery systems nucleic acids such as non-viral vectors, plasmid vectors, and, e.g naked nucleic acid, and nucleic acid complexed with a delivery vehicle such as a liposome, lipid nanoparticle (LNP), or poloxamer. Viral vector delivery systems include DNA and RNA viruses.

Methods and compositions for non-viral delivery of nucleic acids include electroporation, lipofection, microinjection, biolistics, virosomes, liposomes, immunoliposomes, LNPs, polycation or lipid:nucleic acid conjugates, naked nucleic acid (e.g., naked DNA/RNA), artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by AmaxaBiosystems (Cologne, Germany), Maxcyte, Inc. (Rockville, Md.), BTX Molecular Delivery Systems (Holliston, Ma.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). The preparation of lipid:nucleic acid complexes, including targeted liposomes such as immunolipid complexes, is well known in the art, and as described herein.

Various delivery systems (e.g., vectors, liposomes, LNPs) containing the guide RNAs, RNA-guided DNA binding agent, and donor construct, singly or in combination, can also be administered to an organism for delivery to cells in vivo or administered to a cell or cell culture ex vivo. Administration is by any of the routes normally used for introducing a molecule into ultimate contact with blood, fluid, or cells including, but not limited to, injection, infusion, topical application and electroporation. Suitable methods of administering such nucleic acids are available and well known to those of skill in the art.

In certain embodiments, the present disclosure provides DNA or RNA vectors encoding any of the compositions disclosed herein—e.g., a guide RNA comprising any one or more of the guide sequences described herein; or a construct (e.g., bidirectional construct) comprising a sequence encoding Factor IX. In some embodiments, the vector also comprises a sequence encoding an RNA-guided DNA binding agent. In certain embodiments, the invention comprises DNA or RNA vectors encoding any one or more of the compositions described herein, or in any combination. In some embodiments, the vectors further comprise, e.g., promoters, enhancers, and regulatory sequences. In some embodiments, the vector that comprises a bidirectional construct comprising a sequence that encodes Factor IX does not comprise a promoter that drives Factor IX expression. For example, the expression of the Factor IX polypeptide is driven by a promoter of the host cell (e.g., the endogenous albumin promoter when the transgene is integrated into a host cell's albumin locus). In some embodiments, the bidirectional nucleic acid construct includes a first segment and a second segment, each having a splice acceptor upstream of a transgene. In certain embodiments, the splice acceptor is compatible with the splice donor sequence of the host cell's safe harbor site, e.g. the splice donor of intron 1 of a human albumin gene. In some embodiments, the vector that comprises a guide RNA comprising any one or more of the guide sequences described herein also comprises one or more nucleotide sequence(s) encoding a crRNA, a trRNA, or a crRNA and trRNA, as disclosed herein.

In some embodiments, the vector comprises a nucleotide sequence encoding a guide RNA described herein. In some embodiments, the vector comprises one copy of the guide RNA. In other embodiments, the vector comprises more than one copy of the guide RNA. In embodiments with more than one guide RNA, the guide RNAs may be non-identical such that they target different target sequences, or may be identical in that they target the same target sequence. In some embodiments where the vectors comprise more than one guide RNA, each guide RNA may have other different properties, such as activity or stability within a complex with an RNA-guided DNA nuclease, such as a Cas RNP complex. In some embodiments, the nucleotide sequence encoding the guide RNA may be operably linked to at least one transcriptional or translational control sequence, such as a promoter, a 3' UTR, or a 5' UTR. In one embodiment, the promoter may be a tRNA promoter, e.g., $tRNA^{Lys3}$, or a tRNA chimera. See Mefferd et al., *RNA.* 2015 21:1683-9; Scherer et al., Nucleic Acids Res. 2007 35: 2620-2628. In some embodiments, the promoter may be recognized by RNA polymerase M (Pol III). Non-limiting examples of Pol III promoters include U6 and H1 promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In embodiments with more than one guide RNA, the promoters used to drive expression may be the same or different. In some embodiments, the nucleotide encoding the crRNA of the guide RNA and the nucleotide encoding the trRNA of the guide RNA may be provided on the same vector. In some embodiments, the nucleotide encoding the crRNA and the nucleotide encoding the trRNA may be driven by the same promoter. In some embodiments, the crRNA and trRNA may be transcribed into a single transcript. For example, the crRNA and trRNA may be processed from the single transcript to form a double-molecule guide RNA. Alternatively, the crRNA and trRNA may be transcribed into a single-molecule guide RNA (sgRNA). In other embodiments, the crRNA and the trRNA may be driven by their corresponding promoters on the same vector. In yet other embodiments, the crRNA and the trRNA may be encoded by different vectors.

In some embodiments, the nucleotide sequence encoding the guide RNA may be located on the same vector comprising the nucleotide sequence encoding an RNA-guided DNA binding agent such as a Cas protein. In some embodiments, expression of the guide RNA and of the RNA-guided DNA binding agent such as a Cas protein may be driven by their own corresponding promoters. In some embodiments, expression of the guide RNA may be driven by the same promoter that drives expression of the RNA-guided DNA binding agent such as a Cas protein. In some embodiments, the guide RNA and the RNA-guided DNA binding agent such as a Cas protein transcript may be contained within a single transcript. For example, the guide RNA may be within an untranslated region (UTR) of the RNA-guided DNA binding agent such as a Cas protein transcript. In some embodiments, the guide RNA may be within the 5' UTR of the transcript. In other embodiments, the guide RNA may be within the 3' UTR of the transcript. In some embodiments, the intracellular half-life of the transcript may be reduced by containing the guide RNA within its 3' UTR and thereby shortening the length of its 3' UTR. In additional embodiments, the guide RNA may be within an intron of the transcript. In some embodiments, suitable splice sites may be added at the intron within which the guide RNA is located such that the guide RNA is properly spliced out of the transcript. In some embodiments, expression of the RNA-guided DNA binding agent such as a Cas protein and the guide RNA from the same vector in close temporal proximity may facilitate more efficient formation of the CRISPR RNP complex.

In some embodiments, the nucleotide sequence encoding the guide RNA and/or RNA-guided DNA binding agent may be located on the same vector comprising the construct that comprises a Factor IX gene. In some embodiments, proximity of the construct comprising the Factor IX gene and the guide RNA (and/or the RNA-guided DNA binding agent) on the same vector may facilitate more efficient insertion of the construct into a site of insertion created by the guide RNA/RNA-guided DNA binding agent.

In some embodiments, the vector comprises one or more nucleotide sequence(s) encoding a sgRNA and an mRNA encoding an RNA-guided DNA binding agent, which can be a Cas protein, such as Cas9 or Cpf1. In some embodiments, the vector comprises one or more nucleotide sequence(s) encoding a crRNA, a trRNA, and an mRNA encoding an RNA-guided DNA binding agent, which can be a Cas protein, such as, Cas9 or Cpf1. In one embodiment, the Cas9 is from *Streptococcus pyogenes* (i.e., Spy Cas9). In some embodiments, the nucleotide sequence encoding the crRNA, trRNA, or crRNA and trRNA (which may be a sgRNA) comprises or consists of a guide sequence flanked by all or a portion of a repeat sequence from a naturally-occurring CRISPR/Cas system. The nucleic acid comprising or consisting of the crRNA, trRNA, or crRNA and trRNA may further comprise a vector sequence wherein the vector sequence comprises or consists of nucleic acids that are not naturally found together with the crRNA, trRNA, or crRNA and trRNA.

In some embodiments, the crRNA and the trRNA are encoded by non-contiguous nucleic acids within one vector. In other embodiments, the crRNA and the trRNA may be encoded by a contiguous nucleic acid. In some embodiments, the crRNA and the trRNA are encoded by opposite strands of a single nucleic acid. In other embodiments, the crRNA and the trRNA are encoded by the same strand of a single nucleic acid.

In some embodiments, the vector comprises a donor construct (e.g., the bidirectional nucleic acid construct) comprising a sequence that encodes Factor IX, as disclosed herein. In some embodiments, in addition to the donor construct (e.g., bidirectional nucleic acid construct) disclosed herein, the vector may further comprise nucleic acids that encode the guide RNAs described herein and/or nucleic acid encoding an RNA-guided DNA-binding agent (e.g., a Cas nuclease such as Cas9). In some embodiments, a nucleic acid encoding an RNA-guided DNA-binding agent are each or both on a separate vector from a vector that comprises the donor construct (e.g., bidirectional construct) disclosed herein. In any of the embodiments, the vector may include other sequences that include, but are not limited to, promoters, enhancers, regulatory sequences, as described herein. In some embodiments, the promoter does not drive the expression of Factor IX of the donor construct (e.g., bidirectional construct). In some embodiments, the vector comprises one or more nucleotide sequence(s) encoding a crRNA, a trRNA, or a crRNA and trRNA. In some embodiments, the vector comprises one or more nucleotide sequence(s) encoding a sgRNA and an mRNA encoding an RNA-guided DNA nuclease, which can be a Cas nuclease (e.g., Cas9). In some embodiments, the vector comprises one or more nucleotide sequence(s) encoding a crRNA, a trRNA, and an mRNA encoding an RNA-guided DNA nuclease, which can be a Cas nuclease, such as, Cas9. In some embodiments, the Cas9 is from *Streptococcus pyogenes* (i.e., Spy Cas9). In some embodiments, the nucleotide sequence encoding the crRNA, trRNA, or crRNA and trRNA (which may be a sgRNA) comprises or consists of a guide sequence flanked by all or a portion of a repeat sequence from a naturally-occurring CRISPR/Cas system. The nucleic acid comprising or consisting of the crRNA, trRNA, or crRNA and trRNA may further comprise a vector sequence wherein the vector sequence comprises or consists of nucleic acids that are not naturally found together with the crRNA, trRNA, or crRNA and trRNA.

In some embodiments, the vector may be circular. In other embodiments, the vector may be linear. In some embodiments, the vector may be enclosed in a lipid nanoparticle, liposome, non-lipid nanoparticle, or viral capsid. Non-limiting exemplary vectors include plasmids, phagemids, cosmids, artificial chromosomes, minichromosomes, transposons, viral vectors, and expression vectors.

In some embodiments, the vector may be a viral vector. In some embodiments, the viral vector may be genetically modified from its wild type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell or population of host cells along with the vector system described herein. In other embodiments, the virus may be helper-free. For example, the virus may be capable of amplifying and packaging the vectors without a helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, helper dependent adenoviral vectors (HDAd), herpes simplex virus (HSV-1) vectors, bacteriophage T4, baculovirus vectors, and retrovirus vectors. In some embodiments, the viral vector may be an AAV vector. In other embodiments, the viral vector may a lentivirus vector.

In some embodiments, "AAV" refers all serotypes, subtypes, and naturally-occurring AAV as well as recombinant AAV. "AAV" may be used to refer to the virus itself or a derivative thereof. The term "AAV" includes AAV1, AAV2, AAV3, AAV3B, AAV4, AAV5, AAV6, AAV6.2, AAV7, AAVrh.64R1, AAVhu.37, AAVrh.8, AAVrh.32.33, AAV8, AAV9, AAV-DJ, AAV2/8, AAVrh10, AAVLK03, AV10, AAV11, AAV12, rh10, and hybrids thereof, avian AAV, bovine AAV, canine AAV, equine AAV, primate AAV, nonprimate AAV, and ovine AAV. The genomic sequences of various serotypes of AAV, as well as the sequences of the native terminal repeats (TRs), Rep proteins, and capsid subunits are known in the art. Such sequences may be found in the literature or in public databases such as GenBank. A "AAV vector" as used herein refers to an AAV vector comprising a heterologous sequence not of AAV origin (i.e., a nucleic acid sequence heterologous to AAV), typically comprising a sequence encoding a heterologous polypeptide of interest. The construct may comprise an AAV1, AAV2, AAV3, AAV3B, AAV4, AAV5, AAV6, AAV6.2, AAV7, AAVrh.64R1, AAVhu.37, AAVrh.8, AAVrh.32.33, AAV8, AAV9, AAV-DJ, AAV2/8, AAVrh10, AAVLK03, AV10, AAV11, AAV12, rh10, and hybrids thereof, avian AAV, bovine AAV, canine AAV, equine AAV, primate AAV, nonprimate AAV, and ovine AAV capsid sequence. In general, the heterologous nucleic acid sequence (the transgene) is flanked by at least one, and generally by two, AAV inverted terminal repeat sequences (ITRs). An AAV vector may either be single-stranded (ssAAV) or self-complementary (scAAV).

In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal (T) are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding an RNA-guided DNA binding agent such as a Cas protein (e.g., Cas9), while a second AAV vector may contain one or more guide sequences.

In some embodiments, the vector system may be capable of driving expression of one or more nuclease components in a cell. In some embodiments, the bidirectional construct, optionally as part of a vector system, may comprise a promoter capable of driving expression of a coding sequence in a cell. In some embodiments, the vector does not comprise a promoter that drives expression of one or more coding sequences once it is integrated in a cell (e.g., uses the host cell's endogenous promoter such as when inserted at intron 1 of an albumin locus, as exempflied herein). In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding an RNA-guided DNA binding agent such as a Cas protein (e.g., Cas9) described herein. In some embodiments, the nuclease encoded by the vector may be a Cas protein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter.

In some embodiments, the vector may comprise any one or more of the constructs comprising a heterologous Factor IX gene described herein. In some embodiments, the Factor IX gene may be operably linked to at least one transcriptional or translational control sequence. In some embodiments, the Factor IX gene may be operably linked to at least one promoter. In some embodiments, the Factor IX gene is not linked to a promoter that drives the expression of the heterologous gene.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1a) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1a promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On* promoter (Clontech).

In some embodiments, the promoter may be a tissue-specific promoter, e.g., a promoter specific for expression in the liver.

In some embodiments, the compositions comprise a vector system. In some embodiments, the vector system may comprise one single vector. In other embodiments, the vector system may comprise two vectors. In additional embodiments, the vector system may comprise three vectors. When different guide RNAs are used for multiplexing, or when multiple copies of the guide RNA are used, the vector system may comprise more than three vectors.

In some embodiments, the vector system may comprise inducible promoters to start expression only after it is delivered to a target cell. Non-limiting exemplary inducible promoters include those inducible by heat shock, light, chemicals, peptides, metals, steroids, antibiotics, or alcohol.

In some embodiments, the inducible promoter may be one that has a low basal (non-induced) expression level, such as, e.g., the Tet-One promoter (Clontech).

In additional embodiments, the vector system may comprise tissue-specific promoters to start expression only after it is delivered into a specific tissue.

The vector comprising: a guide RNA, RNA-binding DNA binding agent, or donor construct comprising a sequence encoding Factor IX, individually or in any combination, may be delivered by liposome, a nanoparticle, an exosome, or a microvesicle. The vector may also be delivered by a lipid nanoparticle (LNP). One or more guide RNA, RNA-binding DNA binding agent (e.g. mRNA), or donor construct comprising a sequence encoding a heterologous protein, individually or in any combination, may be delivered by liposome, a nanoparticle, an exosome, or a microvesicle. One or more guide RNA, RNA-binding DNA binding agent (e.g. mRNA), or donor construct comprising a sequence encoding a heterologous protein, individually or in any combination, may be delivered by LNP.

Lipid nanoparticles (LNPs) are a well-known means for delivery of nucleotide and protein cargo, and may be used for delivery of any of the guide RNAs, RNA-guided DNA binding agent, and/or donor construct (e.g., bidirectional construct) disclosed herein. In some embodiments, the LNPs deliver the compositions in the form of nucleic acid (e.g., DNA or mRNA), or protein (e.g., Cas nuclease), or nucleic acid together with protein, as appropriate.

In some embodiments, provided herein is a method for delivering any of the guide RNAs described herein and/or donor construct (e.g., bidirectional construct) disclosed herein, alone or in combination, to a host cell or a population of host cells or a subject, wherein any one or more of the components is associated with an LNP. In some embodiments, the method further comprises an RNA-guided DNA binding agent (e.g., Cas9 or a sequence encoding Cas9).

In some embodiments, provided herein is a composition comprising any of the guide RNAs described herein and/or donor construct (e.g., bidirectional construct) disclosed herein, alone or in combination, with an LNP. In some embodiments, the composition further comprises an RNA-guided DNA binding agent (e.g., Cas9 or a sequence encoding Cas9).

In some embodiments, the LNPs comprise cationic lipids. In some embodiments, the LNPs comprise (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate) or another ionizable lipid. See, e.g., lipids of PCT/US2018/053559 (filed Sep. 28, 2018), WO/2017/173054, WO2015/095340, and WO2014/136086, as well as references provided therein. In some embodiments, the LNPs comprise molar ratios of a cationic lipid amine to RNA phosphate (N:P) of about 4.5, 5.0, 5.5, 6.0, or 6.5. In some embodiments, the term cationic and ionizable in the context of LNP lipids is interchangeable, e.g., wherein ionizable lipids are cationic depending on the pH.

In some embodiments, LNPs associated with the bidirectional construct disclosed herein are for use in preparing a medicament for treating a disease or disorder. The disease or disorder may be a Factor IX deficiency such as hemophilia B.

In some embodiments, any of the guide RNAs described herein, RNA-guided DNA binding agents, and/or donor construct (e.g., bidirectional construct) disclosed herein, alone or in combination, whether naked or as part of a vector, is formulated in or administered via a lipid nanoparticle; see e.g., WO/2017/173054 the contents of which are hereby incorporated by reference in their entirety.

In some embodiments, an LNP composition is encompassed comprising: an RNA component and a lipid component, wherein the lipid component comprises an amine lipid such as a biodegradable, ionizable lipid. In some instances, the lipid component comprises biodegradable, ionizable lipid, cholesterol, DSPC, and PEG-DMG.

It will be apparent that a guide RNA disclosed herein, an RNA-guided DNA binding agent (e.g., Cas nuclease or a nucleic acid encoding a Cas nuclease), and a donor construct (e.g., bidirectional construct) comprising a sequence encoding Factor IX can be delivered using the same or different systems. For example, the guide RNA, Cas nuclease, and construct can be carried by the same vector (e.g., AAV). Alternatively, the Cas nuclease (as a protein or mRNA) and/or gRNA can be carried by a plasmid or LNP, while the donor construct can be carried by a vector such as AAV. Furthermore, the different delivery systems can be administered by the same or different routes (e.g. by infusion; by injection, such as intramuscular injection, tail vein injection, or other intravenous injection; by intraperitoneal administration and/or intramuscular injection).

The different delivery systems can be delivered in vitro or in vivo simultaneously or in any sequential order. In some embodiments, the donor construct, guide RNA, and Cas nuclease can be delivered in vitro or in vivo simultaneously, e.g., in one vector, two vectors, individual vectors, one LNP, two LNPs, individual LNPs, or a combination thereof. In some embodiments, the donor construct can be delivered in vivo or in vitro, as a vector and/or associated with a LNP, prior to (e.g., about 1, 2, 3, 4, 5, 6, 7, 8, 9, 10, 11, 12, 13, 14, or more days) delivering the guide RNA and/or Cas nuclease, as a vector and/or associated with a LNP singly or together as a ribonucleoprotein (RNP). As a further example, the guide RNA and Cas nuclease, as a vector and/or associated with a LNP singly or together as a ribonucleoprotein (RNP), can be delivered in vivo or in vitro, prior to (e.g., about 1, 2, 3, 4, 5, 6, 7, 8, 9, 10, 11, 12, 13, 14, or more days) delivering the construct, as a vector and/or associated with a LNP.

In some embodiments, the present disclosure also provides pharmaceutical formulations for administering any of the guide RNAs disclosed herein. In some embodiments, the pharmaceutical formulation includes an RNA-guided DNA binding agent (e.g., Cas nuclease) and a donor construct comprising a coding sequence of a therapeutic heterologous gene, as disclosed herein. Pharmaceutical formulations suitable for delivery into a subject (e.g., human subject) are well known in the art.

IV. Methods of Use

The gRNAs, donor construct (e.g., bidirectional construct comprising a sequence encoding Factor IX), and RNA-guided DNA binding agents described herein are useful for introducing a Factor IX nucleic acid to a host cell or population of host cells, in vivo or in vitro. In some embodiments, the gRNAs, donor construct (e.g., bidirectional construct comprising a sequence encoding Factor IX), and RNA-guided DNA binding agents described herein are useful for expressing Factor IX in a host cell or population of host cells, or in a subject in need thereof. In some embodiments, the gRNAs, donor construct (e.g., bidirectional construct comprising a sequence encoding Factor IX), and RNA-guided DNA binding agents described herein are useful for treating hemophilia (e.g., hemophilia B) in a subject in need thereof. Administration of any one or more of the gRNAs, donor construct (e.g., bidirectional construct comprising a sequence encoding Factor IX), and RNA-guided DNA binding agents described herein will increase Factor IX protein levels and/or Factor IX activity levels, e.g. circulating, serum, or plasma levels. In some embodiments, the effectiveness of the treatment can be assessed by measuring serum or plasma Factor IX activity, wherein an increase in the subject's plasma level and/or activity of Factor IX indicates effectiveness of the treatment. In some embodiments, the effectiveness of the treatment can be assessed by measuring serum or plasma Factor IX protein and/or activity levels, wherein an increase in the subject's plasma level and/or activity of Factor IX indicates effectiveness of the treatment. In some embodiments, effectiveness of the treatment can be determined by assessing clotting function in an aPTT assay and/or thrombin generation in an TGA-EA assay. In some embodiments, effectiveness of the treatment can be determined by assessing the level of Factor IX, e.g., circulating Factor IX, can be measured by a coagulation and/or an immunologic assay, e.g., an sandwich immunoassay, ELISA (see, e.g., Example 13), MSD (see, e.g., Example 14).

In normal or healthy individuals, Factor IX activity and antigen levels vary between about 50 and 160% of normal pooled plasma which is about 3-5 μg/ml, based on its purification from adult human plasma Amiral et al., Clin. Chem. 30(9), 1512-16, 1984 at Table 2; see also Osterud et al., 1978. Individuals having less than 50% of normal plasma level of Factor IX activity and/or antigen levels are classified as having hemophilia. In particular, individuals with less than about 1% active factor are classified as having severe haemophilia, while those with about 1-5% active factor have moderate haemophilia. Individuals with mild haemophilia have between about 6-49% of normal levels of active clotting factor. In some embodiments, the level of circulating factor IX can be measured by a coagulation and/or an immunologic assay, which methods are well known in the art (e.g. Simioni et al. NEJM 2009, Adcock et al., Coagulation Handbook, Esoterix Laboratory Services, 2006). An immunologic method for detecting hFIX protein, and a method of functionally normalizing Factor IX activity of a hyperfunctional hFIX variant is found in Example 13. In some embodiments, Factor IX, e.g., circulating Factor IX, can be measured by a coagulation and/or an immunologic assay, e.g., an sandwich immunoassay, ELISA (see, e.g., Example 13), MSD (see, e.g., Example 14).

Accordingly, in some embodiments, the compositions and methods disclosed herein are useful for increasing plasma levels of Factor IX or Factor IX activity levels in a subject having hemophilia to about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more, of normal level.

In some embodiments, the compositions and methods disclosed herein are useful for increasing Factor IX activity and/or levels, for example increasing circulating FIX protein levels to about 0.05, 0.1, 0.2, 0.5, 1, 2, 3, or 4 μg/ml. FIX protein levels may reach about 150 μg/ml, or more. In some embodiments, the compositions and methods disclosed herein are useful for increasing Factor IX protein levels to about 4 μg/ml. In some embodiments, the compositions and methods disclosed herein are useful for increasing Factor IX protein levels to about 4 μg/ml to about 5 μg/ml, about 41 g/ml to 6 μg/ml, about 4 g/ml to 8 μg/ml, about 4 μg/ml to about 10 μg/ml, or more. In some embodiments, the compositions and methods disclosed herein are useful for increasing Factor IX protein levels to about 0.1 μg/ml to about 10 μg/ml, about 1 μg/ml to about 10 μg/ml, about 0.1 μg/ml to about 6 μg/ml, about 1 μg/ml to about 6 μg/ml, about 2 μg/ml to about 5 μg/ml, or about 3 μg/ml to about 5 μg/ml. For example, the compositions and methods disclosed herein are useful for increasing plasma levels of Factor IX in a subject having hemophilia to about 6, 7, 8, 9, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 75, 80, 85, 90, 95, 100, 105, 110, 115, 120, 125, 130, 135, 140, 145, 150 μg/ml, or more.

In some embodiments, the compositions and methods disclosed herein are useful for increasing plasma levels of Factor IX activity and/or levels in a subject having hemophilia by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, 100%, 110%, 120%, 130%, 140%, 150%, 160%, 170%, 180%, 190%, 200%, or more, as compared to the subject's plasma level and/or activity of Factor IX before administration.

In some embodiments, the compositions and methods disclosed herein are useful for increasing Factor IX protein and/or Factor IX activity in a host cell or population of host cells by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, 100%, 110%, 120%, 130%, 140%, 150%, 160%, 170%, 180%, 190%, 200%, or more as compared to a Factor IX level and/or activity before administration to the host cell or population of host cells, e.g. a normal level. In some embodiments, the cell is a liver cell or a population of liver cells. In some embodiments, the liver cell is hepatocyte or the population of liver cells are hepatocytes.

In some embodiments, the method comprises administering a guide RNA and an RNA-guided DNA binding agent (such as an mRNA encoding a Cas9 nuclease) in an LNP. In further embodiments, the method comprises administering an AAV nucleic acid construct encoding a Factor IX protein, such as an bidirectional FIX construct. CRISPR/Cas9 LNP, comprising guide RNA and an mRNA encoding a Cas9, can be administered intravenously. AAV FIX donor construct can be administered intravenously. Exemplary dosing of CRISPR/Cas9 LNP includes about 0.1, 0.25, 0.3, 0.5, 1, 2, 3, 4, 5, 6, 8, or 10 mpk (RNA). The units mg/kg and mpk are being used interchangably herein. Exemplary dosing of AAV comprising a nucleic acid encoding a FIX protein includes an MOI of about $10^{11}$, $10^{12}$, $10^{13}$, and $10^{14}$ vg/kg, optionally the MOI may be about $1\times10^{13}$ to $1\times10^{14}$ vg/kg.

In some embodiments, the method comprises expressing a therapeutically effective amount of the Factor IX protein. In some embodiments, the method comprises achieving a therapeutically effective level of circulating Factor IX coagulation activity in an individual. In particular embodiments, the method comprises achieving Factor IX activity of at least about 5% to about 50% of normal. The method may comprise achieving Factor IX activity of at least about 50% to about 150% of normal. In certain embodiments, the method comprises achieving an increase in Factor IX activity over the patient's baseline Factor IX activity of at least about 1% to about 50% of normal Factor IX activity, or at least about 5% to about 50% of normal Factor IX activity, or at least about 50% to about 150% of normal Factor IX activity.

In some embodiments, the method further comprises achieving a durable effect, e.g. at least 1 month, 2 months, 6 months, 1 year, or 2 year effect. In some embodiments, the method further comprises achieving the therapeutic effect in a durable and sustained manner, e.g. at least 1 month, 2 months, 6 months, 1 year, or 2 year effect. In some embodiments, the level of circulating Factor IX activity and/or level is stable for at least 1 month, 2 months, 6 months, 1 year, or more. In some embodiments a steady-state activity and/or level of FIX protein is achieved by at least 7 days, at least 14 days, or at least 28 days. In additional embodiments, the method comprises maintaining Factor IX activity and/or levels after a single dose for at least 1, 2, 4, or 6 months, or at least 1, 2, 3, 4, or 5 years.

In additional embodiments involving insertion into the albumin locus, the individual's circulating albumin levels are normal. The method may comprise maintaining the individual's circulating albumin levels within ±5%, ±10%, ±15%, ±20%, or ±50% of normal circulating albumin levels. In certain embodiments, the individual's albumin levels are unchanged as compared to the albumin levels of untreated individuals by at least week 4, week 8, week 12, or week 20. In certain embodiments, the individual's albumin levels transiently drop then return to normal levels. In particular, the methods may comprise detecting no significant alterations in levels of plasma albumin.

In some embodiments, the invention comprises a method or use of modifying (e.g., creating a double strand break in) an albumin gene, such as a human albumin gene, comprising, administering or delivering to a host cell or population of host cells any one or more of the gRNAs, donor construct (e.g., bidirectional construct comprising a sequence encoding Factor IX), and RNA-guided DNA binding agents (e.g., Cas nuclease) described herein. In some embodiments, the invention comprises a method or use of modifying (e.g., creating a double strand break in) an albumin intron 1 region, such as a human albumin intron 1, comprising, administering or delivering to a host cell or population of host cells any one or more of the gRNAs, donor construct (e.g., bidirectional construct comprising a sequence encoding Factor IX), and RNA-guided DNA binding agents (e.g., Cas nuclease) described herein. In some embodiments, the invention comprises a method or use of modifying (e.g., creating a double strand break in) a human safe harbor, such as liver tissue or hepatocyte host cell, comprising, administering or delivering to a host cell or population of host cells any one or more of the gRNAs, donor construct (e.g., bidirectional construct comprising a sequence encoding Factor IX), and RNA-guided DNA binding agents (e.g., Cas nuclease) described herein. Insertion within a safe harbor locus, such as an albumin locus, allows overexpression of the Factor IX gene without significant deleterious effects on the host cell or cell population, such as hepatocytes or liver cells. In some embodiments, the invention comprises a method or use of modifying (e.g., creating a double strand break in) intron 1 of a human albumin locus comprising, administering or delivering to a host cell or population of host cells any one or more of the gRNAs, donor construct (e.g., bidirectional construct comprising a sequence encoding Factor IX), and RNA-guided DNA binding agents (e.g., Cas nuclease) described herein. In some embodiments, the guide RNA comprises a guide sequence that contains at least 15, 16, 17, 18, 19, or 20 contiguous nucleotides that bind within intron 1 of a human albumin locus (SEQ ID NO: 1). In some embodiments, the guide RNA comprises at least 15, 16, 17, 18, 19, or 20 contiguous nucleotides of a sequence selected from the group consisting of SEQ ID NOs: 2-33. In some embodiments, the guide RNA comprises a sequence that is at least 95%, 90%, 85%, 80%, or 75% identical to a sequence selected from the group consisting of SEQ ID NOs:2-33. In some embodiments, the guide RNAs disclosed herein comprise a guide sequence selected from the group consisting of SEQ ID NO: 2, 8, 13, 19, 28, 29, 31, 32, 33. In some embodiments, the guide RNAs disclosed herein comprise a guide sequence at least 17, 18, 19, or 20 contiguous nucleotides of a sequence selected from the group consisting of SEQ ID NOs: 2, 8, 13, 19, 28, 29, 31, 32, 33. In some embodiments, the guide RNAs disclosed herein comprise a guide sequence selected from the group consisting of SEQ ID NOs: 34, 40, 45, 51, 60, 61, 63, 64, 65, 66, 72, 77, 83, 92, 93, 95, 96, and 97. In some embodiments, the guide RNAs disclosed herein comprise a guide sequence that is at least 95%, 90%, 85%, 80%, or 75% identical to a sequence selected from the group consisting of SEQ ID NOs: 2-33. In some embodiments, the guide RNAs disclosed herein comprise a guide sequence that is at least 17, 18, 19, or 20 contiguous nucleotides of a sequence selected from the group consisting of SEQ ID NOs: 2-33. In some embodiments, the guide RNAs disclosed herein comprise a guide sequence that is selected from the group consisting of SEQ ID NOs: 34-97. In some embodiments, the guide RNA comprises at least 15, 16, 17, 18, 19, or 20 contiguous nucleotides of a sequence selected from the group consisting of SEQ ID NOs: 2-5, 10-17, 21-27, and 29-33. In some embodiments, the guide RNA comprises a sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 2-5, 10-17, 21-27, and 29-33. In some embodiments, the guide RNAs disclosed herein comprise a guide sequence at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 34-37, 42-49, 53-59, 61-69, 74-81, 85-91, and 93-97. In some embodiments, the guide RNAs disclosed herein comprise a guide sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence that is at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence that is selected from the group consisting of SEQ ID NOs: 34-37, 42-49, 53-59, 61-69, 74-81, 85-91, and 93-97. In some embodiments, the method is performed in vitro. In some embodiments, the method is performed in vivo. In some embodiments, the donor construct is a bidirectional construct that comprises a sequence encoding Factor IX. In some embodiments, the host cell is a liver cell, such as. In additional embodiments, the liver cell is a hepatocyte.

In some embodiments, the invention comprises a method or use of introducing a Factor IX nucleic acid to a host cell or population of host cells comprising, administering or delivering any one or more of the gRNAs, donor construct (e.g., bidirectional construct comprising a sequence encoding Factor IX), and RNA-guided DNA binding agents (e.g., Cas nuclease) described herein. In some embodiments, the guide RNA comprises a guide sequence that contains at least 15, 16, 17, 18, 19, or 20 contiguous nucleotides that are capable of binding to a region within intron 1 of human albumin locus (SEQ ID NO: 1). In some embodiments, the guide RNA comprises at least 15, 16, 17, 18, 19, or 20 contiguous nucleotides of a sequence selected from the group consisting of SEQ ID NOs: 2-33. In some embodiments, the guide RNA comprises a sequence that is at least 95%, 90%, 85%, 80%, or 75% identical to a sequence selected from the group consisting of SEQ ID NOs: 2-33. In some embodiments, the guide RNAs disclosed herein comprise a guide sequence selected from the group consisting of SEQ ID NO: 2, 8, 13, 19, 28, 29, 31, 32, 33. In some embodiments, the guide RNAs disclosed herein comprise a guide sequence at least 17, 18, 19, or 20 contiguous nucleotides of a sequence selected from the group consisting of SEQ ID NOs: 2, 8, 13, 19, 28, 29, 31, 32, 33. In some embodiments, the guide RNAs disclosed herein comprise a guide sequence selected from the group consisting of SEQ ID NOs: 34, 40, 45, 51, 60, 61, 63, 64, 65, 66, 72, 77, 83, 92, 93, 95, 96, and 97. In some embodiments, the guide RNAs disclosed herein comprise a guide sequence that is at least 95%, 90%, 85%, 80%, or 75% identical to a sequence selected from the group consisting of SEQ ID NOs: 2-33. In some embodiments, the guide RNAs disclosed herein comprise a guide sequence that is at least 17, 18, 19, or 20 contiguous nucleotides of a sequence selected from the group consisting of SEQ ID NOs: 2-33. In some embodiments, the guide RNAs disclosed herein comprise a guide sequence that is selected from the group consisting of SEQ ID NOs: 34-97. In some embodiments, the guide RNA comprises at least 15, 16, 17, 18, 19, or 20 contiguous nucleotides of a sequence selected from the group consisting of SEQ ID NOs: 2-5, 10-17, 21-27, and 29-33. In some embodiments, the guide RNA comprises a sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 2-5, 10-17, 21-27, and 29-33. In some embodiments, the guide RNAs disclosed herein comprise a guide sequence at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 34-37, 42-49, 53-59, 61-69, 74-81, 85-91, and 93-97. In some embodiments, the guide RNAs disclosed herein comprise a guide sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence that is at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence that is selected from the group consisting of SEQ ID NOs: 34-37, 42-49, 53-59, 61-69, 74-81, 85-91, and 93-97. In some embodiments, the method is in vitro. In some embodiments, the method is in vivo. In some embodiments, the donor construct is a bidirectional construct that comprises a sequence encoding Factor IX. In some embodiments, the host cell is a liver cell, or the population of host cells are liver cells, such as hepatocyte.

In some embodiments, the invention comprises a method or use of expressing Factor IX in a host cell or a population of host cells comprising, administering or delivering any one or more of the gRNAs, donor construct (e.g., bidirectional construct comprising a sequence encoding Factor IX), and RNA-guided DNA binding agents (e.g., Cas nuclease) described herein. In some embodiments, the guide RNA comprises a guide sequence that contains at least 15, 16, 17, 18, 19, or 20 contiguous nucleotides that are capable of binding to a region within intron 1 of human albumin locus (SEQ ID NO: 1). In some embodiments, the guide RNA comprises at least 15, 16, 17, 18, 19, or 20 contiguous nucleotides of a sequence selected from the group consisting of SEQ ID NOs: 2-33. In some embodiments, the guide RNA comprises a sequence that is at least 95%, 90%, 85%, 80%, or 75% identical to a sequence selected from the group consisting of SEQ ID NOs:2-33. In some embodiments, the guide RNAs disclosed herein comprise a guide sequence selected from the group consisting of SEQ ID NO: 2, 8, 13, 19, 28, 29, 31, 32, 33. In some embodiments, the guide RNAs disclosed herein comprise a guide sequence at least 17, 18, 19, or 20 contiguous nucleotides of a sequence selected from the group consisting of SEQ ID NOs: 2, 8, 13, 19, 28, 29, 31, 32, 33. In some embodiments, the guide RNAs disclosed herein comprise a guide sequence selected from the group consisting of SEQ ID NOs: 34, 40, 45, 51, 60, 61, 63, 64, 65, 66, 72, 77, 83, 92, 93, 95, 96, and 97. In some embodiments, the guide RNAs disclosed herein comprise a guide sequence that is at least 95%, 90%, 85%, 80%, or 75% identical to a sequence selected from the group consisting of SEQ ID NOs: 2-33. In some embodiments, the guide RNAs disclosed herein comprise a guide sequence that is at least 17, 18, 19, or 20 contiguous nucleotides of a sequence selected from the group consisting of SEQ ID NOs: 2-33. In some embodiments, the guide RNAs disclosed herein comprise a guide sequence that is selected from the group consisting of SEQ ID NOs: 34-97. In some embodiments, the guide RNA comprises at least 15, 16, 17, 18, 19, or 20 contiguous nucleotides of a sequence selected from the group consisting of SEQ ID NOs: 2-5, 10-17, 21-27, and 29-33. In some embodiments, the guide RNA comprises a sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 2-5, 10-17, 21-27, and 29-33. In some embodiments, the guide RNAs disclosed herein comprise a guide sequence at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 34-37, 42-49, 53-59, 61-69, 74-81, 85-91, and 93-97. In some embodiments, the guide RNAs disclosed herein comprise a guide sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence that is at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence that is selected from the group consisting of SEQ ID NOs: 34-37, 42-49, 53-59, 61-69, 74-81, 85-91, and 93-97. In some embodiments, the method is in vitro. In some embodiments, the method is in vivo. In some embodiments, the donor construct is a bidirectional construct that comprises a sequence encoding Factor IX. In some embodiments, the host cell is a liver cell, or the population of host cells are liver cells, such as hepatocyte.

In some embodiments, the invention comprises a method or use of treating hemophilia (e.g., hemophilia B) comprising, administering or delivering any one or more of the gRNAs, donor construct (e.g., bidirectional construct comprising a sequence encoding Factor IX), and RNA-guided DNA binding agents (e.g., Cas nuclease) described herein to a subject in need thereof. In some embodiments, the guide RNA comprises a guide sequence that contains at least 15, 16, 17, 18, 19, or 20 contiguous nucleotides that are capable of binding to a region within intron 1 of human albumin locus (SEQ ID NO: 1). In some embodiments, the guide RNA comprises at least 15, 16, 17, 18, 19, or 20 contiguous nucleotides of a sequence selected from the group consisting of SEQ ID NOs: 2-33. In some embodiments, the guide RNA comprises a sequence that is at least 95%, 90%, 85%, 80%, or 75% identical to a sequence selected from the group consisting of SEQ ID NOs: 2-33. In some embodiments, the guide RNAs disclosed herein comprise a guide sequence selected from the group consisting of SEQ ID NO: 2, 8, 13, 19, 28, 29, 31, 32, 33. In some embodiments, the guide RNAs disclosed herein comprise a guide sequence at least 17, 18, 19, or 20 contiguous nucleotides of a sequence selected from the group consisting of SEQ ID NOs: 2, 8, 13, 19, 28, 29, 31, 32, 33. In some embodiments, the guide RNAs disclosed herein comprise a guide sequence selected from the group consisting of SEQ ID NOs: 34, 40, 45, 51, 60, 61, 63, 64, 65, 66, 72, 77, 83, 92, 93, 95, 96, and 97. In some embodiments, the guide RNAs disclosed herein comprise a guide sequence that is at least 95%, 90%, 85%, 80%, or 75% identical to a sequence selected from the group consisting of SEQ ID NOs: 2-33. In some embodiments, the guide RNAs disclosed herein comprise a guide sequence that is at least 17, 18, 19, or 20 contiguous nucleotides of a sequence selected from the group consisting of SEQ ID NOs: 2-33. In some embodiments, the guide RNAs disclosed herein comprise a guide sequence that is selected from the group consisting of SEQ ID NOs: 34-97. In some embodiments, the guide RNA comprises at least 15, 16, 17, 18, 19, or 20 contiguous nucleotides of a sequence selected from the group consisting of SEQ ID NOs: 2-5, 10-17, 21-27, and 29-33. In some embodiments, the guide RNA comprises a sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 2-5, 10-17, 21-27, and 29-33. In some embodiments, the guide RNAs disclosed herein comprise a guide sequence at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence selected from the group consisting of SEQ ID NOs: 34-37, 42-49, 53-59, 61-69, 74-81, 85-91, and 93-97. In some embodiments, the guide RNAs disclosed herein comprise a guide sequence that is at least 95%, 90%, 85%, 80%, or 75% identical to a sequence selected from the group consisting of SEQ ID NOs: 2-5, 10-17, 21-27, and 29-33. In some embodiments, the guide RNAs disclosed herein comprise a guide sequence that is at least 17, 18, 19, or 20 contiguous nucleotides of a sequence selected from the group consisting of SEQ ID NOs: 2-5, 10-17, 21-27, and 29-33. In some embodiments, the guide RNAs disclosed herein comprise a guide sequence that is selected from the group consisting of SEQ ID NOs: 34-37, 42-49, 53-59, 61-69, 74-81, 85-91, and 93-97. In some embodiments, the donor construct is a bidirectional construct that comprises a sequence encoding Factor IX. In some embodiments, the host cell is a liver cell, or the population of host cells are liver cells, such as hepatocytes.

As described herein, the donor construct (e.g., bidirectional construct) comprising a sequence encoding Factor IX, guide RNA, and RNA-guided DNA binding agent can be delivered using any suitable delivery system and method known in the art. The compositions can be delivered in vitro or in vivo simultaneously or in any sequential order. In some embodiments, the donor construct, guide RNA, and Cas nuclease can be delivered in vitro or in vivo simultaneously, e.g., in one vector, two vectors, individual vectors, one LNP, two LNPs, individual LNPs, or a combination thereof. In some embodiments, the donor construct can be delivered in vivo or in vitro, as a vector and/or associated with a LNP, prior to (e.g., about 1, 2, 3, 4, 5, 6, 7, 8, 9, 10, 11, 12, 13, 14, or more days) delivering the guide RNA and/or Cas nuclease, as a vector and/or associated with a LNP singly or together as a ribonucleoprotein (RNP). In some embodiments, the donor construct can be delivered in multiple administrations, e.g., every day, every two days, every three days, every four days, every week, every two weeks, every three weeks, or every four weeks. In some embodiments, the donor construct can be delivered at one-week intervals, e.g., at week 1, week 2, and week 3, etc. As a further example, the guide RNA and Cas nuclease, as a vector and/or associated with a LNP singly or together as a ribonucleoprotein (RNP), can be delivered in vivo or in vitro, prior to (e.g., about 1, 2, 3, 4, 5, 6, 7, 8, 9, 10, 11, 12, 13, 14, or more days) delivering the construct, as a vector and/or associated with a LNP. In some embodiments, the albumin guide RNA can be delivered in multiple administrations, e.g., every day, every two days, every three days, every four days, every week, every two weeks, every three weeks, or every four weeks. In some embodiments, the the albumin guide RNA can be delivered at one-week intervals, e.g., at week 1, week 2, and week 3, etc. In some embodiments, the Cas nuclease can be delivered in multiple administrations, e.g., can be delivered every day, every two days, every three days, every four days, every week, every two weeks, every three weeks, or every four weeks. In some embodiments, the Cas nuclease can be delivered at one-week intervals, e.g., at week 1, week 2, and week 3, etc. In some embodiments, the guide RNA and Cas nuclease are associated with an LNP and delivered to the host cell or the population of host cells prior to delivering the Factor IX donor construct.

In some embodiments, the donor construct comprises a sequence encoding Factor IX, wherein the Factor IX sequence is wild type Factor IX, e.g., SEQ ID NO: 700. In some embodiments, the donor construct comprises a sequence encoding Factor IX, wherein the Factor IX sequence is wild type Factor IX, e.g., SEQ ID NO: 701. In some embodiments, the sequence encodes a variant of Factor IX. For example, the variant possesses increased coagulation activity than wild type Factor IX. For example, the variant Factor IX comprises one or more mutations, such as an amino acid substitution in position R338 (e.g., R338L), relative to SEQ ID NO: 701. In some embodiments, the sequence encodes a Factor IX variant that is 80%, 85%, 90%, 93%, 95%, 97%, 99% identical to SEQ ID NO: 700, SEQ ID NO: 701, or SEQ ID NO: 702, having at least 80%, 85%, 90%, 92%, 94%, 96%, 98%, 99%, 100%, or more, activity as compared to wild type Factor IX. In some embodiments, the sequence encodes a fragment of Factor IX, wherein the fragment possesses at least 80%, 85%, 90%, 92%, 94%, 96%, 98%, 99%, 100%, or more, activity as compared to wild type Factor IX.

In one example, the Factor IX protein can comprise amino acid substitutions at positions L6 and V181. In another example, the Factor IX protein can comprise amino acid substitutions at positions L6 and K265. In another example, the Factor IX protein can comprise amino acid substitutions at positions L6 and 1383. In another example, the Factor IX protein can comprise amino acid substitutions at positions L6 and E185. In another example, the Factor IX protein can comprise amino acid substitutions at positions V181 and K265. In another example, the Factor IX protein can comprise amino acid substitutions at positions V181 and an 1383. In another example, the Factor IX protein can comprise amino acid substitutions at positions V181 and E185. In another example, the Factor IX protein can comprise amino acid substitutions at positions K265 and 1383. In another example, the Factor IX protein can comprise amino acid substitutions at positions K265 and E185. In another example, the Factor IX protein can comprise amino acid substitutions at positions 1383 and E185. In another example, the Factor IX protein can comprise amino acid substitutions at positions L6, V181, and K265. In another example, the Factor IX protein can comprise amino acid substitutions at positions L6, V181, and 1383. In another example, the Factor IX protein can comprise amino acid substitutions at positions L6, V181, and E185. In another example, the Factor IX protein can comprise amino acid substitutions at positions L6, K265, and 1383. In another example, the Factor IX protein can comprise amino acid substitutions at positions L6, K265, and E185. In another example, the Factor IX protein can comprise amino acid substitutions at positions L6, 1383, and E186. In another example, the Factor IX protein can comprise amino acid substitutions at positions V181, K265, and 1383. In another example, the Factor IX protein can comprise amino acid substitutions at positions V181, K265, and E185. In another example, the Factor IX protein can comprise amino acid substitutions at positions V181, 1383, and E186. In another example, the Factor IX protein can comprise amino acid substitutions at positions K265, 1383, and E185. In another example, the Factor IX protein can comprise amino acid substitutions at positions L6, V181, K265, and 1383. In another example, the Factor IX protein can comprise amino acid substitutions at positions L6, V181, I383, and E185. In another example, the Factor IX protein can comprise amino acid substitutions at positions L6, K265, 1383, and E185. In another example, the Factor IX protein can comprise amino acid substitutions at positions V181, K265, 1383, and E185.

In some embodiments, the donor construct comprises a sequence encoding a Factor IX variant, wherein the Factor IX variant activates coagulation in the absence of its cofactor, Factor VIII (expression results in therapeutically relevant FVIII mimetic activity). Such Factor IX variants can further maintain the activity of wild type Factor IX. For example, such a Factor IX variant can comprise an amino acid substation at position L6, V181, K265, 1383, E185, or a combination thereof relative to wild type Factor IX (e.g., relative to SEQ ID NO: 701). For example, such a Factor IX variant can comprise an L6F mutation, a V181I mutation, a K265A mutation, an I383V mutation, an E185D mutation, or a combination thereof relative to wild type Factor IX (e.g., relative to SEQ ID NO: 701).

In a specific example, the Factor IX protein can comprise amino acid substitutions at positions V181, K265, and 1383. In another specific example, the Factor IX protein can comprise amino acid substitutions at positions V181, K265, I383, and E185. In another specific example, the Factor IX protein can comprise amino acid substitutions at positions L6, V181, K265, and I383.

In one example, the Factor IX protein can comprise an L6F mutation and a V181I mutation. In another example, the Factor IX protein can comprise an L6F mutation and a K265A mutation. In another example, the Factor IX protein can comprise an L6F mutation and an I383V mutation. In another example, the Factor IX protein can comprise an L6F mutation and an E185D mutation. In another example, the Factor IX protein can comprise a V181I mutation and a K265A mutation. In another example, the Factor IX protein can comprise a V181I mutation and an I383V mutation. In another example, the Factor IX protein can comprise a V181I mutation and an E185D mutation. In another example, the Factor IX protein can comprise a K265A mutation and an I383V mutation. In another example, the Factor IX protein can comprise a K265A mutation and an E185D mutation. In another example, the Factor IX protein can comprise an I383V mutation and an E185D mutation. In another example, the Factor IX protein can comprise an L6F mutation, a V181I mutation, and a K265A mutation. In another example, the Factor IX protein can comprise an L6F mutation, a V181I mutation, and an I383V mutation. In another example, the Factor IX protein can comprise an L6F mutation, a V181I mutation and an E185D mutation. In another example, the Factor IX protein can comprise an L6F mutation, a K265A mutation, and an I383V mutation. In another example, the Factor IX protein can comprise an L6F mutation, a K265A mutation, and an E185D mutation. In another example, the Factor IX protein can comprise an L6F mutation, an I383V mutation, and an E186D mutation. In another example, the Factor IX protein can comprise a V181I mutation, a K265A mutation, and an I383V mutation. In another example, the Factor IX protein can comprise a V181I mutation, a K265A mutation, and an E185D mutation. In another example, the Factor IX protein can comprise a V181I mutation, an I383V mutation, and an E186D mutation. In another example, the Factor IX protein can comprise a K265A mutation, an I383V mutation, and an E185D mutation. In another example, the Factor IX protein can comprise an L6F mutation, a V181I mutation, a K265A mutation, and an I383V mutation. In another example, the Factor IX protein can comprise an L6F mutation, a V181I mutation, an I383V mutation, and an E185D mutation. In another example, the Factor IX protein can comprise an L6F mutation, a K265A mutation, an 1383V mutation, and an E185D mutation. In another example, the Factor IX protein can comprise a V181I mutation, a K265A mutation, an 1383V mutation, and an E185D mutation.

In a specific example, the Factor IX protein can comprise a V181I mutation, an K265A mutation, and an I383V mutation. In another specific example, the Factor IX protein can comprise a V181I mutation, a K265A mutation, an I383V mutation, and an E185D mutation. In some embodiments, the Factor IX protein is at least 80%, 85%, 90%, 93%. 95%, 97%, 99% identical to SEQ ID NO: 700, having at least 80%, 85%, 90%, 92%, 94%, 96%, 98%, 99%, 100%, or more, activity as compared to wild type Factor IX. In certain embodiments, the Factor IX variant is at least 80%, 85%, 90%, 93%, 95%, 97%, 99% identical to SEQ ID NO: 700, having at least 80%, 85%, 90%, 92%, 94%, 96%, 98%, 99%, 100%, or more. activity as compared to wild type Factor IX and comprises a V181I mutation, a K265A mutation, an 1383V mutation, and/or an E185D mutation. In another specific example, the Factor IX protein can comprise an L6F mutation, a V181I mutation, a K265A mutation, and an I383V mutation. In certain embodiments, the Factor IX variant is at least 80%, 85%, 90%, 93%, 95%, 97%, 99% identical to SEQ ID NO: 700, having at least 80%, 85%, 90%, 92%, 94%, 96%, 98%, 99%, 100%, or more, activity as compared to wild type Factor IX and comprises a V181I mutation, a K265A mutation, and an 1383V mutation.

In some embodiments, the host cell is a liver cell, or the population of host cells are liver cells. In some embodiments, the host cell is, or the population of host cells are, any suitable non-dividing cell. As used herein, a "non-dividing cell" refers to cells that are terminally differentiated and do not divide, as well as quiescent cells that do not divide but retains the ability to re-enter cell division and proliferation. Liver cells, for example, retain the ability to divide (e.g., when injured or resected), but do not typically divide. During mitotic cell division, homologous recombination is a mechanism by which the genome is protected and double-stranded breaks are repaired. In some embodiments, a "non-dividing" cell refers to a cell in which homologous recombination (HR) is not the primary mechanism by which double-stranded DNA breaks are repaired in the cell, e.g., as compared to a control dividing cell. In some embodiments, a "non-dividing" cell refers to a cell in which non-homologous end joining (NHEJ) is the primary mechanism by which double-stranded DNA breaks are repaired in the cell, e.g., as compared to a control dividing cell. Non-dividing cell types have been described in the literature, e.g. by active NHEJ double-stranded DNA break repair mechanisms. See, e.g. Iyama, DNA Repair (Amst.) 2013, 12(8): 620-636. In some embodiments, the host cell includes, but is not limited to, a liver cell, a muscle cell, or a neuronal cell. In some embodiments, the host cell, or the population of host cells are, is a hepatocyte, such as a mouse, cyno, or human hepatocyte. In some embodiments, the host cell is a myocyte, such as a mouse, cyno, or human myocyte. In some embodiments, provided herein is a host cell composition comprising any one or more guide RNA described herein, alone or in combination with an RNA-guided DNA binding protein. In some embodiments, provided herein is a host cell composition comprising any one or more of the vectors described herein.

In some embodiments, the donor construct (e.g., bidirectional construct) is administered in a nucleic acid vector, such as an AAV vector, e.g., AAV8. In some embodiments, the donor construct does not comprise a homology arm.

In some embodiments, the subject is a mammal. In some embodiments, the subject is human. In some embodiments, the subject is cow, pig, monkey, sheep, dog, cat, fish, or poultry.

In some embodiments, the donor construct (e.g., bidirectional construct) comprising a sequence encoding Factor IX, guide RNA, and RNA-guided DNA binding agent are administered intravenously. In some embodiments, the donor construct (e.g., bidirectional construct) comprising a sequence encoding Factor IX, guide RNA, and RNA-guided DNA binding agent are administered into the hepatic circulation.

In some embodiments, a single administration of a donor construct (e.g., bidirectional construct) comprising a sequence encoding Factor IX, guide RNA, and RNA-guided DNA binding agent is sufficient to increase expression of Factor IX to a desirable level. In other embodiments, more than one administration of a composition comprising a donor construct (e.g., bidirectional construct) comprising a sequence encoding Factor IX, guide RNA, and RNA-guided DNA binding agent may be beneficial to maximize therapeutic effects.

In some embodiments, the present disclosure includes combination therapies comprising any one or more of the gRNAs, donor construct (e.g., bidirectional construct comprising a sequence encoding Factor IX), and RNA-guided DNA binding agents (e.g., Cas nuclease) described herein together with an additional therapy suitable for treating hemophilia, as described above. For example, the methods of the present disclosure can be combined with the use of other hemostatic agents, blood factors, and medications. For example, the subject may be administered a therapeutically effective amount of one or more factors selected from the group consisting of factor XI, factor XII, prekallikrcin, high molecular weight kininogen (HMWK), factor V, factor VII, factor VIII, factor X, factor XIII, factor II, factor VIa, and von Willebrands factor.

In some embodiments, treatment may further comprise administering a procoagulant, such as an activator of the intrinsic coagulation pathway, including factor Xa, factor IXa, factorXIa, factor XIa, and VIIIa, prekallekrein, and high-molecular weight kininogen; or an activator of the extrinsic coagulation pathway, including tissue factor, factor VIIa, factor Va, and factor Xa.

This description and exemplary embodiments should not be taken as limiting. For the purposes of this specification and appended embodiments, unless otherwise indicated, all numbers expressing quantities, percentages, or proportions, and other numerical values used in the specification and embodiments, are to be understood as being modified in all instances by the term "about," to the extent they are not already so modified. Accordingly, unless indicated to the contrary, the numerical parameters set forth in the following specification and attached embodiments are approximations that may vary depending upon the desired properties sought to be obtained. At the very least, and not as an attempt to limit the application of the doctrine of equivalents to the scope of the embodiments, each numerical parameter should at least be construed in light of the number of reported significant digits and by applying ordinary rounding techniques.

```
Human Factor IX Protein Sequence (SEQ ID NO: 700) NCBI Ref: NP_000124:
MQRVNMIMAESPGLITICLLGYLLSAECTVFLDHENANKILNRPKRYNSGKLEEFVQGNL

ERECMEEKCSFEEAREVFENTERTTEFWKQYVDGDQCESNPCLNGGSCKDDINSYECWCP

FGFEGKNCELDVTCNIKNGRCEQFCKNSADNKVVCSCTEGYRLAENQKSCEPAVPFPCGR

VSVSQTSKLTRAETVFPDVDYVNSTEAETILDNITQSTQSFNDFTRVVGGEDAKPGQFPW
```

-continued

QVVLNGKVDAFCGGSIVNEKWIVTAAHCVETGVKITVVAGEHNIEETEHTEQKRNVIRII

PHHNYNAAINKYNHDIALLELDEPLVLNSYVTPICIADKEYTNIFLKFGSGYVSGWGRVF

HKGRSALVLQYLRVPLVDRATCLRSTKFTIYNNMFCAGFHEGGRDSCQGDSGGPHVTEVE

GTSFLTGIISWGEECAMKGKYGIYTKVSRYVNWIKEKTKLT

Human Factor IX Nucleotide Sequence (SEQ ID NO: 706) NCBI Ref: NM_000133):

```
   1 accactttca caatctgcta gcaaaggtta tgcagcgcgt gaacatgatc atggcagaat
  61 caccaggcct catcaccatc tgccttttag gatatctact cagtgctgaa tgtacagttt
 121 ttcttgatca tgaaaacgcc aacaaaattc tgaatcggcc aaagaggtat aattcaggta
 181 aattggaaga gtttgttcaa gggaaccttg agagagaatg tatggaagaa aagtgtagtt
 241 ttgaagaagc acgagaagtt tttgaaaaca ctgaaagaac aactgaattt tggaagcagt
 301 atgttgatgg agatcagtgt gagtccaatc catgtttaaa tggcggcagt tgcaaggatg
 361 acattaattc ctatgaatgt tggtgtccct ttggatttga aggaaagaac tgtgaattag
 421 atgtaacatg taacattaag aatggcagat gcgagcagtt ttgtaaaaat agtgctgata
 481 acaaggtggt ttgctcctgt actgagggat atcgacttgc agaaaaccag aagtcctgtg
 541 aaccagcagt gccatttcca tgtggaagag tttctgtttc acaaacttct aagctcaccc
 601 gtgctgagac tgtttttcct gatgtggact atgtaaattc tactgaagct gaaaccattt
 661 tggataacat cactcaaagc acccaatcat ttaatgactt cactcgggtt gttggtggag
 721 aagatgccaa accaggtcaa ttcccttggc aggttgtttt gaatggtaaa gttgatgcat
 781 tctgtggagg ctctatcgtt aatgaaaaat ggattgtaac tgctgcccac tgtgttgaaa
 841 ctggtgttaa aattacagtt gtcgcaggtg aacataatat tgaggagaca gaacatacag
 901 agcaaaagcg aaatgtgatt cgaattattc ctcaccacaa ctacaatgca gctattaata
 961 agtacaacca tgacattgcc cttctggaac tggacgaacc cttagtgcta aacagctacg
1021 ttacacctat ttgcattgct gacaaggaat acacgaacat cttcctcaaa tttggatctg
1081 gctatgtaag tggctgggga agagtcttcc acaaagggag atcagcttta gttcttcagt
1141 accttagagt tccacttgtt gaccgagcca catgtcttcg atctacaaag ttcaccatct
1201 ataacaacat gttctgtgct ggcttccatg aaggaggtag agattcatgt caaggagata
1261 gtgggggacc ccatgttact gaagtggaag ggaccagttt cttaactgga attattagct
1321 ggggtgaaga gtgtgcaatg aaaggcaaat atggaatata taccaaggta tcccggtatg
1381 tcaactggat taaggaaaaa acaaagctca cttaatgaaa gatggatttc caaggttaat
1441 tcattggaat tgaaaattaa cagggcctct cactaactaa tcactttccc atcttttgtt
1501 agatttgaat atatacattc tatgatcatt gctttttctc tttacagggg agaatttcat
1561 attttacctg agcaaattga ttagaaaatg gaaccactag aggaatataa tgtgttagga
1621 aattacagtc atttctaagg gcccagccct tgacaaaatt gtgaagttaa attctccact
1681 ctgtccatca gatactatgg ttctccacta tggcaactaa ctcactcaat tttccctcct
1741 tagcagcatt ccatcttccc gatcttcttt gcttctccaa ccaaaacatc aatgtttatt
1801 agttctgtat acagtacagg atctttggtc tactctatca caaggccagt accacactca
1861 tgaagaaaga acacaggagt agctgagagg ctaaaactca tcaaaaacac tactcctttt
1921 cctctaccct attcctcaat cttttacctt ttccaaatcc caatccccaa atcagttttt
1981 ctctttctta ctccctctct ccccttttacc ctccatggtc gttaaaggag agatggggag
2041 catcattctg ttatacttct gtacacagtt atacatgtct atcaaaccca gacttgcttc
2101 cgtagtggag acttgctttt cagaacatag ggatgaagta aggtgcctga aaagtttggg
```

-continued

```
2161    ggaaaagttt ctttcagaga gttaagttat tttatatata taatatatat ataaaatata

2221    taatatacaa tataaatata tagtgtgtgt gtatgcgtgt gtgtagacac acacgcatac

2281    acacatataa tggaagcaat aagccattct aagagcttgt atggttatgg aggtctgact

2341    aggcatgatt tcacgaaggc aagattggca tatcattgta actaaaaaag ctgacattga

2401    cccagacata ttgtactctt tctaaaaata ataataataa tgctaacaga aagaagagaa

2461    ccgttcgttt gcaatctaca gctagtagag actttgagga agaattcaac agtgtgtctt

2521    cagcagtgtt cagagccaag caagaagttg aagttgccta gaccagagga cataagtatc

2581    atgtctcctt taactagcat accccgaagt ggagaagggt gcagcaggct caaaggcata

2641    agtcattcca atcagccaac taagttgtcc ttttctggtt tcgtgttcac catggaacat

2701    tttgattata gttaatcctt ctatcttgaa tcttctagag agttgctgac caactgacgt

2761    atgtttccct ttgtgaatta ataaactggt gttctggttc at
```

Human Factor IX polypeptide (SEQ ID No: 701)

```
YNSGKLEEFVQGNLERECMEEKCSFEEAREVFENTERTTEFWKQYVDGDQCESNPCLNGGSCKDDINSYE

CWCPFGFEGKNCELDVTCNIKNGRCEQFCKNSADNKVVCSCTEGYRLAENQKSCEPAVPFPCGRVSVSQT

SKLTRAETVFPDVDYVNSTEAETILDNITQSTQSFNDFTRVVGGEDAKPGQFPWQVVLNGKVDAFCGGSI

VNEKWIVTAAHCVETGVKITVVAGEHNIEETEHTEQKRNVIRIIPHHNYNAAINKYNHDIALLELDEPLV

LNSYVTPICIADKEYTNIFLKFGSGYVSGWGRVFHKGRSALVLQYLRVPLVDRATCLRSTKFTIYNNMFC

AGFHEGGRDSCQGDSGGPHVTEVEGTSFLTGIISWGEECAMKGKYGIYTKVSRYVNWIKEKTKLT
```

EXAMPLES

The following examples are provided to illustrate certain disclosed embodiments and are not to be construed as limiting the scope of this disclosure in any way.

Example 1—Materials and Methods

Cloning and Plasmid Preparation

A bidirectional insertion construct flanked by ITRs was synthesized and cloned into pUC57-Kan by a commercial vendor. The resulting construct (P00147) was used as the parental cloning vector for other vectors. The other insertion constructs (without ITRs) were also commercially synthesized and cloned into pUC57. Purified plasmid was digested with BglII restriction enzyme (New England BioLabs, cat #R0144S), and the insertion constructs were cloned into the parental vector. Plasmid was propagated in Stbl3™ Chemically Competent *E. coli* (Thermo Fisher, Cat #C737303).

AAV Production

Triple transfection in HEK293 cells was used to package genomes with constructs of interest for AAV8 and AAV-DJ production and resulting vectors were purified from both lysed cells and culture media through iodixanol gradient ultracentrifugation method (See, e.g., Lock et al., Hum Gene Ther. 2010 October; 21(10):1259-71). The plasmids used in the triple transfection that contained the genome with constructs of interest are referenced in the Examples by a "PXXXX" number, see also e.g., Table 9. Isolated AAV was dialyzed in storage buffer (PBS with 0.001% Pluronic F68). AAV titer was determined by qPCR using primers/probe located within the ITR region.

In Vitro Transcription ("IVT") of Nuclease mRNA

Capped and polyadenylated *Streptococcus pyogenes* ("Spy") Cas9 mRNA containing N1-methyl pseudo-U was generated by in vitro transcription using a linearized plasmid DNA template and T7 RNA polymerase. Generally, plasmid DNA containing a T7 promoter and a 100 nt poly (A/T) region was linearized by incubating at 37° C. with XbaI to complete digestion followed by heat inactivation of XbaI at 65° C. The linearized plasmid was purified from enzyme and buffer salts. The IVT reaction to generate Cas9 modified mRNA was incubated at 37° C. for 4 hours in the following conditions: 50 ng/μL linearized plasmid; 2 mM each of GTP, ATP, CTP, and N1-methyl pseudo-UTP (Trilink); 10 mM ARCA (Trilink); 5 U/μL T7 RNA polymerase (NEB); 1 U/μL Murine Rnase inhibitor (NEB); 0.004 U/μL Inorganic *E. coli* pyrophosphatase (NEB); and 1× reaction buffer. TURBO Dnase (ThermoFisher) was added to a final concentration of 0.01 U/μL, and the reaction was incubated for an additional 30 minutes to remove the DNA template. The Cas9 mRNA was purified using a MegaClear Transcription Clean-up kit according to the manufacturer's protocol (ThermoFisher). Alternatively, the Cas9 mRNA was purified using LiCl precipitation, ammonium acetate precipitation, and sodium acetate precipitation or using a LiCl precipitation method followed by further purification by tangential flow filtration. The transcript concentration was determined by measuring the light absorbance at 260 nm (Nanodrop), and the transcript was analyzed by capillary electrophoresis by Bioanlayzer (Agilent).

Cas9 mRNAs below comprise Cas9 ORF SEQ ID NO: 703 or SEQ ID NO: 704 or a sequence of Table 24 of PCT/US2019/053423 (which is hereby incorporated by reference).

Lipid Formulations for Delivery of Cas9 mRNA and gRNA

Cas9 mRNA and gRNA were delivered to cells and animals utilizing lipid formulations comprising ionizable lipid ((9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy) methyl)propyl (9Z,12Z)-octadeca-9,12-dienoate), cholesterol, DSPC, and PEG2k-DMG.

For experiments utilizing pre-mixed lipid formulations (referred to herein as "lipid packets"), the components were reconstituted in 100% ethanol at a molar ratio of ionizable lipid:cholesterol:DSPC:PEG2k-DMG of 50:38:9:3, prior to being mixed with RNA cargos (e.g., Cas9 mRNA and gRNA) at a lipid amine to RNA phosphate (N:P) molar ratio of about 6.0, as further described herein.

For experiments utilizing the components formulated as lipid nanoparticles (LNPs), the components were dissolved in 100% ethanol at various molar ratios. The RNA cargos (e.g., Cas9 mRNA and gRNA) were dissolved in 25 mM citrate, 100 mM NaCl, pH 5.0, resulting in a concentration of RNA cargo of approximately 0.45 mg/mL.

For the experiments described in Example 2, the LNPs were formed by microfluidic mixing of the lipid and RNA solutions using a Precision Nanosystems NanoAssemblr™ Benchtop Instrument, according to the manufacturer's protocol. A 2:1 ratio of aqueous to organic solvent was maintained during mixing using differential flow rates. After mixing, the LNPs were collected, diluted in water (approximately 1:1 v/v), held for 1 hour at room temperature, and further diluted with water (approximately 1:1 v/v) before final buffer exchange. The final buffer exchange into 50 mM Tris, 45 mM NaCl, 5% (w/v) sucrose, pH 7.5 (TSS) was completed with PD-10 desalting columns (GE). If required, formulations were concentrated by centrifugation with Amicon 100 kDa centrifugal filters (Millipore). The resulting mixture was then filtered using a 0.2 m sterile filter. The final LNP was stored at −80° C. until further use. The LNPs were formulated at a molar ratio of ionizable lipid:cholesterol: DSPC:PEG2k-DMG of 45:44:9:2, with a lipid amine to RNA phosphate (N:P) molar ratio of about 4.5, and a ratio of gRNA to mRNA of 1:1 by weight.

For the experiments described in other examples, the LNPs were prepared using a cross-flow technique utilizing impinging jet mixing of the lipid in ethanol with two volumes of RNA solutions and one volume of water. The lipid in ethanol was mixed through a mixing cross with the two volumes of RNA solution. A fourth stream of water was mixed with the outlet stream of the cross through an inline tee (See WO2016010840 FIG. 2.). The LNPs were held for 1 hour at room temperature, and further diluted with water (approximately 1:1 v/v). Diluted LNPs were concentrated using tangential flow filtration on a flat sheet cartridge (Sartorius, 100 kD MWCO) and then buffer exchanged by diafiltration into 50 mM Tris, 45 mM NaCl, 5% (w/v) sucrose, pH 7.5 (TSS). Alternatively, the final buffer exchange into TSS was completed with PD-10 desalting columns (GE). If required, formulations were concentrated by centrifugation with Amicon 100 kDa centrifugal filters (Millipore). The resulting mixture was then filtered using a 0.2 μm sterile filter. The final LNP was stored at 4° C. or −80° C. until further use. The LNPs were formulated at a molar ratio of ionizable lipid:cholesterol:DSPC:PEG2k-DMG of 50:38:9:3, with a lipid amine to RNA phosphate (N:P) molar ratio of about 6.0, and a ratio of gRNA to mRNA of 1:1 by weight.

Cell Culture and In Vitro Delivery of Cas9 mRNA, gRNA, and Insertion Constructs

Hepa1-6 Cells

Hepa 1-6 cells were plated at density of 10,000 cells/well in 96-well plates. 24 hours later, cells were treated with LNP and AAV. Before treatment the media was aspirated off from the wells. LNP was diluted to 4 ng/ul in DMEM+10% FBS media and further diluted to 2 ng/ul in 10% FBS (in DMEM) and incubated at 37° C. for 10 min (at a final concentration of 5% FBS). Target MOI of AAV was 1e6, diluted in DMEM+10% FBS media. 50 μl of the above diluted LNP at 2 ng/ul was added to the cells (delivering a total of 100 ng of RNA cargo) followed by 50 μl of AAV. The treatment of LNP and AAV were minutes apart. Total volume of media in cells was 100 μl. After 72 hours post-treatment and 30 days post-treatment, supernatant from these treated cells were collected for human FIX ELISA analysis as described below.

Primary Hepatocytes

Primary mouse hepatocytes (PMH), primary cyno hepatocytes (PCH) and primary human hepatocytes (PHH) were thawed and resuspended in hepatocyte thawing medium with supplements (ThermoFisher) followed by centrifugation. The supernatant was discarded, and the pelleted cells resuspended in hepatocyte plating medium plus supplement pack (ThermoFisher). Cells were counted and plated on Bio-coat collagen I coated 96-well plates at a density of 33,000 cells/well for PHH and 50,000 cells/well for PCH and 15,000 cells/well for PMH. Plated cells were allowed to settle and adhere for 5 hours in a tissue culture incubator at 37° C. and 5% C02 atmosphere. After incubation cells were checked for monolayer formation and were washed thrice with hepatocyte maintenance prior and incubated at 37° C.

For experiments utilizing lipid packet delivery, Cas9 mRNA and gRNA were each separately diluted to 2 mg/ml in maintenance media and 2.9 μl of each were added to wells (in a 96-well Eppendorf plate) containing 12.5 μl of 50 mM sodium citrate, 200 mM sodium chloride at pH 5 and 6.9 μl of water. 12.5 μl of lipid packet formulation was then added, followed by 12.5 μl of water and 150 μl of TSS. Each well was diluted to 20 ng/μl (with respect to total RNA content) using hepatocyte maintenance media, and then diluted to 10 ng/μl (with respect to total RNA content) with 6% fresh mouse serum. Media was aspirated from the cells prior to transfection and 40 μl of the lipid packet/RNA mixtures were added to the cells, followed by addition of AAV (diluted in maintenance media) at an MOI of 1e5. Media was collected 72 hours post-treatment for analysis and cells were harvested for further analysis, as described herein.

Luciferase Assays

For experiments involving NanoLuc detection in cell media, one volume of Nano-Glo® Luciferase Assay Substrate was combined with 50 volumes of Nano-Glo® Luciferase Assay Buffer. The assay was run on a Promega Glomax runner at an integration time of 0.5 sec using 1:10 dilution of samples (50 μl of reagent+40 μl water+10 μl cell media).

For experiments involving detection of the HiBit tag in cell media, LgBiT Protein and Nano-GloR HiBiT Extracellular Substrate were diluted 1:100 and 1:50, respectively, in room temperature Nano-GloR HiBiT Extracellular Buffer. The assay was run on a Promega Glomax runner at an integration time of 1.0 sec using 1:10 dilution of samples (50 μl of reagent+40 μl water+10 μl cell media).

In Vivo Delivery of LNP and/or AAV

Mice were dosed with AAV, LNP, both AAV and LNP, or vehicle (PBS+0.001% Pluronic for AAV vehicle, TSS for LNP vehicle) via the lateral tail vein. AAV were administered in a volume of 0.1 mL per animal with amounts (vector genomes/mouse, "vg/ms") as described herein. LNPs were diluted in TSS and administered at amounts as indicated herein, at about 5 μl/gram body weight. Typically, mice were injected first with AAV and then with LNP, if applicable. At various times points post-treatment, serum and/or liver tissue was collected for certain analyses as described further below.

Human Factor IX (hFIX) ELSA Analysis

For in vitro studies, total human Factor IX levels secreted in cell media were determined using a Human Factor IX ELISA Kit (Abcam, Cat #ab188393) according to manufacturer's protocol. Secreted hFIX levels were quantitated off a standard curve using 4 parameter logistic fit and expressed as ng/ml of media.

For in vivo studies, blood was collected and the serum or plasma was isolated as indicated. The total human Factor IX levels were determined using a Human Factor IX ELISA Kit (Abcam, Cat #ab188393) according to manufacturer's protocol. Serum or plasma hFIX levels were quantitated off a standard curve using 4 parameter logistic fit and expressed as μg/mL of serum.

Next-Generation Sequencing ("NGS") and Analysis for On-Target Cleavage Efficiency Deep sequencing was utilized to identify the presence of insertions and deletions introduced by gene editing, e.g., within intron 1 of albumin. PCR primers were designed around the target site and the genomic area of interest was amplified. Primer sequence design was done as is standard in the field.

Additional PCR was performed according to the manufacturer's protocols (Illumina) to add chemistry for sequencing. The amplicons were sequenced on an Illumina MiSeq instrument. The reads were aligned to the reference genome after eliminating those having low quality scores. The resulting files containing the reads were mapped to the reference genome (BAM files), where reads that overlapped the target region of interest were selected and the number of wild type reads versus the number of reads which contain an insertion or deletion ("indel") was calculated.

The editing percentage (e.g., the "editing efficiency" or "percent editing") is defined as the total number of sequence reads with insertions or deletions ("indels") over the total number of sequence reads, including wild type.

In Situ Hybridization Analysis

BaseScope (ACDbio, Newark, CA) is a specialized RNA in situ hybridization technology that can provide specific detection of exon junctions, e.g., in a hybrid mRNA transcript that contains an insertion transgene (hFIX) and coding sequence from the site of insertion (e.g. exon 1 of albumin). BaseScope was used to measure the percentage of liver cells expressing the hybrid mRNA.

To detect the hybrid mRNA, two probes against the hybrid mRNAs that may arise following insertion of a bidirectional construct were designed by ACDbio (Newark, CA). One of the probes was designed to detect a hybrid mRNA resulting from insertion of the construct in one orientation, while the other probe was designed to detect a hybrid mRNA resulting from insertion of the construct in the other orientation. Livers from different groups of mice were collected and fresh-frozen sectioned. The BaseScope assay, using a single probe or pooled probes was performed according to the manufacture's protocol. Slides were scanned and analyzed by the HALO software. The background (saline treated group) of this assay was 0.58%.

Example 2—In Vitro Testing of Insertion Templates with and without Homology Arms In this Example, Hepa1-6 cells were cultured and treated with AAV harboring insertion templates of various forms (e.g., having either a single-stranded genome ("ssAAV") or a self-complementary genome ("scAAV")), in the presence or absence of LNP delivering Cas9 mRNA and G000551 e.g., as described in Example 1 (n=3). The AAV and LNP were prepared as described in Example 1. Following treatment, the media was collected for human Factor IX levels as described in Example 1.

Figure 2:
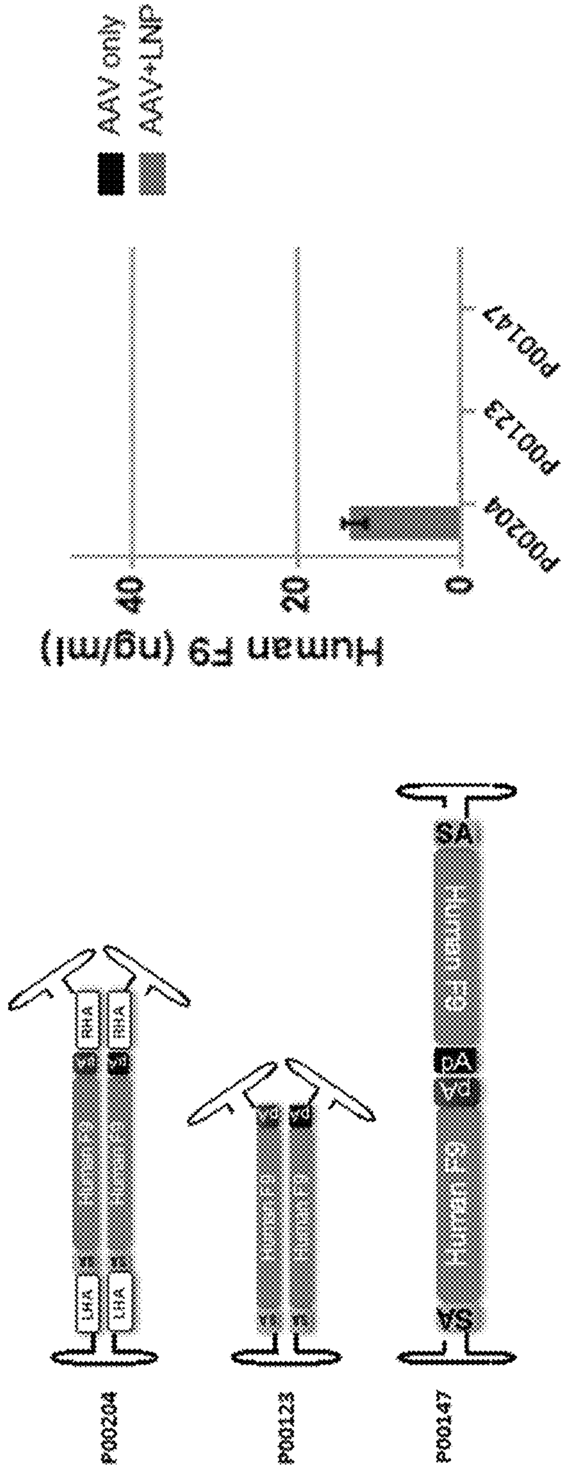
FIG. 2 shows vectors without homology arms are not effective in an immortalized liver cell line (Hepa1-6). An scAAV derived from plasmid P00204 comprising 200 bp homology arms resulted in expression of hFIX in the dividing cells. Use of the AAV vectors derived from P00123 (scAAV lacking homology arms) and P00147 (ssAAV bidirectional construct lacking homology arms) did not result in detectable expression of hFIX.

Hepa1-6 cells are an immortalized mouse liver cell line that continues to divide in culture. As shown in FIG. 2 (72 hour post-treatment time point), only the vector (scAAV derived from plasmid P00204) comprising 200 bp homology arms resulted in detectable expression of hFIX. Use of the AAV vectors derived from P00123 (scAAV lacking homology arms) and P00147 (ssAAV bidirectional construct lacking homology arms) did not result in any detectable expression of hFIX in this experiment. The cells were kept in culture and these results were confirmed when re-assayed at 30 days post-treatment (data not shown).

Example 3—In Vivo Testing of Insertion Templates with and without Homology Arms In this Example, mice were treated with AAV derived from the same plasmids (P00123, P00204, and P00147) as tested in vitro in Example 2. The dosing materials were prepared and dosed as described in Example 1. C57Bl/6 mice were dosed (n=5 for each group) with 3e11 vector genomes each (vg/ms) followed by LNP comprising G000551 ("G551") at a dose of 4 mg/kg (with respect to total RNA cargo content). Four weeks post dose, the animals were euthanized and liver tissue and sera were collected for editing and hFIX expression, respectively.

Figure 3B:
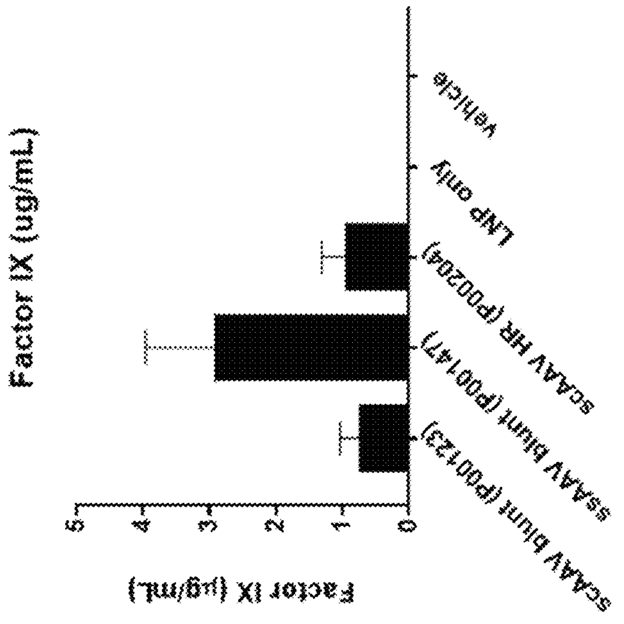
FIGS. 3A and 3B show results from in vivo testing of insertion templates with and without homology arms using vectors derived from P00123, P00147, or P00204.
Figure 3A:
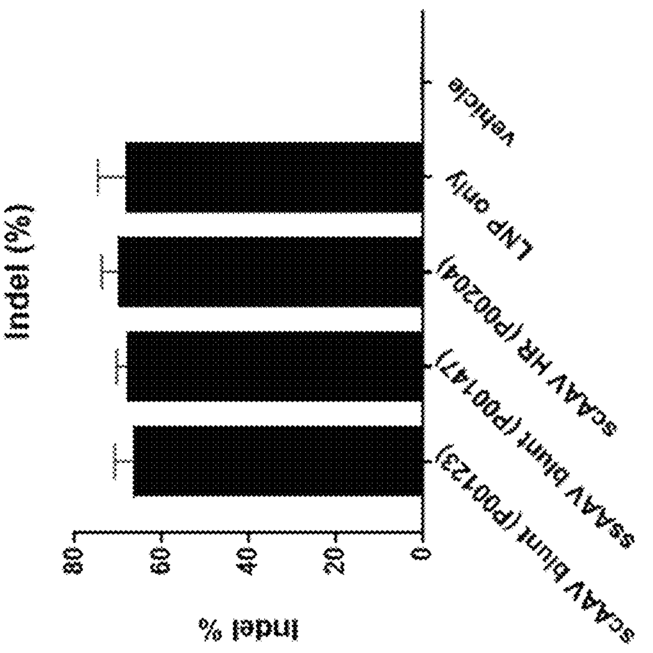

As shown in FIG. 3A and Table 12, liver editing levels of ~60% were detected in each group of animals treated with LNP comprising gRNA targeting intron 1 of murine albumin. However, despite robust and consistent levels of editing in each treatment group, animals receiving the bi-directional vector without homology arms (ssAAV vector derived from P00147) in combination with LNP treatment resulted in the highest level of hFIX expression in serum (FIG. 3B and Table 13).

TABLE 12

| | % Indel | |
|---|---|---|
| Template | Average Indel (%) | St. Dev Indel (%) |
| scAAV Blunt (P00123) | 66.72 | 4.09 |
| ssAAV Blunt (P00147) | 68.10 | 2.27 |
| ssAAV HR (P00204) | 70.16 | 3.68 |
| LNP only | 68.24 | 6.47 |
| Vehicle | 0.28 | 0.08 |

TABLE 13

| | Factor IX Levels | |
|---|---|---|
| Template | Average Factor IX (ug/mL) | St.Dev Factor IX (ug/mL) |
| scAAV Blunt (P00123) | 0.75 | 0.28 |
| ssAAV Blunt (P00147) | 2.92 | 1.04 |
| ssAAV HR (P00204) | 0.96 | 0.35 |
| LNP only | 0 | 0 |
| Vehicle | 0 | 0 |

Example 4—In Vivo Testing of ssAAV Insertion Templates with and without Homology Arms The experiment described in this example examined the effect of incorporating homology arms into ssAAV vectors in vivo.

The dosing materials used in this experiment were prepared and dosed as described in Example 1. C57Bl/6 mice were dosed (n=5 for each group) with 3e11 vg/ms followed by LNP comprising G000666 ("G666") or G000551 ("G551") at a dose of 0.5 mg/kg (with respect to total RNA cargo content). Four weeks post dose, the animals sera was collected for hFIX expression.

Figure 4A:
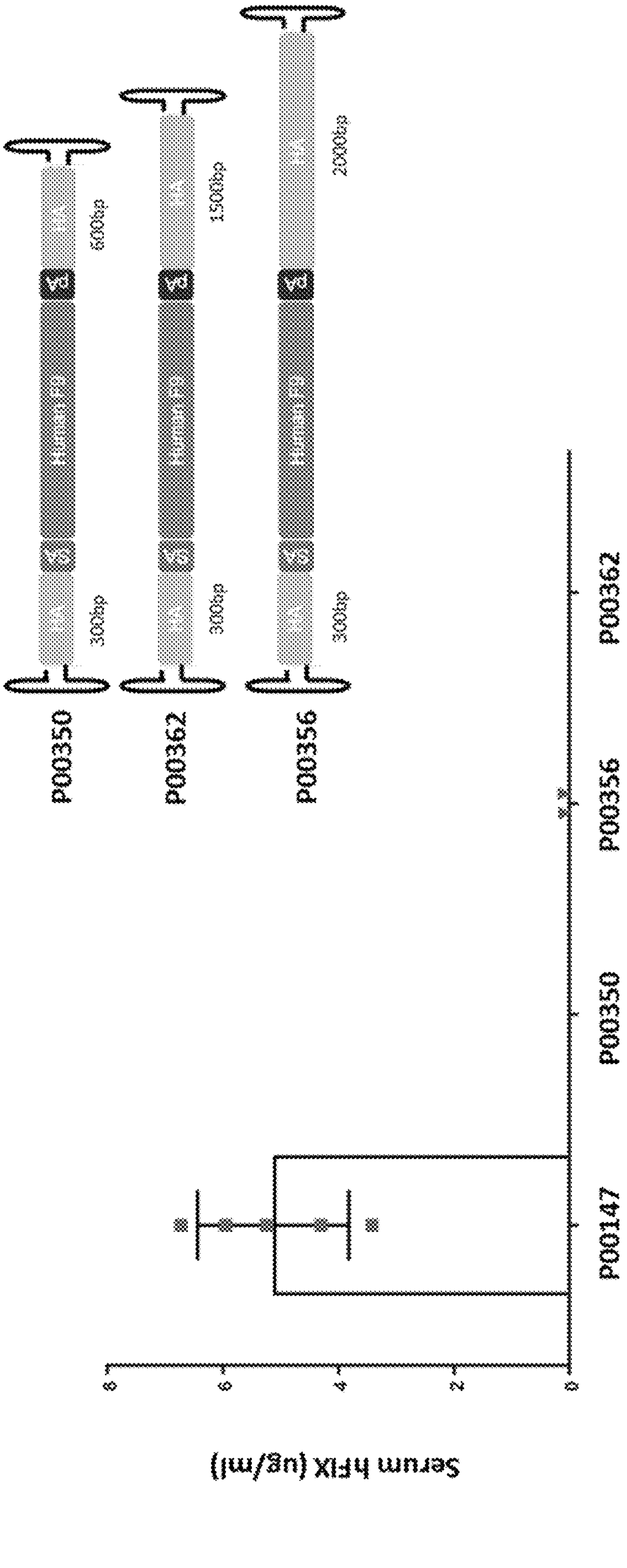
FIGS. 4A and 4B show results from in vivo testing of ssAAV insertion templates with and without homology arms.

As shown in FIG. 4A and Table 14, use of the ssAAV vectors with asymmetrical homology arms (300/600 bp arms, 300/2000 bp arms, and 300/1500 bp arms for vectors derived from plasmids P00350, P00356, and P00362, respectively) for insertion into the site targeted by G551 resulted in levels of circulating hFIX that were below the lower limit of detection for the assay. However, use of the ssAAV vector (derived from P00147) without homology arms and having two hFIX open reading frames (ORF) in a bidirectional orientation resulted in detectable levels of circulating hFIX in each animal.

Figure 4B:
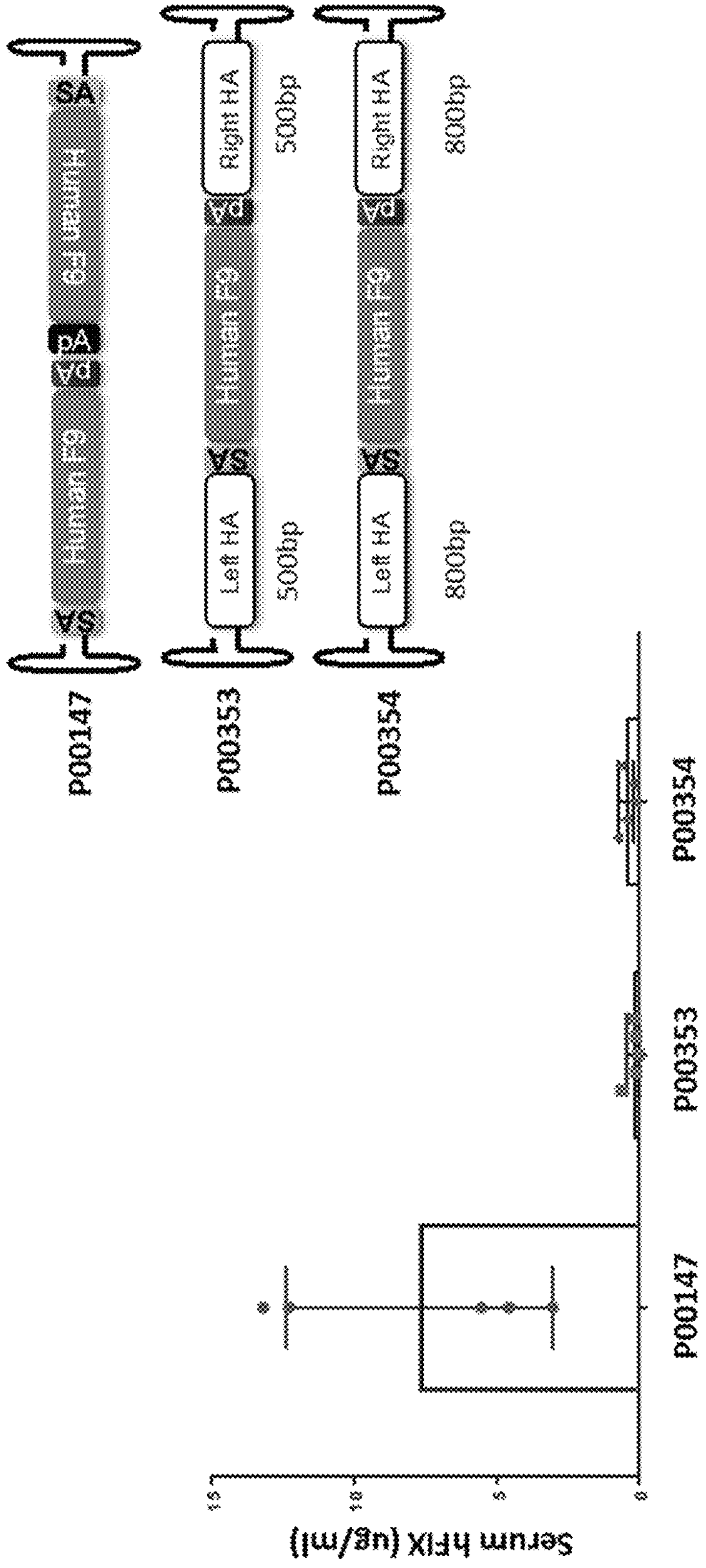

Similarly, use of the ssAAV vectors with asymmetrical homology arms (500 bp arms and 800 bp arms for vectors derived from plasmids P00353 and P00354, respectively) for insertion into the site targeted by G666 resulted in lower but detectable levels, as compared to use of the bidirectional vector without homology arms (derived from P00147) (see FIG. 4B and Table 15).

TABLE 14

| Serum hFIX Levels | | |
|---|---|---|
| AAV | Average Serum FIX (ug/mL) | St.Dev Serum FIX (ug/mL) |
| P00147 | 5.13 | 1.31 |
| P00350 | −0.22 | 0.08 |
| P00356 | −0.23 | 0.04 |
| P00362 | −0.09 | 0.16 |

TABLE 15

| Serum hFIX Levels | | |
|---|---|---|
| AAV | Average Serum FIX (ug/mL) | St.Dev Serum FIX (ug/mL) |
| P00147 | 7.72 | 4.67 |
| P00353 | 0.20 | 0.23 |
| P00354 | 0.46 | 0.26 |

Example 5—In Vitro Screening of Bidirectional Constructs Across Target Sites in Primary Mouse Hepatocytes Having demonstrated that bidirectional constructs lacking homology arms outperformed vectors with other configurations, the experiment described in this Example examined the effects of altering the splice acceptors used to form the hybrid transcript between hFIX and exon 1 of albumin and altering the gRNAs for targeting CRISPR/Cas9-mediated insertion. These varied bidirectional constructs were tested across a panel of target sites utilizing 20 different gRNAs targeting intron 1 of murine albumin in primary mouse hepatocytes (PMH).

Figure 5A:
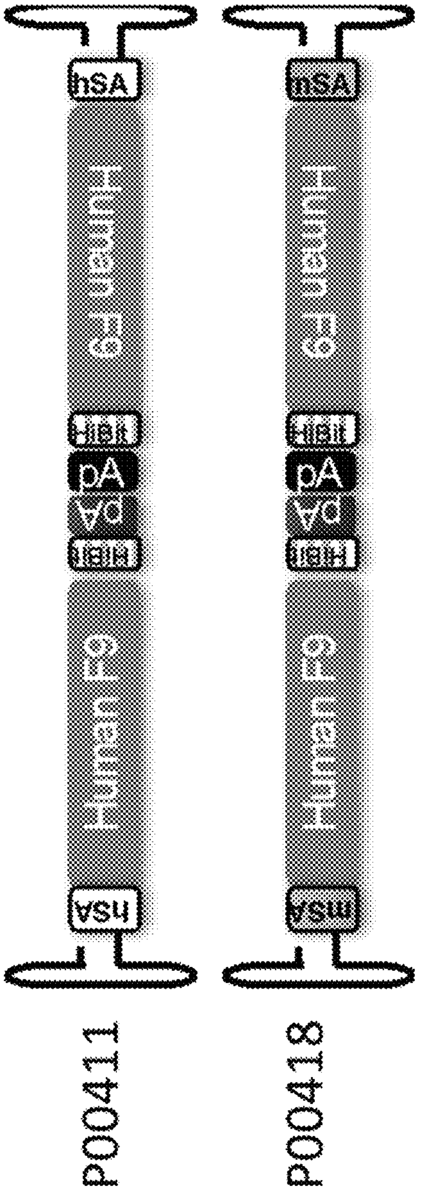
FIGS. 5A-5D show results of targeted insertion of bidirectional constructs across 20 target sites in primary mouse hepatocytes.

The ssAAV and lipid packet delivery materials tested in this Example were prepared and delivered to PMH as described in Example 1, with the AAV at an MOI of 1e5. Following treatment, isolated genomic DNA and cell media was collected for editing and transgene expression analysis, respectively. Each of the vectors comprised a reporter that can be measured through luciferase-based fluorescence detection as described in Example 1, plotted in FIG. 5C as relative luciferase units ("RLU"). The vectors comprised a HiBit peptide fused at the 3' ends of the hFIX ORF, which allows for sensitive detection of relative expression. Schematics of each vector tested are provided in FIG. 5A. The gRNAs tested are shown in FIGS. 5B and SC, using a shortened number for those listed in Table 5 (e.g., where the leading zeros are omitted, for example where "G551" corresponds to "G000551" in Table 5).

Figure 5B:
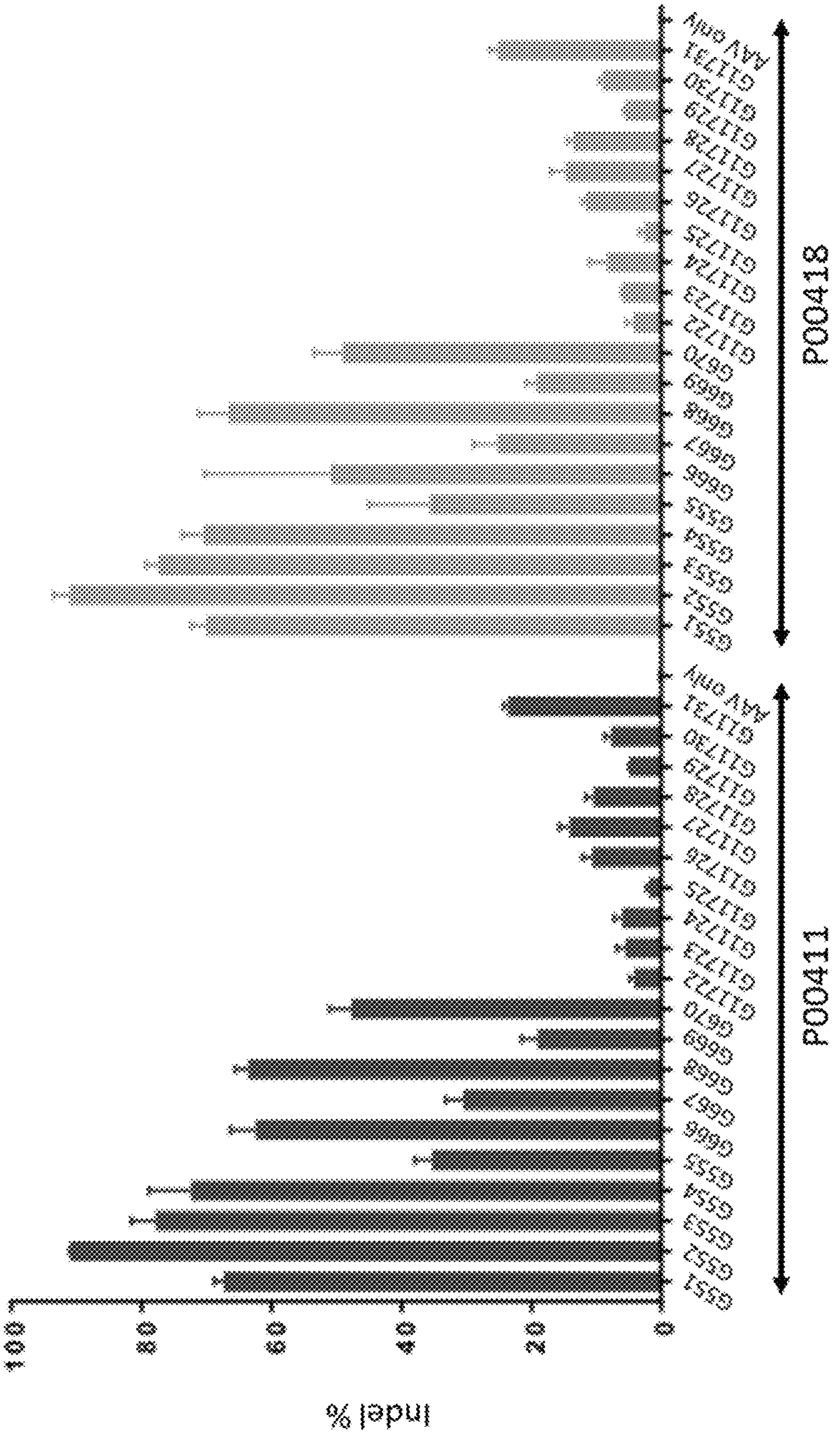
Figure 5C:
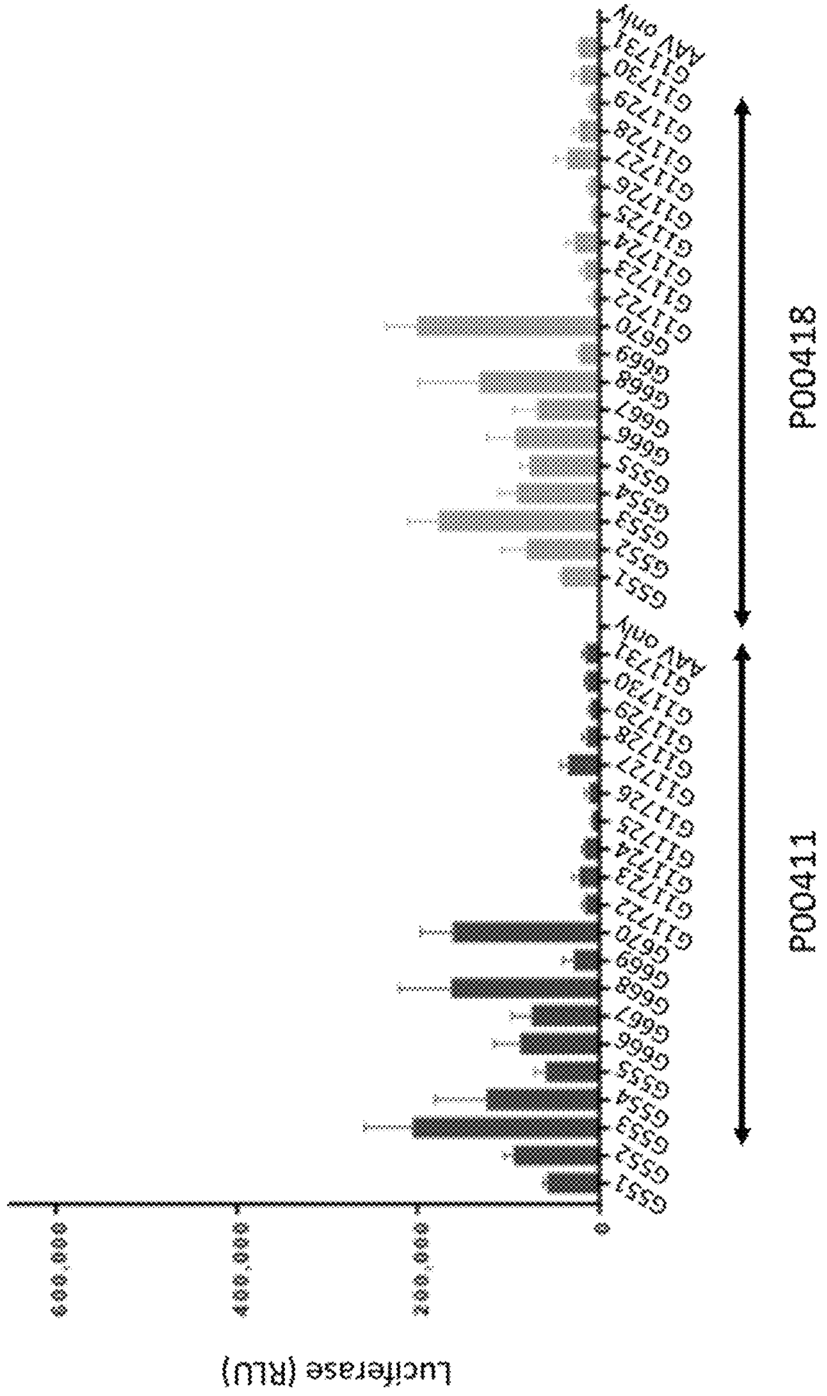
Figure 5D:
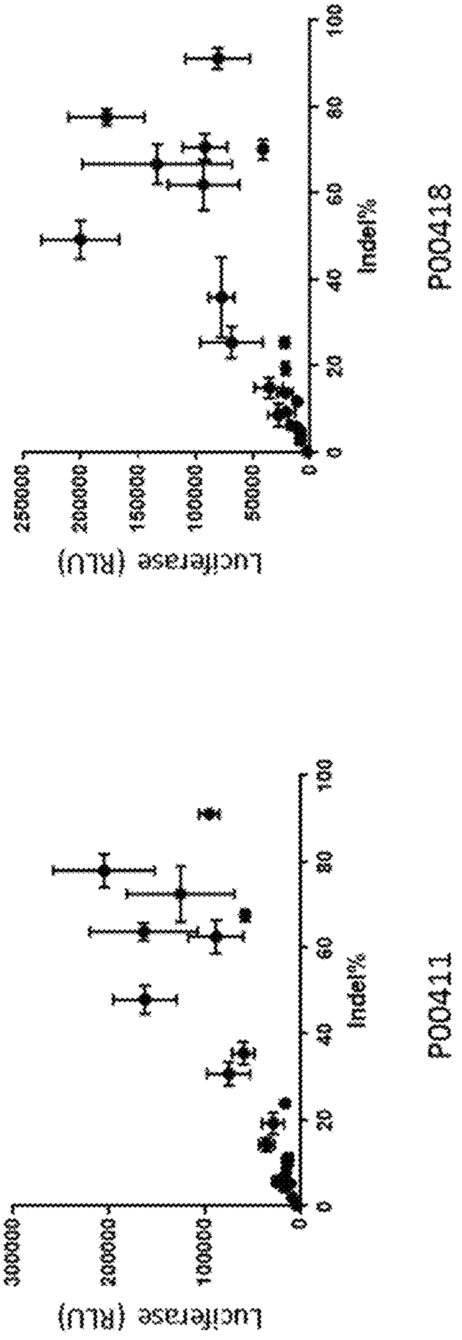

As shown in FIG. 5B and Table 16, consistent but varied levels of editing were detected for each of the treatment groups across each combination tested. Tansgene expression using various combinations of template and guide RNA is shown in FIG. 5C and Table 17. As shown in FIG. 5D, a significant level of indel formation did not necessarily result in more efficient expression of the transgenes. Using P00411- and P00418-derived templates, the $R^2$ values were 0.54 and 0.37, respectively, when guides with less than 10% editing are not included. The mouse albumin splice acceptor and human FIX splice acceptor each resulted in effective transgene expression.

TABLE 16

| % Indel | | | | | | |
|---|---|---|---|---|---|---|
| | P00411 | | P00418 | | P00415 | |
| Guide ID | Average Indel (%) | St. Dev Indel (%) | Average Indel (%) | St. Dev Indel (%) | Average Indel (%) | St. Dev Indel (%) |
| G000551 | 67.4 | 1.42 | 70.67 | 2.29 | 66.73 | 4.90 |
| G000552 | 90.93 | 0.15 | 91.10 | 2.43 | 90.37 | 1.01 |
| G000553 | 77.80 | 3.83 | 77.47 | 1.87 | 80.50 | 0.85 |
| G000554 | 72.37 | 6.49 | 70.53 | 3.16 | 70.60 | 2.91 |
| G000555 | 35.37 | 2.63 | 35.77 | 9.34 | 40.47 | 4.75 |
| G000666 | 62.47 | 3.87 | 50.90 | 19.41 | 65.90 | 3.99 |
| G000667 | 30.57 | 2.73 | 25.30 | 3.67 | 31.67 | 2.29 |
| G000668 | 63.60 | 2.02 | 66.65 | 4.60 | 68.30 | 4.90 |
| G000669 | 19.10 | 2.51 | 19.33 | 1.53 | 18.70 | 1.25 |
| G000670 | 47.80 | 3.27 | 49.10 | 4.42 | 51.97 | 2.06 |
| G011722 | 4.20 | 0.72 | 4.27 | 1.20 | 4.20 | 0.26 |
| G011723 | 5.63 | 1.27 | 6.07 | 0.15 | 5.93 | 0.15 |
| G011724 | 6.10 | 1.28 | 8.50 | 2.69 | 7.13 | 1.27 |

TABLE 16-continued

| % Indel | | | | | | |
|---|---|---|---|---|---|---|
| | P00411 | | P00418 | | P00415 | |
| Guide ID | Average Indel (%) | St. Dev Indel (%) | Average Indel (%) | St. Dev Indel (%) | Average Indel (%) | St. Dev Indel (%) |
| G011725 | 1.93 | 0.29 | 2.60 | 0.79 | 2.53 | 0.65 |
| G011726 | 10.73 | 1.46 | 11.70 | 0.50 | 12.43 | 1.33 |
| G011727 | 14.20 | 1.56 | 14.80 | 2.36 | 16.20 | 2.69 |
| G011728 | 10.55 | 1.20 | 13.65 | 0.92 | 15.50 | 1.56 |
| G011729 | 5.00 | 0.10 | 5.63 | 0.25 | 6.00 | 1.01 |
| G011730 | 7.83 | 0.97 | 9.13 | 0.59 | 7.33 | 0.59 |
| G011731 | 23.70 | 0.66 | 25.27 | 1.21 | 24.87 | 1.01 |
| AAV Only | 0.15 | 0.07 | 0.05 | 0.07 | 0.10 | 0.00 |

TABLE 17

| Luciferase Levels | | | | | | |
|---|---|---|---|---|---|---|
| | P00411 | | P00418 | | P00415 | |
| Guide ID | Average Luciferase (RLU) | St. Dev Luciferase (RLU) | Average Luciferase (RLU) | St. Dev Luciferase (RLU) | Average Luciferase (RLU) | St. Dev Luciferase (RLU) |
| G000551 | 58000.00 | 4331.28 | 41800.00 | 2165.64 | 78633.33 | 20274.70 |
| G000552 | 95700.00 | 10573.08 | 80866.67 | 27911.35 | 205333.33 | 30664.86 |
| G000553 | 205333.33 | 52993.71 | 177333.33 | 32929.22 | 471666.67 | 134001.00 |
| G000554 | 125333.33 | 55949.38 | 91933.33 | 19194.10 | 232666.67 | 67002.49 |
| G000555 | 59933.33 | 11566.04 | 77733.33 | 11061.80 | 155666.67 | 15947.83 |
| G000666 | 88500.00 | 28735.87 | 93266.67 | 30861.19 | 313000.00 | 15394.80 |
| G000667 | 75333.33 | 22653.11 | 68966.67 | 27222.11 | 153000.00 | 30805.84 |
| G000668 | 164000.00 | 56320.51 | 133400.00 | 65111.29 | 429000.00 | 120751.80 |
| G000669 | 28933.33 | 11636.29 | 22033.33 | 2413.16 | 46466.67 | 6543.19 |
| G000670 | 162666.67 | 32959.57 | 200000.00 | 33867.39 | 424666.67 | 36473.73 |
| G011722 | 16766.67 | 3384.28 | 8583.33 | 4103.10 | 24000.00 | 8915.16 |
| G011723 | 22733.33 | 7252.82 | 17133.33 | 4905.44 | 26100.00 | 8109.87 |
| G011724 | 17300.00 | 2400.00 | 28033.33 | 9091.94 | 30933.33 | 3365.02 |
| G011725 | 8253.33 | 1163.20 | 8890.00 | 1429.27 | 20366.67 | 13955.05 |
| G011726 | 12223.33 | 3742.54 | 11610.00 | 2490.44 | 14950.00 | 8176.03 |
| G011727 | 35600.00 | 8128.35 | 36300.00 | 12301.22 | 86700.00 | 5023.94 |
| G011728 | 14900.00 | 5011.99 | 22466.67 | 7130.45 | 38166.67 | 13829.08 |
| G011729 | 10460.00 | 2543.95 | 11223.33 | 2220.28 | 26966.67 | 16085.50 |
| G011730 | 14833.33 | 2307.24 | 21700.00 | 8681.59 | 41233.33 | 25687.03 |
| G011731 | 16433.33 | 3274.65 | 22566.67 | 2205.30 | 20756.67 | 13096.20 |
| AAV Only | 217.00 | 15.56 | 215.00 | 15.56 | 207.00 | 1.41 |

Example 6— In Vivo Screening of Bidirectional Constructs Across Target Sites

The ssAAV and LNPs tested in this Example were prepared and delivered to C57Bl/6 mice as described in Example 1 to assess the performance of the bidirectional constructs across target sites in vivo. Four weeks post dose, the animals were euthanized and liver tissue and sera were collected for editing and hFIX expression, respectively.

Figure 6:
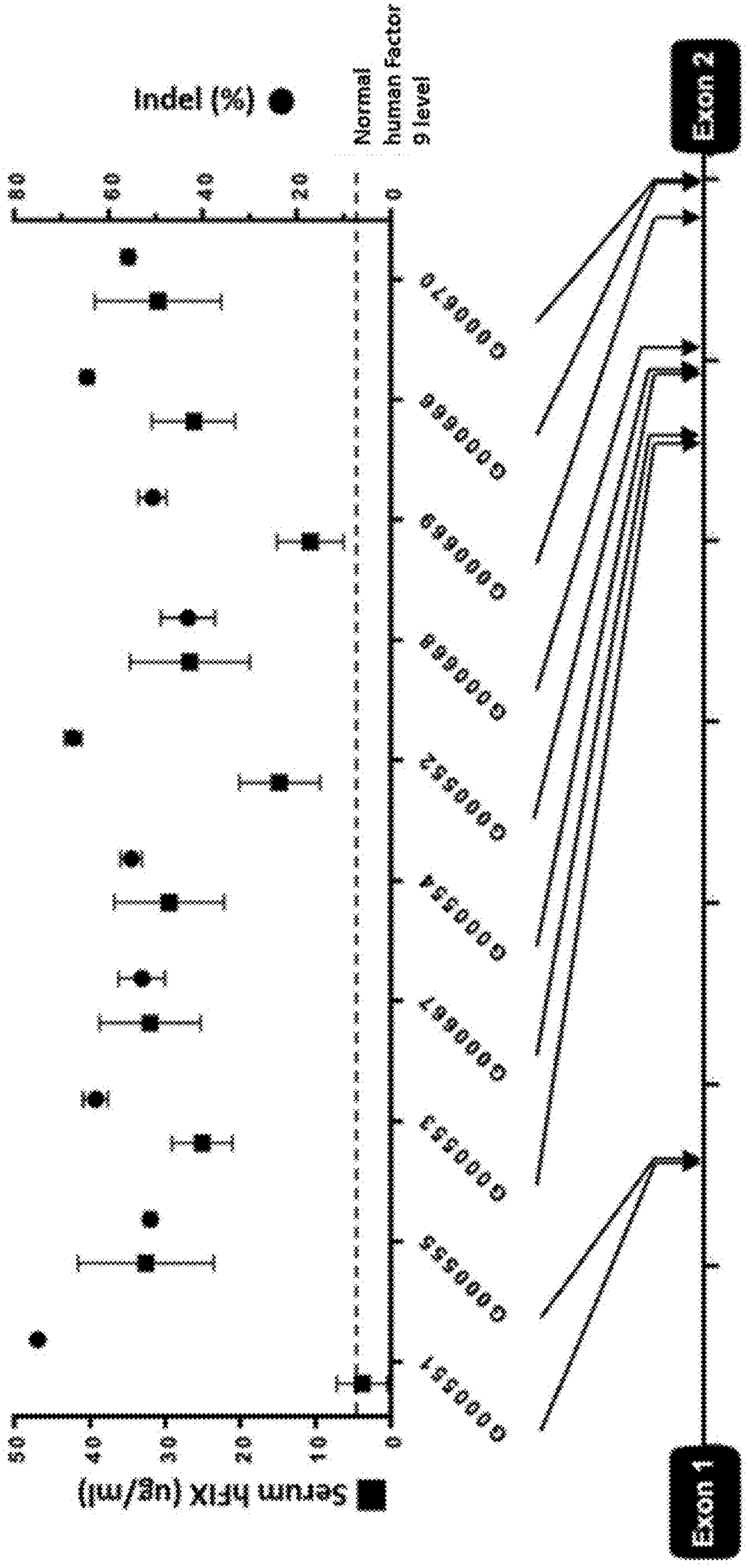
FIG. 6 shows results from in vivo screening of targeted insertion with bidirectional constructs across 10 target sites using with ssAAV derived from P00147. As shown, significant levels of indel formation do not necessarily result in high levels of transgene expression.

In an initial experiment, 10 different LNP formulations containing 10 different gRNA targeting intron 1 of albumin were delivered to mice along with ssAAV derived from P00147. The AAV and LNP were delivered at 3e11 vg/ms and 4 mg/kg (with respect to total RNA cargo content), respectively (n=5 for each group). The gRNAs tested in this experiment are shown in FIG. 6 and tabulated in Table 18. As shown in FIG. 6 and as observed in vitro, a significant level of indel formation was not predictive for insertion or expression of the transgenes.

In a separate experiment, a panel of 20 gRNAs targeting the 20 different target sites tested in vitro in Example 5 were tested in vivo. To this end, LNP formulations containing the 20 gRNAs targeting intron 1 of albumin were delivered to mice along with ssAAV derived from P00147. The AAV and LNP were delivered at 3e11 vg/ms and 1 mg/kg (with respect to total RNA cargo content), respectively. The gRNAs tested in this experiment are shown in FIGS. 7A and 7B.

Figure 7A:
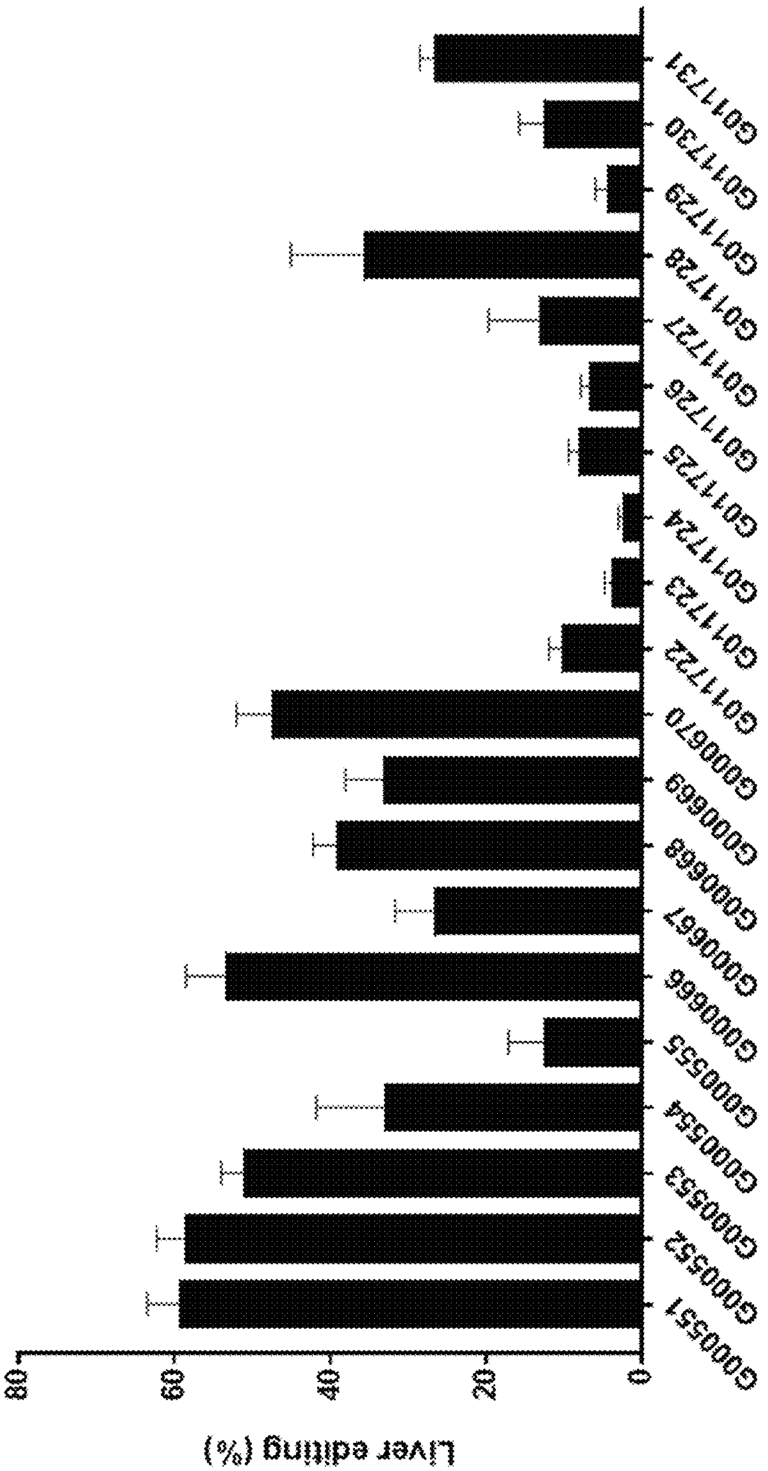
FIGS. 7A-7D show results from in vivo screening of bidirectional constructs across 20 target sites using ssAAV derived from P00147.
Figure 7B:
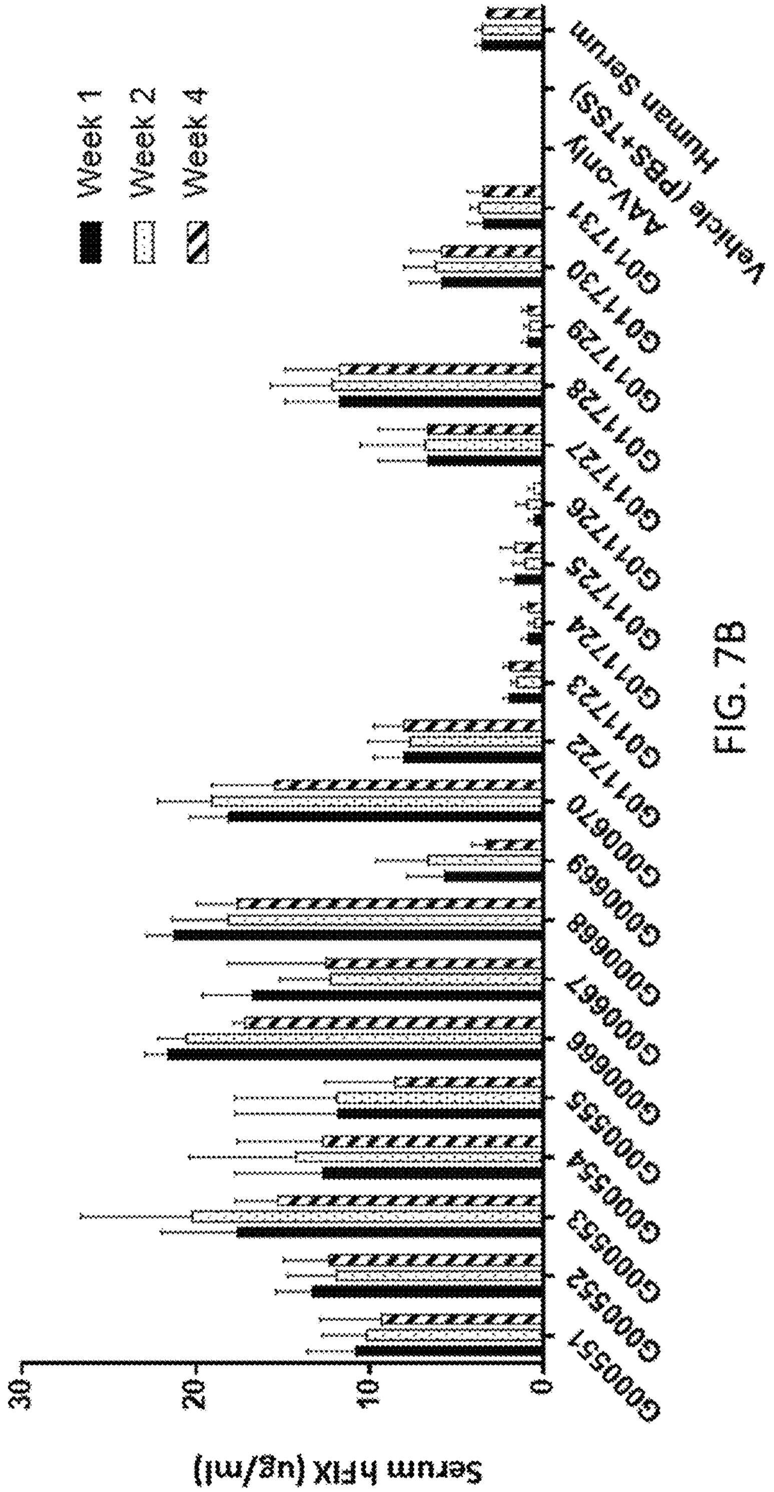
Figure 7D:
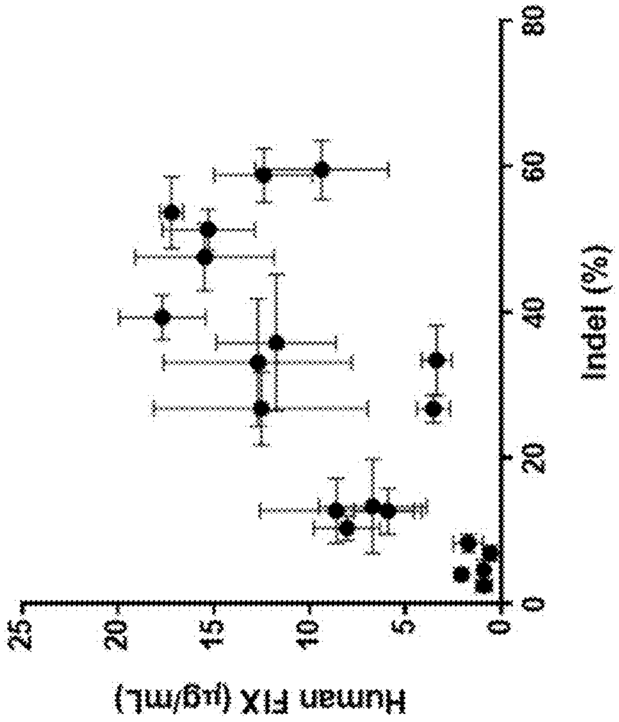
Figure 7C:
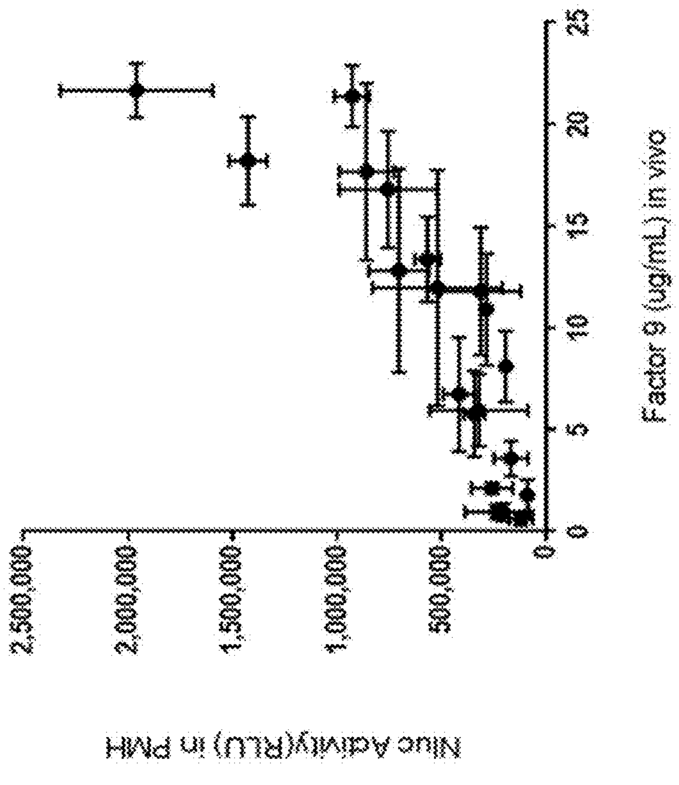

As shown, in FIG. 7A and tabulated in Table 19, varied levels of editing were detected for each of the treatment groups across each LNP/vector combination tested. However, as shown in FIG. 7B and Table 20 and consistent with the in vitro data described in Example 5, higher levels of editing did not necessarily result in higher levels of expression of the transgenes in vivo, indicating a lack of correlation between editing and insertion/expression of the bidirectional hFIX constructs. Indeed, very little correlation exists between the amount of editing achieved and the amount of hFIX expression as viewed in the plot provided in FIG. 7D. In particular, an $R^2$ value of only 0.34 is calculated between the editing and expression data sets for this experiment, when those gRNAs achieving less than 10% editing are removed from the analysis. Interestingly, as shown in FIG. 7C, a correlation plot is provided comparing the levels of expression as measured in RLU from the in vitro experiment of Example 5 to the transgene expression levels in vivo detected in this experiment, with an $R^2$ value of 0.70, demonstrating a positive correlation between the primary cell screening and the in vivo treatments.

Figure 8A:
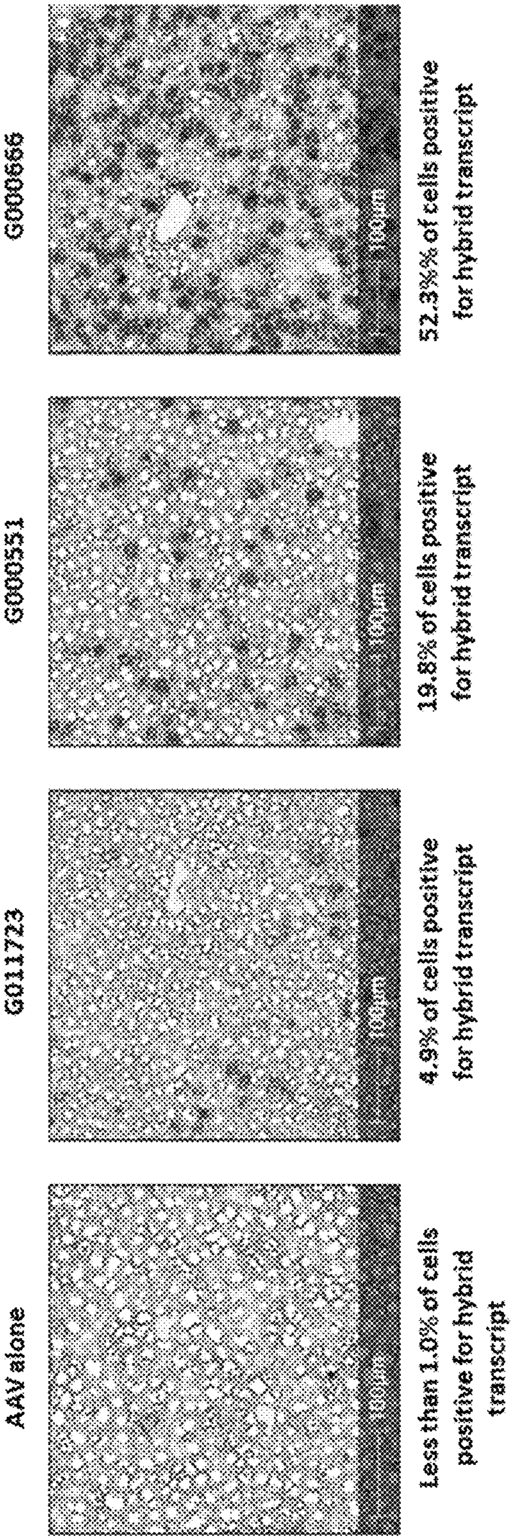
FIGS. 8A and 8B show insertion of the bidirectional construct at the cellular level using in situ hybridization method using probes that can detect the junctions between the hFIX transgene and the mouse albumin exon 1 sequence (FIG. 8A). Circulating hFIX levels correlated with the number of cells that were positive for the hybrid transcript (FIG. 8B).
Figure 8B:
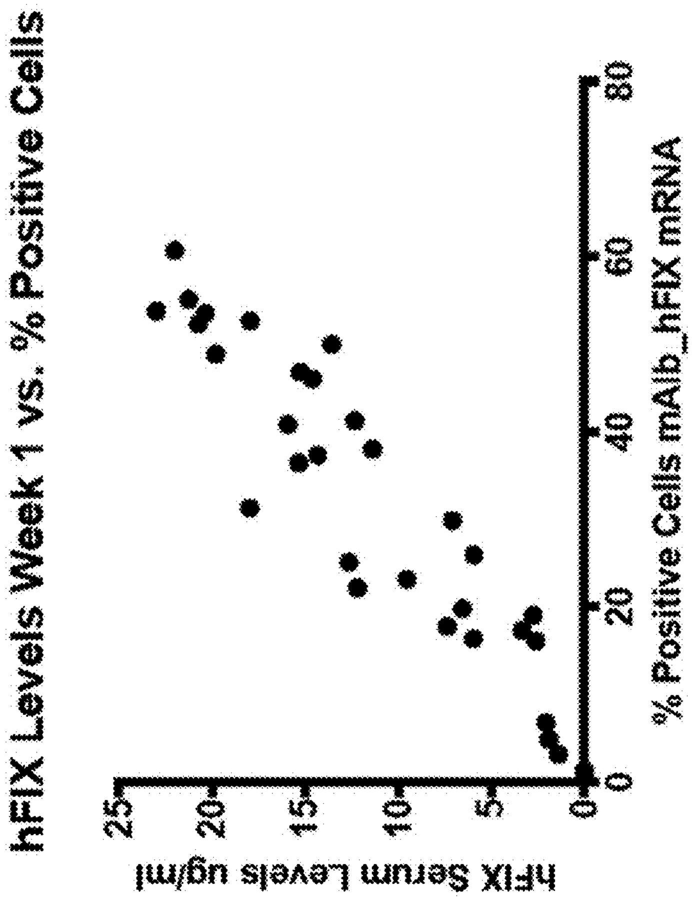

To assess insertion of the bidirectional construct at the cellular level, liver tissues from treated animals were assayed using an in situ hybridization method (BaseScope), e.g., as described in Example 1. This assay utilized probes that can detect the junctions between the hFIX transgene and the mouse albumin exon 1 sequence, as a hybrid transcript. As shown in FIG. 8A, cells positive for the hybrid transcript were detected in animals that received both AAV and LNP. Specifically, when AAV alone is administered, less than 1.0% of cells were positive for the hybrid transcript. With administration of LNPs comprising G011723, G000551, or G000666, 4.9%, 19.8%, or 52.3% of cells were positive for the hybrid transcript. Additionally, as shown in FIG. 8B, circulating hFIX levels correlated with the number of cells that were positive for the hybrid transcript. Lastly, the assay utilized pooled probes that can detect insertion of the bidirectional hFIX construct in either orientation. However, when a single probe was used that only detects a single orientation, the amount of cells that were positive for the hybrid transcript was about half that detected using the pooled probes (in one example, 4.46% vs 9.68%), suggesting that the bidirectional construct indeed is capable of inserting in either orientation giving rise to expressed hybrid transcripts that correlate with the amount of transgene expression at the protein level. These data show that the circulating hFIX levels achieved are dependent on the guide used for insertion.

TABLE 18 hFIX Serum Levels and % Indel

| Guide | Average Indel (%) | St. Dev Indel (%) | Average hFIX Serum Levels | St. Dev hFIX Serum Levels |
|---|---|---|---|---|
| G000551 | 75.02 | 1.27 | 3.82 | 3.38 |
| G000555 | 51.18 | 1.19 | 32.56 | 9.05 |
| G000553 | 62.78 | 2.64 | 25.07 | 4.04 |
| G000667 | 52.96 | 4.96 | 32.03 | 6.74 |
| G000554 | 55.24 | 2.28 | 29.48 | 7.34 |
| G000552 | 67.56 | 1.73 | 14.79 | 5.34 |
| G000668 | 43.14 | 5.78 | 26.72 | 7.97 |
| G000669 | 50.68 | 2.97 | 10.70 | 4.43 |
| G000666 | 64.62 | 1.34 | 26.19 | 5.56 |
| G000670 | 55.90 | 1.30 | 30.96 | 8.44 |

TABLE 19

% Liver Editing

| Guide | Average Liver Editing (%) | St. Dev Liver Editing (%) |
|---|---|---|
| G000551 | 59.48 | 4.02 |
| G000555 | 58.72 | 3.65 |
| G000553 | 51.26 | 2.81 |
| G000554 | 33.04 | 8.76 |
| G000555 | 12.72 | 4.46 |
| G000666 | 53.60 | 4.92 |
| G000667 | 26.74 | 4.98 |
| G000668 | 39.22 | 3.04 |
| G000669 | 33.34 | 4.77 |
| G000670 | 47.50 | 5.58 |
| G011722 | 10.34 | 1.68 |
| G011723 | 4.02 | 0.84 |
| G011724 | 2.46 | 0.64 |
| G011725 | 8.26 | 1.24 |
| G011726 | 6.90 | 1.01 |
| G011727 | 13.33 | 6.43 |
| G011728 | 35.78 | 9.34 |
| G011729 | 4.62 | 1.46 |
| G011730 | 12.68 | 3.14 |
| G011731 | 26.70 | 1.86 |

TABLE 20

Serum hFIX Levels

| | Week 1 | | Week 2 | | Week 4 | |
|---|---|---|---|---|---|---|
| Guide | Average FIX (ug/mL) | St.Dev FIX (ug/mL) | Average FIX (ug/mL) | St.Dev FIX (ug/mL) | Average FIX (ug/mL) | St.Dev FIX (ug/mL) |
| G000551 | 10.88 | 2.74 | 10.25 | 2.51 | 9.39 | 3.48 |
| G000555 | 13.34 | 2.09 | 12.00 | 2.75 | 12.43 | 2.57 |
| G000553 | 17.64 | 4.34 | 20.27 | 6.35 | 15.31 | 2.43 |
| G000554 | 12.79 | 4.99 | 14.29 | 6.09 | 12.74 | 4.93 |
| G000555 | 11.94 | 5.79 | 11.99 | 5.76 | 8.61 | 4.02 |
| G000666 | 21.63 | 1.32 | 20.65 | 1.55 | 17.23 | 0.62 |
| G000667 | 16.77 | 2.86 | 12.35 | 2.85 | 12.57 | 5.60 |
| G000668 | 21.35 | 1.51 | 18.20 | 3.18 | 17.72 | 2.25 |
| G000669 | 5.76 | 2.10 | 6.72 | 2.93 | 3.39 | 0.78 |

TABLE 20-continued

| Serum hFIX Levels | | | | | | |
|---|---|---|---|---|---|---|
| | Week 1 | | Week 2 | | Week 4 | |
| Guide | Average FIX (ug/mL) | St.Dev FIX (ug/mL) | Average FIX (ug/mL) | St.Dev FIX (ug/mL) | Average FIX (ug/mL) | St.Dev FIX (ug/mL) |
| G000670 | 18.18 | 2.17 | 19.16 | 3.05 | 15.49 | 3.61 |
| G011722 | 8.07 | 1.74 | 7.74 | 2.41 | 8.07 | 1.74 |
| G011723 | 2.11 | 0.28 | 1.65 | 0.28 | 2.11 | 0.28 |
| G011724 | 0.92 | 0.43 | 0.60 | 0.30 | 0.92 | 0.43 |
| G011725 | 1.75 | 0.77 | 1.14 | 0.67 | 1.75 | 0.77 |
| G011726 | 0.59 | 0.30 | 1.01 | 0.64 | 0.59 | 0.30 |
| G011727 | 6.71 | 2.80 | 6.90 | 3.68 | 6.71 | 2.80 |
| G011728 | 11.77 | 3.12 | 12.29 | 3.43 | 11.77 | 3.12 |
| G011729 | 0.94 | 0.35 | 0.89 | 0.29 | 0.94 | 0.35 |
| G011730 | 5.93 | 1.77 | 6.33 | 1.73 | 5.93 | 1.77 |
| G011731 | 3.56 | 0.87 | 3.78 | 0.50 | 3.56 | 0.87 |
| AAV Only | 0.00 | 0.00 | 0.00 | 0.00 | 0.00 | 0.00 |
| Vehicle | 0.00 | 0.00 | 0.00 | 0.00 | 0.00 | 0.00 |
| Human Serum | 3.63 | 0.32 | 3.61 | 0.35 | 3.28 | 0.03 |

Example 7—Timing of AAV and LNP Delivery In Vivo

In this Example, the timing between delivery of ssAAV comprising the bidirectional hFIX construct and LNP was examined in C57BV6 mice.

The ssAAV and LNPs tested in this Example were prepared and delivered to mice as described in Example 1. The LNP formulation contained G000551 and the bidirectional template was delivered as ssAAV derived from P00147. The AAV and LNP were delivered at 3e11 vg/ms and 4 mg/kg (with respect to total RNA cargo content), respectively (n=5 for each group). A "Template only" cohort received AAV only, and a "PBS" cohort received no AAV or LNP. One cohort received AAV and LNP sequentially (minutes apart) at day 0 ("Template+LNP day 0"); another cohort received AAV at day 0 and LNP at day 1 ("Template+LNP day 1"); and a final cohort received AAV at day 0 and LNP at day 7("Template+LNP day 7"). At 1 week, 2 weeks and 6 weeks, plasma was collected for hFIX expression analysis.

Figure 9:
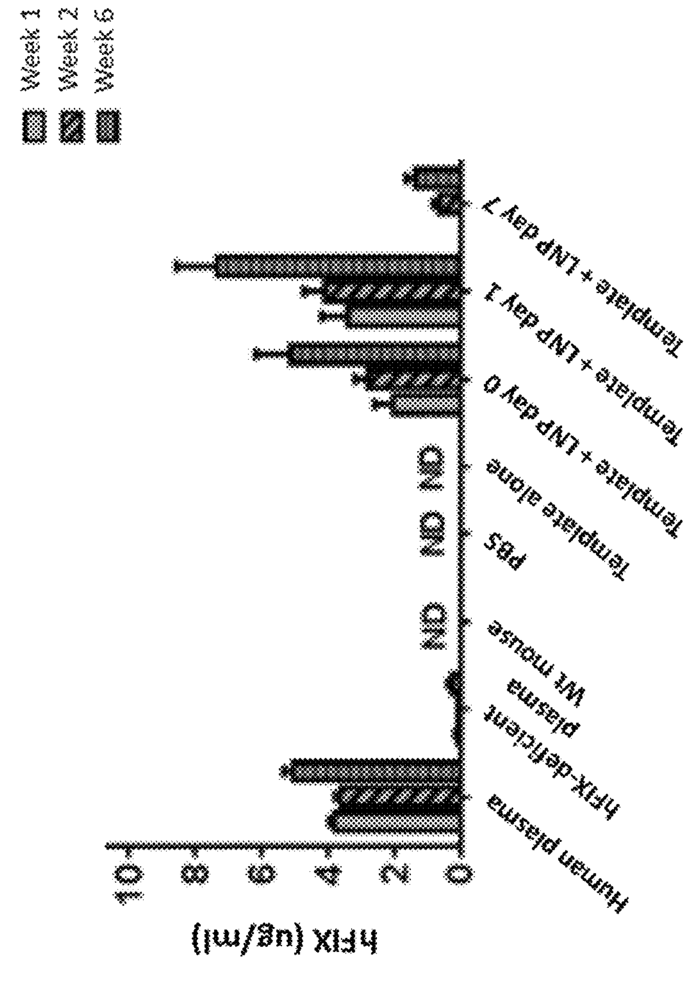
FIG. 9 shows the effect on targeted insertion of varying the timing between delivery of the ssAAV comprising the bidirectional hFIX construct and LNP.

As shown in FIG. 9, hFIX was detected in each cohort at each time assayed, except for the 1 week timepoint for the cohort that received the LNP at day 7 post AAV delivery.

Example 8—Multiple Dosing of LNP Following Delivery of AAV

In this Example, the effects of repeat dosing of LNP following administration of ssAAV was examined.

The ssAAV and LNPs tested in this Example were prepared and delivered to C57Bl/6 mice as described in Example 1. The LNP formulation contained G000551 and the ssAAV was derived from P00147. The AAV and LNP were delivered at 3e11 vg/ms and 0.5 mg/kg (with respect to total RNA cargo content), respectively (n=5 for each group). A "Template only" cohort received AAV only, and a "PBS" cohort received no AAV or LNP. One cohort received AAV and LNP sequentially (minutes apart) at day 0 with no further treatments ("Template+LNP(1x)" in FIG. 10); another cohort received AAV and LNP sequentially (minutes apart) at day 0 and a second dose at day 7 ("Template+LNP (2x)" in FIG. 10); and a final cohort received AAV and LNP sequentially (minutes apart) at day 0, a second dose of LNP at day 7 and a third dose of LNP at day 14 ("Template+ LNP(3x)" in FIG. 10). At 1, 2, 4 and 6 weeks post-administration of AAV, plasma was collected for hFIX expression analysis.

Figure 10:
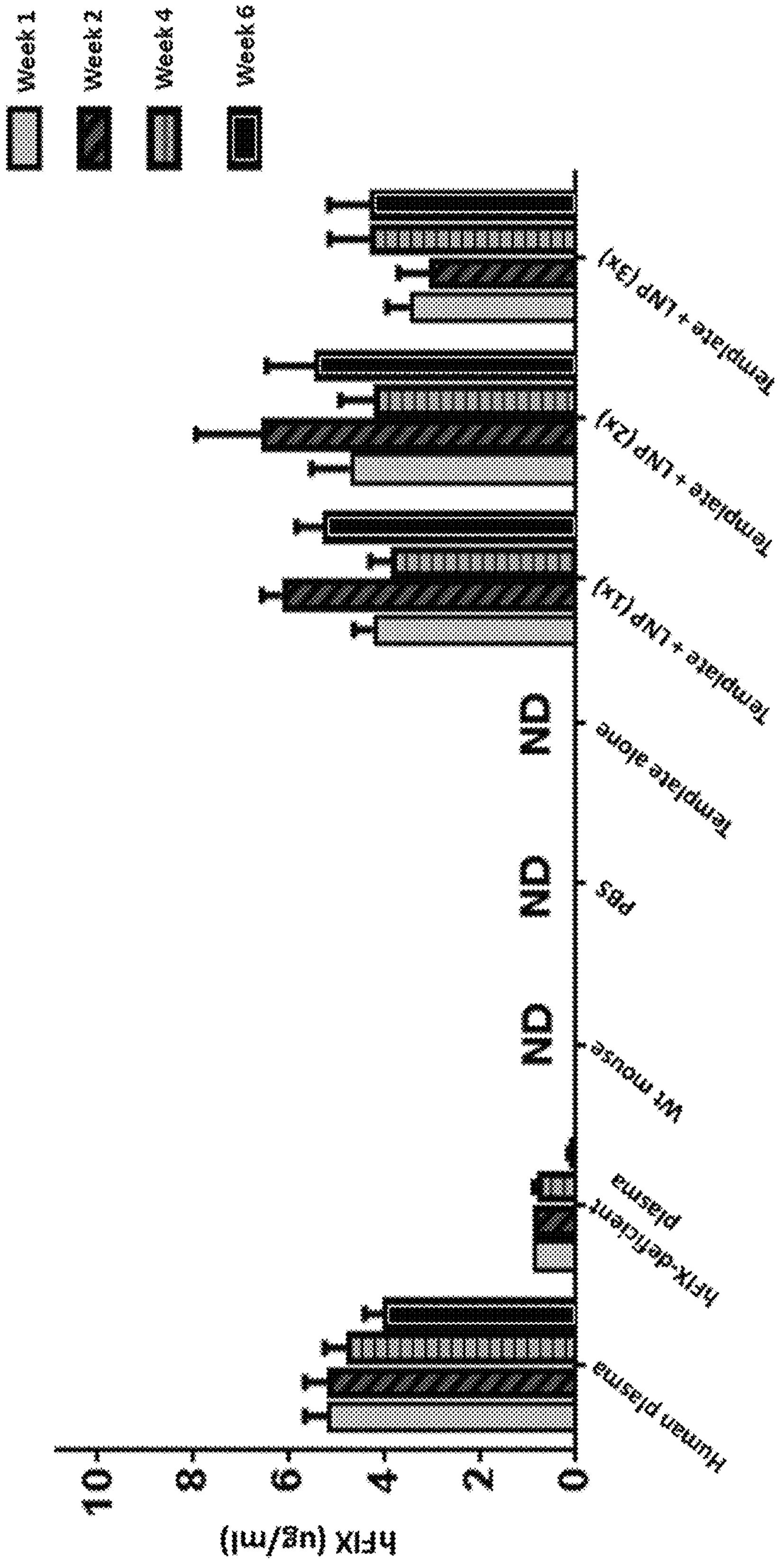
FIG. 10 shows the effect on targeted insertion of varying the number of LNP doses (e.g., 1, 2, or 3) following delivery of the bidirectional hFIX construct.

As shown in FIG. 10, hFIX was detected in each cohort at each time assayed, and multiple subsequent doses of LNP did not significantly increase the amount of hFIX expression.

Example 9—Durability of hFIX Expression In Vivo

The durability of hFIX expression over time in treated animals was assessed in this Example. To this end, hFIX was measured in the serum of treated animals post-dose, as part of a one-year durability study.

The ssAAV and LNPs tested in this Example were prepared and delivered to C57Bl/6 mice as described in Example 1. The LNP formulation contained G000551 and the ssAAV was derived from P00147. The AAV was delivered at 3e11 vg/ms and the LNP was delivered at either 0.25 or 1.0 mg/kg (with respect to total RNA cargo content) (n=5 for each group).

Figure 11A:
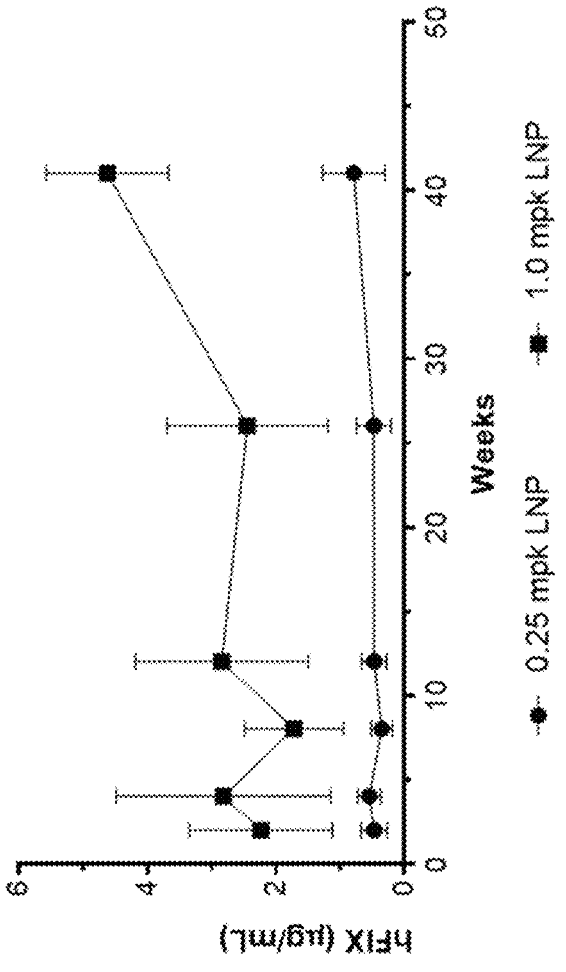
FIG. 11A shows the durability of hFIX expression in vivo.

As shown in FIG. 11A and Table 21, hFIX expression was sustained at each time point assessed for both groups out to 41 weeks. A drop in the levels observed at 8 weeks is believed to be due to the variability of the ELISA assay. Serum albumin levels were measured by ELISA at week 2 and week 41, showing that circulating albumin levels are maintained across the study.

Figure 11B:
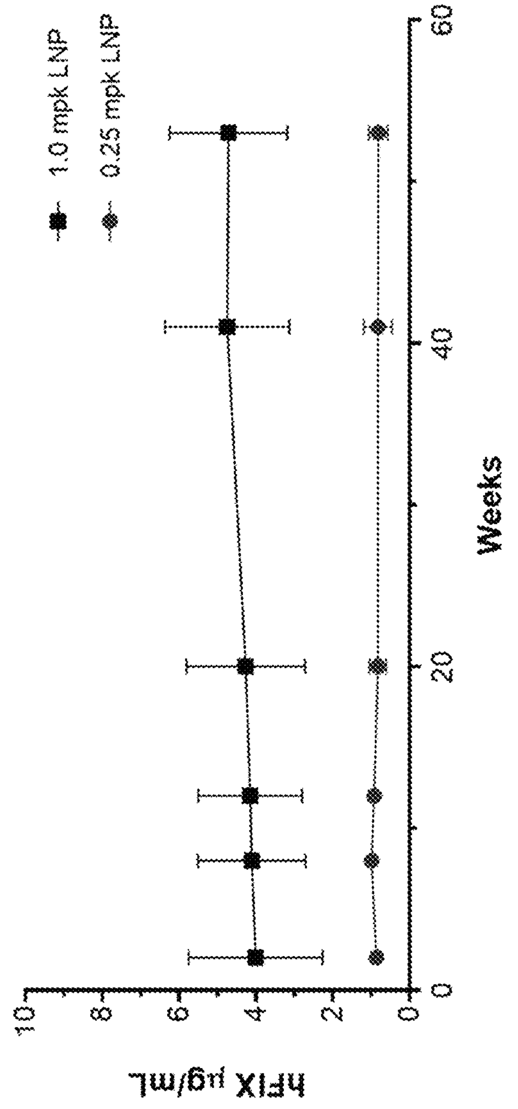
FIG. 11B demonstrates expression from intron 1 of albumin was sustained.

As shown in FIG. 11B and Table 22, hFIX expression was sustained at each time point assessed for both groups out to 52 weeks.

TABLE 21

| FIX Levels | | | | |
|---|---|---|---|---|
| | Dose | | | |
| | 0.25 mpk LNP | | 1 mpk LNP | |
| Week | Average hFIX (ug/mL) | StDev hFIX (ug/mL) | Average hFIX (ug/mL) | StDev hFIX (ug/mL) |
| 2 | 0.48 | 0.21 | 2.24 | 1.12 |
| 4 | 0.55 | 0.18 | 2.82 | 1.67 |
| 8 | 0.40 | 0.17 | 1.72 | 0.77 |
| 12 | 0.48 | 0.20 | 2.85 | 1.34 |
| 20 | 0.48 | 0.27 | 2.45 | 1.26 |
| 41 | 0.79 | 0.49 | 4.63 | 0.95 |

TABLE 22

| FIX Levels | | | | |
|---|---|---|---|---|
| | Dose | | | |
| | 0.25 mpk LNP | | 1 mpk LNP | |
| Week | Average hFIX (ug/mL) | StDev hFIX (ug/mL) | Average hFIX (ug/mL) | StDev hFIX (ug/mL) |
| 2 | 0.87 | 0.15 | 4.02 | 1.75 |
| 8 | 0.99 | 0.15 | 4.11 | 1.41 |
| 12 | 0.93 | 0.14 | 4.15 | 1.35 |
| 20 | 0.83 | 0.22 | 4.27 | 1.54 |
| 41 | 0.83 | 0.37 | 4.76 | 1.62 |
| 52 | 0.82 | 0.25 | 4.72 | 1.54 |

Example 10—Effects of Varied Doses of AAV and LNP to Modulate hFIX Expression In Vivo In this Example, the effects of varying the dose of both AAV and LNP to modulate expression of hFIX was assessed in C57Bl/6 mice.

The ssAAV and LNPs tested in this Example were prepared and delivered to mice as described in Example 1. The LNP formulation contained G000553 and the ssAAV was derived from P00147. The AAV was delivered at 0e, 3e11, 1e12 or 3e12 vg/ms and the LNP was delivered at 0.1, 0.3, or 1.0 mg/kg (with respect to total RNA cargo content) (n=5 for each group). Two weeks post-dose, the animals were euthanized. Sera were collected at two timepoints for hFIX expression analysis.

Figure 12A:
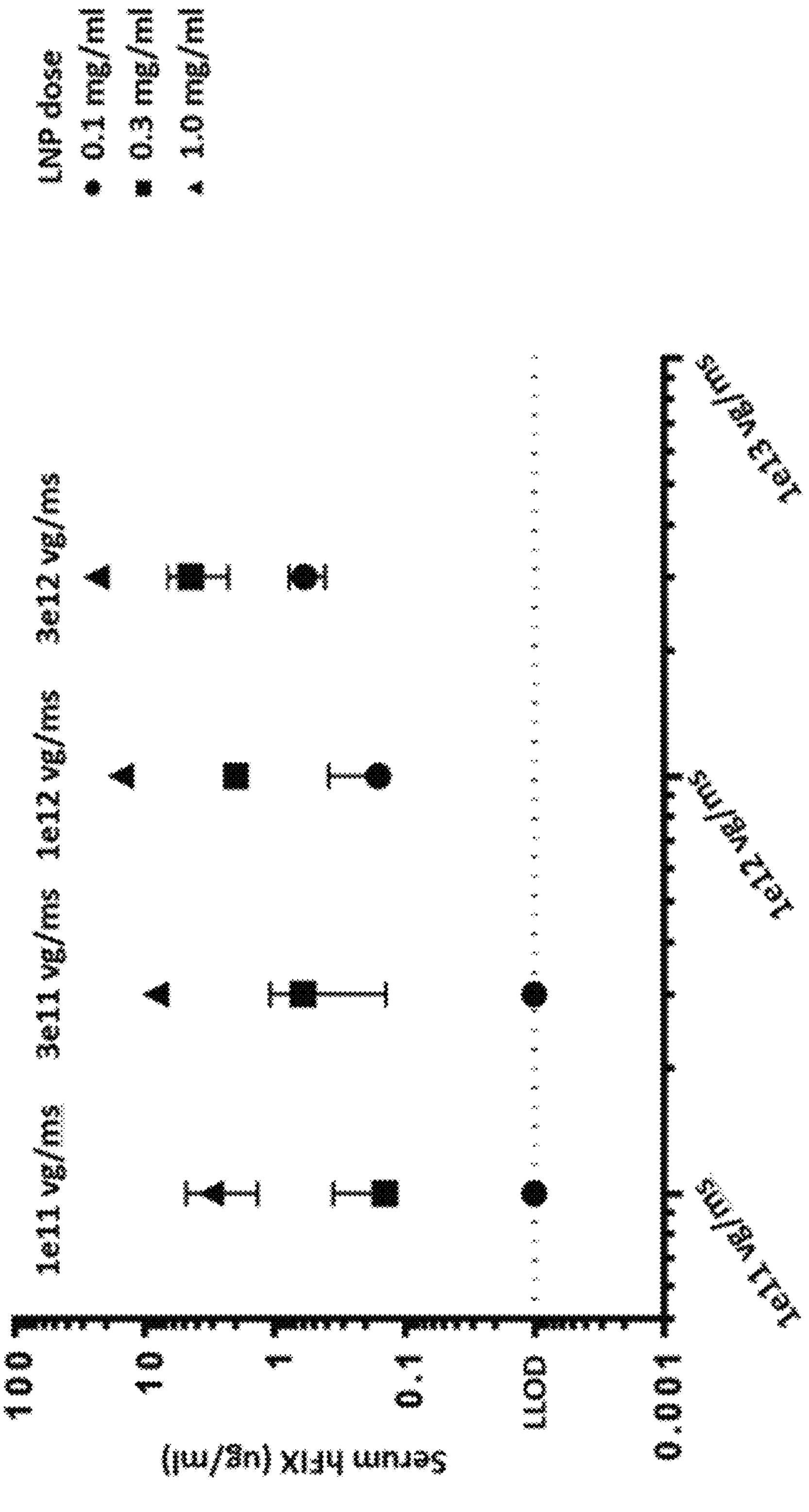
FIG. 12A and FIG. 12B show that varying AAV or LNP dose can modulate the amount of expression of hFIX from intron 1 of the albumin gene in vivo.
Figure 12B:
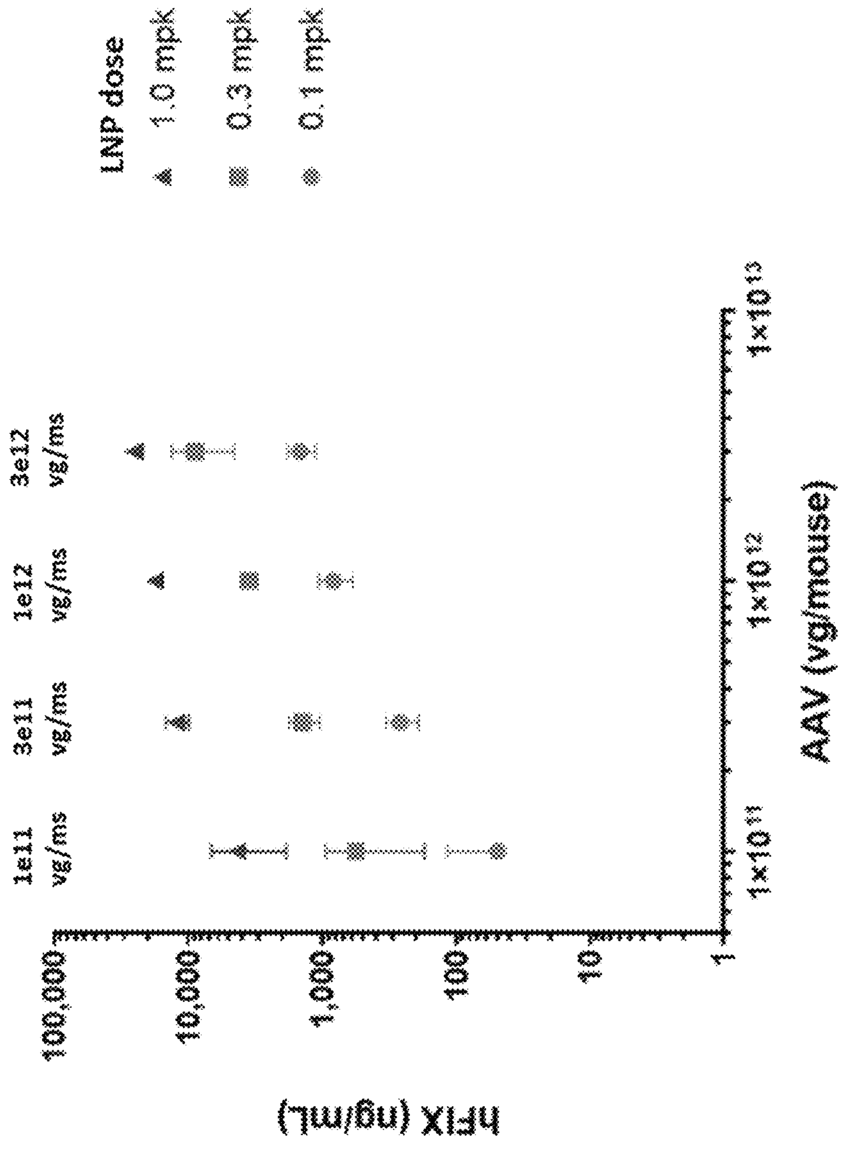

As shown in FIG. 12A (week), FIG. 2B (2 weeks) and Table 23, varying the dose of either AAV or LNP can modulate the amount of expression of hFIX in vivo.

TABLE 23

| Serum hFIX | | | | | |
|---|---|---|---|---|---|
| Timepoint | RNP Dose (mg/kg) | AAV Dose (MOI) | Mean FIX (ng/ml) | SD | N |
| Week 1 | 0.1 | 1E+11 | 0.08 | 0.02 | 2 |
| | | 3E+11 | 0.11 | 0.04 | 5 |
| | | 1E+12 | 0.41 | 0.15 | 5 |
| | | 3E+12 | 0.61 | 0.17 | 5 |
| | 0.3 | 1E+11 | 0.36 | 0.14 | 5 |
| | | 3E+11 | 0.67 | 0.26 | 5 |
| | | 1E+12 | 1.76 | 0.14 | 5 |
| | | 3E+12 | 4.70 | 2.40 | 5 |
| | 1.0 | 1E+11 | 3.71 | 0.31 | 4 |
| | | 3E+11 | 8.00 | 0.51 | 5 |
| | | 1E+12 | 14.17 | 1.38 | 5 |
| | | 3E+12 | 20.70 | 2.79 | 5 |
| | Human serum 1:1000 | | 6.62 | — | 1 |
| Week 2 | 0.1 | 1E+11 | 0.12 | 0.01 | 2 |
| | | 3E+11 | 0.26 | 0.07 | 5 |
| | | 1E+12 | 0.83 | 0.24 | 5 |
| | | 3E+12 | 1.48 | 0.35 | 5 |
| | 0.3 | 1E+11 | 0.70 | 0.26 | 4 |
| | | 3E+11 | 1.42 | 0.37 | 5 |
| | | 1E+12 | 3.53 | 0.49 | 5 |
| | | 3E+12 | 8.94 | 4.39 | 5 |
| | 1.0 | 1E+11 | 5.40 | 0.47 | 4 |
| | | 3E+11 | 12.31 | 2.45 | 5 |
| | | 1E+12 | 17.89 | 1.95 | 5 |
| | | 3E+12 | 25.52 | 3.62 | 5 |
| | Human serum 1:1000 | | 4.47 | — | 1 |

Example 11—In Vitro Screening of Bidirectional Constructs Across Target Sites in Primary Cynomolgus and Primary Human Hepatocytes In this Example, ssAAV vectors comprising a bidirectional construct were tested across a panel of target sites utilizing gRNAs targeting intron 1 of cynomolgus ("cyno") and human albumin in primary cyno (PCH) and primary human hepatocytes (PHH), respectively.

The ssAAV and lipid packet delivery materials tested in this Example were prepared and delivered to PCH and PHH as described in Example 1. Following treatment, isolated genomic DNA and cell media was collected for editing and transgene expression analysis, respectively. Each of the vectors comprised a reporter that can be measured through luciferase-based fluorescence detection as described in Example 1 (derived from plasmid P00415), plotted in FIGS. 13B and 14B as relative luciferase units ("RLU"). For example, the AAV vectors contained the NanoLuc ORF (in addition to GFP). Schematics of the vectors tested are provided in FIGS. 13B and 14B. The gRNAs tested are shown in each of the Figures using a shortened number for those listed in Table 1 and Table 7.

Figure 13A:
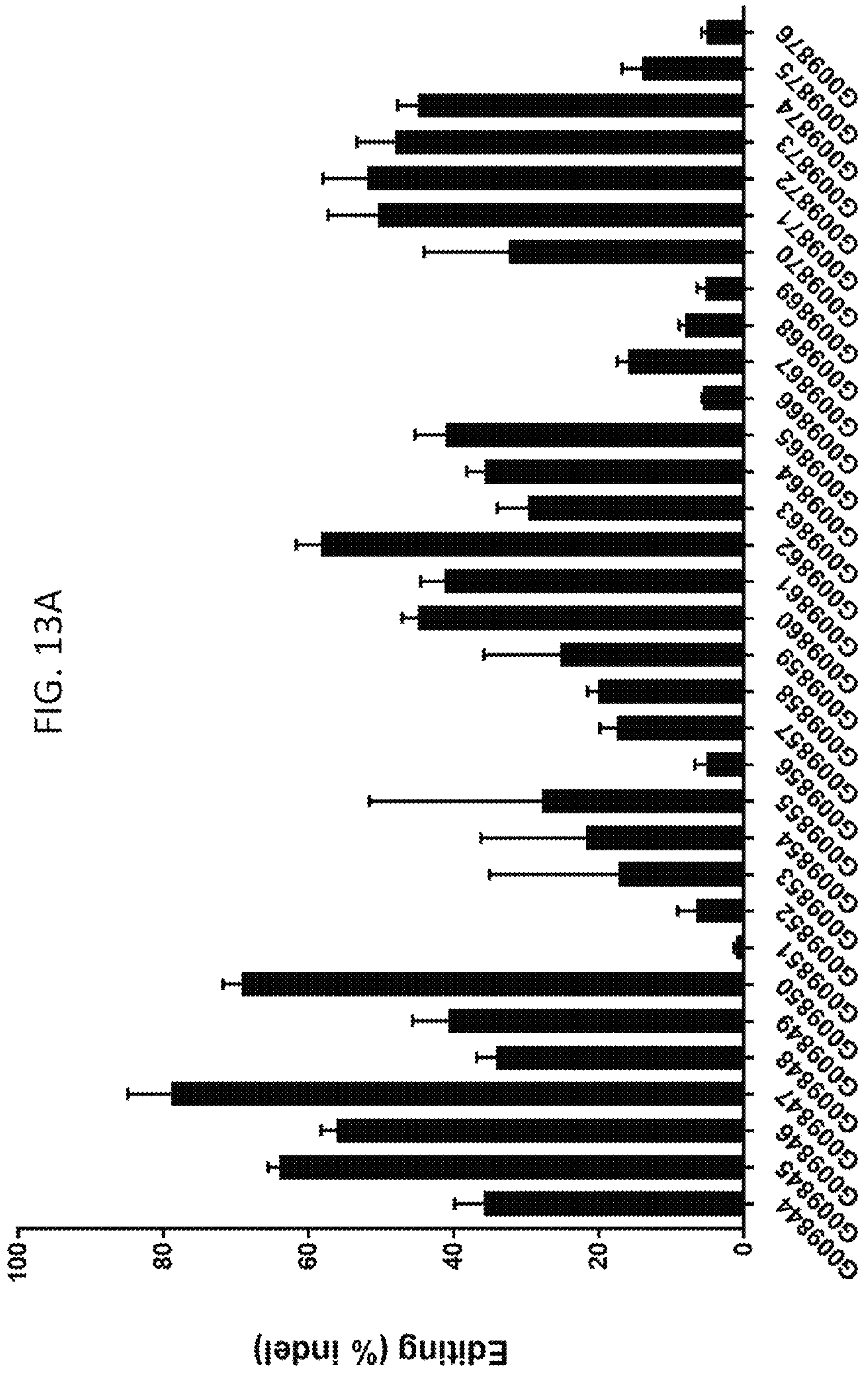
FIGS. 13A-13C show results from screening bidirectional constructs across target sites in primary cynomolgus hepatocytes.
Figure 13B:
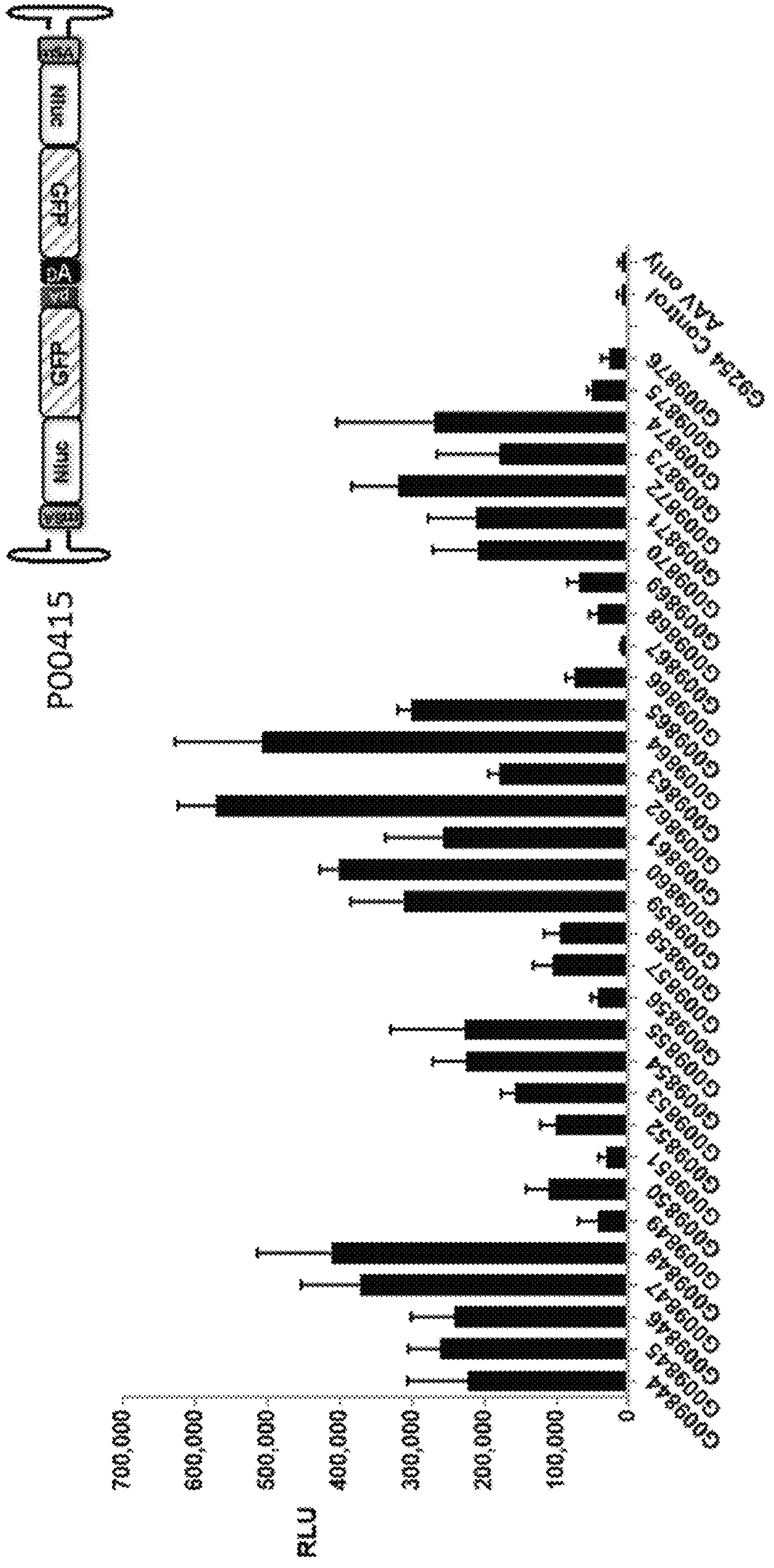
Figure 13C:
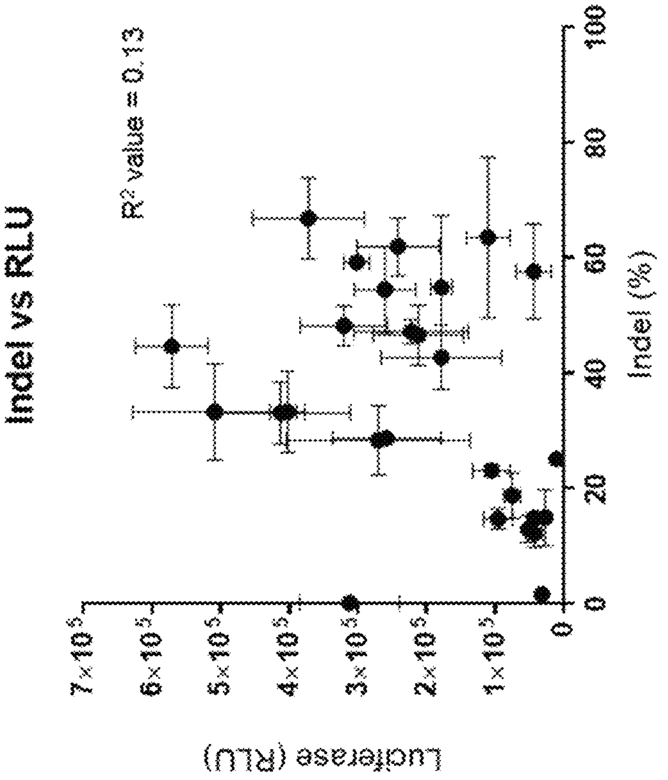
Figure 14A:
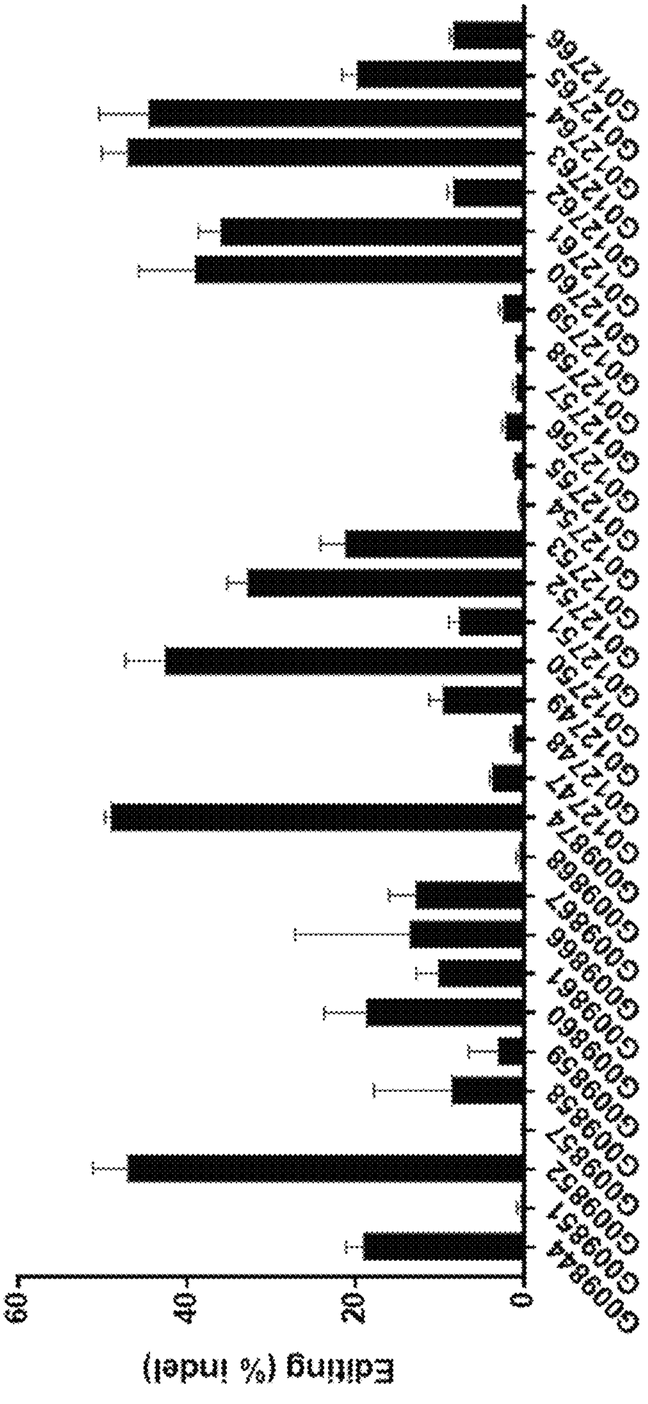
FIGS. 14A-14C show results from screening bidirectional constructs across target sites in primary human hepatocytes.
Figure 14B:
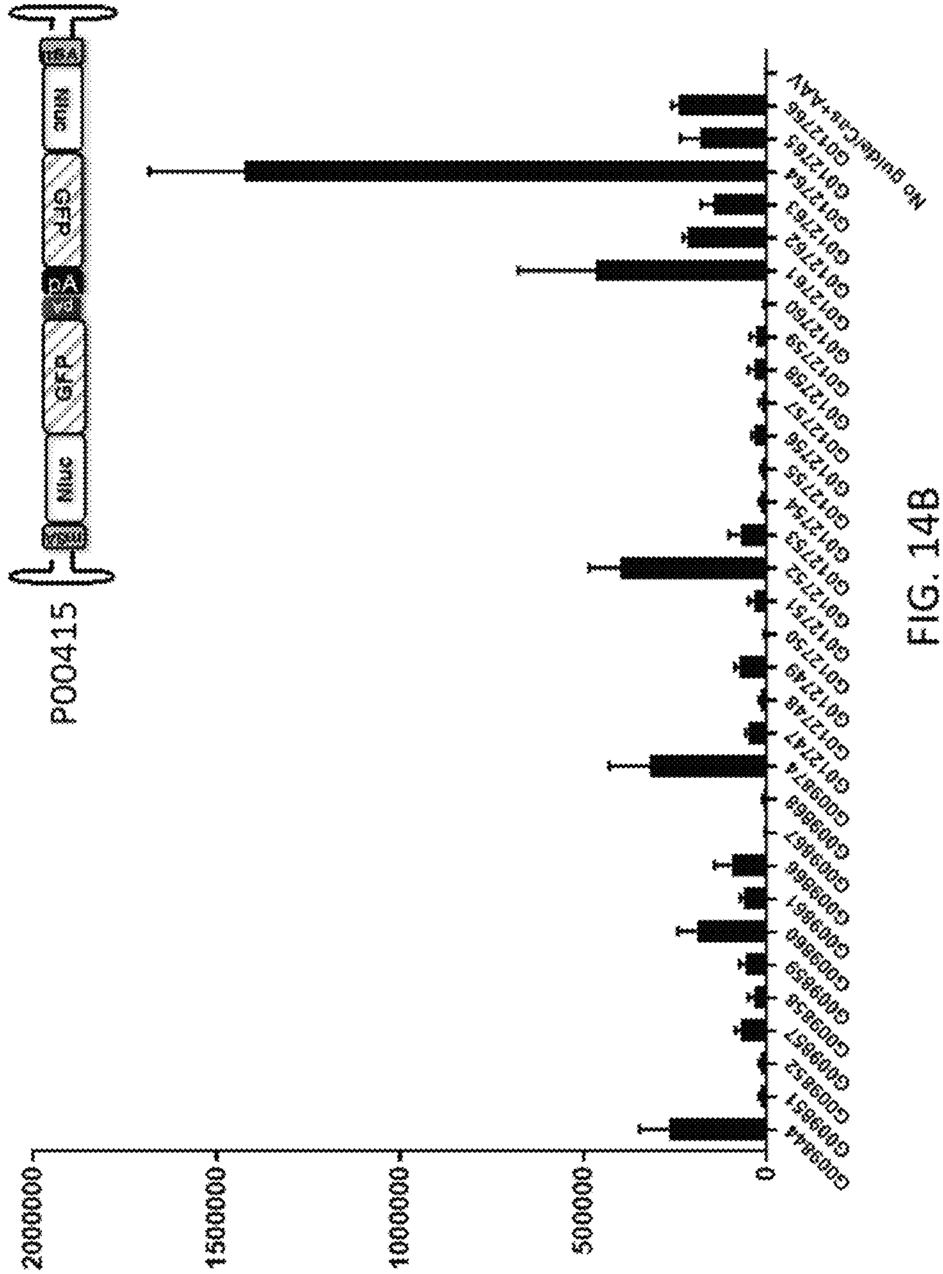
Figure 14C:
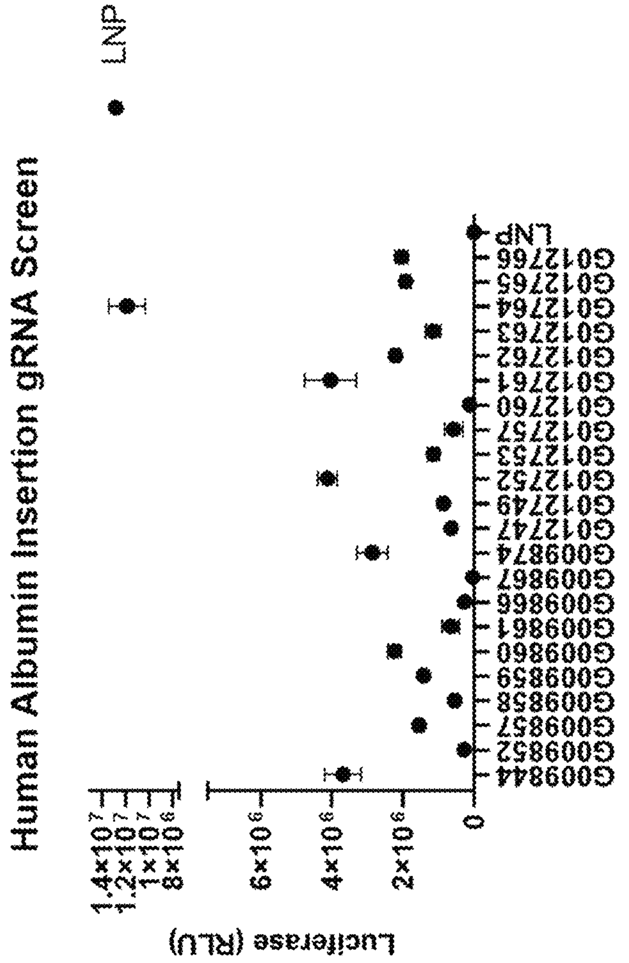
Figure 14D:
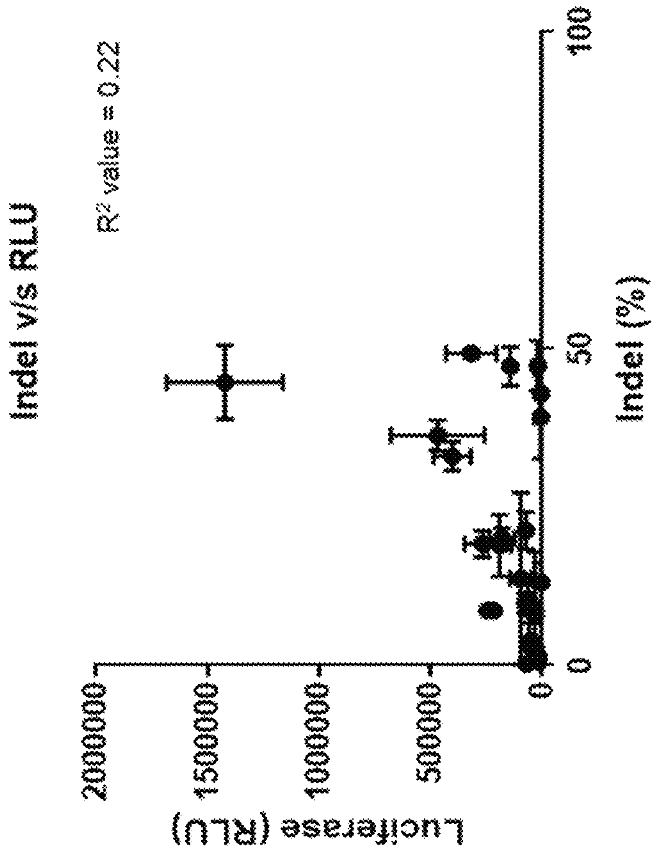

As shown in FIG. 13A for PCH and FIG. 14A for PHH, varied levels of editing were detected for each of the combinations tested (editing data for some combinations tested in the PCH experiment are not reported in FIG. 13A and Table 3 due to failure of certain primer pairs used for the amplicon based sequencing). The editing data shown in FIGS. 13A and 14A graphically, are reproduced numerically in Table 3 and Table 4 below. However, as shown in FIGS. 13B, 13C and FIGS. 14B and 14C, a significant level of indel formation was not predictive for insertion or expression of the transgenes, indicating little correlation between editing and insertion/expression of the bidirectional constructs in PCH and PHH, respectively. As one measure, the $R^2$ value calculated in FIG. 13C is 0.13, and the $R^2$ value of FIG. 14D is 0.22.

Additionally, ssAAV vectors comprising a bidirectional construct were tested across a panel of target sites utilizing single guide RNAs targeting intron 1 of human albumin in primary human hepatocytes (PHH).

The ssAAV and LNP materials were prepared and delivered to PHH as described in Example 1. Following treatment, isolated genomic DNA and cell media was collected for editing and transgene expression analysis, respectively. Each of the vectors comprised a reporter that can be measured through luciferase-based fluorescence detection as described in Example 1 (derived from plasmid P00415), plotted in FIG. 14D as relative luciferase units ("RLU") and tabulated in Table 24 below. For example, the AAV vectors contained the NanoLuc ORF (in addition to GFP). Schematics of the vectors tested are provided in FIGS. 13B and 14B. The gRNAs tested are shown in FIG. 14D using a shortened number for those listed in Table 1 and Table 7.

TABLE 3

Albumin intron 1 editing data for sgRNAs delivered to primary cynomolgus hepatocytes

| GUIDE ID | Avg % Edit | Std Dev % Edit |
|---|---|---|
| G009867 | 25.05 | 0.21 |
| G009866 | 18.7 | 3.96 |
| G009876 | 14.85 | 4.88 |
| G009875 | 12.85 | 2.33 |
| G009874 | 28.25 | 6.01 |
| G009873 | 42.65 | 5.59 |
| G009865 | 59.15 | 0.21 |
| G009872 | 48.15 | 3.46 |
| G009871 | 46.5 | 5.23 |
| G009864 | 33.2 | 8.34 |
| G009863 | 54.8 | 12.45 |
| G009862 | 44.6 | 7.21 |
| G009861 | 28.65 | 0.21 |
| G009860 | 33.2 | 7.07 |
| G009859 | 0.05 | 0.07 |
| G009858 | 14.65 | 1.77 |
| G009857 | 23 | 0.99 |
| G009856 | 14.8 | 0.99 |
| G009851 | 1.5 | 0.42 |
| G009868 | 12.15 | 2.47 |
| G009850 | 63.45 | 13.93 |
| G009849 | 57.55 | 8.27 |
| G009848 | 33 | 5.37 |
| G009847 | 66.75 | 7 |
| G009846 | 61.85 | 5.02 |
| G009845 | 54.4 | 7.5 |
| G009844 | 47.15 | 2.05 |

TABLE 4

Albumin intron 1 editing data for sgRNAs delivered to primary human hepatocytes

| GUIDE ID | Avg % Edit | Std Dev % Edit |
|---|---|---|
| G009844 | 19.07 | 2.07 |
| G009851 | 0.43 | 0.35 |
| G009852 | 47.20 | 3.96 |
| G009857 | 0.10 | 0.14 |
| G009858 | 8.63 | 9.16 |
| G009859 | 3.07 | 3.50 |
| G009860 | 18.80 | 4.90 |
| G009861 | 10.27 | 2.51 |
| G009866 | 13.60 | 13.55 |
| G009867 | 12.97 | 3.04 |
| G009868 | 0.63 | 0.32 |
| G009874 | 49.13 | 0.60 |
| G012747 | 3.83 | 0.23 |
| G012748 | 1.30 | 0.35 |
| G012749 | 9.77 | 1.50 |

TABLE 4-continued

Albumin intron 1 editing data for sgRNAs delivered to primary human hepatocytes

| GUIDE ID | Avg % Edit | Std Dev % Edit |
|---|---|---|
| G012750 | 42.73 | 4.58 |
| G012751 | 7.77 | 1.16 |
| G012752 | 32.93 | 2.27 |
| G012753 | 21.20 | 2.95 |
| G012754 | 0.60 | 0.10 |
| G012755 | 1.10 | 0.10 |
| G012756 | 2.17 | 0.40 |
| G012757 | 1.07 | 0.25 |
| G012758 | 0.90 | 0.10 |
| G012759 | 2.60 | 0.35 |
| G012760 | 39.10 | 6.58 |
| G012761 | 36.17 | 2.43 |
| G012762 | 8.50 | 0.57 |
| G012763 | 47.07 | 3.07 |
| G012764 | 44.57 | 5.83 |
| G012765 | 19.90 | 1.68 |
| G012766 | 8.50 | 0.28 |

TABLE 24 hAlb Guide Screen Luciferase

| Guide | Average Luciferase (RLU) | St. Dev Luciferase (RLU) |
|---|---|---|
| G009844 | 3700000 | 509116.9 |
| G009852 | 281000 | 69296.46 |
| G009857 | 1550000 | 127279.2 |
| G009858 | 551000 | 108894.4 |
| G009859 | 1425000 | 77781.75 |
| G009860 | 2240000 | 183847.8 |
| G009861 | 663500 | 238295 |
| G009866 | 274000 | 11313.71 |
| G009867 | 44700 | 565.6854 |
| G009874 | 2865000 | 431335.1 |
| G012747 | 651000 | 59396.97 |
| G012749 | 867000 | 93338.1 |
| G012752 | 4130000 | 268700.6 |
| G012753 | 1145000 | 162634.6 |
| G012757 | 579000 | 257386.9 |
| G012760 | 129000 | 36769.55 |
| G012761 | 4045000 | 728320 |
| G012762 | 2220000 | 127279.2 |
| G012763 | 1155000 | 205061 |
| G012764 | 11900000 | 1555635 |
| G012765 | 1935000 | 134350.3 |
| G012766 | 2050000 | 169705.6 |
| LNP | 8430 | 212.132 |

Example 12—In Vivo Testing of Factor IX Expression from an Alternative Safe Harbor Locus In this Example, insertion of ssAAV comprising a bidirectional hFIX construct at an alternative safe harbor locus was evaluated. To test the insertion into an alternative safe harbor locus, AAV was prepared as described above. Mice were administered with AAVs at a dose of 3e11 vg/mouse immediately followed by administration of LNPs formulated with Cas9 mRNAs and guide RNAs at a dose of 0.3 mg/kg. Animals were sacrificed 4 weeks post-dose, and liver and blood samples were collected. Editing in the liver samples was determined by NGS. Human hFIX levels in the serum was determined by ELISA. The NGS and ELISA data showed effective insertion and expression of hFIX within the alternative safe harbor locus.

Example 13—In Vivo Testing of the Human Factor IX Gene Insertion in Non-Human Primates In this example, an 8 week study was performed to evaluate the human Factor IX gene insertion and hFIX protein expression in cynomolgus monkeys through administration of adeno-associated virus (AAV) and/or lipid nanoparticles (LNP) with various guides. This study was conducted with LNP formulations and AAV formulations prepared as described above. Each LNP formulation contained Cas9 mRNA and guide RNA (gRNA) with an mRNA:gRNA ratio of 2:1 by weight. The ssAAV was derived from P00147.

Male cynomologus monkeys were treated in cohorts of n=3. Animals were dosed with AAV by slow bolus injection or infusion in the doses described in Table 10. Following AAV treatment, animals received buffer or LNP as described in Table 10 by slow bolus or infusion.

Two weeks post-dose, liver specimens were collected through single ultrasound-guided percutaneous biopsy. Each biopsy specimen was flash frozen in liquid nitrogen and stored at −86 to −60° C. Editing analysis of the liver specimens was performed by NGS Sequencing as previously described.

For Factor IX ELISA analysis, blood samples were collected from the animals on days 7, 14, 28, and 56 post-dose. Blood samples were collected and processed to plasma following blood draw and stored at −86 to −60° C. until analysis.

The total human Factor IX levels were determined from plasma samples by ELISA. Briefly, Reacti-Bind 96-well microplate (VWR Cat #PI15041) were coated with capture antibody (mouse mAB to human Factor IX antibody (HTI, Cat #AHIX-5041)) at a concentration of 1 μg/ml then blocked using 1×PBS with 5% Bovine Serum Albumin. Test samples or standards of purified human Factor IX protein (ERL, Cat #HFIX 1009, Lot #HFIX4840) diluted in Cynomolgus monkey plasma were next incubated in individual wells. The detection antibody (Sheep anti-human Factor 9 polyclonal antibody, Abcam, Cat #ab128048) was adsorbed at a concentration of 100 ng/ml. The secondary antibody (Donkey anti-Sheep IgG pAbs with HRP, Abcam, Cat #ab97125) was used at 100 ng/mL. TMB Substrate Reagent set (BD OptEIA Cat #555214) was used to develop the plate. Optical density was assessed spectrophotometrically at 450 nm on a microplate reader (Molecular Devices i3 system) and analyzed using SoftMax pro 6.4.

Indel formation was detected, confirming that editing occurred. The NGS data showed effective indel formation. Expression of hFIX from the albumin locus in NHPs was measured by ELISA and is depicted in Table 1 I and FIG. 15. Plasma levels of hFIX reached levels previously described as therapeutically effective (George, et al., NEJM 377(23), 2215-27, 2017).

Figure 15:
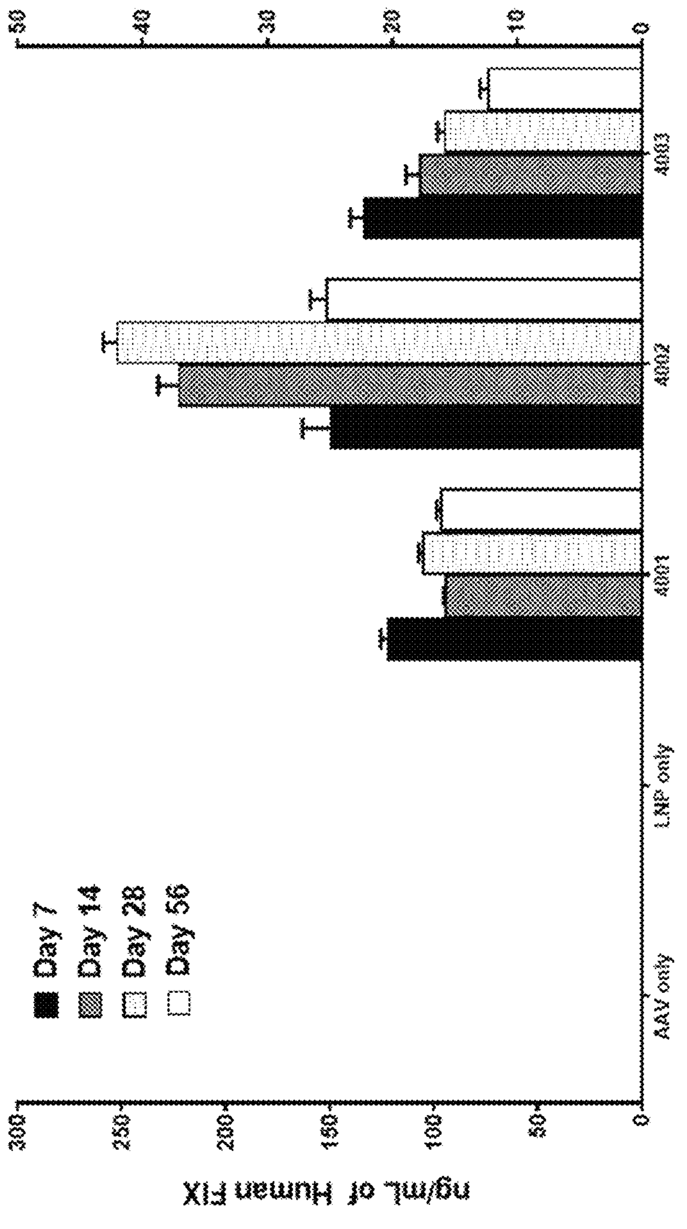
FIG. 15 shows the results of in vivo studies where non-human primates were dosed with LNPs along with a bi-directional hFIX insertion template (derived from P00147). Systemic hFIX levels were achieved only in animals treated with both LNPs and AAV, with no hFIX detectable using AAV or LNPs alone.

As measured, circulating hFIX protein levels were sustained through the eight week study (see FIG. 15, showing day 7, 14, 28, and 56 average levels of ~135, ~140, ~150, and ~110 ng/mL, respectively), achieving protein levels ranging from ~75 ng/mL to −250 ng/mL. Plasma hFIX levels were calculated using a specific activity of ~8 fold higher for the R338L hyperfunctional hFIX variant (Simioni et al., NEJM 361(17), 1671-75, 2009) (which reports a protein-specific activity of hFIX-R338L of 390±28 U per milligram, and a protein-specific activity for wild-type factor IX of 45±2.4 U per milligram). Calculating the functionally normalized Factor IX activity for the hyperfunctional Factor IX variant tested in this example, the experiment achieved stable levels of human Factor IX protein in the NHPs over the 8 week study that correspond to about 20-40% of wild type Factor IX activity (range spans 12-67% of wild type Factor IX activity).

TABLE 10

| Editing in liver | | | | | |
|---|---|---|---|---|---|
| Animal ID | Guide ID | F9-AAV (vg/kg) | F9-AAV Volume (mL/kg) | LNP (mg/kg) | LNP Volume (mL/kg) |
| 4001 | G009860 | 3E+13 | 1 | 3 | 2 |
| 4002 | G009860 | 3E+13 | 1 | 3 | 2 |
| 4003 | G009860 | 3E+13 | 1 | 3 | 2 |
| 5001 | TSS | 3E+13 | 1 | 0 | 0 |
| 5002 | TSS | 3E+13 | 1 | 0 | 0 |
| 5003 | TSS | 3E+13 | 1 | 0 | 0 |
| 6001 | G009862 | 0 | 0 | 3 | 2 |
| 6002 | G009862 | 0 | 0 | 3 | 2 |
| 6003 | G009862 | 0 | 0 | 3 | 2 |

TABLE 11

| hFIX expression | | | | |
|---|---|---|---|---|
| Animal ID | Day 7 Factor IX (ng/mL) | Day 14 Factor IX (ng/mL) | Day 28 Factor IX (ng/mL) | Day 56 Factor IX (ng/mL) |
| 4001 | 122.84/+−2.85 | 94.93/+−0.56 | 105.65/+−1.94 | 97.31/+−1.49 |
| 4002 | 149.77/+−13.5 | 222.92/+−9.61 | 252.49/+−6.46 | 152.05/+−7.46 |
| 4003 | 134.06/+−6.17 | 107.04/+−6.46 | 95.30/+−3.18 | 74.23/+−3.53 |
| 5001 | ND | ND | ND | ND |
| 5002 | ND | ND | ND | ND |
| 5003 | ND | ND | ND | ND |
| 6001 | ND | ND | ND | ND |
| 6002 | ND | ND | ND | ND |
| 6003 | ND | ND | ND | ND |

Example 14 In Vivo Testing of Factor IX Insertion in Non-Human Primates

In this example, a study was performed to evaluate the Factor IX gene insertion and hFIX protein expression in cynomolgus monkeys following administration of ssAAV derived from P00147 and/or CRISPR/Cas9 lipid nanoparticles (LNP) with various guides including G009860 and various LNP components.

Indel formation was measured by NGS, confirming that editing occurred. Total human Factor IX levels were determined from plasma samples by ELISA using a mouse mAB to human Factor IX antibody (HTI, Cat #AHIX-5041), sheep anti-human Factor 9 polyclonal antibody (Abcam, Cat #ab128048), and donkey anti-Sheep IgG pAbs with HRP (Abcam, Cat #ab97125), as described in Example 13. Human FIX protein levels>3 fold higher than those achieved in the experiment of Example 13 were obtained from the bidirectional template using alternative CRISPR/Cas9 LNP. In the study, ELISA assay results indicate that circulating hFIX protein levels at or above the normal range of human FIX levels (3-5 ug/mL; Amiral et al., Clin. Chem., 30(9), 1512-16, 1984) were achieved using G009860 in the NHPs by at least the day 14 and 28 timepoints. Initial data indicated circulating human FIX protein levels of ~3-4 μg/mL at day 14 after a single dose, with levels sustained through the first 28 days (~3-5 μg/mL) of the study. The human FIX levels were measured at the conclusion of the study by the same method and data are presented in the Table 25. Additional guides G009847, G009862, and G009864 were also tested and shown to facilitate insertion of a FIX-expressing template in the NHP study.

TABLE 25

| Serum human Factor IX protein levels -ELISA Method of Example 13 | | | | | | | | | | |
|---|---|---|---|---|---|---|---|---|---|---|
| | Day 7 FIX ng/mL | STD DEV | Day 14 FIX ng/mL | STD DEV | Day 28 FIX ng/mL | STD DEV | Day 42 FIX ng/mL | STD DEV | Day 56 FIX ng/mL | STD DEV |
| 3001 | 2532.8 | 145.6 | 2562.6 | 99.0 | 3011.7 | 62.7 | 2936.7 | 72.4 | 2748.5 | 86.0 |
| 3002 | 2211.4 | 95.8 | 2958.5 | 119.2 | 3350.2 | 98.4 | 3049.7 | 112.7 | 3036.7 | 90.6 |
| 3003 | 3195.1 | 475.6 | 4433.9 | 238.7 | 3367.2 | 157.7 | 3746.1 | 95.6 | 3925.0 | 157.4 |

Circulating albumin levels were measured by ELISA, indicating that baseline albumin levels are maintained at 28 days. Tested albumin levels in untreated animals varied ±~15% in the study. In treated animals, circulating albumin levels changed minimally and did not drop out of the normal range, and the levels recovered to baseline within one month.

Circulating human FIX protein levels were also determined by a sandwich immunoassay with a greater dynamic range. Briefly, an MSD GOLD 96-well Streptavidin SECTOR Plate (Meso Scale Diagnostics, Cat. L15SA-1) was blocked with 1% ECL Blocking Agent (Sigma, GERPN2125). After tapping out the blocking solution, biotinylated capture antibody (Sino Biological, 11503-R044) was immobilized on the plate. Recombinant human FIX protein (Enzyme Research Laboratories, HFIX 1009) was used to prepare a calibration standard in 0.5% ECL Blocking Agent. Following a wash, calibration standards and plasma samples were added to the plate and incubated. Following a wash, a detection antibody (Haematologic Technologies, AHIX-5041) conjugated with a sulfo-tag label was added to the wells and incubated. After washing away any unbound detection antibody, Read Buffer T was applied to the wells. Without any additional incubation, the plate was imaged with an MSD Quick Plex SQ120 instrument and data was analyzed with Discovery Workbench 4.0 software package (Meso Scale Discovery). Concentrations are expressed as mean calculated concentrations in ug/m. For the samples, N=3 unless indicated with an asterisk, in which case N=2. Expression of hFIX from the albumin locus in the treated study group as measured by the MSD ELISA is depicted in Table 26.

TABLE 26

| Serum human Factor IX protein levels - MSD ELISA | | | | | | |
|---|---|---|---|---|---|---|
| | Mean Calc. Conc. (ug/mL) | | | | | |
| | 3001 | | 3002 | | 3003 | |
| Time Point | Conc. | Inter-Assay CV | Conc. | Inter-Assay CV | Conc. | Inter-Assay CV |
| Day 7 | 7.85 | 20% | 5.63 | 14% | 11.20 | 26% |
| Day 14 | 8.65 | 15% | 11.06 | 18% | 14.70 | 28% |
| Day 28 | 9.14 | 7% | 14.12 | 7% | 10.85 | 25% |
| Day 42 | 9.03 | 10% | 33.12* | 0% | 13.22 | 13% |
| Day 56 | 10.24 | 13% | 16.72 | 12% | 33.84* | 4% |

Example 15—Off-Target Analysis of Albumin Human Guides

A biochemical method (See, e.g., Cameron et al., Nature Methods. 6, 600-606; 2017) was used to determine potential off-target genomic sites cleaved by Cas9 targeting Albumin. In this experiment, 13 sgRNA targeting human Albumin and two control guides with known off-target profiles were screened using isolated HEK293 genomic DNA. The number of potential off-target sites detected using a guide concentration of 16 nM in the biochemical assay were shown in Table 27. The assay identified potential off-target sites for the sgRNAs tested.

TABLE 27

Off-Target Analysis

| gRNA ID | Target | Guide Sequence (SEQ ID NO:) | Off-Target Site Count |
|---|---|---|---|
| G012753 | Albumin | GACUGAAACUUCACAGAAUA (SEQ ID NO: 20) | 62 |
| G012761 | Albumin | AGUGCAAUGGAUAGGUCUUU (SEQ ID NO: 28) | 75 |
| G012752 | Albumin | UGACUGAAACUUCACAGAAU (SEQ ID NO: 19) | 223 |
| G012764 | Albumin | CCUCACUCUUGUCUGGGCAA (SEQ ID NO: 31) | 3985 |
| G012763 | Albumin | UGGGCAAGGGAAGAAAAAAA (SEQ ID NO: 30) | 5443 |
| G009857 | Albumin | AUUUAUGAGAUCAACAGCAC (SEQ ID NO: 5) | 131 |
| G009859 | Albumin | UUAAAUAAAGCAUAGUGCAA (SEQ ID NO: 7) | 91 |
| G009860 | Albumin | UAAAGCAUAGUGCAAUGGAU (SEQ ID NO: 8) | 133 |
| G012762 | Albumin | UGAUUCCUACAGAAAAACUC (SEQ ID NO: 29) | 68 |
| G009844 | Albumin | GAGCAACCUCACUCUUGUCU (SEQ ID NO: 2) | 107 |
| G012765 | Albumin | ACCUCACUCUUGUCUGGGCA (SEQ ID NO: 32) | 41 |
| G012766 | Albumin | UGAGCAACCUCACUCUUGUC (SEQ ID NO: 33) | 78 |
| G009874 | Albumin | UAAUAAAAUUCAAACAUCCU (SEQ ID NO: 13) | 53 |
| G000644 | EMX1 | GAGUCCGAGCAGAAGAAGAA (SEQ ID NO: 1129) | 304 |
| G000645 | VEGFA | GACCCCCUCCACCCCGCCUC (SEQ ID NO: 1130) | 1641 |

In known off-target detection assays such as the biochemical method used above, a large number of potential off-target sites are typically recovered, by design, so as to “cast a wide net” for potential sites that can be validated in other contexts, e.g., in a primary cell of interest. For example, the biochemical method typically over represents the number of potential off-target sites as the assay utilizes purified high molecular weight genomic DNA free of the cell environment and is dependent on the dose of Cas9 RNP used. Accordingly, potential off-target sites identified by these methods may be validated using targeted sequencing of the identified potential off-target sites.

Example 16. Use of Humanized Albumin Mice to Screen Guide RNAs for Human F9 Insertion In Vivo We aimed to identify effective guide RNAs for hF9 insertion into the human albumin locus. To this end, we utilized mice in which the mouse albumin locus was replaced with the corresponding human albumin genomic sequence, including the first intron ($ALB^{hu/hu}$ mice). This allowed us to test the insertion efficiency of guide RNAs targeting the first intron of human albumin in the context of an adult liver in vivo. Two separate mouse experiments were set up using the $ALB^{hu/hu}$ mice to screen a total of 11 guide RNAs, each targeting the first intron of the human albumin locus. All mice were weighed and injected via tail vein at day 0 of the experiment. Blood was collected at weeks 1, 3, 4, and 6 via tail bleed, and plasma was separated. Mice were terminated at week 7. Blood was collected via the vena cava, and plasma was separated. Livers and spleens were dissected as well.

In the first experiment, 6 LNPs comprising Cas9 mRNA and the following guides were prepared as in Example 1 and tested: G009852, G009859, G009860, G009864, G009874, and G012764. LNPs were diluted to 0.3 mg/kg (using an average weight of 30 grams) and co-injected with AAV8 packaged with the bi-directional hF9 insertion template at a dose of 3E11 viral genomes per mouse. Five $ALB^{hu/hu}$ male mice between 12 and 14 weeks old were injected per group. Five mice from same cohort were injected with AAV8 packaged with a CAGG promoter operably linked to hF9, which leads to episomal expression of hF9 (at 3E11 viral genomes per mouse). There were three negative control groups with three mice per group that were injected with buffer alone, AAV8 packaged with the bi-directional hF9 insertion template alone, or LNP-G009874 alone.

In the experiment, the following LNPs comprising Cas9 mRNA and the following guides were prepared as in Example 1 and tested: G009860, G012764, G009844, G009857, G012752, G012753, and G012761. All were diluted to 0.3 mg/kg (using an average weight of 40 grams) and co-injected with AAV8 packaged with the bi-directional hF9 insertion template at a dose of 3E11 viral genomes per mouse. Five $ALB^{hu/hu}$ male mice 30 weeks old were injected per group. Five mice from same cohort were injected with AAV8 packaged with a CAGG promoter operably linked to hF9, which leads to episomal expression of hF9 (at 3E11 viral genomes per mouse). There were three negative control groups with three mice per group that were injected with buffer alone, AAV8 packaged with the bi-directional hF9 insertion template alone, or LNP-G009874 alone.

Figure 16A:
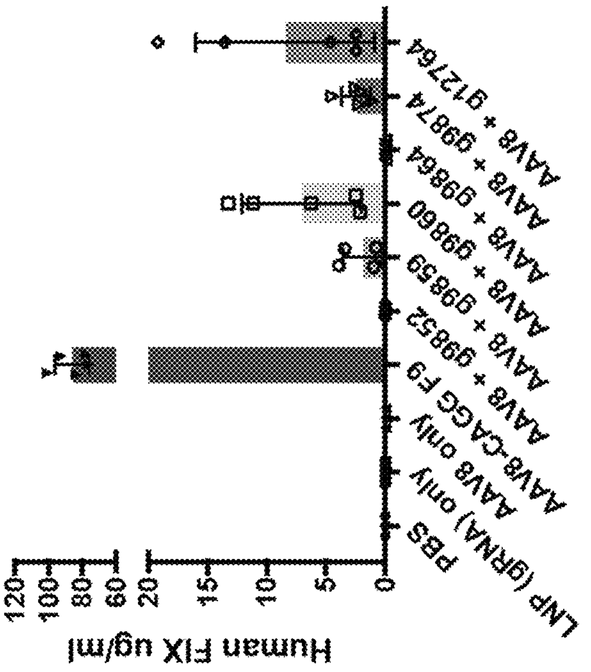
FIG. 16A and FIG. 16B show human Factor IX expression levels in the plasma samples at week 6 post-injection.
Figure 16B:
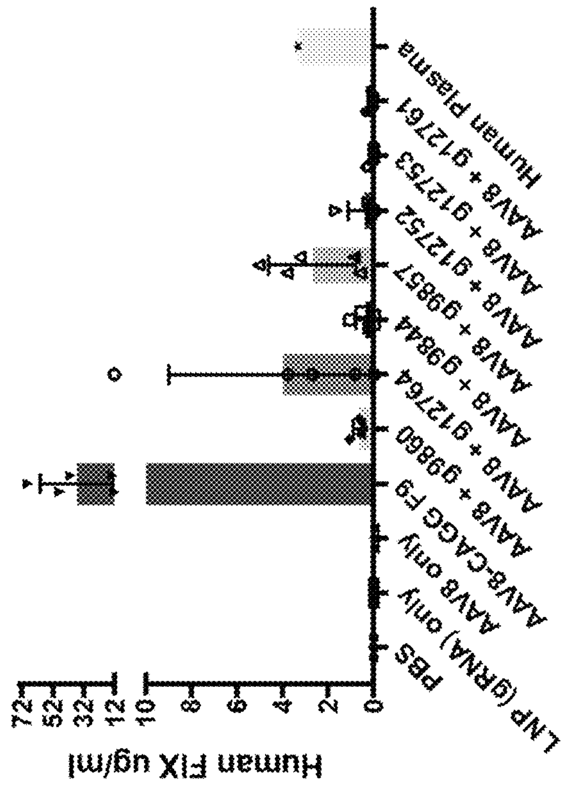

For analysis, an ELISA was performed to measure levels of hFIX circulating in the mice at each timepoint. Human Factor IX ELISA Kits (ab188393) were used for this purpose, and all plates were run with human pooled normal plasma from George King Bio-Medical as a positive assay control. Human Factor IX expression levels in the plasma samples in each group at week 6 post-injection are shown in FIG. 16A and FIG. 16B. Consistent with the in vitro insertion data, low to no Factor IX serum levels were detected when guide RNA G009852 was used. Consistent with the lack of an adjacent PAM sequence in human albumin, Factor IX serum levels were not detectable when guide RNA G009864 was used. Factor IX expression in the serum was observed for the groups using guide RNAs G009859, G009860, G009874, and G0012764.

Spleens and a portion of the left lateral lobe of all livers were submitted for next-generation sequencing (NGS) analysis. NGS was used to assess the percentage of liver cells with insertions/deletions (indels) at the humanized albumin locus at week 7 post-injection with AAV-hF9 donor and LNP-CRISPR/Cas9. Consistent with the lack of an adjacent PAM sequence in human albumin, no editing was detectable in the liver when guide RNA G009864 was used. Editing in the liver was observed for the groups using guide RNAs G009859, G009860, G009874, and G012764 (data not shown).

Figure 17:
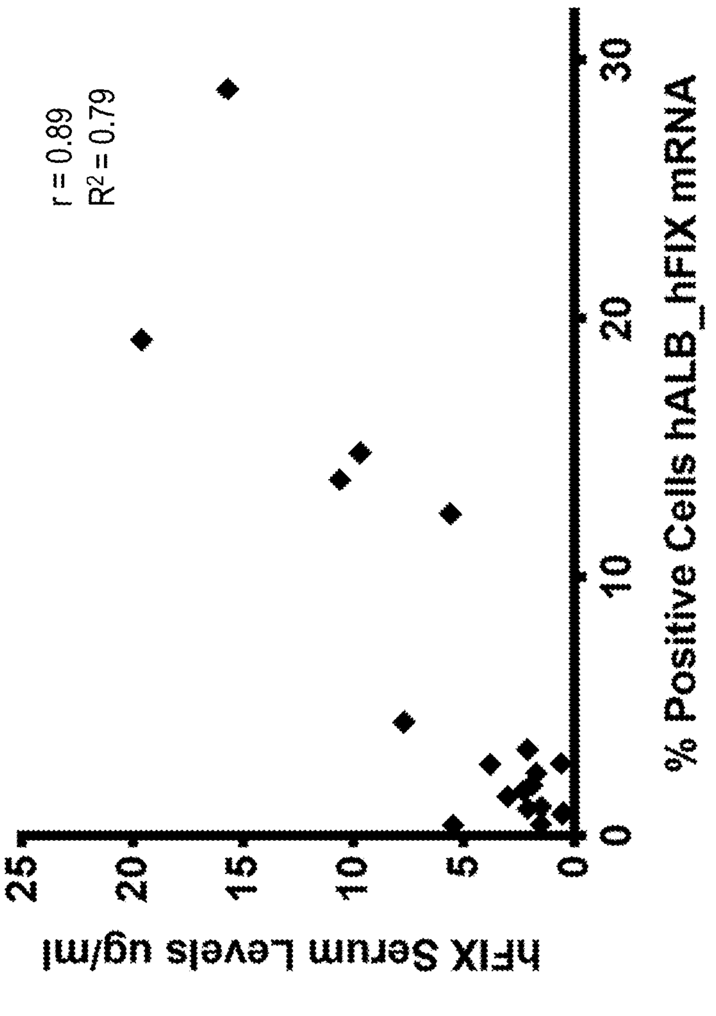
FIG. 17 shows week 7 serum levels and % positive cells across the multiple lobes for each animal.

The remaining liver was fixed for 24 hours in 10% neutral buffered formalin and then transferred to 70% ethanol. Four to five samples from separate lobes were cut and shipped to HistoWisz and were processed and embedded in paraffin blocks. Five-micron sections were then cut from each paraffin block, and BASESCOPE™ was performed on the Ventana Ultra Discovery (Roche) using the universal BASESCOPE™ procedure and reagents by Advanced Cell Diagnostics and a custom designed probe that targets the unique mRNA junction formed between the human albumin signal sequence from the first intron of the $ALB^{hu/hu}$ albumin locus and the hF9 transgene when successful integration and transcription is achieved. HALO imaging software (Indica Labs) was then used to quantify the percentage of positive cells in each sample. The average of percentage positive cells across the multiple lobes for each animal was then correlated to the hFIX levels in the serum at week 7. The results are shown in FIG. 17 and Table 28. The week 7 serum levels and the % positive cells for the hALB-hFIX mRNA strongly correlated (r=0.89; $R^2$=0.79).

TABLE 28

Week 7 hFIX and BASESCOPE ™ Data.

| Mouse | Guide | hFIX ug/mL (Week 7) | % mRNA Probe (4-5 Sections) | STD % mRNA Probe | Total Cells Counted |
|---|---|---|---|---|---|
| 1 | Buffer | ND | 0.09 | 0.03 | 152833 |
| 4 | AAV Only | ND | 0.53 | 0.67 | 351084 |
| 7 | LNP Only | ND | 0.48 | 0.33 | 75160 |
| 10 | CAG F9 | 211.8 | 0.20 | 0.22 | 190277 |
| 15 | G009852 | ND | 0.30 | 0.09 | 144518 |
| 20 | G009859 | 0.5 | 0.82 | 0.45 | 143817 |
| 21 | G009859 | 0.5 | 0.88 | 0.43 | 160172 |
| 22 | G009859 | 2.3 | 1.71 | 1.54 | 26015 |
| 23 | G009859 | 3.8 | 2.74 | 0.59 | 183085 |
| 24 | G009859 | 0.6 | 2.78 | 1.96 | 152424 |
| 25 | G009860 | 5.6 | 12.46 | 5.80 | 78935 |
| 26 | G009860 | 10.6 | 13.76 | 5.32 | 112252 |
| 27 | G009860 | 9.7 | 14.80 | 5.45 | 201592 |
| 28 | G009860 | 2.1 | 3.32 | 0.76 | 84710 |
| 29 | G009860 | 3.0 | 1.52 | 0.35 | 203277 |
| 30 | G009864 | ND | 1.94 | 1.78 | 145807 |
| 35 | G009874 | 1.7 | 2.42 | 1.14 | 126665 |
| 36 | G009874 | 1.5 | 1.08 | 0.53 | 195861 |
| 37 | G009874 | 2.1 | 1.02 | 1.29 | 181679 |
| 38 | G009874 | 5.5 | 0.40 | 0.43 | 175359 |
| 39 | G009874 | 1.5 | 0.44 | 0.18 | 205417 |
| 40 | G012764 | 15.7 | 28.85 | 7.11 | 167824 |
| 41 | G012764 | 19.6 | 19.17 | 8.23 | 70081 |
| 42 | G012764 | 1.9 | 1.95 | 1.79 | 154742 |
| 43 | G012764 | 7.7 | 4.38 | 0.68 | 114060 |
| 44 | G012764 | 3.0 | 1.64 | 1.04 | 238623 |
| 43 | DapB (−) | — | 0.12 | 0.07 | 144730 |

Example 17—Use of Humanized Albumin Mice Crossed with F9 Knockout Mice to Assess Functionality of Inserted Human F9 In Vivo For a next study, functionality of inserted hF9 was tested in male $ALB^{ms/hu}$×$F9^{-/-}$ mice. LNPs comprising Cas9 mRNA and the following guides were prepared as in Example 1 and tested: G009860 (targeting the first intron of the human albumin locus) and G000666 (targeting the first intron of the mouse albumin locus). G009860 was diluted to 0.3 mg/kg, and G000666 was diluted to 1.0 mg/kg (using an average weight of 31.2 grams), and both were co-injected with AAV8 packaged with the bi-directional h9 insertion template at a dose of 3E11 viral genomes per mouse. Five $ALB^{ms/hu}$×$F9^{-/-}$ male mice (16 weeks old) were injected per group. Five mice from same cohort were injected with AAV8 packaged with a CAGG promoter operably linked to hF9, which leads to episomal expression of hF9 (at 3E11 viral genomes per mouse). There were six negative control animals with one mouse per group that was injected with buffer alone or AAV8 packaged with the bi-directional hF9 insertion template alone, and two mice per group that were injected with LNP-G009860 or LNP-G000666 alone at 0.3 mg/kg and 1.0 mg/kg, respectively.

For analysis, an ELISA was performed to measure levels of hFIX circulating in the mice at each timepoint. Human Factor IX ELISA Kits (ab188393) were used for this purpose, and all plates were run with human pooled normal plasma from George King Bio-Medical as a positive assay control. Spleens and a portion of the left lateral lobe of all livers were submitted for NGS analysis.

Figure 18:
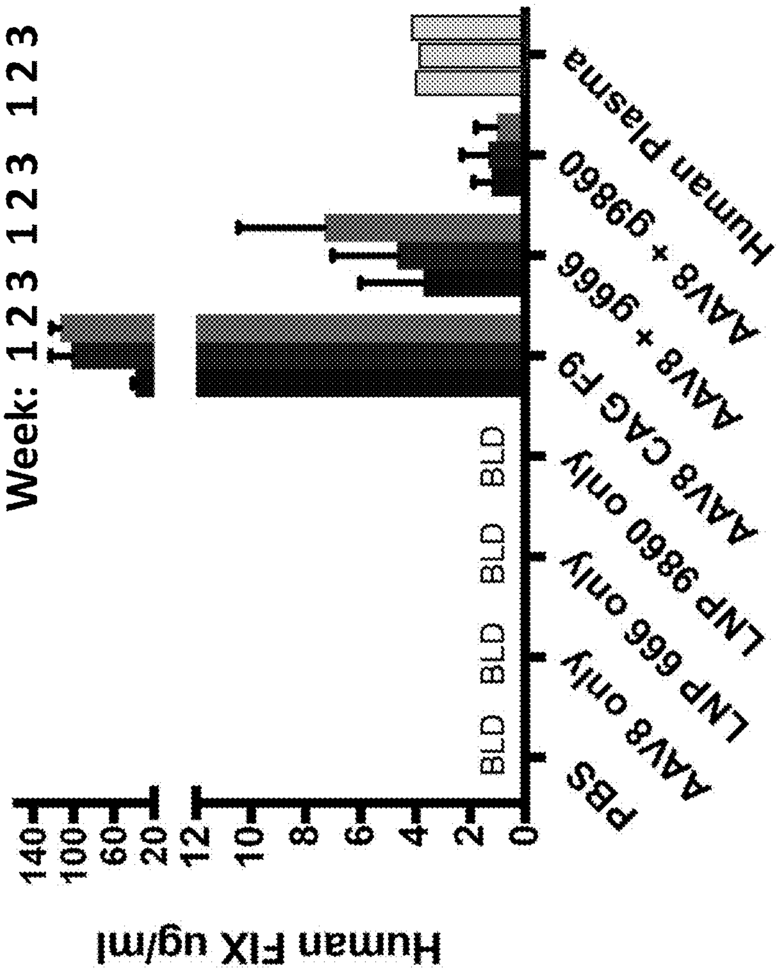
FIG. 18 shows human Factor IX expression levels in the plasma samples in each group at weeks 1, 2, and 4 post-injection.

Human Factor IX expression levels in the plasma samples in each group at weeks 1, 2, and 4 post-injection are shown in FIG. 18 and in Table 29. In addition, NGS results showing insertion and deletion (indel) levels at the albumin locus in the liver and spleen are shown in Table 29. As shown in FIG. 18 and Table 29, hFIX was detected in the plasma of treated $Alb^{+/hu}$/$F9^{-/-}$ mice at 1, 3, and 4 weeks, with ELISA showing expression values of 0.5-10 μg/mL at 1, 3 and 4 weeks

TABLE 29

Human FIX Plasma Levels and NGS Results.

| Sample | Week 1 (μg/mL) | Week 3 (μg/mL) | Week 4 (μg/mL) | INDEL Liver | INDEL Spleen |
|---|---|---|---|---|---|
| S1 PBS | BLD | BLD | BLD | 6.12 | 0.12 |
| S18 AAV8 only | BLD | BLD | BLD | 0.73 | 0.10 |
| S2 G000666 only | BLD | BLD | BLD | 37.48 | 0.92 |
| S4 G000666 only | BLD | BLD | BLD | 30.67 | 1.17 |
| S19 G009860 only | BLD | BLD | BLD | 12.25 | 0.31 |
| S20 G009860 only | BLD | BLD | BLD | 10.73 | 0.45 |
| S10 CAG | 42.60 | 129.83 | 117.74 | 1.45 | 0.12 |
| S14 CAG | 35.55 | 82.25 | 100.95 | 0.08 | 0.11 |
| S15 CAG | 37.30 | 115.51 | 107.26 | 0.10 | 0.05 |
| S16 CAG | 36.39 | 81.27 | 116.24 | 0.05 | 0.10 |
| S17 CAG | 40.50 | 101.38 | 124.15 | 0.16 | 0.06 |
| S5 AAV8 + G000666 | 2.90 | 5.00 | 8.79 | 41.46 | 1.43 |
| S6 AAV8 + G000666 | 4.67 | 6.11 | 10.29 | 33.81 | 1.59 |
| S7 AAV8 + G000666 | 2.88 | 3.15 | 3.01 | 33.47 | 1.04 |
| S8 AAV8 + G000666 | 0.94 | 1.61 | No sample | 36.54 | 1.34 |
| S9 AAV8 + G000666 | 7.14 | 7.53 | 7.23 | 30.63 | 1.38 |
| S11 AAV8 + G009860 | 0.73 | 0.62 | 0.86 | 11.15 | 0.52 |
| S12 AAV8 + G009860 | 0.52 | 0.43 | 0.47 | 7.05 | 0.39 |
| S13 AAV8 + G009860 | 1.71 | 1.89 | 0.93 | 18.38 | 0.57 |
| S21 AAV8 + G009860 | 1.21 | 2.79 | 0.59 | 13.44 | 0.22 |

TABLE 29-continued

Human FIX Plasma Levels and NGS Results.

| Sample | Week 1 (μg/mL) | Week 3 (μg/mL) | Week 4 (μg/mL) | INDEL Liver | INDEL Spleen |
|---|---|---|---|---|---|
| S22 AAV8 + G009860 | 2.06 | 1.03 | 2.37 | 18.06 | 0.19 |
| Human | 4.00 | 3.91 | 4.12 | N/A | N/A |

The remaining liver was fixed for 24 hours in 10% neutral buffered formalin and then transferred to 70% ethanol. Four to five samples from separate lobes were cut and shipped to HistoWiz and were processed and embedded in paraffin blocks. Five-micron sections were then cut from each paraffin block for analysis via BASESCOPE™ on the Ventana Ultra Discovery (Roche) using the universal BASESCOPE™ procedure and reagents by Advanced Cell Diagnostics and a custom designed probe that targets the unique mRNA junction formed between either the human or the mouse albumin signal sequence from the first intron of each respective albumin locus in the $ALB^{ms/hu}$ mouse and the hF9 transgene when successful integration and transcription is achieved. HALO imaging software (Indica Labs) is used to quantify the percentage of positive cells in each sample.

Next, terminal blood was used for assessment of functional coagulation activity by activated partial thromboplastin time (aPIT) and Thrombin Generation Assay (TGA). Activated partial thromboplastin time (aPTT) is a clinical measurement of intrinsic pathway clotting activity in plasma. Plasma is induced to clot by the addition of ellagic acid or kaolin, both of which activate coagulation factor XII in the intrinsic pathway (as known as the contact pathway) of coagulation, that subsequently results in the generation of fibrin from fibrinogen once thrombin is activated. The aPTT assay provides an estimation of an individual's ability to generate a clot, and this information can be used to determine risk of bleeding or thrombosis. To test aPTT, a semi-automated benchtop system (Diagnostica Stago STart 4) with an electro-mechanical clot detection method (viscosity-based detection system) was used to assess clotting in plasma. To each cuvette with a steel ball, 50 μL of citrated plasma was added and incubated at 37° C. for 5 min, and then clotting was triggered with the addition of 50 μL of ellagic acid (final concentration of 30 μM) at 37° C. for 300 seconds. Following final activation of clotting by adding 50 μL of 0.025 M calcium chloride (final concentration of 8 mM) to each cuvette, the steal ball began to oscillate back and forth between the two drive coils. The movement of the ball was detected by the receiver coil. The generation of fibrin increased plasma viscosity until the ball ceased to move, which was recorded as the clotting time. The only parameter measured was clotting time. Runs were conducted in duplicate.

Thrombin generation assay (TGA) is a non-clinical assessment of the kinetics of thrombin generation in activated plasma. Thrombin generation is an essential process of coagulation because thrombin is responsible for activation of other coagulation factors and propagation of additional thrombin (via FXI activation) for the conversion of fibrinogen to fibrin. Thrombin generation assay provides an estimation of an individual's ability to generate thrombin, and this information can be used to determine risk of bleeding or thrombosis. To perform the TGA, a calibrated automated thrombogram was used to assess thrombin generation levels in a spectrophotometer (Thrombinograph™, Thermo Scientific). For high throughput experimentation, 96-well plates (Immulon II HB) were used. To each well, 55 μL of citrated plasma (4× diluted with saline for mouse plasma) was added and incubated at 37° C. for 30 min. Thrombin generation is triggered with the addition of 15 μL of 2 μM ellagic acid (final concentration of 0.33 μM) at 37° C. for 45 min. Thrombin generation was determined following the automated injection of 15 μL of the fluorogenic substrate with 16 mM $CaCl_2$) (FluCa; Thrombinoscope BV) into each well. The fluorogenic substrate reacted with the generated thrombin, which was measured continuously in the plasma every 33 sec for 90 min at 460 nn. The fluorescence intensity was proportional to the proteolytic activity of thrombin. The main parameters measured in the tracing were lag time, peak thrombin generation, time to peak thrombin generation, and endogcnous thrombin potential (ETP). The lag time provides an estimation of time required for initial detection of thrombin in plasma. The peak is the maximum amount of thrombin generated at a given time after activation. Time to peak thrombin generation is time from initiation of the coagulation cascade to the peak generation of thrombin. ETP is the total amount of thrombin generated during the 60 minutes measured. Runs were conducted in duplicate.

Figure 19:
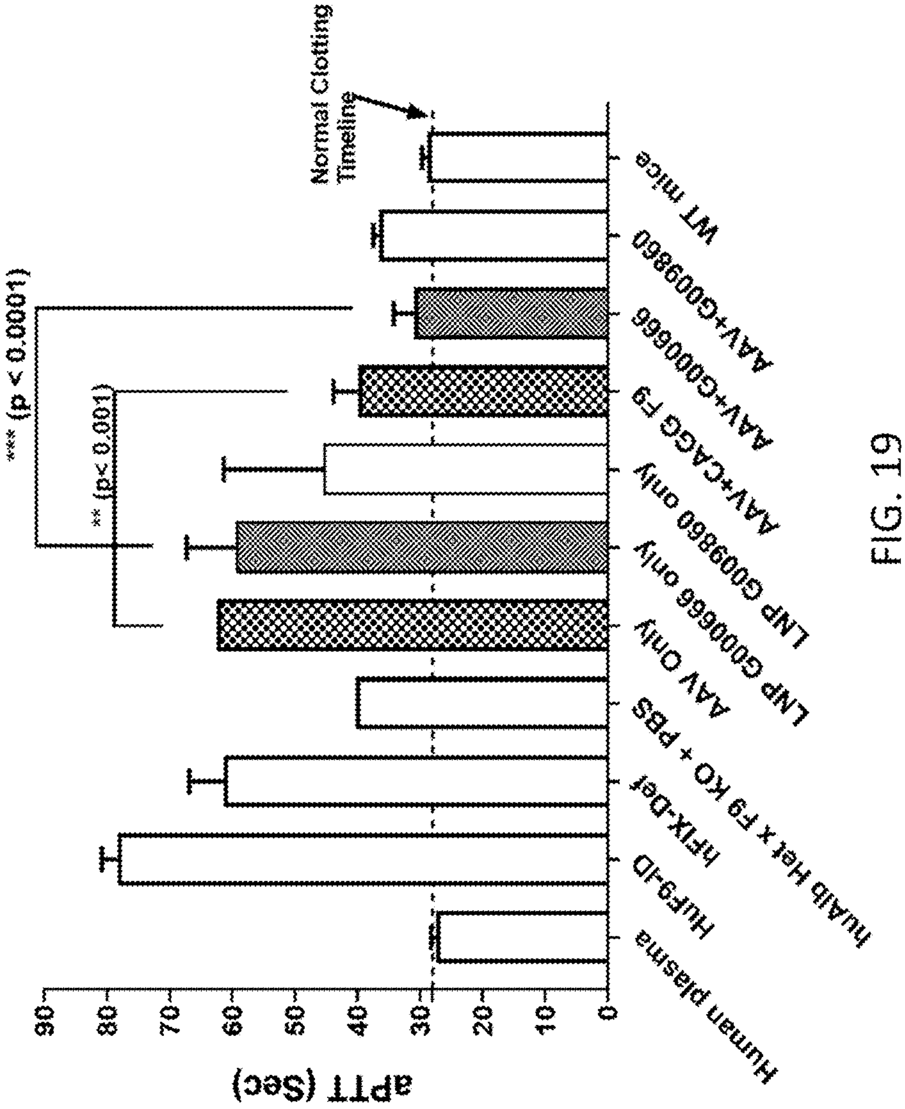
FIG. 19 shows insertion of the hF9 transgene and clotting function in the aPTT assay.

As shown in FIG. 19 and Table 30, insertion of the hF9 transgene using for example G000666 showed recovered clotting function in the aPIT assay. AAV only and LNP only negative control samples showed prolonged aPTT times of 45-60 seconds in saline. The positive control CAGG and test samples AAV8+LNP were closer to the normal human aPTT of 28-34 seconds.

TABLE 30 aPTT and TGA-EA.

| Sample # | I.V. Injection | Week 4 F9 μg/mL | Average aPTT (sec) | TGA-EA Peak (nM) |
|---|---|---|---|---|
| 1 | PBS | BLD | 40.2 | 11.13 |
| 18 | AAV Only | BLD | 62.5 | −1 |
| 2 | LNP g666 only | BLD | 53.9 | −1 |
| 4 | LNP g666 only | BLD | 65.0 | 2.45 |
| 19 | LNP G009860 only | BLD | 34.1 | 42.83 |
| 20 | LNP G009860 only | BLD | 56.7 | 18.07 |
| 10 | AAV + CAGG F9 | 117.74 | 41.1 | 42.65 |
| 14 | AAV + CAGG F9 | 100.95 | 34.1 | 49.96 |
| 15 | AAV + CAGG F9 | 107.26 | 42.2 | 49.49 |
| 16 | AAV + CAGG F9 | 116.24 | 37.9 | 44.46 |
| 17 | AAV + CAGG F9 | 124.15 | 44.1 | 38.02 |
| 5 | AAV + g666 | 8.79 | 31.3 | 72.11 |
| 6 | AAV + g666 | 10.29 | 32.6 | 90.14 |
| 7 | AAV + g666 | 3.01 | 33.5 | 58.33 |
| 8 | AAV + g666 | no sample | NA | NA |
| 9 | AAV + g666 | 7.23 | 25.9 | 67.23 |
| 11 | AAV + G009860 | 0.86 | 36.8 | 56.92 |
| 12 | AAV + G009860 | 0.47 | 37.7 | 45.16 |
| 13 | AAV + G009860 | 0.93 | 35.3 | 60.45 |
| 21 | AAV + G009860 | 0.59 | 36.1 | 47.44 |
| 22 | AAV + G009860 | 2.37 | >300 | Clots in tube |

Figure 20A:
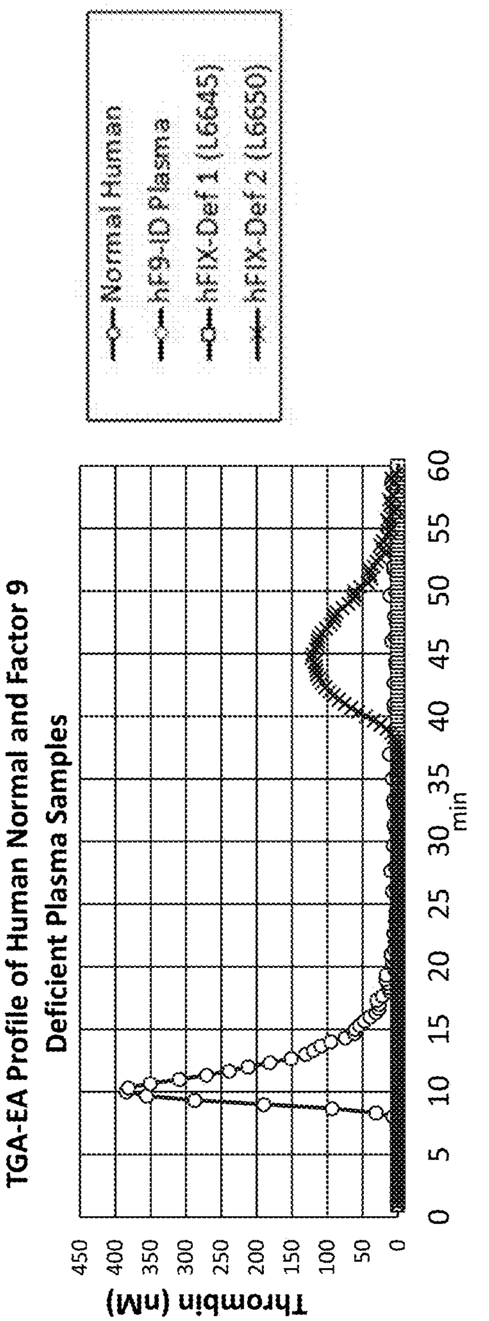
FIG. 20A and FIG. 20B show insertion of the hF9 transgene and thrombin generation in TGA-EA analysis.
Figure 20B:
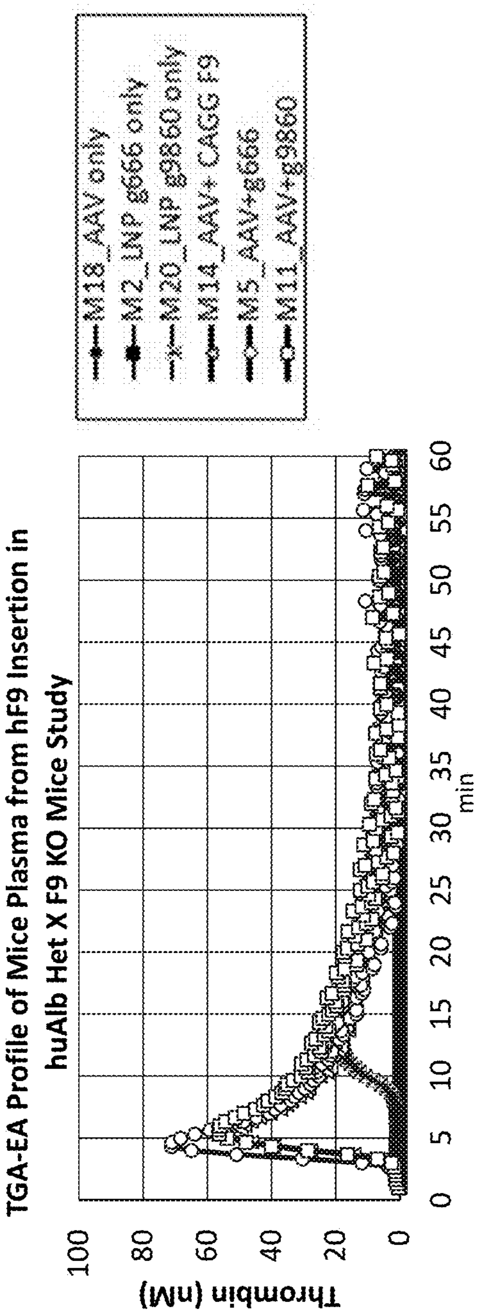
Figure 21:
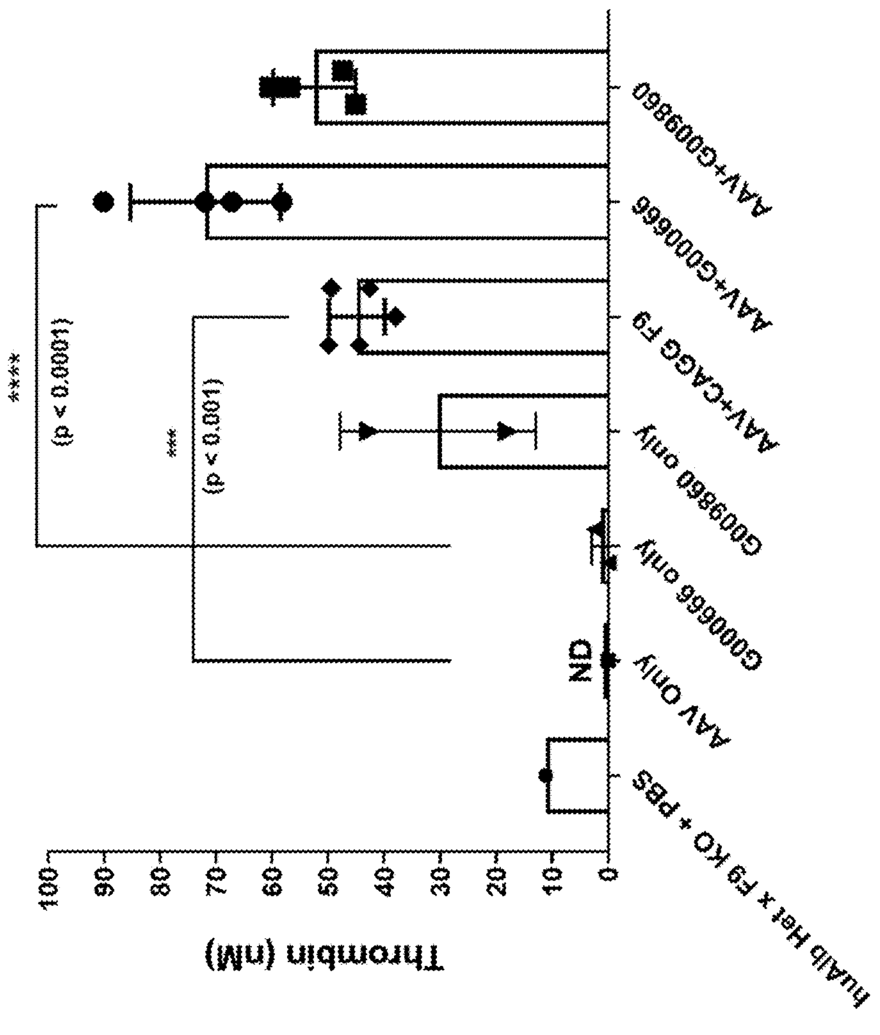
FIG. 21 shows insertion of the hF9 transgene and thrombin generation.

As shown in FIG. 20A, FIG. 20B, and FIG. 21 and in Table 30, insertion of the hF9 transgene using for example G000666 showed increased thrombin generation in TGA-EA analysis. Thrombin concentrations were higher in the positive control CAGG and AAV8+LNP as compared to the negative control samples.

In conclusion, hFIX was detected in the plasma of $Alb^{+/hu}F9^{-/-}$ mice at 1, 3, and 4 weeks, and the expressed hFIX-R338L was found to be functional since thrombin was generated in a TGA assay, and aPTT clotting time was improved.

Human albumin intron 1:

(SEQ ID NO: 1)

GTAAGAAATCCATTTTTCTATTGTTCAACTTTTATTCTATTTTCCCAG

TAAAATAAAGTTTTAGTAAACTCTGCATCTTTAAAGAATTATTTTGGC

ATTTATTTCTAAAATGGCATAGTATTTTGTATTTGTGAAGTCTTACAA

GGTTATCTTATTAATAAAATTCAAACATCCTAGGTAAAAAAAAAAAAA

GGTCAGAATTGTTTAGTGACTGTAATTTTCTTTTGCGCACTAAGGAAA

GTGCAAAGTAACTTAGAGTGACTGAAACTTCACAGAATAGGGTTGAAG

ATTGAATTCATAACTATCCCAAAGACCTATCCATTGCACTATGCTTTA

-continued

TTTAAAAACCACAAAACCTGTGCTGTTGATCTCATAAATAGAACTTGT

ATTTATATTTATTTTCATTTTAGTCTGTCTTCTTGGTTGCTGTTGATA

GACACTAAAAGAGTATTAGATATTATCTAAGTTTGAATATAAGGCTAT

AAATATTTAATAATTTTTAAAATAGTATTCTTGGTAATTGAATTATTC

TTCTGTTTAAAGGCAGAAGAAATAATTGAACATCATCCTGAGTTTTTC

TGTAGGAATCAGAGCCCAATATTTTGAAACAAATGCATAATCTAAGTC

AAATGGAAAGAAATATAAAAAGTAACATTATTACTTCTTGTTTTCTTC

AGTATTTAACAATCCTTTTTTTTCTTCCCTTGCCCAG

TABLE 5

Mouse albumin guide RNA

| Guide ID | Guide Sequence | Mouse Genomic Coordinates (mm10) | SEQ ID NO: |
|---|---|---|---|
| G000551 | AUUUGCAUCUGAGAACCCUU | chr5:90461148-90461168 | 98 |
| G000552 | AUCGGGAACUGGCAUCUUCA | chr5:90461590-90461610 | 99 |
| G000553 | GUUACAGGAAAAUCUGAAGG | chr5:90461569-90461589 | 100 |
| G000554 | GAUCGGGAACUGGCAUCUUC | chr5:90461589-90461609 | 101 |
| G000555 | UGCAUCUGAGAACCCUUAGG | chr5:90461151-90461171 | 102 |
| G000666 | CACUCUUGUCUGUGGAAACA | chr5:90461709-90461729 | 103 |
| G000667 | AUCGUUACAGGAAAAUCUGA | chr5:90461572-90461592 | 104 |
| G000668 | GCAUCUUCAGGGAGUAGCUU | chr5:90461601-90461621 | 105 |
| G000669 | CAAUCUUUAAAUAUGUUGUG | chr5:90461674-90461694 | 106 |
| G000670 | UCACUCUUGUCUGUGGAAAC | chr5:90461710-90461730 | 107 |
| G011722 | UGCUUGUAUUUUUCUAGUAA | chr5:90461039-90461059 | 108 |
| G011723 | GUAAAUAUCUACUAAGACAA | chr5:90461425-90461445 | 109 |
| G011724 | UUUUUCUAGUAAUGGAAGCC | chr5:90461047-90461067 | 110 |
| G011725 | UUAUAUUAUUGAUAUAUUUU | chr5:90461174-90461194 | 111 |
| G011726 | GCACAGAUAUAAACACUUAA | chr5:90461480-90461500 | 112 |
| G011727 | CACAGAUAUAAACACUUAAC | chr5:90461481-90461501 | 113 |
| G011728 | GGUUUUAAAAAUAAUAAUGU | chr5:90461502-90461522 | 114 |
| G011729 | UCAGAUUUUCCUGUAACGAU | chr5:90461572-90461592 | 115 |
| G011730 | CAGAUUUUCCUGUAACGAUC | chr5:90461573-90461593 | 116 |
| G011731 | CAAUGGUAAAUAAGAAAUAA | chr5:90461408-90461428 | 117 |
| G013018 | GGAAAAUCUGAAGGUGGCAA | chr5:90461563-90461583 | 118 |
| G013019 | GGCGAUCUCACUCUUGUCUG | chr5:90461717-90461737 | 119 |

TABLE 6

Mouse albumin sgRNAs and modification pattern

| Guide ID | Full Sequence | SEQ ID NO: | Full Sequence Modified | SEQ ID NO: |
|---|---|---|---|---|
| G000551 | AUUUGCAUCUGAGAACCCUUGUUUUAGAGCUAGAAAUAGCAAGUUAAAAUAAGGCUAGUCCGUUAUCAACUUGAAAAAGUGGCACCGAGUCGGUGCUUUU | 120 | mA*mU*mU*UGCAUCUGAGAACCCUUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 142 |
| G000552 | AUCGGGAACUGGCAUCUUCAGUUUUAGAGCUAGAAAUAGCAAGUUAAAAUAAGGCUAGUCCGUUAUCAACUUGAAAAAGUGGCACCGAGUCGGUGCUUUU | 121 | mA*mU*mC*GGGAACUGGCAUCUUCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 143 |
| G000553 | GUUACAGGAAAAUCUGAAGGGUUUUAGAGCUAGAAAUAGCAAGUUAAAAUAAGGCUAGUCCGUUAUCAACUUGAAAAAGUGGCACCGAGUCGGUGCUUUU | 122 | mG*mU*mU*ACAGGAAAAUCUGAAGGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 144 |
| G000554 | GAUCGGGAACUGGCAUCUUCGUUUUAGAGCUAGAAAUAGCAAGUUAAAAUAAGGCUAGUCCGUUAUCAACUUGAAAAAGUGGCACCGAGUCGGUGCUUUU | 123 | mG*mA*mU*CGGGAACUGGCAUCUUCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 145 |
| G000555 | UGCAUCUGAGAACCCUUAGGGUUUUAGAGCUAGAAAUAGCAAGUUAAAAUAAGGCUAGUCCGUUAUCAACUUGAAAAAGUGGCACCGAGUCGGUGCUUUU | 124 | mU*mG*mC*AUCUGAGAACCCUUAGGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 146 |
| G000666 | CACUCUUGUCUGUGGAAACAGUUUUAGAGCUAGAAAUAGCAAGUUAAAAUAAGGCUAGUCCGUUAUCAACUUGAAAAAGUGGCACCGAGUCGGUGCUUUU | 125 | mC*mA*mC*UCUUGUCUGUGGAAACAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 147 |
| G000667 | AUCGUUACAGGAAAAUCUGAGUUUUAGAGCUAGAAAUAGCAAGUUAAAAUAAGGCUAGUCCGUUAUCAACUUGAAAAAGUGGCACCGAGUCGGUGCUUUU | 126 | mA*mU*mC*GUUACAGGAAAAUCUGAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 148 |
| G000668 | GCAUCUUCAGGGAGUAGCUUGUUUUAGAGCUAGAAAUAGCAAGUUAAAAUAAGGCUAGUCCGUUAUCAACUUGAAAAAGUGGCACCGAGUCGGUGCUUUU | 127 | mG*mC*mA*UCUUCAGGGAGUAGCUUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 149 |
| G000669 | CAAUCUUUAAAUAUGUUGUGGUUUUAGAGCUAGAAAUAGCAAGUUAAAAUAAGGCUAGUCCGUUAUCAACUUGAAAAAGUGGCACCGAGUCGGUGCUUUU | 128 | mC*mA*mA*UCUUUAAAUAUGUUGUGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 150 |
| G000670 | UCACUCUUGUCUGUGGAAACGUUUUAGAGCUAGAAAUAGCAAGUUAAAAUAAGGCUAGUCCGUUAUCAACUUGAAAAAGUGGCACCGAGUCGGUGCUUUU | 129 | mU*mC*mA*CUCUUGUCUGUGGAAACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 151 |
| G011722 | UGCUUGUAUUUUUCUAGUAAGUUUUAGAGCUAGAAAUAGCAAGUUAAAAUAAGGCUAGUCCGUUAUCAACUUGAAAAAGUGGCACCGAGUCGGUGCUUUU | 130 | mU*mG*mC*UUGUAUUUUUCUAGUAAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 152 |
| G011723 | GUAAAUAUCUACUAAGACAAGUUUUAGAGCUAGAAAUAGCAAGUUAAAAUAAGGCUAGUCCGUUAUCAACUUGAAAAAGUGGCACCGAGUCGGUGCUUUU | 131 | mG*mU*mA*AAUAUCUACUAAGACAAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | 153 |
| G011724 | UUUUUCUAGUAAUGGAAGCCGUUUUAGAGCUAGAAAUAGC | 132 | mU*mU*mU*UUCUAGUAAUGGAAGCCGUUUUAGAmGmCmUmAmGmAmAmAmUmAmGmCAAGUUAAAA | 154 |

TABLE 6-continued

| Mouse albumin sgRNAs and modification pattern | | | | |
|---|---|---|---|---|
| Guide ID | Full Sequence | SEQ ID NO: | Full Sequence Modified | SEQ ID NO: |
| | AAGUUAAAAUAAGGCUAGUC CGUUAUCAACUUGAAAAAGU GGCACCGAGUCGGUGCUUUU | | UAAGGCUAGUCCGUUAUCAmAmCmUmUmGmAmA mAmAmAmGmUmGmGmCmAmCmCmGmAmGmUmCm GmGmUmGmCmU*mU*mU*mU | |
| G011725 | UUAUAUUAUUGAUAUAUUUU GUUUUAGAGCUAGAAAUAGC AAGUUAAAAUAAGGCUAGUC CGUUAUCAACUUGAAAAAGU GGCACCGAGUCGGUGCUUUU | 133 | mU*mU*mA*UAUUAUUGAUAUAUUUUGUUUUAGA mGmCmUmAmGmAmAmAmUmAmGmCAAGUUAAAA UAAGGCUAGUCCGUUAUCAmAmCmUmUmGmAmA mAmAmAmGmUmGmGmCmAmCmCmGmAmGmUmCm GmGmUmGmCmU*mU*mU*mU | 155 |
| G011726 | GCACAGAUAUAAACACUUAA GUUUUAGAGCUAGAAAUAGC AAGUUAAAAUAAGGCUAGUC CGUUAUCAACUUGAAAAAGU GGCACCGAGUCGGUGCUUUU | 134 | mG*mC*mA*CAGAUAUAAACACUUAAGUUUUAGA mGmCmUmAmGmAmAmAmUmAmGmCAAGUUAAAA UAAGGCUAGUCCGUUAUCAmAmCmUmUmGmAmA mAmAmAmGmUmGmGmCmAmCmCmGmAmGmUmCm GmGmUmGmCmU*mU*mU*mU | 156 |
| G011727 | CACAGAUAUAAACACUUAAC GUUUUAGAGCUAGAAAUAGC AAGUUAAAAUAAGGCUAGUC CGUUAUCAACUUGAAAAAGU GGCACCGAGUCGGUGCUUUU | 135 | mC*mA*mC*AGAUAUAAACACUUAACGUUUUAGAm GmCmUmAmGmAmAmAmUmAmGmCAAGUUAAAAU AAGGCUAGUCCGUUAUCAmAmCmUmUmGmAmAm AmAmAmGmUmGmGmCmAmCmCmGmAmGmUmCmG mGmUmGmCmU*mU*mU*mU | 157 |
| G011728 | GGUUUUAAAAAUAAUAAUGU GUUUUAGAGCUAGAAAUAGC AAGUUAAAAUAAGGCUAGUC CGUUAUCAACUUGAAAAAGU GGCACCGAGUCGGUGCUUUU | 136 | mG*mG*mU*UUUAAAAAUAAUAAUGUGUUUUAGA mGmCmUmAmGmAmAmAmUmAmGmCAAGUUAAAA UAAGGCUAGUCCGUUAUCAmAmCmUmUmGmAmA mAmAmAmGmUmGmGmCmAmCmCmGmAmGmUmCm GmGmUmGmCmU*mU*mU*mU | 158 |
| G011729 | UCAGAUUUUCCUGUAACGAU GUUUUAGAGCUAGAAAUAGC AAGUUAAAAUAAGGCUAGUC CGUUAUCAACUUGAAAAAGU GGCACCGAGUCGGUGCUUUU | 137 | mU*mC*mA*GAUUUUCCUGUAACGAUGUUUUAGA mGmCmUmAmGmAmAmAmUmAmGmCAAGUUAAAA UAAGGCUAGUCCGUUAUCAmAmCmUmUmGmAmA mAmAmAmGmUmGmGmCmAmCmCmGmAmGmUmCm GmGmUmGmCmU*mU*mU*mU | 159 |
| G011730 | CAGAUUUUCCUGUAACGAUC GUUUUAGAGCUAGAAAUAGC AAGUUAAAAUAAGGCUAGUC CGUUAUCAACUUGAAAAAGU GGCACCGAGUCGGUGCUUUU | 138 | mC*mA*mG*AUUUUCCUGUAACGAUCGUUUUAGAm GmCmUmAmGmAmAmAmUmAmGmCAAGUUAAAAU AAGGCUAGUCCGUUAUCAmAmCmUmUmGmAmAm AmAmAmGmUmGmGmCmAmCmCmGmAmGmUmCmG mGmUmGmCmU*mU*mU*mU | 160 |
| G011731 | CAAUGGUAAAUAAGAAAUAA GUUUUAGAGCUAGAAAUAGC AAGUUAAAAUAAGGCUAGUC CGUUAUCAACUUGAAAAAGU GGCACCGAGUCGGUGCUUUU | 139 | mC*mA*mA*UGGUAAAUAAGAAAUAAGUUUUAGA mGmCmUmAmGmAmAmAmUmAmGmCAAGUUAAAA UAAGGCUAGUCCGUUAUCAmAmCmUmUmGmAmA mAmAmAmGmUmGmGmCmAmCmCmGmAmGmUmCm GmGmUmGmCmU*mU*mU*mU | 161 |
| G013018 | GGAAAAUCUGAAGGUGGCAA GUUUUAGAGCUAGAAAUAGC AAGUUAAAAUAAGGCUAGUC CGUUAUCAACUUGAAAAAGU GGCACCGAGUCGGUGCUUUU | 140 | mG*mG*mA*AAAUCUGAAGGUGGCAAGUUUUAGA mGmCmUmAmGmAmAmAmUmAmGmCAAGUUAAAA UAAGGCUAGUCCGUUAUCAmAmCmUmUmGmAmA mAmAmAmGmUmGmGmCmAmCmCmGmAmGmUmCm GmGmUmGmCmU*mU*mU*mU | 162 |
| G013019 | GGCGAUCUCACUCUUGUCUG GUUUUAGAGCUAGAAAUAGC AAGUUAAAAUAAGGCUAGUC CGUUAUCAACUUGAAAAAGU GGCACCGAGUCGGUGCUUUU | 141 | mG*mG*mC*GAUCUCACUCUUGUCUGGUUUUAGAm GmCmUmAmGmAmAmAmUmAmGmCAAGUUAAAAU AAGGCUAGUCCGUUAUCAmAmCmUmUmGmAmAm AmAmAmGmUmGmGmCmAmCmCmGmAmGmUmCmG mGmUmGmCmU*mU*mU*mU | 163 |

TABLE 7

| Cyno albumin guide RNA | | | |
|---|---|---|---|
| Guide ID | Guide Sequence | Cyno Genomic Coordinates (mf5) | SEQ ID NO: |
| G009844 | GAGCAACCUCACUCUUGUCU | chr5:61198711-61198731 | 2 |
| G009845 | AGCAACCUCACUCUUGUCUG | chr5:61198712-61198732 | 165 |
| G009846 | ACCUCACUCUUGUCUGGGGA | chr5:61198716-61198736 | 166 |

TABLE 7-continued

Cyno albumin guide RNA

| Guide ID | Guide Sequence | Cyno Genomic Coordinates (mf5) | SEQ ID NO: |
|---|---|---|---|
| G009847 | CCUCACUCUUGUCUGGGGAA | chr5:61198717-61198737 | 167 |
| G009848 | CUCACUCUUGUCUGGGGAAG | chr5:61198718-61198738 | 168 |
| G009849 | GGGGAAGGGGAGAAAAAAAA | chr5:61198731-61198751 | 169 |
| G009850 | GGGAAGGGGAGAAAAAAAAA | chr5:61198732-61198752 | 170 |
| G009851 | AUGCAUUUGUUUCAAAAUAU | chr5:61198825-61198845 | 3 |
| G009852 | UGCAUUUGUUUCAAAAUAUU | chr5:61198826-61198846 | 172 |
| G009853 | UGAUUCCUACAGAAAAAGUC | chr5:61198852-61198872 | 173 |
| G009854 | UACAGAAAAAGUCAGGAUAA | chr5:61198859-61198879 | 174 |
| G009855 | UUUCUUCUGCCUUUAAACAG | chr5:61198889-61198909 | 175 |
| G009856 | UUAUAGUUUUAUAUUCAAAC | chr5:61198957-61198977 | 176 |
| G009857 | AUUUAUGAGAUCAACAGCAC | chr5:61199062-61199082 | 5 |
| G009858 | GAUCAACAGCACAGGUUUUG | chr5:61199070-61199090 | 6 |
| G009859 | UUAAAUAAAGCAUAGUGCAA | chr5:61199096-61199116 | 7 |
| G009860 | UAAAGCAUAGUGCAAUGGAU | chr5:61199101-61199121 | 8 |
| G009861 | UAGUGCAAUGGAUAGGUCUU | chr5:61199108-61199128 | 9 |
| G009862 | AGUGCAAUGGAUAGGUCUUA | chr5:61199109-61199129 | 182 |
| G009863 | UUACUUUGCACUUUCCUUAG | chr5:61199186-61199206 | 183 |
| G009864 | UACUUUGCACUUUCCUUAGU | chr5:61199187-61199207 | 184 |
| G009865 | UCUGACCUUUUAUUUUACCU | chr5:61199238-61199258 | 185 |
| G009866 | UACUAAAACUUUAUUUUACU | chr5:61199367-61199387 | 10 |
| G009867 | AAAGUUGAACAAUAGAAAAA | chr5:61199401-61199421 | 11 |
| G009868 | AAUGCAUAAUCUAAGUCAAA | chr5:61198812-61198832 | 12 |
| G009869 | AUUAUCCUGACUUUUUCUGU | chr5:61198860-61198880 | 189 |
| G009870 | UGAAUUAUUCCUCUGUUUAA | chr5:61198901-61198921 | 190 |
| G009871 | UAAUUUUCUUUUGCCCACUA | chr5:61199203-61199223 | 191 |
| G009872 | AAAAGGUCAGAAUUGUUUAG | chr5:61199229-61199249 | 192 |
| G009873 | AACAUCCUAGGUAAAAUAAA | chr5:61199246-61199266 | 193 |
| G009874 | UAAUAAAAUUCAAACAUCCU | chr5:61199258-61199278 | 13 |
| G009875 | UUGUCAUGUAUUUCUAAAAU | chr5:61199322-61199342 | 195 |
| G009876 | UUUGUCAUGUAUUUCUAAAA | chr5:61199323-61199343 | 196 |

TABLE 8

Cyno sgRNA and modification patterns

| Guide ID | Full Sequence | SEQ ID NO: | Full Sequence Modified | SEQ ID NO: |
|---|---|---|---|---|
| G009844 | GAGCAACCUCACUCUUGUCU GUUUUAGAGCUAGAAAUAGC | 34 | mG*mA*mG*CAACCUCACUCUUGUCUGUUUUAG AmGmCmUmAmGmAmAmAmUmAmGmCAAGUUA | 66 |

TABLE 8-continued

| Cyno sgRNA and modification patterns | | | | |
|---|---|---|---|---|
| Guide ID | Full Sequence | SEQ ID NO: | Full Sequence Modified | SEQ ID NO: |
| | AAGUUAAAAUAAGGCUAGUC CGUUAUCAACUUGAAAAAGU GGCACCGAGUCGGUGCUUUU | | AAAUAAGGCUAGUCCGUUAUCAmAmCmUmUm GmAmAmAmAmAmGmUmGmGmCmAmCmCmGm AmGmUmCmGmGmUmGmCmU*mU*mU*mU | |
| G009845 | AGCAACCUCACUCUUGUCUG GUUUUAGAGCUAGAAAUAGC AAGUUAAAAUAAGGCUAGUC CGUUAUCAACUUGAAAAAGU GGCACCGAGUCGGUGCUUUU | 198 | mA*mG*mC*AACCUCACUCUUGUCUGGUUUUAG AmGmCmUmAmGmAmAmAmUmAmGmCAAGUUA AAAUAAGGCUAGUCCGUUAUCAmAmCmUmUm GmAmAmAmAmAmGmUmGmGmCmAmCmCmGm AmGmUmCmGmGmUmGmCmU*mU*mU*mU | 231 |
| G009846 | ACCUCACUCUUGUCUGGGGA GUUUUAGAGCUAGAAAUAGC AAGUUAAAAUAAGGCUAGUC CGUUAUCAACUUGAAAAAGU GGCACCGAGUCGGUGCUUUU | 199 | mA*mC*mC*UCACUCUUGUCUGGGGAGUUUU AGAmGmCmUmAmGmAmAmAmUmAmGmCAA GUUAAAAUAAGGCUAGUCCGUUAUCAmAmCm UmUmGmAmAmAmAmAmGmUmGmGmCmAmCm CmGmAmGmUmCmGmGmUmGmCmU*mU*mU*mU | 232 |
| G009847 | CCUCACUCUUGUCUGGGGAA GUUUUAGAGCUAGAAAUAGC AAGUUAAAAUAAGGCUAGUC CGUUAUCAACUUGAAAAAGU GGCACCGAGUCGGUGCUUUU | 200 | mC*mC*mU*CACUCUUGUCUGGGGAAGUUUUA GAmGmCmUmAmGmAmAmAmUmAmGmCAAGU UAAAAUAAGGCUAGUCCGUUAUCAmAmCmUm UmGmAmAmAmAmAmGmUmGmGmCmAmCmCm GmAmGmUmCmGmGmUmGmCmU*mU*mU*mU | 233 |
| G009848 | CUCACUCUUGUCUGGGGAAG GUUUUAGAGCUAGAAAUAGC AAGUUAAAAUAAGGCUAGUC CGUUAUCAACUUGAAAAAGU GGCACCGAGUCGGUGCUUUU | 201 | mC*mU*mC*ACUCUUGUCUGGGGAAGGUUUU AGAmGmCmUmAmGmAmAmAmUmAmGmCAA GUUAAAAUAAGGCUAGUCCGUUAUCAmAmCm UmUmGmAmAmAmAmAmGmUmGmGmCmAmCm CmGmAmGmUmCmGmGmUmGmCmU*mU*mU*mU | 234 |
| G009849 | GGGGAAGGGGAGAAAAAAAA GUUUUAGAGCUAGAAAUAGC AAGUUAAAAUAAGGCUAGUC CGUUAUCAACUUGAAAAAGU GGCACCGAGUCGGUGCUUUU | 202 | mG*mG*mG*GAAGGGGAGAAAAAAAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 235 |
| G009850 | GGGAAGGGGAGAAAAAAAAA GUUUUAGAGCUAGAAAUAGC AAGUUAAAAUAAGGCUAGUC CGUUAUCAACUUGAAAAAGU GGCACCGAGUCGGUGCUUUU | 203 | mG*mG*mG*AAGGGGAGAAAAAAAAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 236 |
| G009851 | AUGCAUUUGUUUCAAAAUAU GUUUUAGAGCUAGAAAUAGC AAGUUAAAAUAAGGCUAGUC CGUUAUCAACUUGAAAAAGU GGCACCGAGUCGGUGCUUUU | 35 | mA*mU*mG*CAUUUGUUUCAAAAUAUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 67 |
| G009852 | UGCAUUUGUUUCAAAAUAUU GUUUUAGAGCUAGAAAUAGC AAGUUAAAAUAAGGCUAGUC CGUUAUCAACUUGAAAAAGU GGCACCGAGUCGGUGCUUUU | 36 | mU*mG*mC*AUUUGUUUCAAAAUAUUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 68 |
| G009853 | UGAUUCCUACAGAAAAAGUC GUUUUAGAGCUAGAAAUAGC AAGUUAAAAUAAGGCUAGUC CGUUAUCAACUUGAAAAAGU GGCACCGAGUCGGUGCUUUU | 206 | mU*mG*mA*UUCCUACAGAAAAAGUCGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 239 |
| G009854 | UACAGAAAAAGUCAGGAUAA GUUUUAGAGCUAGAAAUAGC AAGUUAAAAUAAGGCUAGUC CGUUAUCAACUUGAAAAAGU GGCACCGAGUCGGUGCUUUU | 207 | mU*mA*mC*AGAAAAAGUCAGGAUAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 240 |
| G009855 | UUUCUUCUGCCUUUAAACAG GUUUUAGAGCUAGAAAUAGC AAGUUAAAAUAAGGCUAGUC CGUUAUCAACUUGAAAAAGU GGCACCGAGUCGGUGCUUUU | 208 | mU*mU*mU*CUUCUGCCUUUAAACAGGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 241 |

TABLE 8-continued

Cyno sgRNA and modification patterns

| Guide ID | Full Sequence | SEQ ID NO: | Full Sequence Modified | SEQ ID NO: |
|---|---|---|---|---|
| G009856 | UUAUAGUUUUAUAUUCAAAC GUUUUAGAGCUAGAAAUAGC AAGUUAAAAUAAGGCUAGUC CGUUAUCAACUUGAAAAAGU GGCACCGAGUCGGUGCUUUU | 209 | mU*mU*mA*UAGUUUUAUAUUCAAACGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 242 |
| G009857 | AUUUAUGAGAUCAACAGCAC GUUUUAGAGCUAGAAAUAGC AAGUUAAAAUAAGGCUAGUC CGUUAUCAACUUGAAAAAGU GGCACCGAGUCGGUGCUUUU | 37 | mA*mU*mU*UAUGAGAUCAACAGCACGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 69 |
| G009858 | GAUCAACAGCACAGGUUUUG GUUUUAGAGCUAGAAAUAGC AAGUUAAAAUAAGGCUAGUC CGUUAUCAACUUGAAAAAGU GGCACCGAGUCGGUGCUUUU | 38 | mG*mA*mU*CAACAGCACAGGUUUUGGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 70 |
| G009859 | UUAAAUAAAGCAUAGUGCAA GUUUUAGAGCUAGAAAUAGC AAGUUAAAAUAAGGCUAGUC CGUUAUCAACUUGAAAAAGU GGCACCGAGUCGGUGCUUUU | 39 | mU*mU*mA*AAUAAAGCAUAGUGCAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 71 |
| G009860 | UAAAGCAUAGUGCAAUGGAU GUUUUAGAGCUAGAAAUAGC AAGUUAAAAUAAGGCUAGUC CGUUAUCAACUUGAAAAAGU GGCACCGAGUCGGUGCUUUU | 40 | mU*mA*mA*AGCAUAGUGCAAUGGAUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 72 |
| G009861 | UAGUGCAAUGGAUAGGUCUU GUUUUAGAGCUAGAAAUAGC AAGUUAAAAUAAGGCUAGUC CGUUAUCAACUUGAAAAAGU GGCACCGAGUCGGUGCUUUU | 41 | mU*mA*mG*UGCAAUGGAUAGGUCUUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 73 |
| G009862 | AGUGCAAUGGAUAGGUCUUA GUUUUAGAGCUAGAAAUAGC AAGUUAAAAUAAGGCUAGUC CGUUAUCAACUUGAAAAAGU GGCACCGAGUCGGUGCUUUU | 215 | mA*mG*mU*GCAAUGGAUAGGUCUUAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 248 |
| G009863 | UUACUUUGCACUUUCCUUAG GUUUUAGAGCUAGAAAUAGC AAGUUAAAAUAAGGCUAGUC CGUUAUCAACUUGAAAAAGU GGCACCGAGUCGGUGCUUUU | 216 | mU*mU*mA*CUUUGCACUUUCCUUAGGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 249 |
| G009864 | UACUUUGCACUUUCCUUAGU GUUUUAGAGCUAGAAAUAGC AAGUUAAAAUAAGGCUAGUC CGUUAUCAACUUGAAAAAGU GGCACCGAGUCGGUGCUUUU | 217 | mU*mA*mC*UUUGCACUUUCCUUAGUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 250 |
| G009865 | UCUGACCUUUUAUUUUACCU GUUUUAGAGCUAGAAAUAGC AAGUUAAAAUAAGGCUAGUC CGUUAUCAACUUGAAAAAGU GGCACCGAGUCGGUGCUUUU | 218 | mU*mC*mU*GACCUUUUAUUUUACCUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 251 |
| G009866 | UACUAAAACUUUAUUUUACU GUUUUAGAGCUAGAAAUAGC AAGUUAAAAUAAGGCUAGUC CGUUAUCAACUUGAAAAAGU GGCACCGAGUCGGUGCUUUU | 42 | mU*mA*mC*UAAAACUUUAUUUUACUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 74 |
| G009867 | AAAGUUGAACAAUAGAAAAA GUUUUAGAGCUAGAAAUAGC AAGUUAAAAUAAGGCUAGUC CGUUAUCAACUUGAAAAAGU GGCACCGAGUCGGUGCUUUU | 43 | mA*mA*mA*GUUGAACAAUAGAAAAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 75 |

TABLE 8-continued

| Cyno sgRNA and modification patterns | | | | |
|---|---|---|---|---|
| Guide ID | Full Sequence | SEQ ID NO: | Full Sequence Modified | SEQ ID NO: |
| G009868 | AAUGCAUAAUCUAAGUCAAA GUUUUAGAGCUAGAAAUAGC AAGUUAAAAUAAGGCUAGUC CGUUAUCAACUUGAAAAAGU GGCACCGAGUCGGUGCUUUU | 44 | mA*mA*mU*GCAUAAUCUAAGUCAAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 76 |
| G009869 | AUUAUCCUGACUUUUUCUGU GUUUUAGAGCUAGAAAUAGC AAGUUAAAAUAAGGCUAGUC CGUUAUCAACUUGAAAAAGU GGCACCGAGUCGGUGCUUUU | 222 | mA*mU*mU*AUCCUGACUUUUUCUGUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 255 |
| G009870 | UGAAUUAUUCCUCUGUUUAA GUUUUAGAGCUAGAAAUAGC AAGUUAAAAUAAGGCUAGUC CGUUAUCAACUUGAAAAAGU GGCACCGAGUCGGUGCUUUU | 223 | mU*mG*mA*AUUAUUCCUCUGUUUAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 256 |
| G009871 | UAAUUUUCUUUUGCCCACUA GUUUUAGAGCUAGAAAUAGC AAGUUAAAAUAAGGCUAGUC CGUUAUCAACUUGAAAAAGU GGCACCGAGUCGGUGCUUUU | 224 | mU*mA*mA*UUUUCUUUUGCCCACUAGUUUUAG AmGmCmUmAmGmAmAmAmUmAmGmCAAGUUAA AAUAAGGCUAGUCCGUUAUCAmAmCmUmUm GmAmAmAmAmAmGmUmGmGmCmAmCmCmGm AmGmUmCmGmGmUmGmCmU*mU*mU*mU | 257 |
| G009872 | AAAAGGUCAGAAUUGUUUAG GUUUUAGAGCUAGAAAUAGC AAGUUAAAAUAAGGCUAGUC CGUUAUCAACUUGAAAAAGU GGCACCGAGUCGGUGCUUUU | 225 | mA*mA*mA*AGGUCAGAAUUGUUUAGGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 258 |
| G009873 | AACAUCCUAGGUAAAAUAAA GUUUUAGAGCUAGAAAUAGC AAGUUAAAAUAAGGCUAGUC CGUUAUCAACUUGAAAAAGU GGCACCGAGUCGGUGCUUUU | 226 | mA*mA*mC*AUCCUAGGUAAAAUAAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 259 |
| G009874 | UAAUAAAAUUCAAACAUCCU GUUUUAGAGCUAGAAAUAGC AAGUUAAAAUAAGGCUAGUC CGUUAUCAACUUGAAAAAGU GGCACCGAGUCGGUGCUUUU | 45 | mU*mA*mA*UAAAAUUCAAACAUCCUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 77 |
| G009875 | UUGUCAUGUAUUUCUAAAAU GUUUUAGAGCUAGAAAUAGC AAGUUAAAAUAAGGCUAGUC CGUUAUCAACUUGAAAAAGU GGCACCGAGUCGGUGCUUUU | 228 | mU*mU*mG*UCAUGUAUUUCUAAAAUGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 261 |
| G009876 | UUUGUCAUGUAUUUCUAAAA GUUUUAGAGCUAGAAAUAGC AAGUUAAAAUAAGGCUAGUC CGUUAUCAACUUGAAAAAGU GGCACCGAGUCGGUGCUUUU | 229 | mU*mU*mU*GUCAUGUAUUUCUAAAAGUUUUAG AmGmCmUmAmGmAmAmAmUmAmGmCAAGUUAA AAUAAGGCUAGUCCGUUAUCAmAmCmUmUmGm AmAmAmAmAmGmUmGmGmCmAmCmCmGmAmGm UmCmGmGmUmGmCmU*mU*mU*mU | 262 |

TABLE 9

| Vector Components and Sequences | | | | | | | | |
|---|---|---|---|---|---|---|---|---|
| | | 1st orientation | | | 2nd orientation | | | |
| Plasmid ID | 5' ITR | Splice Acceptor | Transgene | Poly-A | Poly-A | Transgene | Splice Acceptor | 3' ITR |
| P00147 | (SEQ ID NO: 263) | Mouse Albumin Splice Acceptor (SEQ ID NO: 264) | Human Factor IX (R338L) (SEQ ID NO: 265) | SEQ ID NO: 266 | SEQ ID NO: 267 | Human Factor IX (R338L) (SEQ ID NO: 268) | Mouse Albumin Splice Acceptor (SEQ ID NO: 269) | (SEQ ID NO: 270) |

TABLE 9-continued

Vector Components and Sequences

| | | 1st orientation | | | 2nd orientation | | | |
|---|---|---|---|---|---|---|---|---|
| Plasmid ID | 5' ITR | Splice Acceptor | Transgene | Poly-A | Poly-A | Transgene | Splice Acceptor | 3' ITR |
| P00411 | (SEQ ID NO: 263) | Human Factor IX Splice Acceptor (SEQ ID NO: 271) | Human Factor IX (R338L)-HiBit (SEQ ID NO: 272) | SEQ ID NO: 266 | SEQ ID NO: 267 | Human Factor IX (R338L)-HiBit (SEQ ID NO: 273) | Human Factor IX Splice Acceptor (SEQ ID NO: 274) | (SEQ ID NO: 270) |
| P00415 | (SEQ ID NO: 263) | Mouse Albumin Splice Acceptor (SEQ ID NO: 264) | Nluc-P2A-GFP (SEQ ID NO: 275) | SEQ ID NO: 266 | SEQ ID NO: 267 | Nluc-P2A-GFP (SEQ ID NO: 276) | Mouse Albumin Splice Acceptor (SEQ ID NO: 269) | (SEQ ID NO: 270) |
| P00418 | (SEQ ID NO: 263) | Mouse Albumin Splice Acceptor (SEQ ID NO: 264) | Human Factor IX (R338L)-HiBit (SEQ ID NO: 272) | SEQ ID NO: 266 | SEQ ID NO: 267 | Human Factor IX (R338L)-HiBit (SEQ ID NO: 273) | Mouse Albumin Splice Acceptor (SEQ ID NO: 269) | (SEQ ID NO: 270) |

5' ITR Sequence (SEQ ID NO: 263):
TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCT

Mouse Albumin Splice Acceptor (1st orientation) (SEQ ID NO: 264):
TAGGTCAGTGAAGAGAAGAACAAAAAGCAGCATATTACAGTTAGTTGTCTTCATCA

ATCTTTAAATATGTTGTGTGGTTTTTCTCTCCCTGTTTCCACAG

Human Factor IX (R338L), 1st Orientation (SEQ ID NO: 265):
TTTCTTGATCATGAAAACGCCAACAAAATTCTGAATCGGCCAAAGAGGTATAATTCA

GGTAAATTGGAAGAGTTTGTTCAAGGGAACCTTGAGAGAGAATGTATGGAAGAAAA

GTGTAGTTTTGAAGAAGCACGAGAAGTTTTTGAAAACACTGAAAGAACAACTGAAT

TTTGGAAGCAGTATGTTGATGGAGATCAGTGTGAGTCCAATCCATGTTTAAATGGCG

GCAGTTGCAAGGATGACATTAATTCCTATGAATGTTGGTGTCCCTTTGGATTTGAAG

GAAAGAACTGTGAATTAGATGTAACATGTAACATTAAGAATGGCAGATGCGAGCAG

TTTTGTAAAAATAGTGCTGATAACAAGGTGGTTTGCTCCTGTACTGAGGGATATCGA

CTTGCAGAAAACCAGAAGTCCTGTGAACCAGCAGTGCCATTTCCATGTGGAAGAGTT

TCTGTTTCACAAACTTCTAAGCTCACCCGTGCTGAGACTGTTTTTCCTGATGTGGACT

ATGTAAATTCTACTGAAGCTGAAACCATTTTGGATAACATCACTCAAAGCACCCAAT

CATTTAATGACTTCACTCGGGTTGTTGGTGGAGAAGATGCCAAACCAGGTCAATTCC

CTTGGCAGGTTGTTTTGAATGGTAAAGTTGATGCATTCTGTGGAGGCTCTATCGTTA

ATGAAAAATGGATTGTAACTGCTGCCCACTGTGTTGAAACTGGTGTTAAAATTACAG

TTGTCGCAGGTGAACATAATATTGAGGAGACAGAACATACAGAGCAAAAGCGAAAT

GTGATTCGAATTATTCCTCACCACAACTACAATGCAGCTATTAATAAGTACAACCAT

GACATTGCCCTTCTGGAACTGGACGAACCCTTAGTGCTAAACAGCTACGTTACACCT

ATTTGCATTGCTGACAAGGAATACACGAACATCTTCCTCAAATTTGGATCTGGCTAT

-continued

GTAAGTGGCTGGGGAAGAGTCTTCCACAAAGGGAGATCAGCTTTAGTTCTTCAGTAC

CTTAGAGTTCCACTTGTTGACCGAGCCACATGTCTTCTATCTACAAAGTTCACCATCT

ATAACAACATGTTCTGTGCTGGCTTCCATGAAGGAGGTAGAGATTCATGTCAAGGAG

ATAGTGGGGGACCCCATGTTACTGAAGTGGAAGGGACCAGTTTCTTAACTGGAATTA

TTAGCTGGGGTGAAGAGTGTGCAATGAAAGGCAAATATGGAATATATACCAAGGTA

TCCCGGTATGTCAACTGGATTAAGGAAAAAACAAAGCTCACTTAA

Poly-A (1$^{st}$ orientation) (SEQ ID NO: 266):
CCTCGACTGTGCCTTCTAGTTGCCAGCCATCTGTTGTTTGCCCCTCCCCCGTGCCTTC

CTTGACCCTGGAAGGTGCCACTCCCACTGTCCTTTCCTAATAAAATGAGGAAATTGC

ATCGCATTGTCTGAGTAGGTGTCATTCTATTCTGGGGGGTGGGGTGGGGCAGGACAG

CAAGGGGGAGGATTGGGAAGACAATAGCAGGCATGCTGGGGATGCGGTGGGCTCTA

TGGCTTCTGAGGCGGAAAGAACCAGCTGGGGCTCTAGGGGGTATCCCC

Poly-A (2$^{nd}$ orientation) (SEQ ID NO: 267):
AAAAAACCTCCCACACCTCCCCCTGAACCTGAAACATAAAATGAATGCAATTGTTGT

TGTTAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATC

AATGTATCTTATCATGTCTG

Human Factor IX (R338L), 2$^{nd}$ Orientation (SEQ ID NO: 268):
TTAGGTGAGCTTAGTCTTTTCTTTTATCCAATTCACGTAGCGAGAGACCTTCGTATAG

ATGCCATATTTCCCCTTCATCGCACATTCCTCCCCCCAACTTATTATCCCGGTCAAGA

AACTTGTTCCTTCGACTTCAGTGACGTGTGGTCCACCTGAATCACCTTGGCATGAGTC

GCGACCGCCCTCGTGAAACCCAGCACAAAACATGTTATTGTAAATCGTAAATTTCGT

GGACAGAAGACAGGTCGCTCTATCGACCAACGGGACGCGCAAATATTGCAGAACGA

GGGCTGATCGACCTTTGTGGAAGACCCGCCCCCACCCACTCACATATCCGCTCCCAA

ATTTCAAGAAGATATTTGTATATTCTTTATCGGCTATACAAATCGGGGTAACATAGG

AGTTAAGTACGAGTGGCTCGTCCAGCTCCAGGAGGGCTATATCATGGTTGTACTTGT

TTATAGCGGCATTATAATTGTGATGGGGTATGATCCTGATAACATTCCTTTTCTGTTC

AGTATGCTCAGTTTCTTCAATGTTGTGTTCGCCAGCCACGACCGTAATCTTAACCCCC

GTCTCGACACAGTGTGCGGCCGTTACAATCCACTTTTCATTGACTATGGAGCCCCCA

CAAAACGCGTCGACTTTTCCGTTGAGCACCACCTGCCATGGAAATTGGCCAGGTTTA

GCGTCCTCGCCCCCGACAACCCTAGTAAAGTCATTAAATGACTGTGTGGATTGTGTT

ATATTATCAAGAATCGTTTCGGCTTCAGTAGAGTTAACGTAGTCCACATCGGGAAAA

ACTGTCTCGGCCCTTGTCAACTTTGATGTCTGGGACACACTTACCCGACCGCACGGG

AAGGGCACCGCCGGTTCACAGCTCTTTTGATTCTCAGCGAGCCGGTAGCCCTCAGTG

CAACTACACACAACTTTGTTGTCGGCGGAATTTTTACAGAATTGCTCGCATCGTCCA

TTTTTAATGTTGCAGGTGACGTCCAACTCGCAGTTTTTTCCTTCAAAACCAAAAGGG

CACCAACACTCGTAGGAATTTATATCGTCTTTACAACTCCCCCCATTCAGACATGGA

TTAGATTCGCATTGGTCCCCATCGACATATTGCTTCCAGAACTCAGTGGTCCGTTCTG

TATTCTCAAACACCTCGCGCGCTTCTTCAAAACTGCATTTTTCCTCCATACACTCTCG

CTCCAAGTTCCCTTGCACGAATTCTTCAAGCTTTCCTGAGTTATACCTTTTAGGCCGG

TTAAGTATCTTATTCGCGTTTTCGTGGTCCAGAAA

-continued

Mouse Albumin Splice Acceptor (2nd orientation) (SEQ ID NO: 269):
CTGTGGAAACAGGGAGAGAAAAACCACACAACATATTTAAAGATTGATGAAGACAA

CTAACTGTAATATGCTGCTTTTTGTTCTTCTCTTCACTGACCTA

3' ITR Sequence (SEQ ID NO: 270):
AGGAACCCCTAGTGATGGAGTTGGCCACTCCCTCTCTGCGCGCTCGCTCGCTCACTG

AGGCCGCCCGGGCAAAGCCCGGGCGTCGGGCGACCTTTGGTCGCCCGGCCTCAGTG

AGCGAGCGAGCGCGCAGAGAGGGAGTGGCCAA

Human Factor IX Splice Acceptor (1st Orientation) (SEQ ID NO: 271):
GATTATTTGGATTAAAAACAAAGACTTTCTTAAGAGATGTAAAATTTTCATGATGTT

TTCTTTTTTGCTAAAACTAAAGAATTATTCTTTTACATTTCAG

Human Factor IX (R338L)-HiBit (1st Orientation) (SEQ ID NO: 272):
TTTCTTGATCATGAAAACGCCAACAAAATTCTGAATCGGCCAAAGAGGTATAATTCA

GGTAAATTGGAAGAGTTTGTTCAAGGGAACCTTGAGAGAGAATGTATGGAAGAAAA

GTGTAGTTTTGAAGAAGCACGAGAAGTTTTTGAAAACACTGAAAGAACAACTGAAT

TTTGGAAGCAGTATGTTGATGGAGATCAGTGTGAGTCCAATCCATGTTTAAATGGCG

GCAGTTGCAAGGATGACATTAATTCCTATGAATGTTGGTGTCCCTTTGGATTTGAAG

GAAAGAACTGTGAATTAGATGTAACATGTAACATTAAGAATGGCAGATGCGAGCAG

TTTTGTAAAAATAGTGCTGATAACAAGGTGGTTTGCTCCTGTACTGAGGGATATCGA

CTTGCAGAAAACCAGAAGTCCTGTGAACCAGCAGTGCCATTTCCATGTGGAAGAGTT

TCTGTTTCACAAACTTCTAAGCTCACCCGTGCTGAGACTGTTTTTCCTGATGTGGACT

ATGTAAATTCTACTGAAGCTGAAACCATTTTGGATAACATCACTCAAAGCACCCAAT

CATTTAATGACTTCACTCGGGTTGTTGGTGGAGAAGATGCCAAACCAGGTCAATTCC

CTTGGCAGGTTGTTTTGAATGGTAAAGTTGATGCATTCTGTGGAGGCTCTATCGTTA

ATGAAAAATGGATTGTAACTGCTGCCCACTGTGTTGAAACTGGTGTTAAAATTACAG

TTGTCGCAGGTGAACATAATATTGAGGAGACAGAACATACAGAGCAAAAGCGAAAT

GTGATTCGAATTATTCCTCACCACAACTACAATGCAGCTATTAATAAGTACAACCAT

GACATTGCCCTTCTGGAACTGGACGAACCCTTAGTGCTAAACAGCTACGTTACACCT

ATTTGCATTGCTGACAAGGAATACACGAACATCTTCCTCAAATTTGGATCTGGCTAT

GTAAGTGGCTGGGGAAGAGTCTTCCACAAAGGGAGATCAGCTTTAGTTCTTCAGTAC

CTTAGAGTTCCACTTGTTGACCGAGCCACATGTCTTCTATCTACAAAGTTCACCATCT

ATAACAACATGTTCTGTGCTGGCTTCCATGAAGGAGGTAGAGATTCATGTCAAGGAG

ATAGTGGGGGACCCCATGTTACTGAAGTGGAAGGGACCAGTTTCTTAACTGGAATTA

TTAGCTGGGGTGAAGAGTGTGCAATGAAAGGCAAATATGGAATATATACCAAGGTC

TCCCGGTATGTCAACTGGATTAAGGAAAAAACAAAGCTCACTGTCAGCGGATGGAG

ACTGTTCAAGAAGATCAGCTAA

Human Factor IX (R338L)-HiBit (2nd Orientation) (SEQ ID NO: 273):
TTAGGAAATCTTCTTAAACAGCCGCCAGCCGCTCACGGTGAGCTTAGTCTTTTCTTTT

ATCCAATTCACGTAGCGAGAGACCTTCGTATAGATGCCATATTTCCCCTTCATCGCA

CATTCCTCCCCCCAACTTATTATCCCGGTCAAGAAACTTGTTCCTTCGACTTCAGTGA

CGTGTGGTCCACCTGAATCACCTTGGCATGAGTCGCGACCGCCCTCGTGAAACCCAG

CACAAAACATGTTATTGTAAATCGTAAATTTCGTGGACAGAAGACAGGTCGCTCTAT

CGACCAACGGGACGCGCAAATATTGCAGAACGAGGGCTGATCGACCTTTGTGGAAG

ACCCGCCCCCACCCACTCACATATCCGCTCCCAAATTTCAAGAAGATATTTGTATAT

-continued

TCTTTATCGGCTATACAAATCGGGGTAACATAGGAGTTAAGTACGAGTGGCTCGTCC

AGCTCCAGGAGGGCTATATCATGGTTGTACTTGTTTATAGCGGCATTATAATTGTGA

TGGGGTATGATCCTGATAACATTCCTTTTCTGTTCAGTATGCTCAGTTTCTTCAATGT

TGTGTTCGCCAGCCACGACCGTAATCTTAACCCCCGTCTCGACACAGTGTGCGGCCG

TTACAATCCACTTTTCATTGACTATGGAGCCCCCACAAAACGCGTCGACTTTTCCGTT

GAGCACCACCTGCCATGGAAATTGGCCAGGTTTAGCGTCCTCGCCCCCGACAACCCT

AGTAAAGTCATTAAATGACTGTGTGGATTGTGTTATATTATCAAGAATCGTTTCGGC

TTCAGTAGAGTTAACGTAGTCCACATCGGGAAAAACTGTCTCGGCCCTTGTCAACTT

TGATGTCTGGGACACACTTACCCGACCGCACGGGAAGGGCACCGCCGGTTCACAGC

TCTTTTGATTCTCAGCGAGCCGGTAGCCCTCAGTGCAACTACACACAACTTTGTTGTC

GGCGGAATTTTTACAGAATTGCTCGCATCGTCCATTTTTAATGTTGCAGGTGACGTCC

AACTCGCAGTTTTTTCCTTCAAAACCAAAAGGGCACCAACACTCGTAGGAATTTATA

TCGTCTTTACAACTCCCCCCATTCAGACATGGATTAGATTCGCATTGGTCCCCATCGA

CATATTGCTTCCAGAACTCAGTGGTCCGTTCTGTATTCTCAAACACCTCGCGCGCTTC

TTCAAAACTGCATTTTTCCTCCATACACTCTCGCTCCAAGTTCCCTTGCACGAATTCT

TCAAGCTTTCCTGAGTTATACCTTTTAGGCCGGTTAAGTATCTTATTCGCGTTTTCGT

GGTCCAGAAA

Human Factor IX Splice Acceptor (2nd Orientation) (SEQ ID NO: 274):
CTGAAATGTAAAAGAATAATTCTTTAGTTTTAGCAAAAAAGAAAACATCATGAAAA

TTTTACATCTCTTAAGAAAGTCTTTGTTTTTAATCCAAATAATC

Nluc-P2A-GFP (1st Orientation) (SEQ ID NO: 275):
TTTCTTGATCATGAAAACGCCAACAAAATTCTGAATCGGCCAAAGAGGTATAATTCA

GGTAAATTGGAAGAGTTTGTTCAAGGGAACCTTGAGAGAGAATGTATGGAAGAAAA

GTGTAGTTTTGAAGAAGCAGTATTCACTTTGGAGGACTTTGTCGGTGACTGGAGGCA

AACCGCTGGTTATAATCTCGACCAAGTACTGGAACAGGGCGGGGTAAGTTCCCTCTT

TCAGAATTTGGGTGTAAGCGTCACACCAATCCAGCGGATTGTGTTGTCTGGAGAGAA

CGGACTCAAAATTGACATCCATGTTATCATTCCATATGAAGGTCTCAGTGGAGACCA

AATGGGGCAGATCGAGAAGATTTTCAAGGTAGTTTACCCAGTCGACGATCACCACTT

CAAAGTCATTCTCCACTATGGCACACTTGTTATCGACGGAGTAACTCCTAATATGAT

TGATTACTTTGGTCGCCCGTATGAGGGCATCGCAGTGTTTGATGGCAAAAAGATCAC

CGTAACAGGAACGTTGTGGAATGGGAACAAGATAATCGACGAGAGATTGATAAATC

CAGACGGGTCACTCCTGTTCAGGGTTACAATTAACGGCGTCACAGGATGGAGACTCT

GTGAACGAATACTGGCCACAAATTTTTCACTCCTGAAGCAGGCCGGAGACGTGGAG

GAAAACCCAGGGCCCGTGAGCAAGGGCGAGGAGCTGTTCACCGGGGTGGTGCCCAT

CCTGGTCGAGCTGGACGGCGACGTAAACGGCCACAAGTTCAGCGTGTCCGGCGAGG

GCGAGGGCGATGCCACCTACGGCAAGCTGACCCTGAAGTTCATCTGCACCACCGGC

AAGCTGCCCGTGCCCTGGCCCACCCTCGTGACCACCCTGACCTACGGCGTGCAGTGC

TTCAGCCGCTACCCCGACCACATGAAGCAGCACGACTTCTTCAAGTCCGCCATGCCC

GAAGGCTACGTCCAGGAGCGCACCATCTTCTTCAAGGACGACGGCAACTACAAGAC

CCGCGCCGAGGTGAAGTTCGAGGGCGACACCCTGGTGAACCGCATCGAGCTGAAGG

GCATCGACTTCAAGGAGGACGGCAACATCCTGGGGCACAAGCTGGAGTACAACTAC

-continued

AACAGCCACAACGTCTATATCATGGCCGACAAGCAGAAGAACGGCATCAAGGTGAA

CTTCAAGATCCGCCACAACATCGAGGACGGCAGCGTGCAGCTCGCCGACCACTACC

AGCAGAACACCCCCATCGGCGACGGCCCCGTGCTGCTGCCCGACAACCACTACCTG

AGCACCCAGTCCGCCCTGAGCAAAGACCCCAACGAGAAGCGCGATCACATGGTCCT

GCTGGAGTTCGTGACCGCCGCCGGGATCACTCTCGGCATGGACGAGCTGTACAAGG

GAGGAGGAAGCCCGAAGAAGAAGAGAAAGGTCTAA

Nluc-P2A-GFP (2nd Orientation) (SEQ ID NO: 276):

TTACACCTTCCTCTTCTTCTTGGGGCTGCCGCCGCCCTTGTACAGCTCGTCCATGCCC

AGGGTGATGCCGGCGGCGGTCACGAACTCCAGCAGCACCATGTGGTCCCTCTTCTCG

TTGGGGTCCTTGCTCAGGGCGCTCTGGGTGCTCAGGTAGTGGTTGTCGGGCAGCAGC

ACGGGGCCGTCGCCGATGGGGGTGTTCTGCTGGTAGTGGTCGGCCAGCTGCACGCTG

CCGTCCTCGATGTTGTGCCTGATCTTGAAGTTCACCTTGATGCCGTTCTTCTGCTTGT

CGGCCATGATGTACACGTTGTGGCTGTTGTAGTTGTACTCCAGCTTGTGGCCCAGGA

TGTTGCCGTCCTCCTTGAAGTCGATGCCCTTCAGCTCGATCCTGTTCACCAGGGTGTC

GCCCTCGAACTTCACCTCGGCCCTGGTCTTGTAGTTGCCGTCGTCCTTGAAGAAGAT

GGTCCTCTCCTGCACGTAGCCCTCGGGCATGGCGCTCTTGAAGAAGTCGTGCTGCTT

CATGTGGTCGGGGTACCTGCTGAAGCACTGCACGCCGTAGGTCAGGGTGGTCACCA

GGGTGGGCCAGGGCACGGGCAGCTTGCCGGTGGTGCAGATGAACTTCAGGGTCAGC

TTGCCGTAGGTGGCGTCGCCCTCGCCCTCGCCGCTCACGCTGAACTTGTGGCCGTTC

ACGTCGCCGTCCAGCTCCACCAGGATGGGCACCACGCCGGTGAACAGCTCCTCGCC

CTTGCTCACGGGGCCGGGGTTCTCCTCCACGTCGCCGGCCTGCTTCAGCAGGCTGAA

GTTGGTGGCCAGGATCCTCTCGCACAGCCTCCAGCCGGTCACGCCGTTGATGGTCAC

CCTGAACAGCAGGCTGCCGTCGGGGTTGATCAGCCTCTCGTCGATGATCTTGTTGCC

GTTCCACAGGGTGCCGGTCACGGTGATCTTCTTGCCGTCGAACACGGCGATGCCCTC

GTAGGGCCTGCCGAAGTAGTCGATCATGTTGGGGGTCACGCCGTCGATCACCAGGG

TGCCGTAGTGCAGGATCACCTTGAAGTGGTGGTCGTCCACGGGGTACACCACCTTGA

AAATCTTCTCGATCTGGCCCATCTGGTCGCCGCTCAGGCCCTCGTAGGGGATGATCA

CGTGGATGTCGATCTTCAGGCCGTTCTCGCCGCTCAGCACGATCCTCTGGATGGGGG

TCACGCTCACGCCCAGGTTCTGGAACAGGCTGCTCACGCCGCCCTGCTCCAGCACCT

GGTCCAGGTTGTAGCCGGCGGTCTGCCTCCAGTCGCCCACGAAGTCCTCCAGGGTGA

ACACGGCCTCCTCGAAGCTGCACTTCTCCTCCATGCACTCCCTCTCCAGGTTGCCCTG

CACGAACTCCTCCAGCTTGCCGCTGTTGTACCTCTTGGGCCTGTTCAGGATCTTGTTG

GCGTTCTCGTGGTCCAGGAA

P00147 full sequence (from ITR to ITR):

(SEQ ID NO: 277)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTCTTAGGTCAGTGAAGAGA

AGAACAAAAAGCAGCATATTACAGTTAGTTGTCTTCATCAATCTTTAAATATGTTGT

GTGGTTTTTCTCTCCCTGTTTCCACAGTTTTTCTTGATCATGAAAACGCCAACAAAAT

TCTGAATCGGCCAAAGAGGTATAATTCAGGTAAATTGGAAGAGTTTGTTCAAGGGA

ACCTTGAGAGAGAATGTATGGAAGAAAAGTGTAGTTTTGAAGAAGCACGAGAAGTT

-continued

TTTGAAAACACTGAAAGAACAACTGAATTTTGGAAGCAGTATGTTGATGGAGATCA

GTGTGAGTCCAATCCATGTTTAAATGGCGGCAGTTGCAAGGATGACATTAATTCCTA

TGAATGTTGGTGTCCCTTTGGATTTGAAGGAAAGAACTGTGAATTAGATGTAACATG

TAACATTAAGAATGGCAGATGCGAGCAGTTTTGTAAAAATAGTGCTGATAACAAGG

TGGTTTGCTCCTGTACTGAGGGATATCGACTTGCAGAAAACCAGAAGTCCTGTGAAC

CAGCAGTGCCATTTCCATGTGGAAGAGTTTCTGTTTCACAAACTTCTAAGCTCACCC

GTGCTGAGACTGTTTTTCCTGATGTGGACTATGTAAATTCTACTGAAGCTGAAACCA

TTTTGGATAACATCACTCAAAGCACCCAATCATTTAATGACTTCACTCGGGTTGTTG

GTGGAGAAGATGCCAAACCAGGTCAATTCCCTTGGCAGGTTGTTTTGAATGGTAAAG

TTGATGCATTCTGTGGAGGCTCTATCGTTAATGAAAAATGGATTGTAACTGCTGCCC

ACTGTGTTGAAACTGGTGTTAAAATTACAGTTGTCGCAGGTGAACATAATATTGAGG

AGACAGAACATACAGAGCAAAAGCGAAATGTGATTCGAATTATTCCTCACCACAAC

TACAATGCAGCTATTAATAAGTACAACCATGACATTGCCCTTCTGGAACTGGACGAA

CCCTTAGTGCTAAACAGCTACGTTACACCTATTTGCATTGCTGACAAGGAATACACG

AACATCTTCCTCAAATTTGGATCTGGCTATGTAAGTGGCTGGGGAAGAGTCTTCCAC

AAAGGGAGATCAGCTTTAGTTCTTCAGTACCTTAGAGTTCCACTTGTTGACCGAGCC

ACATGTCTTCTATCTACAAAGTTCACCATCTATAACAACATGTTCTGTGCTGGCTTCC

ATGAAGGAGGTAGAGATTCATGTCAAGGAGATAGTGGGGGACCCCATGTTACTGAA

GTGGAAGGGACCAGTTTCTTAACTGGAATTATTAGCTGGGGTGAAGAGTGTGCAAT

GAAAGGCAAATATGGAATATATACCAAGGTATCCCGGTATGTCAACTGGATTAAGG

AAAAAACAAAGCTCACTTAACCTCGACTGTGCCTTCTAGTTGCCAGCCATCTGTTGT

TTGCCCCTCCCCCGTGCCTTCCTTGACCCTGGAAGGTGCCACTCCCACTGTCCTTTCC

TAATAAAATGAGGAAATTGCATCGCATTGTCTGAGTAGGTGTCATTCTATTCTGGGG

GGTGGGGTGGGGCAGGACAGCAAGGGGGAGGATTGGGAAGACAATAGCAGGCATG

CTGGGGATGCGGTGGGCTCTATGGCTTCTGAGGCGGAAAGAACCAGCTGGGGCTCT

AGGGGGTATCCCCAAAAAACCTCCCACACCTCCCCCTGAACCTGAAACATAAAATG

AATGCAATTGTTGTTGTTAACTTGTTTATTGCAGCTTATAATGGTTACAAATAAAGCA

ATAGCATCACAAATTTCACAAATAAAGCATTTTTTTCACTGCATTCTAGTTGTGGTTT

GTCCAAACTCATCAATGTATCTTATCATGTCTGTTAGGTGAGCTTAGTCTTTTCTTTT

ATCCAATTCACGTAGCGAGAGACCTTCGTATAGATGCCATATTTCCCCTTCATCGCA

CATTCCTCCCCCCAACTTATTATCCCGGTCAAGAAACTTGTTCCTTCGACTTCAGTGA

CGTGTGGTCCACCTGAATCACCTTGGCATGAGTCGCGACCGCCCTCGTGAAACCCAG

CACAAAACATGTTATTGTAAATCGTAAATTTCGTGGACAGAAGACAGGTCGCTCTAT

CGACCAACGGGACGCGCAAATATTGCAGAACGAGGGCTGATCGACCTTTGTGGAAG

ACCCGCCCCCACCCACTCACATATCCGCTCCCAAATTTCAAGAAGATATTTGTATAT

TCTTTATCGGCTATACAAATCGGGGTAACATAGGAGTTAAGTACGAGTGGCTCGTCC

AGCTCCAGGAGGGCTATATCATGGTTGTACTTGTTTATAGCGGCATTATAATTGTGA

TGGGGTATGATCCTGATAACATTCCTTTTCTGTTCAGTATGCTCAGTTTCTTCAATGT

TGTGTTCGCCAGCCACGACCGTAATCTTAACCCCCGTCTCGACACAGTGTGCGGCCG

TTACAATCCACTTTTCATTGACTATGGAGCCCCCACAAAACGCGTCGACTTTTCCGTT

GAGCACCACCTGCCATGGAAATTGGCCAGGTTTAGCGTCCTCGCCCCCGACAACCCT

-continued

AGTAAAGTCATTAAATGACTGTGTGGATTGTGTTATATTATCAAGAATCGTTTCGGC

TTCAGTAGAGTTAACGTAGTCCACATCGGGAAAAACTGTCTCGGCCCTTGTCAACTT

TGATGTCTGGGACACACTTACCCGACCGCACGGGAAGGGCACCGCCGGTTCACAGC

TCTTTTGATTCTCAGCGAGCCGGTAGCCCTCAGTGCAACTACACACAACTTTGTTGTC

GGCGGAATTTTTACAGAATTGCTCGCATCGTCCATTTTTAATGTTGCAGGTGACGTCC

AACTCGCAGTTTTTTCCTTCAAAACCAAAAGGGCACCAACACTCGTAGGAATTTATA

TCGTCTTTACAACTCCCCCCATTCAGACATGGATTAGATTCGCATTGGTCCCCATCGA

CATATTGCTTCCAGAACTCAGTGGTCCGTTCTGTATTCTCAAACACCTCGCGCGCTTC

TTCAAAACTGCATTTTTCCTCCATACACTCTCGCTCCAAGTTCCCTTGCACGAATTCT

TCAAGCTTTCCTGAGTTATACCTTTTAGGCCGGTTAAGTATCTTATTCGCGTTTTCGT

GGTCCAGAAAAACTGTGGAAACAGGGAGAGAAAAACCACACAACATATTTAAAGA

TTGATGAAGACAACTAACTGTAATATGCTGCTTTTTGTTCTTCTCTTCACTGACCTAA

GAGATCTAGGAACCCCTAGTGATGGAGTTGGCCACTCCCTCTCTGCGCGCTCGCTCG

CTCACTGAGGCCGCCCGGGCAAAGCCCGGGCGTCGGGCGACCTTTGGTCGCCCGGC

CTCAGTGAGCGAGCGAGCGCGCAGAGAGGGAGTGGCCAA

P00411 full sequence (form ITR to ITR):

(SEQ ID NO: 278)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTCTGATTATTTGGATTAAAA

ACAAAGACTTTCTTAAGAGATGTAAAATTTTCATGATGTTTTCTTTTTTGCTAAAACT

AAAGAATTATTCTTTTACATTTCAGTTTTTCTTGATCATGAAAACGCCAACAAAATTC

TGAATCGGCCAAAGAGGTATAATTCAGGTAAATTGGAAGAGTTTGTTCAAGGGAAC

CTTGAGAGAGAATGTATGGAAGAAAAGTGTAGTTTTGAAGAAGCACGAGAAGTTT

TGAAAACACTGAAAGAACAACTGAATTTTGGAAGCAGTATGTTGATGGAGATCAGT

GTGAGTCCAATCCATGTTTAAATGGCGGCAGTTGCAAGGATGACATTAATTCCTATG

AATGTTGGTGTCCCTTTGGATTTGAAGGAAAGAACTGTGAATTAGATGTAACATGTA

ACATTAAGAATGGCAGATGCGAGCAGTTTTGTAAAAATAGTGCTGATAACAAGGTG

GTTTGCTCCTGTACTGAGGGATATCGACTTGCAGAAAACCAGAAGTCCTGTGAACCA

GCAGTGCCATTTCCATGTGGAAGAGTTTCTGTTTCACAAACTTCTAAGCTCACCCGT

GCTGAGACTGTTTTTCCTGATGTGGACTATGTAAATTCTACTGAAGCTGAAACCATTT

TGGATAACATCACTCAAAGCACCCAATCATTTAATGACTTCACTCGGGTTGTTGGTG

GAGAAGATGCCAAACCAGGTCAATTCCCTTGGCAGGTTGTTTTGAATGGTAAAGTTG

ATGCATTCTGTGGAGGCTCTATCGTTAATGAAAAATGGATTGTAACTGCTGCCCACT

GTGTTGAAACTGGTGTTAAAATTACAGTTGTCGCAGGTGAACATAATATTGAGGAGA

CAGAACATACAGAGCAAAAGCGAAATGTGATTCGAATTATTCCTCACCACAACTAC

AATGCAGCTATTAATAAGTACAACCATGACATTGCCCTTCTGGAACTGGACGAACCC

TTAGTGCTAAACAGCTACGTTACACCTATTTGCATTGCTGACAAGGAATACACGAAC

ATCTTCCTCAAATTTGGATCTGGCTATGTAAGTGGCTGGGGAAGAGTCTTCCACAAA

GGGAGATCAGCTTTAGTTCTTCAGTACCTTAGAGTTCCACTTGTTGACCGAGCCACA

TGTCTTCTATCTACAAAGTTCACCATCTATAACAACATGTTCTGTGCTGGCTTCCATG

-continued

AAGGAGGTAGAGATTCATGTCAAGGAGATAGTGGGGGACCCCATGTTACTGAAGTG

GAAGGGACCAGTTTCTTAACTGGAATTATTAGCTGGGGTGAAGAGTGTGCAATGAA

AGGCAAATATGGAATATATACCAAGGTCTCCCGGTATGTCAACTGGATTAAGGAAA

AAACAAAGCTCACTGTCAGCGGATGGAGACTGTTCAAGAAGATCAGCTAACCTCGA

CTGTGCCTTCTAGTTGCCAGCCATCTGTTGTTTGCCCCTCCCCCGTGCCTTCCTTGAC

CCTGGAAGGTGCCACTCCCACTGTCCTTTCCTAATAAAATGAGGAAATTGCATCGCA

TTGTCTGAGTAGGTGTCATTCTATTCTGGGGGGTGGGGTGGGGCAGGACAGCAAGG

GGGAGGATTGGGAAGACAATAGCAGGCATGCTGGGGATGCGGTGGGCTCTATGGCT

TCTGAGGCGGAAAGAACCAGCTGGGGCTCTAGGGGGTATCCCCAAAAAACCTCCCA

CACCTCCCCCTGAACCTGAAACATAAAATGAATGCAATTGTTGTTGTTAACTTGTTT

ATTGCAGCTTATAATGGTTACAAATAAAGCAATAGCATCACAAATTTCACAAATAAA

GCATTTTTTTCACTGCATTCTAGTTGTGGTTTGTCCAAACTCATCAATGTATCTTATC

ATGTCTGTTAGGAAATCTTCTTAAACAGCCGCCAGCCGCTCACGGTGAGCTTAGTCT

TTTCTTTTATCCAATTCACGTAGCGAGAGACCTTCGTATAGATGCCATATTTCCCCTT

CATCGCACATTCCTCCCCCCAACTTATTATCCCGGTCAAGAAACTTGTTCCTTCGACT

TCAGTGACGTGTGGTCCACCTGAATCACCTTGGCATGAGTCGCGACCGCCCTCGTGA

AACCCAGCACAAAACATGTTATTGTAAATCGTAAATTTCGTGGACAGAAGACAGGT

CGCTCTATCGACCAACGGGACGCGCAAATATTGCAGAACGAGGGCTGATCGACCTT

TGTGGAAGACCCGCCCCCACCCACTCACATATCCGCTCCCAAATTTCAAGAAGATAT

TTGTATATTCTTTATCGGCTATACAAATCGGGGTAACATAGGAGTTAAGTACGAGTG

GCTCGTCCAGCTCCAGGAGGGCTATATCATGGTTGTACTTGTTTATAGCGGCATTAT

AATTGTGATGGGGTATGATCCTGATAACATTCCTTTTCTGTTCAGTATGCTCAGTTTC

TTCAATGTTGTGTTCGCCAGCCACGACCGTAATCTTAACCCCCGTCTCGACACAGTG

TGCGGCCGTTACAATCCACTTTTCATTGACTATGGAGCCCCCACAAAACGCGTCGAC

TTTTCCGTTGAGCACCACCTGCCATGGAAATTGGCCAGGTTTAGCGTCCTCGCCCCC

GACAACCCTAGTAAAGTCATTAAATGACTGTGTGGATTGTGTTATATTATCAAGAAT

CGTTTCGGCTTCAGTAGAGTTAACGTAGTCCACATCGGGAAAAAACTGTCTCGGCCCT

TGTCAACTTTGATGTCTGGGACACACTTACCCGACCGCACGGGAAGGGCACCGCCG

GTTCACAGCTCTTTTGATTCTCAGCGAGCCGGTAGCCCTCAGTGCAACTACACACAA

CTTTGTTGTCGGCGGAATTTTTACAGAATTGCTCGCATCGTCCATTTTTAATGTTGCA

GGTGACGTCCAACTCGCAGTTTTTTCCTTCAAAACCAAAAGGGCACCAACACTCGTA

GGAATTTATATCGTCTTTACAACTCCCCCCATTCAGACATGGATTAGATTCGCATTGG

TCCCCATCGACATATTGCTTCCAGAACTCAGTGGTCCGTTCTGTATTCTCAAACACCT

CGCGCGCTTCTTCAAAACTGCATTTTTCCTCCATACACTCTCGCTCCAAGTTCCCTTG

CACGAATTCTTCAAGCTTTCCTGAGTTATACCTTTTAGGCCGGTTAAGTATCTTATTC

GCGTTTTCGTGGTCCAGAAAAACTGAAATGTAAAAGAATAATTCTTTAGTTTTAGCA

AAAAAGAAAACATCATGAAAATTTTACATCTCTTAAGAAAGTCTTTGTTTTTAATCC

AAATAATCAGAGATCTAGGAACCCCTAGTGATGGAGTTGGCCACTCCCTCTCTGCGC

GCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAA

-continued

P00415 full sequence (from ITR to ITR):

(SEQ ID NO: 279)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTCTTAGGTCAGTGAAGAGA

AGAACAAAAAGCAGCATATTACAGTTAGTTGTCTTCATCAATCTTTAAATATGTTGT

GTGGTTTTTCTCTCCCTGTTTCCACAGTTTTTCTTGATCATGAAAACGCCAACAAAAT

TCTGAATCGGCCAAAGAGGTATAATTCAGGTAAATTGGAAGAGTTTGTTCAAGGGA

ACCTTGAGAGAGAATGTATGGAAGAAAAGTGTAGTTTTGAAGAAGCAGTATTCACT

TTGGAGGACTTTGTCGGTGACTGGAGGCAAACCGCTGGTTATAATCTCGACCAAGTA

CTGGAACAGGGCGGGGTAAGTTCCCTCTTTCAGAATTTGGGTGTAAGCGTCACACCA

ATCCAGCGGATTGTGTTGTCTGGAGAGAACGGACTCAAAATTGACATCCATGTTATC

ATTCCATATGAAGGTCTCAGTGGAGACCAAATGGGGCAGATCGAGAAGATTTTCAA

GGTAGTTTACCCAGTCGACGATCACCACTTCAAAGTCATTCTCCACTATGGCACACT

TGTTATCGACGGAGTAACTCCTAATATGATTGATTACTTTGGTCGCCCGTATGAGGG

CATCGCAGTGTTTGATGGCAAAAAGATCACCGTAACAGGAACGTTGTGGAATGGGA

ACAAGATAATCGACGAGAGATTGATAAATCCAGACGGGTCACTCCTGTTCAGGGTT

ACAATTAACGGCGTCACAGGATGGAGACTCTGTGAACGAATACTGGCCACAAATTT

TTCACTCCTGAAGCAGGCCGGAGACGTGGAGGAAAACCCAGGGCCCGTGAGCAAGG

GCGAGGAGCTGTTCACCGGGGTGGTGCCCATCCTGGTCGAGCTGGACGGCGACGTA

AACGGCCACAAGTTCAGCGTGTCCGGCGAGGGCGAGGGCGATGCCACCTACGGCAA

GCTGACCCTGAAGTTCATCTGCACCACCGGCAAGCTGCCCGTGCCCTGGCCCACCCT

CGTGACCACCCTGACCTACGGCGTGCAGTGCTTCAGCCGCTACCCCGACCACATGAA

GCAGCACGACTTCTTCAAGTCCGCCATGCCCGAAGGCTACGTCCAGGAGCGCACCA

TCTTCTTCAAGGACGACGGCAACTACAAGACCCGCGCCGAGGTGAAGTTCGAGGGC

GACACCCTGGTGAACCGCATCGAGCTGAAGGGCATCGACTTCAAGGAGGACGGCAA

CATCCTGGGGCACAAGCTGGAGTACAACTACAACAGCCACAACGTCTATATCATGG

CCGACAAGCAGAAGAACGGCATCAAGGTGAACTTCAAGATCCGCCACAACATCGAG

GACGGCAGCGTGCAGCTCGCCGACCACTACCAGCAGAACACCCCCATCGGCGACGG

CCCCGTGCTGCTGCCCGACAACCACTACCTGAGCACCCAGTCCGCCCTGAGCAAAG

ACCCCAACGAGAAGCGCGATCACATGGTCCTGCTGGAGTTCGTGACCGCCGCCGGG

ATCACTCTCGGCATGGACGAGCTGTACAAGGGAGGAGGAAGCCCGAAGAAGAAGA

GAAAGGTCTAACCTCGACTGTGCCTTCTAGTTGCCAGCCATCTGTTGTTTGCCCCTCC

CCCGTGCCTTCCTTGACCCTGGAAGGTGCCACTCCCACTGTCCTTTCCTAATAAAATG

AGGAAATTGCATCGCATTGTCTGAGTAGGTGTCATTCTATTCTGGGGGGTGGGGTGG

GGCAGGACAGCAAGGGGGAGGATTGGGAAGACAATAGCAGGCATGCTGGGGATGC

GGTGGGCTCTATGGCTTCTGAGGCGGAAAGAACCAGCTGGGGCTCTAGGGGGTATC

CCCAAAAAACCTCCCACACCTCCCCCTGAACCTGAAACATAAAATGAATGCAATTGT

TGTTGTTAACTTGTTTATTGCAGCTTATAATGGTTACAAATAAAGCAATAGCATCAC

AAATTTCACAAATAAAGCATTTTTTTCACTGCATTCTAGTTGTGGTTTGTCCAAACTC

ATCAATGTATCTTATCATGTCTGTTACACCTTCCTCTTCTTCTTGGGGCTGCCGCCGC

-continued

CCTTGTACAGCTCGTCCATGCCCAGGGTGATGCCGGCGGCGGTCACGAACTCCAGCA

GCACCATGTGGTCCCTCTTCTCGTTGGGGTCCTTGCTCAGGGCGCTCTGGGTGCTCAG

GTAGTGGTTGTCGGGCAGCAGCACGGGGCCGTCGCCGATGGGGGTGTTCTGCTGGT

AGTGGTCGGCCAGCTGCACGCTGCCGTCCTCGATGTTGTGCCTGATCTTGAAGTTCA

CCTTGATGCCGTTCTTCTGCTTGTCGGCCATGATGTACACGTTGTGGCTGTTGTAGTT

GTACTCCAGCTTGTGGCCCAGGATGTTGCCGTCCTCCTTGAAGTCGATGCCCTTCAG

CTCGATCCTGTTCACCAGGGTGTCGCCCTCGAACTTCACCTCGGCCCTGGTCTTGTAG

TTGCCGTCGTCCTTGAAGAAGATGGTCCTCTCCTGCACGTAGCCCTCGGGCATGGCG

CTCTTGAAGAAGTCGTGCTGCTTCATGTGGTCGGGGTACCTGCTGAAGCACTGCACG

CCGTAGGTCAGGGTGGTCACCAGGGTGGGCCAGGGCACGGGCAGCTTGCCGGTGGT

GCAGATGAACTTCAGGGTCAGCTTGCCGTAGGTGGCGTCGCCCTCGCCCTCGCCGCT

CACGCTGAACTTGTGGCCGTTCACGTCGCCGTCCAGCTCCACCAGGATGGGCACCAC

GCCGGTGAACAGCTCCTCGCCCTTGCTCACGGGGCCGGGGTTCTCCTCCACGTCGCC

GGCCTGCTTCAGCAGGCTGAAGTTGGTGGCCAGGATCCTCTCGCACAGCCTCCAGCC

GGTCACGCCGTTGATGGTCACCCTGAACAGCAGGCTGCCGTCGGGGTTGATCAGCCT

CTCGTCGATGATCTTGTTGCCGTTCCACAGGGTGCCGGTCACGGTGATCTTCTTGCCG

TCGAACACGGCGATGCCCTCGTAGGGCCTGCCGAAGTAGTCGATCATGTTGGGGGTC

ACGCCGTCGATCACCAGGGTGCCGTAGTGCAGGATCACCTTGAAGTGGTGGTCGTCC

ACGGGGTACACCACCTTGAAAATCTTCTCGATCTGGCCCATCTGGTCGCCGCTCAGG

CCCTCGTAGGGGATGATCACGTGGATGTCGATCTTCAGGCCGTTCTCGCCGCTCAGC

ACGATCCTCTGGATGGGGGTCACGCTCACGCCCAGGTTCTGGAACAGGCTGCTCACG

CCGCCCTGCTCCAGCACCTGGTCCAGGTTGTAGCCGGCGGTCTGCCTCCAGTCGCCC

ACGAAGTCCTCCAGGGTGAACACGGCCTCCTCGAAGCTGCACTTCTCCTCCATGCAC

TCCCTCTCCAGGTTGCCCTGCACGAACTCCTCCAGCTTGCCGCTGTTGTACCTCTTGG

GCCTGTTCAGGATCTTGTTGGCGTTCTCGTGGTCCAGGAA

P00418 full sequence (from ITR to ITR):

(SEQ ID NO: 280)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTCTTAGGTCAGTGAAGAGA

AGAACAAAAAGCAGCATATTACAGTTAGTTGTCTTCATCAATCTTTAAATATGTTGT

GTGGTTTTTCTCTCCCTGTTTCCACAGTTTTTCTTGATCATGAAAACGCCAACAAAAT

TCTGAATCGGCCAAAGAGGTATAATTCAGGTAAATTGGAAGAGTTTGTTCAAGGGA

ACCTTGAGAGAGAATGTATGGAAGAAAAGTGTAGTTTTGAAGAAGCACGAGAAGTT

TTTGAAAACACTGAAAGAACAACTGAATTTTGGAAGCAGTATGTTGATGGAGATCA

GTGTGAGTCCAATCCATGTTTAAATGGCGGCAGTTGCAAGGATGACATTAATTCCTA

TGAATGTTGGTGTCCCTTTGGATTTGAAGGAAAGAACTGTGAATTAGATGTAACATG

TAACATTAAGAATGGCAGATGCGAGCAGTTTTGTAAAAATAGTGCTGATAACAAGG

TGGTTTGCTCCTGTACTGAGGGATATCGACTTGCAGAAAACCAGAAGTCCTGTGAAC

CAGCAGTGCCATTTCCATGTGGAAGAGTTTCTGTTTCACAAACTTCTAAGCTCACCC

GTGCTGAGACTGTTTTTCCTGATGTGGACTATGTAAATTCTACTGAAGCTGAAACCA

TTTTGGATAACATCACTCAAAGCACCCAATCATTTAATGACTTCACTCGGGTTGTTG

-continued

GTGGAGAAGATGCCAAACCAGGTCAATTCCCTTGGCAGGTTGTTTTGAATGGTAAAG

TTGATGCATTCTGTGGAGGCTCTATCGTTAATGAAAAATGGATTGTAACTGCTGCCC

ACTGTGTTGAAACTGGTGTTAAAATTACAGTTGTCGCAGGTGAACATAATATTGAGG

AGACAGAACATACAGAGCAAAAGCGAAATGTGATTCGAATTATTCCTCACCACAAC

TACAATGCAGCTATTAATAAGTACAACCATGACATTGCCCTTCTGGAACTGGACGAA

CCCTTAGTGCTAAACAGCTACGTTACACCTATTTGCATTGCTGACAAGGAATACACG

AACATCTTCCTCAAATTTGGATCTGGCTATGTAAGTGGCTGGGGAAGAGTCTTCCAC

AAAGGGAGATCAGCTTTAGTTCTTCAGTACCTTAGAGTTCCACTTGTTGACCGAGCC

ACATGTCTTCTATCTACAAAGTTCACCATCTATAACAACATGTTCTGTGCTGGCTTCC

ATGAAGGAGGTAGAGATTCATGTCAAGGAGATAGTGGGGGACCCCATGTTACTGAA

GTGGAAGGGACCAGTTTCTTAACTGGAATTATTAGCTGGGGTGAAGAGTGTGCAAT

GAAAGGCAAATATGGAATATATACCAAGGTCTCCCGGTATGTCAACTGGATTAAGG

AAAAAACAAAGCTCACTGTCAGCGGATGGAGACTGTTCAAGAAGATCAGCTAACCT

CGACTGTGCCTTCTAGTTGCCAGCCATCTGTTGTTTGCCCCTCCCCCGTGCCTTCCTT

GACCCTGGAAGGTGCCACTCCCACTGTCCTTTCCTAATAAAATGAGGAAATTGCATC

GCATTGTCTGAGTAGGTGTCATTCTATTCTGGGGGGTGGGGTGGGGCAGGACAGCA

AGGGGGAGGATTGGGAAGACAATAGCAGGCATGCTGGGGATGCGGTGGGCTCTATG

GCTTCTGAGGCGGAAAGAACCAGCTGGGGCTCTAGGGGGTATCCCCAAAAAACCTC

CCACACCTCCCCCTGAACCTGAAACATAAAATGAATGCAATTGTTGTTGTTAACTTG

TTTATTGCAGCTTATAATGGTTACAAATAAAGCAATAGCATCACAAATTTCACAAAT

AAAGCATTTTTTTCACTGCATTCTAGTTGTGGTTTGTCCAAACTCATCAATGTATCTT

ATCATGTCTGTTAGGAAATCTTCTTAAACAGCCGCCAGCCGCTCACGGTGAGCTTAG

TCTTTTCTTTTATCCAATTCACGTAGCGAGAGACCTTCGTATAGATGCCATATTTCCC

CTTCATCGCACATTCCTCCCCCCAACTTATTATCCCGGTCAAGAAACTTGTTCCTTCG

ACTTCAGTGACGTGTGGTCCACCTGAATCACCTTGGCATGAGTCGCGACCGCCCTCG

TGAAACCCAGCACAAAACATGTTATTGTAAATCGTAAATTTCGTGGACAGAAGACA

GGTCGCTCTATCGACCAACGGGACGCGCAAATATTGCAGAACGAGGGCTGATCGAC

CTTTGTGGAAGACCCGCCCCCACCCACTCACATATCCGCTCCCAAATTTCAAGAAGA

TATTTGTATATTCTTTATCGGCTATACAAATCGGGGTAACATAGGAGTTAAGTACGA

GTGGCTCGTCCAGCTCCAGGAGGGCTATATCATGGTTGTACTTGTTTATAGCGGCAT

TATAATTGTGATGGGGTATGATCCTGATAACATTCCTTTTCTGTTCAGTATGCTCAGT

TTCTTCAATGTTGTGTTCGCCAGCCACGACCGTAATCTTAACCCCCGTCTCGACACA

GTGTGCGGCCGTTACAATCCACTTTTCATTGACTATGGAGCCCCCACAAAACGCGTC

GACTTTTCCGTTGAGCACCACCTGCCATGGAAATTGGCCAGGTTTAGCGTCCTCGCC

CCCGACAACCCTAGTAAAGTCATTAAATGACTGTGTGGATTGTGTTATATTATCAAG

AATCGTTTCGGCTTCAGTAGAGTTAACGTAGTCCACATCGGGAAAAACTGTCTCGGC

CCTTGTCAACTTTGATGTCTGGGACACACTTACCCGACCGCACGGGAAGGGCACCGC

CGGTTCACAGCTCTTTTGATTCTCAGCGAGCCGGTAGCCCTCAGTGCAACTACACAC

AACTTTGTTGTCGGCGGAATTTTTACAGAATTGCTCGCATCGTCCATTTTTAATGTTG

CAGGTGACGTCCAACTCGCAGTTTTTTCCTTCAAAACCAAAAGGGCACCAACACTCG

-continued

TAGGAATTTATATCGTCTTTACAACTCCCCCCATTCAGACATGGATTAGATTCGCATT

GGTCCCCATCGACATATTGCTTCCAGAACTCAGTGGTCCGTTCTGTATTCTCAAACAC

CTCGCGCGCTTCTTCAAAACTGCATTTTTCCTCCATACACTCTCGCTCCAAGTTCCCT

TGCACGAATTCTTCAAGCTTTCCTGAGTTATACCTTTTAGGCCGGTTAAGTATCTTAT

TCGCGTTTTCGTGGTCCAGAAAAACTGTGGAAACAGGGAGAGAAAAACCACACAAC

ATATTTAAAGATTGATGAAGACAACTAACTGTAATATGCTGCTTTTTGTTCTTCTCTT

CACTGACCTAAGAGATCTAGGAACCCCTAGTGATGGAGTTGGCCACTCCCTCTCTGC

GCGCTCGCTCGCTCACTGAGGCCGCCCGGGCAAAGCCCGGGCGTCGGGCGACCTTT

GGTCGCCCGGCCTCAGTGAGCGAGCGAGCGCGCAGAGAGGGAGTGGCCAA

P00123 full sequence (from ITR to ITR):

(SEQ ID NO: 281)

GGCCACTCCCTCTCTGCGCGCTCGCTCGCTCACTGAGGCCGGGCGACCAAAGGTCGC

CCGACGCCCGGGCTTTGCCCGGGCGGCCTCAGTGAGCGAGCGAGCGCGCAGAGAGG

GAGTGGCCAACTCCATCACTAGGGGTTCCTGGAGGGGTGGAGTCGTGATAGGTCAG

TGAAGAGAAGAACAAAAAGCAGCATATTACAGTTAGTTGTCTTCATCAATCTTTAAA

TATGTTGTGTGGTTTTTCTCTCCCTGTTTCCACAGTTTTTCTTGATCATGAAAACGCCA

ACAAAATTCTGAATCGGCCAAAGAGGTATAATTCAGGTAAATTGGAAGAGTTTGTTC

AAGGGAACCTTGAGAGAGAATGTATGGAAGAAAAGTGTAGTTTTGAAGAAGCACGA

GAAGTTTTTGAAAACACTGAAAGAACAACTGAATTTTGGAAGCAGTATGTTGATGG

AGATCAGTGTGAGTCCAATCCATGTTTAAATGGCGGCAGTTGCAAGGATGACATTAA

TTCCTATGAATGTTGGTGTCCCTTTGGATTTGAAGGAAAGAACTGTGAATTAGATGT

AACATGTAACATTAAGAATGGCAGATGCGAGCAGTTTTGTAAAAATAGTGCTGATA

ACAAGGTGGTTTGCTCCTGTACTGAGGGATATCGACTTGCAGAAAACCAGAAGTCCT

GTGAACCAGCAGTGCCATTTCCATGTGGAAGAGTTTCTGTTTCACAAACTTCTAAGC

TCACCCGTGCTGAGACTGTTTTTCCTGATGTGGACTATGTAAATTCTACTGAAGCTGA

AACCATTTTGGATAACATCACTCAAAGCACCCAATCATTTAATGACTTCACTCGGGT

TGTTGGTGGAGAAGATGCCAAACCAGGTCAATTCCCTTGGCAGGTTGTTTTGAATGG

TAAAGTTGATGCATTCTGTGGAGGCTCTATCGTTAATGAAAAATGGATTGTAACTGC

TGCCCACTGTGTTGAAACTGGTGTTAAAATTACAGTTGTCGCAGGTGAACATAATAT

TGAGGAGACAGAACATACAGAGCAAAAGCGAAATGTGATTCGAATTATTCCTCACC

ACAACTACAATGCAGCTATTAATAAGTACAACCATGACATTGCCCTTCTGGAACTGG

ACGAACCCTTAGTGCTAAACAGCTACGTTACACCTATTTGCATTGCTGACAAGGAAT

ACACGAACATCTTCCTCAAATTTGGATCTGGCTATGTAAGTGGCTGGGGAAGAGTCT

TCCACAAAGGGAGATCAGCTTTAGTTCTTCAGTACCTTAGAGTTCCACTTGTTGACC

GAGCCACATGTCTTCTATCTACAAAGTTCACCATCTATAACAACATGTTCTGTGCTG

GCTTCCATGAAGGAGGTAGAGATTCATGTCAAGGAGATAGTGGGGGACCCCATGTT

ACTGAAGTGGAAGGGACCAGTTTCTTAACTGGAATTATTAGCTGGGGTGAAGAGTG

TGCAATGAAAGGCAAATATGGAATATATACCAAGGTATCCCGGTATGTCAACTGGA

TTAAGGAAAAAACAAAGCTCACTTAACCTCGACTGTGCCTTCTAGTTGCCAGCCATC

TGTTGTTTGCCCCTCCCCCGTGCCTTCCTTGACCCTGGAAGGTGCCACTCCCACTGTC

CTTTCCTAATAAAATGAGGAAATTGCATCGCATTGTCTGAGTAGGTGTCATTCTATTC

TGGGGGGTGGGGTGGGGCAGGACAGCAAGGGGGAGGATTGGGAAGACAATAGCAG

-continued

GCATGCTGGGGATGCGGTGGGCTCTATGGCTTCTGAGGCGGAAAGAACCAGCTGGG

GCTCTAGGGGGTATCCCCACTAGTCCACTCCCTCTCTGCGCGCTCGCTCGCTCACTG

AGGCCGGGCGACCAAAGGTCGCCCGACGCCCGGGCTTTGCCCGGGCGGCCTCAGTG

AGCGAGCGAGCGCGCAGAGAGGGA

P00204 full sequence (from ITR to ITR):

(SEQ ID NO: 282)

GGCCACTCCCTCTCTGCGCGCTCGCTCGCTCACTGAGGCCGGGCGACCAAAGGTCGC

CCGACGCCCGGGCTTTGCCCGGGCGGCCTCAGTGAGCGAGCGAGCGCGCAGAGAGG

GAGTGGCCAACTCCATCACTAGGGGTTCCTGGAGGGGTGGAGTCGTGACCTAGGTC

GTCTCCGGCTCTGCTTTTTCCAGGGGTGTGTTTCGCCGAGAAGCACGTAAGAGTTTT

ATGTTTTTTCATCTCTGCTTGTATTTTTCTAGTAATGGAAGCCTGGTATTTTAAAATA

GTTAAATTTTCCTTTAGTGCTGATTTCTAGATTATTATTACTGTTGTTGTTGTTATTAT

TGTCATTATTTGCATCTGAGAACTAGGTCAGTGAAGAGAAGAACAAAAAGCAGCAT

ATTACAGTTAGTTGTCTTCATCAATCTTTAAATATGTTGTGTGGTTTTTCTCTCCCTGT

TTCCACAGTTTTTCTTGATCATGAAAACGCCAACAAAATTCTGAATCGGCCAAAGAG

GTATAATTCAGGTAAATTGGAAGAGTTTGTTCAAGGGAACCTTGAGAGAGAATGTA

TGGAAGAAAAGTGTAGTTTTGAAGAAGCACGAGAAGTTTTTGAAAACACTGAAAGA

ACAACTGAATTTTGGAAGCAGTATGTTGATGGAGATCAGTGTGAGTCCAATCCATGT

TTAAATGGCGGCAGTTGCAAGGATGACATTAATTCCTATGAATGTTGGTGTCCCTTT

GGATTTGAAGGAAAGAACTGTGAATTAGATGTAACATGTAACATTAAGAATGGCAG

ATGCGAGCAGTTTTGTAAAAATAGTGCTGATAACAAGGTGGTTTGCTCCTGTACTGA

GGGATATCGACTTGCAGAAAACCAGAAGTCCTGTGAACCAGCAGTGCCATTTCCAT

GTGGAAGAGTTTCTGTTTCACAAACTTCTAAGCTCACCCGTGCTGAGACTGTTTTTCC

TGATGTGGACTATGTAAATTCTACTGAAGCTGAAACCATTTTGGATAACATCACTCA

AAGCACCCAATCATTTAATGACTTCACTCGGGTTGTTGGTGGAGAAGATGCCAAACC

AGGTCAATTCCCTTGGCAGGTTGTTTTGAATGGTAAAGTTGATGCATTCTGTGGAGG

CTCTATCGTTAATGAAAAATGGATTGTAACTGCTGCCCACTGTGTTGAAACTGGTGT

TAAAATTACAGTTGTCGCAGGTGAACATAATATTGAGGAGACAGAACATACAGAGC

AAAAGCGAAATGTGATTCGAATTATTCCTCACCACAACTACAATGCAGCTATTAATA

AGTACAACCATGACATTGCCCTTCTGGAACTGGACGAACCCTTAGTGCTAAACAGCT

ACGTTACACCTATTTGCATTGCTGACAAGGAATACACGAACATCTTCCTCAAATTTG

GATCTGGCTATGTAAGTGGCTGGGGAAGAGTCTTCCACAAAGGGAGATCAGCTTTA

GTTCTTCAGTACCTTAGAGTTCCACTTGTTGACCGAGCCACATGTCTTCTATCTACAA

AGTTCACCATCTATAACAACATGTTCTGTGCTGGCTTCCATGAAGGAGGTAGAGATT

CATGTCAAGGAGATAGTGGGGGACCCCATGTTACTGAAGTGGAAGGGACCAGTTTC

TTAACTGGAATTATTAGCTGGGGTGAAGAGTGTGCAATGAAAGGCAAATATGGAAT

ATATACCAAGGTATCCCGGTATGTCAACTGGATTAAGGAAAAAACAAAGCTCACTT

AACCTCGACTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGAGGAAATT

GCATCGCATTGTCTGAGTAGGTGTCATTCTATTCTGGGGGGTGGGGTGGGGCAGGAC

AGCAAGGGGGAGGATTGGGAAGACAATAGCAGGCATGCTGGGGATGCGGTGGGCT

-continued

CTATGGCTTCTGAGGCGGAAAGAACCAGCTGGGGCTCTAGGGGGTATCCCCCTTAG

GTGGTTATATTATTGATATATTTTTGGTATCTTTGATGACAATAATGGGGGATTTTGA

AAGCTTAGCTTTAAATTTCTTTTAATTAAAAAAAAATGCTAGGCAGAATGACTCAAA

TTACGTTGGATACAGTTGAATTTATTACGGTCTCATAGGGCCTGCCTGCTCGACCAT

GCTATACTAAAAATTAAAAGTGTACTAGTCCACTCCCTCTCTGCGCGCTCGCTCGCT

CACTGAGGCCGGGCGACCAAAGGTCGCCCGACGCCCGGGCTTTGCCCGGGCGGCCT

CAGTGAGCGAGCGAGCGCGCAGAGAGGGA

P00353 full sequence (from ITR to ITR):

(SEQ ID NO: 283)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTGATTTTGAAAGCTTAGCTT

TAAATTTCTTTTAATTAAAAAAAAATGCTAGGCAGAATGACTCAAATTACGTTGGAT

ACAGTTGAATTTATTACGGTCTCATAGGGCCTGCCTGCTCGACCATGCTATACTAAA

AATTAAAAGTGTGTGTTACTAATTTTATAAATGGAGTTTCCATTTATATTTACCTTTA

TTTCTTATTTACCATTGTCTTAGTAGATATTTACAAACATGACAGAAACACTAAATCT

TGAGTTTGAATGCACAGATATAAACACTTAACGGGTTTTAAAAATAATAATGTTGGT

GAAAAAATATAACTTTGAGTGTAGCAGAGAGGAACCATTGCCACCTTCAGATTTTCC

TGTAACGATCGGGAACTGGCATCTTCAGGGAGTAGCTTAGGTCAGTGAAGAGAAGA

ACAAAAAGCAGCATATTACAGTTAGTTGTCTTCATCAATCTTTAAATATGTTGTGTG

GTTTTTCTCTCCCTGTTTCCACAGTTTTTCTTGATCATGAAAACGCCAACAAAATTCT

GAATCGGCCAAAGAGGTTTCTTGATCATGAAAACGCCAACAAAATTCTGAATCGGC

CAAAGAGGTATAATTCAGGTAAATTGGAAGAGTTTGTTCAAGGGAACCTTGAGAGA

GAATGTATGGAAGAAAAGTGTAGTTTTGAAGAAGCACGAGAAGTTTTTGAAAACAC

TGAAAGAACAACTGAATTTTGGAAGCAGTATGTTGATGGAGATCAGTGTGAGTCCA

ATCCATGTTTAAATGGCGGCAGTTGCAAGGATGACATTAATTCCTATGAATGTTGGT

GTCCCTTTGGATTTGAAGGAAAGAACTGTGAATTAGATGTAACATGTAACATTAAGA

ATGGCAGATGCGAGCAGTTTTGTAAAAATAGTGCTGATAACAAGGTGGTTTGCTCCT

GTACTGAGGGATATCGACTTGCAGAAAACCAGAAGTCCTGTGAACCAGCAGTGCCA

TTTCCATGTGGAAGAGTTTCTGTTTCACAAACTTCTAAGCTCACCCGTGCTGAGACTG

TTTTTCCTGATGTGGACTATGTAAATTCTACTGAAGCTGAAACCATTTTGGATAACAT

CACTCAAAGCACCCAATCATTTAATGACTTCACTCGGGTTGTTGGTGGAGAAGATGC

CAAACCAGGTCAATTCCCTTGGCAGGTTGTTTTGAATGGTAAAGTTGATGCATTCTG

TGGAGGCTCTATCGTTAATGAAAAATGGATTGTAACTGCTGCCCACTGTGTTGAAAC

TGGTGTTAAAATTACAGTTGTCGCAGGTGAACATAATATTGAGGAGACAGAACATA

CAGAGCAAAAGCGAAATGTGATTCGAATTATTCCTCACCACAACTACAATGCAGCT

ATTAATAAGTACAACCATGACATTGCCCTTCTGGAACTGGACGAACCCTTAGTGCTA

AACAGCTACGTTACACCTATTTGCATTGCTGACAAGGAATACACGAACATCTTCCTC

AAATTTGGATCTGGCTATGTAAGTGGCTGGGGAAGAGTCTTCCACAAAGGGAGATC

AGCTTTAGTTCTTCAGTACCTTAGAGTTCCACTTGTTGACCGAGCCACATGTCTTCTA

TCTACAAAGTTCACCATCTATAACAACATGTTCTGTGCTGGCTTCCATGAAGGAGGT

AGAGATTCATGTCAAGGAGATAGTGGGGGACCCCATGTTACTGAAGTGGAAGGGAC

-continued

CAGTTTCTTAACTGGAATTATTAGCTGGGGTGAAGAGTGTGCAATGAAAGGCAAAT

ATGGAATATATACCAAGGTATCCCGGTATGTCAACTGGATTAAGGAAAAAACAAAG

CTCACTTAACCTCGACTGTGCCTTCTAGTTGCCAGCCATCTGTTGTTTGCCCCTCCCC

CGTGCCTTCCTTGACCCTGGAAGGTGCCACTCCCACTGTCCTTTCCTAATAAAATGA

GGAAATTGCATCGCATTGTCTGAGTAGGTGTCATTCTATTCTGGGGGGTGGGGTGGG

GCAGGACAGCAAGGGGGAGGATTGGGAAGACAATAGCAGGCATGCTGGGGATGCG

GTGGGCTCTATGGCTTCTGAGGCGGAAAGAACCAGCTGGGGCTCTAGGGGGTATCC

CCGTGAGATCGCCCATCGGTATAATGATTTGGGAGAACAACATTTCAAAGGCCTGTA

AGTTATAATGCTGAAAGCCCACTTAATATTTCTGGTAGTATTAGTTAAAGTTTTAAA

ACACCTTTTTCCACCTTGAGTGTGAGAATTGTAGAGCAGTGCTGTCCAGTAGAAATG

TGTGCATTGACAGAAAGACTGTGGATCTGTGCTGAGCAATGTGGCAGCCAGAGATC

ACAAGGCTATCAAGCACTTTGCACATGGCAAGTGTAACTGAGAAGCACACATTCAA

ATAATAGTTAATTTTAATTGAATGTATCTAGCCATGTGTGGCTAGTAGCTCCTTTCCT

GGAGAGAGAATCTGGAGCCCACATCTAACTTGTTAAGTCTGGAATCTTATTTTTTAT

TTCTGGAAAGGTCTATGAACTATAGTTTTGGGGGCAGCTCACTTACTAACTTTTAAT

GCAATAAGAATCTCATGGTATCTTGAGAACATTATTTTGTCTCTTTGTAGATCTAGGA

ACCCCTAGTGATGGAGTTGGCCACTCCCTCTCTGCGCGCTCGCTCGCTCACTGAGGC

CGCCCGGGCAAAGCCCGGGCGTCGGGCGACCTTTGGTCGCCCGGCCTCAGTGAGCG

AGCGAGCGCGCAGAGAGGGAGTGGCCAA

P00354 full sequence (from ITR to ITR):

(SEQ ID NO: 284)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTTAGCCTCTGGCAAAATGAA

GTGGGTAACCTTTCTCCTCCTCCTCTTCGTCTCCGGCTCTGCTTTTTCCAGGGGTGTGT

TTCGCCGAGAAGCACGTAAGAGTTTTATGTTTTTTCATCTCTGCTTGTATTTTTCTAG

TAATGGAAGCCTGGTATTTTAAAATAGTTAAATTTTCCTTTAGTGCTGATTTCTAGAT

TATTATTACTGTTGTTGTTGTTATTATTGTCATTATTTGCATCTGAGAACCCTTAGGTG

GTTATATTATTGATATATTTTTGGTATCTTTGATGACAATAATGGGGGATTTTGAAAG

CTTAGCTTTAAATTTCTTTTAATTAAAAAAAAATGCTAGGCAGAATGACTCAAATTA

CGTTGGATACAGTTGAATTTATTACGGTCTCATAGGGCCTGCCTGCTCGACCATGCT

ATACTAAAAATTAAAAGTGTGTGTTACTAATTTTATAAATGGAGTTTCCATTTATATT

TACCTTTATTTCTTATTTACCATTGTCTTAGTAGATATTTACAAACATGACAGAAACA

CTAAATCTTGAGTTTGAATGCACAGATATAAACACTTAACGGGTTTTAAAAATAATA

ATGTTGGTGAAAAAATATAACTTTGAGTGTAGCAGAGAGGAACCATTGCCACCTTCA

GATTTTCCTGTAACGATCGGGAACTGGCATCTTCAGGGAGTAGCTTAGGTCAGTGAA

GAGAAGAACAAAAAGCAGCATATTACAGTTAGTTGTCTTCATCAATCTTTAAATATG

TTGTGTGGTTTTTCTCTCCCTGTTTCCACAGTTTTTCTTGATCATGAAAACGCCAACA

AAATTCTGAATCGGCCAAAGAGGTATAATTCAGGTAAATTGGAAGAGTTTGTTCAA

GGGAACCTTGAGAGAGAATGTATGGAAGAAAAGTGTAGTTTTGAAGAAGCACGAGA

AGTTTTTGAAAACACTGAAAGAACAACTGAATTTTGGAAGCAGTATGTTGATGGAG

-continued

ATCAGTGTGAGTCCAATCCATGTTTAAATGGCGGCAGTTGCAAGGATGACATTAATT

CCTATGAATGTTGGTGTCCCTTTGGATTTGAAGGAAAGAACTGTGAATTAGATGTAA

CATGTAACATTAAGAATGGCAGATGCGAGCAGTTTTGTAAAAATAGTGCTGATAAC

AAGGTGGTTTGCTCCTGTACTGAGGGATATCGACTTGCAGAAAACCAGAAGTCCTGT

GAACCAGCAGTGCCATTTCCATGTGGAAGAGTTTCTGTTTCACAAACTTCTAAGCTC

ACCCGTGCTGAGACTGTTTTTCCTGATGTGGACTATGTAAATTCTACTGAAGCTGAA

ACCATTTTGGATAACATCACTCAAAGCACCCAATCATTTAATGACTTCACTCGGGTT

GTTGGTGGAGAAGATGCCAAACCAGGTCAATTCCCTTGGCAGGTTGTTTTGAATGGT

AAAGTTGATGCATTCTGTGGAGGCTCTATCGTTAATGAAAAATGGATTGTAACTGCT

GCCCACTGTGTTGAAACTGGTGTTAAAATTACAGTTGTCGCAGGTGAACATAATATT

GAGGAGACAGAACATACAGAGCAAAAGCGAAATGTGATTCGAATTATTCCTCACCA

CAACTACAATGCAGCTATTAATAAGTACAACCATGACATTGCCCTTCTGGAACTGGA

CGAACCCTTAGTGCTAAACAGCTACGTTACACCTATTTGCATTGCTGACAAGGAATA

CACGAACATCTTCCTCAAATTTGGATCTGGCTATGTAAGTGGCTGGGGAAGAGTCTT

CCACAAAGGGAGATCAGCTTTAGTTCTTCAGTACCTTAGAGTTCCACTTGTTGACCG

AGCCACATGTCTTCTATCTACAAAGTTCACCATCTATAACAACATGTTCTGTGCTGGC

TTCCATGAAGGAGGTAGAGATTCATGTCAAGGAGATAGTGGGGGACCCCATGTTAC

TGAAGTGGAAGGGACCAGTTTCTTAACTGGAATTATTAGCTGGGGTGAAGAGTGTG

CAATGAAAGGCAAATATGGAATATATACCAAGGTATCCCGGTATGTCAACTGGATT

AAGGAAAAAACAAAGCTCACTTAACCTCGACTGTGCCTTCTAGTTGCCAGCCATCTG

TTGTTTGCCCCTCCCCCGTGCCTTCCTTGACCCTGGAAGGTGCCACTCCCACTGTCCT

TTCCTAATAAAATGAGGAAATTGCATCGCATTGTCTGAGTAGGTGTCATTCTATTCT

GGGGGGTGGGGTGGGGCAGGACAGCAAGGGGGAGGATTGGGAAGACAATAGCAGG

CATGCTGGGGATGCGGTGGGCTCTATGGCTTCTGAGGCGGAAAGAACCAGCTGGGG

CTCTAGGGGGTATCCCCGTGAGATCGCCCATCGGTATAATGATTTGGGAGAACAACA

TTTCAAAGGCCTGTAAGTTATAATGCTGAAAGCCCACTTAATATTTCTGGTAGTATT

AGTTAAAGTTTTAAAACACCTTTTTCCACCTTGAGTGTGAGAATTGTAGAGCAGTGC

TGTCCAGTAGAAATGTGTGCATTGACAGAAAGACTGTGGATCTGTGCTGAGCAATGT

GGCAGCCAGAGATCACAAGGCTATCAAGCACTTTGCACATGGCAAGTGTAACTGAG

AAGCACACATTCAAATAATAGTTAATTTTAATTGAATGTATCTAGCCATGTGTGGCT

AGTAGCTCCTTTCCTGGAGAGAGAATCTGGAGCCCACATCTAACTTGTTAAGTCTGG

AATCTTATTTTTTATTTCTGGAAAGGTCTATGAACTATAGTTTTGGGGGCAGCTCACT

TACTAACTTTTAATGCAATAAGAATCTCATGGTATCTTGAGAACATTATTTTGTCTCT

TTGTAGTACTGAAACCTTATACATGTGAAGTAAGGGGTCTATACTTAAGTCACATCT

CCAACCTTAGTAATGTTTTAATGTAGTAAAAAAATGAGTAATTAATTTATTTTTAGA

AGGTCAATAGTATCATGTATTCCAAATAACAGAGGTATATGGTTAGAAAAGAAACA

ATTCAAAGGACTTATATAATATCTAGCCTTGACAATGAATAAATTTAGAGAGTAGTT

TGCCTGTTTGCCTCATGTTCATAAATCTATTGACACATATGTGCATCTGCACTTCAGC

ATGGTAGAAGTCCATATTCAGATCTAGGAACCCCTAGTGATGGAGTTGGCCACTCCC

TCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCA

-continued

A

P00350: The 300/600 bp HA F9 construct (for G551)

(SEQ ID NO: 285)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTAAGTATATTAGAGCGAGTC

TTTCTGCACACAGATCACCTTTCCTATCAACCCCACTAGCCTCTGGCAAAATGAAGT

GGGTAACCTTTCTCCTCCTCCTCTTCGTCTCCGGCTCTGCTTTTTCCAGGGGTGTGTTT

CGCCGAGAAGCACGTAAGAGTTTTATGTTTTTTCATCTCTGCTTGTATTTTTCTAGTA

ATGGAAGCCTGGTATTTTAAAATAGTTAAATTTTCCTTTAGTGCTGATTTCTAGATTA

TTATTACTGTTGTTGTTGTTATTATTGTCATTATTTGCATCTGAGAACCTTTTTCTTGA

TCATGAAAACGCCAACAAAATTCTGAATCGGCCAAAGAGGTATAATTCAGGTAAAT

TGGAAGAGTTTGTTCAAGGGAACCTTGAGAGAGAATGTATGGAAGAAAAGTGTAGT

TTTGAAGAAGCACGAGAAGTTTTTGAAAACACTGAAAGAACAACTGAATTTTGGAA

GCAGTATGTTGATGGAGATCAGTGTGAGTCCAATCCATGTTTAAATGGCGGCAGTTG

CAAGGATGACATTAATTCCTATGAATGTTGGTGTCCCTTTGGATTTGAAGGAAAGAA

CTGTGAATTAGATGTAACATGTAACATTAAGAATGGCAGATGCGAGCAGTTTTGTAA

AAATAGTGCTGATAACAAGGTGGTTTGCTCCTGTACTGAGGGATATCGACTTGCAGA

AAACCAGAAGTCCTGTGAACCAGCAGTGCCATTTCCATGTGGAAGAGTTTCTGTTTC

ACAAACTTCTAAGCTCACCCGTGCTGAGACTGTTTTTCCTGATGTGGACTATGTAAA

TTCTACTGAAGCTGAAACCATTTTGGATAACATCACTCAAAGCACCCAATCATTTAA

TGACTTCACTCGGGTTGTTGGTGGAGAAGATGCCAAACCAGGTCAATTCCCTTGGCA

GGTTGTTTTGAATGGTAAAGTTGATGCATTCTGTGGAGGCTCTATCGTTAATGAAAA

ATGGATTGTAACTGCTGCCCACTGTGTTGAAACTGGTGTTAAAATTACAGTTGTCGC

AGGTGAACATAATATTGAGGAGACAGAACATACAGAGCAAAAGCGAAATGTGATTC

GAATTATTCCTCACCACAACTACAATGCAGCTATTAATAAGTACAACCATGACATTG

CCCTTCTGGAACTGGACGAACCCTTAGTGCTAAACAGCTACGTTACACCTATTTGCA

TTGCTGACAAGGAATACACGAACATCTTCCTCAAATTTGGATCTGGCTATGTAAGTG

GCTGGGGAAGAGTCTTCCACAAAGGGAGATCAGCTTTAGTTCTTCAGTACCTTAGAG

TTCCACTTGTTGACCGAGCCACATGTCTTCTATCTACAAAGTTCACCATCTATAACAA

CATGTTCTGTGCTGGCTTCCATGAAGGAGGTAGAGATTCATGTCAAGGAGATAGTGG

GGGACCCCATGTTACTGAAGTGGAAGGGACCAGTTTCTTAACTGGAATTATTAGCTG

GGGTGAAGAGTGTGCAATGAAAGGCAAATATGGAATATATACCAAGGTATCCCGGT

ATGTCAACTGGATTAAGGAAAAAACAAAGCTCACTTAACCTCGACTGTGCCTTCTAG

TTGCCAGCCATCTGTTGTTTGCCCCTCCCCCGTGCCTTCCTTGACCCTGGAAGGTGCC

ACTCCCACTGTCCTTTCCTAATAAAATGAGGAAATTGCATCGCATTGTCTGAGTAGG

TGTCATTCTATTCTGGGGGGTGGGGTGGGGCAGGACAGCAAGGGGGAGGATTGGGA

AGACAATAGCAGGCATGCTGGGGATGCGGTGGGCTCTATGGCTTCTGAGGCGGAAA

GAACCAGCTGGGGCTCTAGGGGGTATCCCCCTTAGGTGGTTATATTATTGATATATT

TTTGGTATCTTTGATGACAATAATGGGGGATTTTGAAAGCTTAGCTTTAAATTTCTTT

TAATTAAAAAAAAATGCTAGGCAGAATGACTCAAATTACGTTGGATACAGTTGAAT

-continued

TTATTACGGTCTCATAGGGCCTGCCTGCTCGACCATGCTATACTAAAAATTAAAAGT

GTGTGTTACTAATTTTATAAATGGAGTTTCCATTTATATTTACCTTTATTTCTTATTTA

CCATTGTCTTAGTAGATATTTACAAACATGACAGAAACACTAAAGATCTAGGAACCC

CTAGTGATGGAGTTGGCCACTCCCTCTCTGCGCGCTCGCTCGCTCACTGAGGCCGCC

CGGGCAAAGCCCGGGCGTCGGGCGACCTTTGGTCGCCCGGCCTCAGTGAGCGAGCG

AGCGCGCAGAGAGGGAGTGGCCAA

P00356: The 300/2000 bp HA F9 construct (for G551)

(SEQ ID NO: 286)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTAAGTATATTAGAGCGAGTC

TTTCTGCACACAGATCACCTTTCCTATCAACCCCACTAGCCTCTGGCAAAATGAAGT

GGGTAACCTTTCTCCTCCTCCTCTTCGTCTCCGGCTCTGCTTTTTCCAGGGGTGTGTTT

CGCCGAGAAGCACGTAAGAGTTTTATGTTTTTTCATCTCTGCTTGTATTTTTCTAGTA

ATGGAAGCCTGGTATTTTAAAATAGTTAAATTTTCCTTTAGTGCTGATTTCTAGATTA

TTATTACTGTTGTTGTTGTTATTATTGTCATTATTTGCATCTGAGAACCTTTTTCTTGA

TCATGAAAACGCCAACAAAATTCTGAATCGGCCAAAGAGGTATAATTCAGGTAAAT

TGGAAGAGTTTGTTCAAGGGAACCTTGAGAGAGAATGTATGGAAGAAAAGTGTAGT

TTTGAAGAAGCACGAGAAGTTTTTGAAAACACTGAAAGAACAACTGAATTTTGGAA

GCAGTATGTTGATGGAGATCAGTGTGAGTCCAATCCATGTTTAAATGGCGGCAGTTG

CAAGGATGACATTAATTCCTATGAATGTTGGTGTCCCTTTGGATTTGAAGGAAAGAA

CTGTGAATTAGATGTAACATGTAACATTAAGAATGGCAGATGCGAGCAGTTTTGTAA

AAATAGTGCTGATAACAAGGTGGTTTGCTCCTGTACTGAGGGATATCGACTTGCAGA

AAACCAGAAGTCCTGTGAACCAGCAGTGCCATTTCCATGTGGAAGAGTTTCTGTTTC

ACAAACTTCTAAGCTCACCCGTGCTGAGACTGTTTTTCCTGATGTGGACTATGTAAA

TTCTACTGAAGCTGAAACCATTTTGGATAACATCACTCAAAGCACCCAATCATTTAA

TGACTTCACTCGGGTTGTTGGTGGAGAAGATGCCAAACCAGGTCAATTCCCTTGGCA

GGTTGTTTTGAATGGTAAAGTTGATGCATTCTGTGGAGGCTCTATCGTTAATGAAAA

ATGGATTGTAACTGCTGCCCACTGTGTTGAAACTGGTGTTAAAATTACAGTTGTCGC

AGGTGAACATAATATTGAGGAGACAGAACATACAGAGCAAAAGCGAAATGTGATTC

GAATTATTCCTCACCACAACTACAATGCAGCTATTAATAAGTACAACCATGACATTG

CCCTTCTGGAACTGGACGAACCCTTAGTGCTAAACAGCTACGTTACACCTATTTGCA

TTGCTGACAAGGAATACACGAACATCTTCCTCAAATTTGGATCTGGCTATGTAAGTG

GCTGGGGAAGAGTCTTCCACAAAGGGAGATCAGCTTTAGTTCTTCAGTACCTTAGAG

TTCCACTTGTTGACCGAGCCACATGTCTTCTATCTACAAAGTTCACCATCTATAACAA

CATGTTCTGTGCTGGCTTCCATGAAGGAGGTAGAGATTCATGTCAAGGAGATAGTGG

GGGACCCCATGTTACTGAAGTGGAAGGGACCAGTTTCTTAACTGGAATTATTAGCTG

GGGTGAAGAGTGTGCAATGAAAGGCAAATATGGAATATATACCAAGGTATCCCGGT

ATGTCAACTGGATTAAGGAAAAAACAAAGCTCACTTAACCTCGACTGTGCCTTCTAG

TTGCCAGCCATCTGTTGTTTGCCCCTCCCCCGTGCCTTCCTTGACCCTGGAAGGTGCC

ACTCCCACTGTCCTTTCCTAATAAAATGAGGAAATTGCATCGCATTGTCTGAGTAGG

TGTCATTCTATTCTGGGGGGTGGGGTGGGGCAGGACAGCAAGGGGGAGGATTGGGA

-continued

AGACAATAGCAGGCATGCTGGGGATGCGGTGGGCTCTATGGCTTCTGAGGCGGAAA

GAACCAGCTGGGGCTCTAGGGGGTATCCCCCTTAGGTGGTTATATTATTGATATATT

TTTGGTATCTTTGATGACAATAATGGGGGATTTTGAAAGCTTAGCTTTAAATTTCTTT

TAATTAAAAAAAAATGCTAGGCAGAATGACTCAAATTACGTTGGATACAGTTGAAT

TTATTACGGTCTCATAGGGCCTGCCTGCTCGACCATGCTATACTAAAAATTAAAAGT

GTGTGTTACTAATTTTATAAATGGAGTTTCCATTTATATTTACCTTTATTTCTTATTTA

CCATTGTCTTAGTAGATATTTACAAACATGACAGAAACACTAAATCTTGAGTTTGAA

TGCACAGATATAAACACTTAACGGGTTTTAAAAATAATAATGTTGGTGAAAAAATAT

AACTTTGAGTGTAGCAGAGAGGAACCATTGCCACCTTCAGATTTTCCTGTAACGATC

GGGAACTGGCATCTTCAGGGAGTAGCTTAGGTCAGTGAAGAGAAGAACAAAAAGCA

GCATATTACAGTTAGTTGTCTTCATCAATCTTTAAATATGTTGTGTGGTTTTTCTCTCC

CTGTTTCCACAGACAAGAGTGAGATCGCCCATCGGTATAATGATTTGGGAGAACAA

CATTTCAAAGGCCTGTAAGTTATAATGCTGAAAGCCCACTTAATATTTCTGGTAGTA

TTAGTTAAAGTTTTAAAACACCTTTTTCCACCTTGAGTGTGAGAATTGTAGAGCAGT

GCTGTCCAGTAGAAATGTGTGCATTGACAGAAAGACTGTGGATCTGTGCTGAGCAAT

GTGGCAGCCAGAGATCACAAGGCTATCAAGCACTTTGCACATGGCAAGTGTAACTG

AGAAGCACACATTCAAATAATAGTTAATTTTAATTGAATGTATCTAGCCATGTGTGG

CTAGTAGCTCCTTTCCTGGAGAGAGAATCTGGAGCCCACATCTAACTTGTTAAGTCT

GGAATCTTATTTTTTATTTCTGGAAAGGTCTATGAACTATAGTTTTGGGGGCAGCTCA

CTTACTAACTTTTAATGCAATAAGATCCATGGTATCTTGAGAACATTATTTTGTCTCT

TTGTAGTACTGAAACCTTATACATGTGAAGTAAGGGGTCTATACTTAAGTCACATCT

CCAACCTTAGTAATGTTTTAATGTAGTAAAAAAATGAGTAATTAATTTATTTTTAGA

AGGTCAATAGTATCATGTATTCCAAATAACAGAGGTATATGGTTAGAAAAGAAACA

ATTCAAAGGACTTATATAATATCTAGCCTTGACAATGAATAAATTTAGAGAGTAGTT

TGCCTGTTTGCCTCATGTTCATAAATCTATTGACACATATGTGCATCTGCACTTCAGC

ATGGTAGAAGTCCATATTCCTTTGCTTGGAAAGGCAGGTGTTCCCATTACGCCTCAG

AGAATAGCTGACGGGAAGAGGCTTTCTAGATAGTTGTATGAAAGATATACAAAATC

TCGCAGGTATACACAGGCATGATTTGCTGGTTGGGAGAGCCACTTGCCTCATACTGA

GGTTTTTGTGTCTGCTTTTCAGAGTCCTGATTGCCTTTTCCCAGTATCTCCAGAAATG

CTCATACGATGAGCATGCCAAATTAGTGCAGGAAGTAACAGACTTTGCAAAGACGT

GTGTTGCCGATGAGTCTGCCGCCAACTGTGACAAATCCCTTGTGAGTACCTTCTGAT

TTTGTGGATCTACTTTCCTGCTTTCTGGAACTCTGTTTCAAAGCCAATCATGACTCCA

TCACTTAAGGCCCCGGGAACACTGTGGCAGAGGGCAGCAGAGAGATTGATAAAGCC

AGGGTGATGGGAATTTTCTGTGGGACTCCATTTCATAGTAATTGCAGAAGCTACAAT

ACACTCAAAAAGTCTCACCACATGACTGCCCAAATGGGAGCTTGACAGTGACAGTG

ACAGTAGATATGCCAAAGTGGATGAGGGAAAGACCACAAGAGCTAAACCCTGTAAA

AAGAACTGTAGGCAACTAAGGAATGCAGAGAGAAAGATCTAGGAACCCCTAGTGAT

GGAGTTGGCCACTCCCTCTCTGCGCGCTCGCTCGCTCACTGAGGCCGCCCGGGCAAA

GCCCGGGCGTCGGGCGACCTTTGGTCGCCCGGCCTCAGTGAGCGAGCGAGCGCGCA

GAGAGGGAGTGGCCAA

-continued

P00362: The 300/1500 bp HA F9 construct (for G551)

(SEQ ID NO: 287)

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTAGATCTAAGTATATTAGAGCGAGTC

TTTCTGCACACAGATCACCTTTCCTATCAACCCCACTAGCCTCTGGCAAAATGAAGT

GGGTAACCTTTCTCCTCCTCCTCTTCGTCTCCGGCTCTGCTTTTTCCAGGGGTGTGTTT

CGCCGAGAAGCACGTAAGAGTTTTATGTTTTTTCATCTCTGCTTGTATTTTTCTAGTA

ATGGAAGCCTGGTATTTTAAAATAGTTAAATTTTCCTTTAGTGCTGATTTCTAGATTA

TTATTACTGTTGTTGTTGTTATTATTGTCATTATTTGCATCTGAGAACCTTTTTCTTGA

TCATGAAAACGCCAACAAAATTCTGAATCGGCCAAAGAGGTATAATTCAGGTAAAT

TGGAAGAGTTTGTTCAAGGGAACCTTGAGAGAGAATGTATGGAAGAAAAGTGTAGT

TTTGAAGAAGCACGAGAAGTTTTTGAAAACACTGAAAGAACAACTGAATTTTGGAA

GCAGTATGTTGATGGAGATCAGTGTGAGTCCAATCCATGTTTAAATGGCGGCAGTTG

CAAGGATGACATTAATTCCTATGAATGTTGGTGTCCCTTTGGATTTGAAGGAAAGAA

CTGTGAATTAGATGTAACATGTAACATTAAGAATGGCAGATGCGAGCAGTTTTGTAA

AAATAGTGCTGATAACAAGGTGGTTTGCTCCTGTACTGAGGGATATCGACTTGCAGA

AAACCAGAAGTCCTGTGAACCAGCAGTGCCATTTCCATGTGGAAGAGTTTCTGTTTC

ACAAACTTCTAAGCTCACCCGTGCTGAGACTGTTTTTCCTGATGTGGACTATGTAAA

TTCTACTGAAGCTGAAACCATTTTGGATAACATCACTCAAAGCACCCAATCATTTAA

TGACTTCACTCGGGTTGTTGGTGGAGAAGATGCCAAACCAGGTCAATTCCCTTGGCA

GGTTGTTTTGAATGGTAAAGTTGATGCATTCTGTGGAGGCTCTATCGTTAATGAAAA

ATGGATTGTAACTGCTGCCCACTGTGTTGAAACTGGTGTTAAAATTACAGTTGTCGC

AGGTGAACATAATATTGAGGAGACAGAACATACAGAGCAAAAGCGAAATGTGATTC

GAATTATTCCTCACCACAACTACAATGCAGCTATTAATAAGTACAACCATGACATTG

CCCTTCTGGAACTGGACGAACCCTTAGTGCTAAACAGCTACGTTACACCTATTTGCA

TTGCTGACAAGGAATACACGAACATCTTCCTCAAATTTGGATCTGGCTATGTAAGTG

GCTGGGGAAGAGTCTTCCACAAAGGGAGATCAGCTTTAGTTCTTCAGTACCTTAGAG

TTCCACTTGTTGACCGAGCCACATGTCTTCTATCTACAAAGTTCACCATCTATAACAA

CATGTTCTGTGCTGGCTTCCATGAAGGAGGTAGAGATTCATGTCAAGGAGATAGTGG

GGGACCCCATGTTACTGAAGTGGAAGGGACCAGTTTCTTAACTGGAATTATTAGCTG

GGGTGAAGAGTGTGCAATGAAAGGCAAATATGGAATATATACCAAGGTATCCCGGT

ATGTCAACTGGATTAAGGAAAAAACAAAGCTCACTTAACCTCGACTGTGCCTTCTAG

TTGCCAGCCATCTGTTGTTTGCCCCTCCCCCGTGCCTTCCTTGACCCTGGAAGGTGCC

ACTCCCACTGTCCTTTCCTAATAAAATGAGGAAATTGCATCGCATTGTCTGAGTAGG

TGTCATTCTATTCTGGGGGGTGGGGTGGGGCAGGACAGCAAGGGGGAGGATTGGGA

AGACAATAGCAGGCATGCTGGGGATGCGGTGGGCTCTATGGCTTCTGAGGCGGAAA

GAACCAGCTGGGGCTCTAGGGGGTATCCCCCTTAGGTGGTTATATTATTGATATATT

TTTGGTATCTTTGATGACAATAATGGGGGATTTTGAAAGCTTAGCTTTAAATTTCTTT

TAATTAAAAAAAAATGCTAGGCAGAATGACTCAAATTACGTTGGATACAGTTGAAT

TTATTACGGTCTCATAGGGCCTGCCTGCTCGACCATGCTATACTAAAAATTAAAAGT

GTGTGTTACTAATTTTATAAATGGAGTTTCCATTTATATTTACCTTTATTTCTTATTTA

-continued

CCATTGTCTTAGTAGATATTTACAAACATGACAGAAACACTAAATCTTGAGTTTGAA

TGCACAGATATAAACACTTAACGGGTTTTAAAAATAATAATGTTGGTGAAAAAATAT

AACTTTGAGTGTAGCAGAGAGGAACCATTGCCACCTTCAGATTTTCCTGTAACGATC

GGGAACTGGCATCTTCAGGGAGTAGCTTAGGTCAGTGAAGAGAAGAACAAAAAGCA

GCATATTACAGTTAGTTGTCTTCATCAATCTTTAAATATGTTGTGTGGTTTTTCTCTCC

CTGTTTCCACAGACAAGAGTGAGATCGCCCATCGGTATAATGATTTGGGAGAACAA

CATTTCAAAGGCCTGTAAGTTATAATGCTGAAAGCCCACTTAATATTTCTGGTAGTA

TTAGTTAAAGTTTTAAAACACCTTTTTCCACCTTGAGTGTGAGAATTGTAGAGCAGT

GCTGTCCAGTAGAAATGTGTGCATTGACAGAAAGACTGTGGATCTGTGCTGAGCAAT

GTGGCAGCCAGAGATCACAAGGCTATCAAGCACTTTGCACATGGCAAGTGTAACTG

AGAAGCACACATTCAAATAATAGTTAATTTTAATTGAATGTATCTAGCCATGTGTGG

CTAGTAGCTCCTTTCCTGGAGAGAGAATCTGGAGCCCACATCTAACTTGTTAAGTCT

GGAATCTTATTTTTTATTTCTGGAAAGGTCTATGAACTATAGTTTTGGGGGCAGCTCA

CTTACTAACTTTTAATGCAATAAGATCCATGGTATCTTGAGAACATTATTTTGTCTCT

TTGTAGTACTGAAACCTTATACATGTGAAGTAAGGGGTCTATACTTAAGTCACATCT

CCAACCTTAGTAATGTTTTAATGTAGTAAAAAAATGAGTAATTAATTTATTTTTAGA

AGGTCAATAGTATCATGTATTCCAAATAACAGAGGTATATGGTTAGAAAAGAAACA

ATTCAAAGGACTTATATAATATCTAGCCTTGACAATGAATAAATTTAGAGAGTAGTT

TGCCTGTTTGCCTCATGTTCATAAATCTATTGACACATATGTGCATCTGCACTTCAGC

ATGGTAGAAGTCCATATTCCTTTGCTTGGAAAGGCAGGTGTTCCCATTACGCCTCAG

AGAATAGCTGACGGGAAGAGGCTTTCTAGATAGTTGTATGAAAGATATACAAAATC

TCGCAGGTATACACAGGCATGATTTGCTGGTTGGGAGAGCCACTTAGATCTAGGAAC

CCCTAGTGATGGAGTTGGCCACTCCCTCTCTGCGCGCTCGCTCGCTCACTGAGGCCG

CCCGGGCAAAGCCCGGGCGTCGGGCGACCTTTGGTCGCCCGGCCTCAGTGAGCGAG

CGAGCGCGCAGAGAGGGAGTGGCCAA

Factor IX R338L polypeptide encoded in P00147

(SEQ ID NO: 702)

YNSGKLEEFVQGNLERECMEEKCSFEEAREVFENTERTTEFWKQYVDGDQCESNPCLNGGSCK

DDINSYECWCPFGFEGKNCELDVTCNIKNGRCEQFCKNSADNKVVCSCTEGYRLAENQKSCEPA

VPFPCGRVSVSQTSKLTRAETVFPDVDYVNSTEAETILDNITQSTQSFNDFTRVVGGEDAKPGQFP

WQVVLNGKVDAFCGGSIVNEKWIVTAAHCVETGVKITVVAGEHNIEETEHTEQKRNVIRIIPHHN

YNAAINKYNHDIALLELDEPLVLNSYVTPICIADKEYTNIFLKFGSGYVSGWGRVFHKGRSALVL

QYLRVPLVDRATCLLSTKFTIYNNMFCAGFHEGGRDSCQGDSGGPHVTEVEGTSFLTGIISWGEE

CAMKGKYGIYTKVSRYVNWIKEKTKLT

Cas9 ORF (SEQ ID NO: 703)

ATGGATAAGAAGTACTCAATCGGGCTGGATATCGGAACTAATTCCGTGGGTTGGGC

AGTGATCACGGATGAATACAAAGTGCCGTCCAAGAAGTTCAAGGTCCTGGGGAACA

CCGATAGACACAGCATCAAGAAAAATCTCATCGGAGCCCTGCTGTTTGACTCCGGC

GAAACCGCAGAAGCGACCCGGCTCAAACGTACCGCGAGGCGACGCTACACCCGGCG

GAAGAATCGCATCTGCTATCTGCAAGAGATCTTTTCGAACGAAATGGCAAAGGTCG

ACGACAGCTTCTTCCACCGCCTGGAAGAATCTTTCCTGGTGGAGGAGGACAAGAAG

-continued

CATGAACGGCATCCTATCTTTGGAAACATCGTCGACGAAGTGGCGTACCACGAAAA

GTACCCGACCATCTACCATCTGCGGAAGAAGTTGGTTGACTCAACTGACAAGGCCG

ACCTCAGATTGATCTACTTGGCCCTCGCCCATATGATCAAATTCCGCGGACACTTCC

TGATCGAAGGCGATCTGAACCCTGATAACTCCGACGTGGATAAGCTTTTCATTCAAC

TGGTGCAGACCTACAACCAACTGTTCGAAGAAAACCCAATCAATGCTAGCGGCGTC

GATGCCAAGGCCATCCTGTCCGCCCGGCTGTCGAAGTCGCGGCGCCTCGAAAACCT

GATCGCACAGCTGCCGGGAGAGAAAAAGAACGGACTTTTCGGCAACTTGATCGCTC

TCTCACTGGGACTCACTCCCAATTTCAAGTCCAATTTTGACCTGGCCGAGGACGCGA

AGCTGCAACTCTCAAAGGACACCTACGACGACGACTTGGACAATTTGCTGGCACAA

ATTGGCGATCAGTACGCGGATCTGTTCCTTGCCGCTAAGAACCTTTCGGACGCAATC

TTGCTGTCCGATATCCTGCGCGTGAACACCGAAATAACCAAAGCGCCGCTTAGCGCC

TCGATGATTAAGCGGTACGACGAGCATCACCAGGATCTCACGCTGCTCAAAGCGCT

CGTGAGACAGCAACTGCCTGAAAAGTACAAGGAGATCTTCTTCGACCAGTCCAAGA

ATGGGTACGCAGGGTACATCGATGGAGGCGCTAGCCAGGAAGAGTTCTATAAGTTC

ATCAAGCCAATCCTGGAAAAGATGGACGGAACCGAAGAACTGCTGGTCAAGCTGAA

CAGGGAGGATCTGCTCCGGAAACAGAGAACCTTTGACAACGGATCCATTCCCCACC

AGATCCATCTGGGTGAGCTGCACGCCATCTTGCGGCGCCAGGAGGACTTTTACCCAT

TCCTCAAGGACAACCGGGAAAAGATCGAGAAAATTCTGACGTTCCGCATCCCGTATT

ACGTGGGCCCACTGGCGCGCGGCAATTCGCGCTTCGCGTGGATGACTAGAAAATCA

GAGGAAACCATCACTCCTTGGAATTTCGAGGAAGTTGTGGATAAGGGAGCTTCGGC

ACAAAGCTTCATCGAACGAATGACCAACTTCGACAAGAATCTCCCAAACGAGAAGG

TGCTTCCTAAGCACAGCCTCCTTTACGAATACTTCACTGTCTACAACGAACTGACTA

AAGTGAAATACGTTACTGAAGGAATGAGGAAGCCGGCCTTTCTGTCCGGAGAACAG

AAGAAAGCAATTGTCGATCTGCTGTTCAAGACCAACCGCAAGGTGACCGTCAAGCA

GCTTAAAGAGGACTACTTCAAGAAGATCGAGTGTTTCGACTCAGTGGAAATCAGCG

GGGTGGAGGACAGATTCAACGCTTCGCTGGGAACCTATCATGATCTCCTGAAGATCA

TCAAGGACAAGGACTTCCTTGACAACGAGGAGAACGAGGACATCCTGGAAGATATC

GTCCTGACCTTGACCCTTTTCGAGGATCGCGAGATGATCGAGGAGAGGCTTAAGACC

TACGCTCATCTCTTCGACGATAAGGTCATGAAACAACTCAAGCGCCGCCGGTACACT

GGTTGGGGCCGCCTCTCCCGCAAGCTGATCAACGGTATTCGCGATAAACAGAGCGG

TAAAACTATCCTGGATTTCCTCAAATCGGATGGCTTCGCTAATCGTAACTTCATGCA

ATTGATCCACGACGACAGCCTGACCTTTAAGGAGGACATCCAAAAAGCACAAGTGT

CCGGACAGGGAGACTCACTCCATGAACACATCGCGAATCTGGCCGGTTCGCCGGCG

ATTAAGAAGGGAATTCTGCAAACTGTGAAGGTGGTCGACGAGCTGGTGAAGGTCAT

GGGACGGCACAAACCGGAGAATATCGTGATTGAAATGGCCCGAGAAAACCAGACTA

CCCAGAAGGGCCAGAAAAACTCCCGCGAAAGGATGAAGCGGATCGAAGAAGGAAT

CAAGGAGCTGGGCAGCCAGATCCTGAAAGAGCACCCGGTGGAAAACACGCAGCTG

CAGAACGAGAAGCTCTACCTGTACTATTTGCAAAATGGACGGGACATGTACGTGGA

CCAAGAGCTGGACATCAATCGGTTGTCTGATTACGACGTGGACCACATCGTTCCACA

GTCCTTTCTGAAGGATGACTCGATCGATAACAAGGTGTTGACTCGCAGCGACAAGA

ACAGAGGGAAGTCAGATAATGTGCCATCGGAGGAGGTCGTGAAGAAGATGAAGAA

-continued

TTACTGGCGGCAGCTCCTGAATGCGAAGCTGATTACCCAGAGAAAGTTTGACAATCT

CACTAAAGCCGAGCGCGGCGGACTCTCAGAGCTGGATAAGGCTGGATTCATCAAAC

GGCAGCTGGTCGAGACTCGGCAGATTACCAAGCACGTGGCGCAGATCTTGGACTCC

CGCATGAACACTAAATACGACGAGAACGATAAGCTCATCCGGGAAGTGAAGGTGAT

TACCCTGAAAAGCAAACTTGTGTCGGACTTTCGGAAGGACTTTCAGTTTTACAAAGT

GAGAGAAATCAACAACTACCATCACGCGCATGACGCATACCTCAACGCTGTGGTCG

GTACCGCCCTGATCAAAAAGTACCCTAAACTTGAATCGGAGTTTGTGTACGGAGACT

ACAAGGTCTACGACGTGAGGAAGATGATAGCCAAGTCCGAACAGGAAATCGGGAA

AGCAACTGCGAAATACTTCTTTTACTCAAACATCATGAACTTTTTCAAGACTGAAAT

TACGCTGGCCAATGGAGAAATCAGGAAGAGGCCACTGATCGAAACTAACGGAGAA

ACGGGCGAAATCGTGTGGGACAAGGGCAGGGACTTCGCAACTGTTCGCAAAGTGCT

CTCTATGCCGCAAGTCAATATTGTGAAGAAAACCGAAGTGCAAACCGGCGGATTTTC

AAAGGAATCGATCCTCCCAAAGAGAAATAGCGACAAGCTCATTGCACGCAAGAAAG

ACTGGGACCCGAAGAAGTACGGAGGATTCGATTCGCCGACTGTCGCATACTCCGTC

CTCGTGGTGGCCAAGGTGGAGAAGGGAAAGAGCAAAAAGCTCAAATCCGTCAAAG

AGCTGCTGGGGATTACCATCATGGAACGATCCTCGTTCGAGAAGAACCCGATTGATT

TCCTCGAGGCGAAGGGTTACAAGGAGGTGAAGAAGGATCTGATCATCAAACTCCCC

AAGTACTCACTGTTCGAACTGGAAAATGGTCGGAAGCGCATGCTGGCTTCGGCCGG

AGAACTCCAAAAAGGAAATGAGCTGGCCTTGCCTAGCAAGTACGTCAACTTCCTCTA

TCTTGCTTCGCACTACGAAAAACTCAAAGGGTCACCGGAAGATAACGAACAGAAGC

AGCTTTTCGTGGAGCAGCACAAGCATTATCTGGATGAAATCATCGAACAAATCTCCG

AGTTTTCAAAGCGCGTGATCCTCGCCGACGCCAACCTCGACAAAGTCCTGTCGGCCT

ACAATAAGCATAGAGATAAGCCGATCAGAGAACAGGCCGAGAACATTATCCACTTG

TTCACCCTGACTAACCTGGGAGCCCCAGCCGCCTTCAAGTACTTCGATACTACTATC

GATCGCAAAAGATACACGTCCACCAAGGAAGTTCTGGACGCGACCCTGATCCACCA

AAGCATCACTGGACTCTACGAAACTAGGATCGATCTGTCGCAGCTGGGTGGCGAT

U-dep Cas9 ORF (SEQ ID NO: 704)

ATGGACAAGAAGTACAGCATCGGACTGGACATCGGAACAAACAGCGTCGGATGGGC

AGTCATCACAGACGAATACAAGGTCCCGAGCAAGAAGTTCAAGGTCCTGGGAAACA

CAGACAGACACAGCATCAAGAAGAACCTGATCGGAGCACTGCTGTTCGACAGCGGA

GAAACAGCAGAAGCAACAAGACTGAAGAGAACAGCAAGAAGAAGATACACAAGAA

GAAAGAACAGAATCTGCTACCTGCAGGAAATCTTCAGCAACGAAATGGCAAAGGTC

GACGACAGCTTCTTCCACAGACTGGAAGAAAGCTTCCTGGTCGAAGAAGACAAGAA

GCACGAAAGACACCCGATCTTCGGAAACATCGTCGACGAAGTCGCATACCACGAAA

AGTACCCGACAATCTACCACCTGAGAAAGAAGCTGGTCGACAGCACAGACAAGGCA

GACCTGAGACTGATCTACCTGGCACTGGCACACATGATCAAGTTCAGAGGACACTTC

CTGATCGAAGGAGACCTGAACCCGGACAACAGCGACGTCGACAAGCTGTTCATCCA

GCTGGTCCAGACATACAACCAGCTGTTCGAAGAAAACCCGATCAACGCAAGCGGAG

TCGACGCAAAGGCAATCCTGAGCGCAAGACTGAGCAAGAGCAGAAGACTGGAAAA

CCTGATCGCACAGCTGCCGGGAGAAAAGAAGAACGGACTGTTCGGAAACCTGATCG

-continued

CACTGAGCCTGGGACTGACACCGAACTTCAAGAGCAACTTCGACCTGGCAGAAGAC

GCAAAGCTGCAGCTGAGCAAGGACACATACGACGACGACCTGGACAACCTGCTGGC

ACAGATCGGAGACCAGTACGCAGACCTGTTCCTGGCAGCAAAGAACCTGAGCGACG

CAATCCTGCTGAGCGACATCCTGAGAGTCAACACAGAAATCACAAAGGCACCGCTG

AGCGCAAGCATGATCAAGAGATACGACGAACACCACCAGGACCTGACACTGCTGAA

GGCACTGGTCAGACAGCAGCTGCCGGAAAAGTACAAGGAAATCTTCTTCGACCAGA

GCAAGAACGGATACGCAGGATACATCGACGGAGGAGCAAGCCAGGAAGAATTCTA

CAAGTTCATCAAGCCGATCCTGGAAAAGATGGACGGAACAGAAGAACTGCTGGTCA

AGCTGAACAGAGAAGACCTGCTGAGAAAGCAGAGAACATTCGACAACGGAAGCAT

CCCGCACCAGATCCACCTGGGAGAACTGCACGCAATCCTGAGAAGACAGGAAGACT

TCTACCCGTTCCTGAAGGACAACAGAGAAAAGATCGAAAAGATCCTGACATTCAGA

ATCCCGTACTACGTCGGACCGCTGGCAAGAGGAAACAGCAGATTCGCATGGATGAC

AAGAAAGAGCGAAGAAACAATCACACCGTGGAACTTCGAAGAAGTCGTCGACAAG

GGAGCAAGCGCACAGAGCTTCATCGAAAGAATGACAAACTTCGACAAGAACCTGCC

GAACGAAAAGGTCCTGCCGAAGCACAGCCTGCTGTACGAATACTTCACAGTCTACA

ACGAACTGACAAAGGTCAAGTACGTCACAGAAGGAATGAGAAAGCCGGCATTCCTG

AGCGGAGAACAGAAGAAGGCAATCGTCGACCTGCTGTTCAAGACAAACAGAAAGG

TCACAGTCAAGCAGCTGAAGGAAGACTACTTCAAGAAGATCGAATGCTTCGACAGC

GTCGAAATCAGCGGAGTCGAAGACAGATTCAACGCAAGCCTGGGAACATACCACGA

CCTGCTGAAGATCATCAAGGACAAGGACTTCCTGGACAACGAAGAAAACGAAGACA

TCCTGGAAGACATCGTCCTGACACTGACACTGTTCGAAGACAGAGAAATGATCGAA

GAAAGACTGAAGACATACGCACACCTGTTCGACGACAAGGTCATGAAGCAGCTGAA

GAGAAGAAGATACACAGGATGGGGAAGACTGAGCAGAAAGCTGATCAACGGAATC

AGAGACAAGCAGAGCGGAAAGACAATCCTGGACTTCCTGAAGAGCGACGGATTCGC

AAACAGAAACTTCATGCAGCTGATCCACGACGACAGCCTGACATTCAAGGAAGACA

TCCAGAAGGCACAGGTCAGCGGACAGGGAGACAGCCTGCACGAACACATCGCAAA

CCTGGCAGGAAGCCCGGCAATCAAGAAGGGAATCCTGCAGACAGTCAAGGTCGTCG

ACGAACTGGTCAAGGTCATGGGAAGACACAAGCCGGAAAACATCGTCATCGAAATG

GCAAGAGAAAACCAGACAACACAGAAGGGACAGAAGAACAGCAGAGAAAGAATG

AAGAGAATCGAAGAAGGAATCAAGGAACTGGGAAGCCAGATCCTGAAGGAACACC

CGGTCGAAAACACACAGCTGCAGAACGAAAAGCTGTACCTGTACTACCTGCAGAAC

GGAAGAGACATGTACGTCGACCAGGAACTGGACATCAACAGACTGAGCGACTACGA

CGTCGACCACATCGTCCCGCAGAGCTTCCTGAAGGACGACAGCATCGACAACAAGG

TCCTGACAAGAAGCGACAAGAACAGAGGAAAGAGCGACAACGTCCCGAGCGAAGA

AGTCGTCAAGAAGATGAAGAACTACTGGAGACAGCTGCTGAACGCAAAGCTGATCA

CACAGAGAAAGTTCGACAACCTGACAAAGGCAGAGAGAGGAGGACTGAGCGAACT

GGACAAGGCAGGATTCATCAAGAGACAGCTGGTCGAAACAAGACAGATCACAAAG

CACGTCGCACAGATCCTGGACAGCAGAATGAACACAAAGTACGACGAAAACGACA

AGCTGATCAGAGAAGTCAAGGTCATCACACTGAAGAGCAAGCTGGTCAGCGACTTC

AGAAAGGACTTCCAGTTCTACAAGGTCAGAGAAATCAACAACTACCACCACGCACA

CGACGCATACCTGAACGCAGTCGTCGGAACAGCACTGATCAAGAAGTACCCGAAGC

-continued

TGGAAAGCGAATTCGTCTACGGAGACTACAAGGTCTACGACGTCAGAAAGATGATC
GCAAAGAGCGAACAGGAAATCGGAAAGGCAACAGCAAAGTACTTCTTCTACAGCAA
CATCATGAACTTCTTCAAGACAGAAATCACACTGGCAAACGGAGAAATCAGAAAGA
GACCGCTGATCGAAACAAACGGAGAAACAGGAGAAATCGTCTGGGACAAGGGAAG
AGACTTCGCAACAGTCAGAAAGGTCCTGAGCATGCCGCAGGTCAACATCGTCAAGA
AGACAGAAGTCCAGACAGGAGGATTCAGCAAGGAAAGCATCCTGCCGAAGAGAAA
CAGCGACAAGCTGATCGCAAGAAAGAAGGACTGGGACCCGAAGAAGTACGGAGGA
TTCGACAGCCCGACAGTCGCATACAGCGTCCTGGTCGTCGCAAAGGTCGAAAAGGG
AAAGAGCAAGAAGCTGAAGAGCGTCAAGGAACTGCTGGGAATCACAATCATGGAA
AGAAGCAGCTTCGAAAAGAACCCGATCGACTTCCTGGAAGCAAAGGGATACAAGGA
AGTCAAGAAGGACCTGATCATCAAGCTGCCGAAGTACAGCCTGTTCGAACTGGAAA
ACGGAAGAAAGAGAATGCTGGCAAGCGCAGGAGAACTGCAGAAGGGAAACGAACT
GGCACTGCCGAGCAAGTACGTCAACTTCCTGTACCTGGCAAGCCACTACGAAAAGC
TGAAGGGAAGCCCGGAAGACAACGAACAGAAGCAGCTGTTCGTCGAACAGCACAA
GCACTACCTGGACGAAATCATCGAACAGATCAGCGAATTCAGCAAGAGAGTCATCC
TGGCAGACGCAAACCTGGACAAGGTCCTGAGCGCATACAACAAGCACAGAGACAA
GCCGATCAGAGAACAGGCAGAAAACATCATCCACCTGTTCACACTGACAAACCTGG
GAGCACCGGCAGCATTCAAGTACTTCGACACAACAATCGACAGAAAGAGATACACA
AGCACAAAGGAAGTCCTGGACGCAACACTGATCCACCAGAGCATCACAGGACTGTA
CGAAACAAGAATCGACCTGAGCCAGCTGGGAGGAGACGGAGGAGGAAGCCCGAAG
AAGAAGAGAAAGGTCTAG mRNA comprising U dep Cas9

(SEQ ID NO: 705)

GGGUCCCGCAGUCGGCGUCCAGCGGCUCUGCUUGUUCGUGUGUGUGUCGUUGCAG
GCCUUAUUCGGAUCCGCCACCAUGGACAAGAAGUACAGCAUCGGACUGGACAUCG
GAACAAACAGCGUCGGAUGGGCAGUCAUCACAGACGAAUACAAGGUCCCGAGCAA
GAAGUUCAAGGUCCUGGGAAACACAGACAGACACAGCAUCAAGAAGAACCUGAU
CGGAGCACUGCUGUUCGACAGCGGAGAAACAGCAGAAGCAACAAGACUGAAGAG
AACAGCAAGAAGAAGAUACACAAGAAGAAAGAACAGAAUCUGCUACCUGCAGGA
AAUCUUCAGCAACGAAAUGGCAAAGGUCGACGACAGCUUCUUCCACAGACUGGAA
GAAAGCUUCCUGGUCGAAGAAGACAAGAAGCACGAAAGACACCCGAUCUUCGGA
AACAUCGUCGACGAAGUCGCAUACCACGAAAAGUACCCGACAAUCUACCACCUGA
GAAAGAAGCUGGUCGACAGCACAGACAAGGCAGACCUGAGACUGAUCUACCUGGC
ACUGGCACACAUGAUCAAGUUCAGAGGACACUUCCUGAUCGAAGGAGACCUGAAC
CCGGACAACAGCGACGUCGACAAGCUGUUCAUCCAGCUGGUCCAGACAUACAACC
AGCUGUUCGAAGAAAACCCGAUCAACGCAAGCGGAGUCGACGCAAAGGCAAUCCU
GAGCGCAAGACUGAGCAAGAGCAGAAGACUGGAAAACCUGAUCGCACAGCUGCCG
GGAGAAAAGAAGAACGGACUGUUCGGAAACCUGAUCGCACUGAGCCUGGGACUG
ACACCGAACUUCAAGAGCAACUUCGACCUGGCAGAAGACGCAAAGCUGCAGCUGA
GCAAGGACACAUACGACGACGACCUGGACAACCUGCUGGCACAGAUCGGAGACCA
GUACGCAGACCUGUUCCUGGCAGCAAAGAACCUGAGCGACGCAAUCCUGCUGAGC

-continued

GACAUCCUGAGAGUCAACACAGAAAUCACAAAGGCACCGCUGAGCGCAAGCAUGA

UCAAGAGAUACGACGAACACCACCAGGACCUGACACUGCUGAAGGCACUGGUCAG

ACAGCAGCUGCCGGAAAAGUACAAGGAAAUCUUCUUCGACCAGAGCAAGAACGG

AUACGCAGGAUACAUCGACGGAGGAGCAAGCCAGGAAGAAUUCUACAAGUUCAU

CAAGCCGAUCCUGGAAAAGAUGGACGGAACAGAAGAACUGCUGGUCAAGCUGAA

CAGAGAAGACCUGCUGAGAAAGCAGAGAACAUUCGACAACGGAAGCAUCCCGCAC

CAGAUCCACCUGGGAGAACUGCACGCAAUCCUGAGAAGACAGGAAGACUUCUACC

CGUUCCUGAAGGACAACAGAGAAAAGAUCGAAAAGAUCCUGACAUUCAGAAUCC

CGUACUACGUCGGACCGCUGGCAAGAGGAAACAGCAGAUUCGCAUGGAUGACAA

GAAAGAGCGAAGAAACAAUCACACCGUGGAACUUCGAAGAAGUCGUCGACAAGG

GAGCAAGCGCACAGAGCUUCAUCGAAAGAAUGACAAACUUCGACAAGAACCUGCC

GAACGAAAAGGUCCUGCCGAAGCACAGCCUGCUGUACGAAUACUUCACAGUCUAC

AACGAACUGACAAAGGUCAAGUACGUCACAGAAGGAAUGAGAAAGCCGGCAUUC

CUGAGCGGAGAACAGAAGAAGGCAAUCGUCGACCUGCUGUUCAAGACAAACAGA

AAGGUCACAGUCAAGCAGCUGAAGGAAGACUACUUCAAGAAGAUCGAAUGCUUC

GACAGCGUCGAAAUCAGCGGAGUCGAAGACAGAUUCAACGCAAGCCUGGGAACA

UACCACGACCUGCUGAAGAUCAUCAAGGACAAGGACUUCCUGGACAACGAAGAAA

ACGAAGACAUCCUGGAAGACAUCGUCCUGACACUGACACUGUUCGAAGACAGAGA

AAUGAUCGAAGAAAGACUGAAGACAUACGCACACCUGUUCGACGACAAGGUCAU

GAAGCAGCUGAAGAGAAGAAGAUACACAGGAUGGGGAAGACUGAGCAGAAAGCU

GAUCAACGGAAUCAGAGACAAGCAGAGCGGAAAGACAAUCCUGGACUUCCUGAA

GAGCGACGGAUUCGCAAACAGAAACUUCAUGCAGCUGAUCCACGACGACAGCCUG

ACAUUCAAGGAAGACAUCCAGAAGGCACAGGUCAGCGGACAGGGAGACAGCCUGC

ACGAACACAUCGCAAACCUGGCAGGAAGCCCGGCAAUCAAGAAGGGAAUCCUGCA

GACAGUCAAGGUCGUCGACGAACUGGUCAAGGUCAUGGGAAGACACAAGCCGGA

AAACAUCGUCAUCGAAAUGGCAAGAGAAAACCAGACAACACAGAAGGGACAGAA

GAACAGCAGAGAAAGAAUGAAGAGAAUCGAAGAAGGAAUCAAGGAACUGGGAAG

CCAGAUCCUGAAGGAACACCCGGUCGAAAACACACAGCUGCAGAACGAAAAGCUG

UACCUGUACUACCUGCAGAACGGAAGAGACAUGUACGUCGACCAGGAACUGGACA

UCAACAGACUGAGCGACUACGACGUCGACCACAUCGUCCCGCAGAGCUUCCUGAA

GGACGACAGCAUCGACAACAAGGUCCUGACAAGAAGCGACAAGAACAGAGGAAA

GAGCGACAACGUCCCGAGCGAAGAAGUCGUCAAGAAGAUGAAGAACUACUGGAG

ACAGCUGCUGAACGCAAAGCUGAUCACACAGAGAAAGUUCGACAACCUGACAAAG

GCAGAGAGAGGAGGACUGAGCGAACUGGACAAGGCAGGAUUCAUCAAGAGACAG

CUGGUCGAAACAAGACAGAUCACAAAGCACGUCGCACAGAUCCUGGACAGCAGAA

UGAACACAAAGUACGACGAAAACGACAAGCUGAUCAGAGAAGUCAAGGUCAUCA

CACUGAAGAGCAAGCUGGUCAGCGACUUCAGAAAGGACUUCCAGUUCUACAAGG

UCAGAGAAAUCAACAACUACCACCACGCACACGACGCAUACCUGAACGCAGUCGU

CGGAACAGCACUGAUCAAGAAGUACCCGAAGCUGGAAAGCGAAUUCGUCUACGG

AGACUACAAGGUCUACGACGUCAGAAAGAUGAUCGCAAAGAGCGAACAGGAAAU

CGGAAAGGCAACAGCAAAGUACUUCUUCUACAGCAACAUCAUGAACUUCUUCAAG

-continued

ACAGAAAUCACACUGGCAAACGGAGAAAUCAGAAAGAGACCGCUGAUCGAAACA

AACGGAGAAACAGGAGAAAUCGUCUGGGACAAGGGAAGAGACUUCGCAACAGUC

AGAAAGGUCCUGAGCAUGCCGCAGGUCAACAUCGUCAAGAAGACAGAAGUCCAG

ACAGGAGGAUUCAGCAAGGAAAGCAUCCUGCCGAAGAGAAACAGCGACAAGCUG

AUCGCAAGAAAGAAGGACUGGGACCCGAAGAAGUACGGAGGAUUCGACAGCCCG

ACAGUCGCAUACAGCGUCCUGGUCGUCGCAAAGGUCGAAAAGGGAAAGAGCAAG

AAGCUGAAGAGCGUCAAGGAACUGCUGGGAAUCACAAUCAUGGAAAGAAGCAGC

UUCGAAAAGAACCCGAUCGACUUCCUGGAAGCAAAGGGAUACAAGGAAGUCAAG

AAGGACCUGAUCAUCAAGCUGCCGAAGUACAGCCUGUUCGAACUGGAAAACGGA

AGAAAGAGAAUGCUGGCAAGCGCAGGAGAACUGCAGAAGGGAAACGAACUGGCA

CUGCCGAGCAAGUACGUCAACUUCCUGUACCUGGCAAGCCACUACGAAAAGCUGA

AGGGAAGCCCGGAAGACAACGAACAGAAGCAGCUGUUCGUCGAACAGCACAAGCA

CUACCUGGACGAAAUCAUCGAACAGAUCAGCGAAUUCAGCAAGAGAGUCAUCCUG

GCAGACGCAAACCUGGACAAGGUCCUGAGCGCAUACAACAAGCACAGAGACAAGC

CGAUCAGAGAACAGGCAGAAAACAUCAUCCACCUGUUCACACUGACAAACCUGGG

AGCACCGGCAGCAUUCAAGUACUUCGACACAACAAUCGACAGAAAGAGAUACACA

AGCACAAAGGAAGUCCUGGACGCAACACUGAUCCACCAGAGCAUCACAGGACUGU

ACGAAACAAGAAUCGACCUGAGCCAGCUGGGAGGAGACGGAGGAGGAAGCCCGA

AGAAGAAGAGAAAGGUCUAGCUAGCCAUCACAUUUAAAAGCAUCUCAGCCUACC

AUGAGAAUAAGAGAAAGAAAAUGAAGAUCAAUAGCUUAUUCAUCUCUUUUUCUU

UUUCGUUGGUGUAAAGCCAACACCCUGUCUAAAAAACAUAAAUUUCUUUAAUCA

UUUUGCCUCUUUUCUCUGUGCUUCAAUUAAUAAAAAAUGGAAAGAACCUCGAGA

AAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

What is claimed is:

1. A method of expressing Factor IX in a cell or population of cells, comprising administering:

i) a nucleic acid construct comprising a Factor IX protein coding sequence;

ii) an RNA-guided DNA binding agent; and iii) a guide RNA (gRNA) comprising the sequence of SEQ ID NO: 8, thereby expressing Factor IX in a cell or population of cells.

2. The method of claim 1, wherein the RNA-guided DNA binding agent is a Cas9 or a nucleic acid encoding a Cas9.

3. The method of claim 1, wherein the RNA-guided DNA binding agent is a nucleic acid encoding the RNA-guided DNA binding agent, and wherein the nucleic acid encoding the RNA-guided DNA binding agent is an mRNA.

4. The method of claim 1, wherein the nucleic acid construct and/or the gRNA is administered as a nucleic acid vector, and wherein the nucleic acid vector is a viral vector.

5. The method of claim 4, wherein the viral vector is selected from the group consisting of an adeno associate viral (AAV) vector, adenoviius vector, retrovirus vector, and lentivirus vector.

6. The method of claim 1, wherein the nucleic acid construct encodes a Factor IX protein having a mutation R338L.

7. A composition for use in expressing Factor IX in a cell, wherein the composition comprises:

i) a nucleic acid construct comprising a Factor IX protein coding sequence;

ii) an RNA-guided DNA binding agent; and iii) a guide RNA (gRNA) comprising the sequence of SEQ ID NO: 8.

8. The composition of claim 7, wherein the RNA-guided DNA binding agent is a Cas nuclease or a nucleic acid encoding a Cas nuclease.

9. The composition of claim 8, wherein the Cas nuclease is an *S. pyogenes* Cas9 nuclease or variant thereof.

10. A method of treating a Factor IX deficiency comprising administering to an individual with the Factor IX deficiency:

i) a nucleic acid construct comprising a Factor IX protein coding sequence;

ii) an RNA-guided DNA binding agent; and iii) a guide RNA (gRNA) comprising the sequence of SEQ ID NO: 8, thereby expressing the Factor IX protein in the individual.

11. The method of claim 1, wherein the gRNA comprises the sequence of SEQ ID NO: 40.

12. The method of claim 1, wherein the gRNA comprises the sequence of:

mU*mA*mA*AGCAUAGUGCAAUGGAUGUUUUA GAmGmCmUmAmGmAmAmAm UmAmGmCAAGUUAAAAUAAGGCUAGU-CCGUUAUCAmAmCmUmUmGmAmAmA mAmAmGmUmGmGmCmAmCmCmGmAmGmUm CmGmGmUmGmCmU*mU*mU*mU (SEQ ID NO: 72), wherein "mA," "mC," "mU," and "mG" represent nucleotides that have been substituted with 2'-O-Me and * indicates a phosphorothioate (PS) bond.

13. The composition of claim 7, wherein the gRNA comprises the sequence of SEQ ID NO: 40.

14. The composition of claim 7, wherein the gRNA comprises the sequence of:

mU*mA*mA*AGCAUAGUGCAAUGGAUGUUUUA GAmGmCmUmAmGmAmAmAm UmAmGmCAAGUUAAAAUAAGGCUAGU-CCGUUAUCAmAmCmUmUmGmAmAmA mAmAmGmUmGmGmCmAmCmCmGmAmGmUm CmGmGmUmGmCmU*mU*mU*mU (SEQ ID NO: 72), wherein "mA," "mC," "mU," and "mG" represent nucleotides that have been substituted with 2'-O-Me and * indicates a phosphorothioate (PS) bond.

15. The method of claim 10, wherein the gRNA comprises the sequence of SEQ ID NO: 40.

16. The method of claim 10, wherein the gRNA comprises the sequence of:

mU*mA*mA*AGCAUAGUGCAAUGGAUGUUUUA GAmGmCmUmAmGmAmAmAm UmAmGmCAAGUUAAAAUAAGGCUAGU-CCGUUAUCAmAmCmUmUmGmAmAmA mAmAmGmUmGmGmCmAmCmCmGmAmGmUm CmGmGmUmGmCmU*mU*mU*mU (SEQ ID NO: 72), wherein "mA," "mC," "mU," and "mG" represent nucleotides that have been substituted with 2'-O-Me and * indicates a phosphorothioate (PS) bond.

* * * * *

UNITED STATES PATENT AND TRADEMARK OFFICE

CERTIFICATE OF CORRECTION

PATENT NO. : 12,214,023 B2
APPLICATION NO. : 16/657961
DATED : February 4, 2025
INVENTOR(S) : Jonathan Douglas Finn et al.

It is certified that error appears in the above-identified patent and that said Letters Patent is hereby corrected as shown below:

In the Claims

In Column 474, Line 56, Claim 5, delete “adenoviius” and insert -- adenovirus --

Signed and Sealed this
Twenty-second Day of April, 2025

Coke Morgan Stewart
*Acting Director of the United States Patent and Trademark Office*

SEQUENCE LISTING

<160> NUMBER OF SEQ ID NOS: 1130

<210> SEQ ID NO 1
<211> LENGTH: 709
<212> TYPE: DNA
<213> ORGANISM: Homo sapiens

<400> SEQUENCE: 1
gtaagaaatc catttttcta ttgttcaact tttattctat tttcccagta aaataaagtt 60
ttagtaaact ctgcatcttt aaagaattat tttggcattt atttctaaaa tggcatagta 120
ttttgtattt gtgaagtctt acaaggttat cttattaata aaattcaaac atcctaggta 180
aaaaaaaaaa aaggtcagaa ttgtttagtg actgtaattt tcttttgcgc actaaggaaa 240
gtgcaaagta acttagagtg actgaaactt cacagaatag ggttgaagat tgaattcata 300
actatcccaa agacctatcc attgcactat gctttattta aaaaccacaa aacctgtgct 360
gttgatctca taaatagaac ttgtatttat atttattttc attttagtct gtcttcttgg 420
ttgctgttga tagacactaa aagagtatta gatattatct aagtttgaat ataaggctat 480
aaatatttaa taatttttaa aatagtattc ttggtaattg aattattctt ctgtttaaag 540
gcagaagaaa taattgaaca tcatcctgag tttttctgta ggaatcagag cccaatattt 600
tgaaacaaat gcataatcta agtcaaatgg aaagaaatat aaaaagtaac attattactt 660
cttgttttct tcagtattta acaatccttt tttttcttcc cttgcccag 709

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2
gagcaaccuc acucuugucu 20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
augcauuugu uucaaaauau 20

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4
ugcauuuguu ucaaaauauu 20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 5
auuuaugaga ucaacagcac 20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 6
gaucaacagc acagguuuug 20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 7
uuaaauaaag cauagugcaa 20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 8
uaaagcauag ugcaauggau 20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 9
uagugcaaug gauaggucuu 20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 10
uacuaaaacu uuauuuuacu 20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 11
aaaguugaac aauagaaaaa 20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 12
aaugcauaau cuaagucaaa 20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 13
uaauaaaauu caaacauccu 20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 14
gcaucuuuaa agaauuauuu 20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 15
uuuggcauuu auuucuaaaa 20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 16
uguauuugug aagucuuaca 20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 17
uccuagguaa aaaaaaaaaa 20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 18
uaauuuucuu uugcgcacua 20

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide -continued

<400> SEQUENCE: 19
ugacugaaac uucacagaau 20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 20
gacugaaacu ucacagaaua 20

<210> SEQ ID NO 21
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 21
uucauuuuag ucugucuucu 20

<210> SEQ ID NO 22
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 22
auuaucuaag uuugaauaua 20

<210> SEQ ID NO 23
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23
aauuuuuaaa auaguauucu 20

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 24
ugaauuauuc uucuguuuaa 20

<210> SEQ ID NO 25
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 25
aucauccuga guuuuucugu 20

<210> SEQ ID NO 26
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
uuacuaaaac uuuauuuuac 20

<210> SEQ ID NO 27
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
accuuuuuuu uuuuuuaccu 20

<210> SEQ ID NO 28
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 28
agugcaaugg auaggucuuu 20

<210> SEQ ID NO 29
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
ugauuccuac agaaaaacuc 20

<210> SEQ ID NO 30
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30
ugggcaaggg aagaaaaaaa 20

<210> SEQ ID NO 31
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 31
ccucacucuu gucugggcaa 20

<210> SEQ ID NO 32
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 32
accucacucu ugucugggca 20

<210> SEQ ID NO 33
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 33
ugagcaaccu cacucuuguc 20

<210> SEQ ID NO 34
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 34
gagcaaccuc acucuugucu guuuuagagc uagaaauagc aaguuaaaau aaggcuaguc 60
cguuaucaac uugaaaaagu ggcaccgagu cggugcuuuu 100

<210> SEQ ID NO 35
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 35
augcauuugu uucaaaauau guuuuagagc uagaaauagc aaguuaaaau aaggcuaguc 60
cguuaucaac uugaaaaagu ggcaccgagu cggugcuuuu 100

<210> SEQ ID NO 36
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 36
ugcauuuguu ucaaaauauu guuuuagagc uagaaauagc aaguuaaaau aaggcuaguc 60
cguuaucaac uugaaaaagu ggcaccgagu cggugcuuuu 100

<210> SEQ ID NO 37
<211> LENGTH: 100
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 37
auuuaugaga ucaacagcac guuuuagagc uagaaauagc aaguuaaaau aaggcuaguc     60
cguuaucaac uugaaaaagu ggcaccgagu cggugcuuuu                           100

<210> SEQ ID NO 38
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 38
gaucaacagc acagguuuug guuuuagagc uagaaauagc aaguuaaaau aaggcuaguc     60
cguuaucaac uugaaaaagu ggcaccgagu cggugcuuuu                           100

<210> SEQ ID NO 39
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 39
uuaaauaaag cauagugcaa guuuuagagc uagaaauagc aaguuaaaau aaggcuaguc     60
cguuaucaac uugaaaaagu ggcaccgagu cggugcuuuu                           100

<210> SEQ ID NO 40
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 40
uaaagcauag ugcaauggau guuuuagagc uagaaauagc aaguuaaaau aaggcuaguc     60
cguuaucaac uugaaaaagu ggcaccgagu cggugcuuuu                           100

<210> SEQ ID NO 41
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 41
uagugcaaug gauaggucuu guuuuagagc uagaaauagc aaguuaaaau aaggcuaguc     60
cguuaucaac uugaaaaagu ggcaccgagu cggugcuuuu                           100

<210> SEQ ID NO 42
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 42

-continued uacuaaaacu uuauuuuacu guuuuagagc uagaaauagc aaguuaaaau aaggcuaguc 60
cguuaucaac uugaaaaagu ggcaccgagu cggugcuuuu 100

<210> SEQ ID NO 43
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 43
aaaguugaac aauagaaaaa guuuuagagc uagaaauagc aaguuaaaau aaggcuaguc 60
cguuaucaac uugaaaaagu ggcaccgagu cggugcuuuu 100

<210> SEQ ID NO 44
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 44
aaugcauaau cuaagucaaa guuuuagagc uagaaauagc aaguuaaaau aaggcuaguc 60
cguuaucaac uugaaaaagu ggcaccgagu cggugcuuuu 100

<210> SEQ ID NO 45
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 45
uaauaaaauu caaacauccu guuuuagagc uagaaauagc aaguuaaaau aaggcuaguc 60
cguuaucaac uugaaaaagu ggcaccgagu cggugcuuuu 100

<210> SEQ ID NO 46
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 46
gcaucuuuaa agaauuauuu guuuuagagc uagaaauagc aaguuaaaau aaggcuaguc 60
cguuaucaac uugaaaaagu ggcaccgagu cggugcuuuu 100

<210> SEQ ID NO 47
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 47
uuuggcauuu auuucuaaaa guuuuagagc uagaaauagc aaguuaaaau aaggcuaguc 60
cguuaucaac uugaaaaagu ggcaccgagu cggugcuuuu 100

-continued

<210> SEQ ID NO 48
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 48
uguauuugug aagucuuaca guuuuagagc uagaaauagc aaguuaaaau aaggcuaguc 60
cguuaucaac uugaaaaagu ggcaccgagu cggugcuuuu 100

<210> SEQ ID NO 49
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 49
uccuagguaa aaaaaaaaaa guuuuagagc uagaaauagc aaguuaaaau aaggcuaguc 60
cguuaucaac uugaaaaagu ggcaccgagu cggugcuuuu 100

<210> SEQ ID NO 50
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 50
uaauuuucuu uugcgcacua guuuuagagc uagaaauagc aaguuaaaau aaggcuaguc 60
cguuaucaac uugaaaaagu ggcaccgagu cggugcuuuu 100

<210> SEQ ID NO 51
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 51
ugacugaaac uucacagaau guuuuagagc uagaaauagc aaguuaaaau aaggcuaguc 60
cguuaucaac uugaaaaagu ggcaccgagu cggugcuuuu 100

<210> SEQ ID NO 52
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 52
gacugaaacu ucacagaaua guuuuagagc uagaaauagc aaguuaaaau aaggcuaguc 60
cguuaucaac uugaaaaagu ggcaccgagu cggugcuuuu 100

<210> SEQ ID NO 53
<211> LENGTH: 100

<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 53
uucauuuuag ucugucuucu guuuuagagc uagaaauagc aaguuaaaau aaggcuaguc 60
cguuaucaac uugaaaaagu ggcaccgagu cggugcuuuu 100

<210> SEQ ID NO 54
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 54
auuaucuaag uuugaauaua guuuuagagc uagaaauagc aaguuaaaau aaggcuaguc 60
cguuaucaac uugaaaaagu ggcaccgagu cggugcuuuu 100

<210> SEQ ID NO 55
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 55
aauuuuuaaa auaguauucu guuuuagagc uagaaauagc aaguuaaaau aaggcuaguc 60
cguuaucaac uugaaaaagu ggcaccgagu cggugcuuuu 100

<210> SEQ ID NO 56
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 56
ugaauuauuc uucuguuuaa guuuuagagc uagaaauagc aaguuaaaau aaggcuaguc 60
cguuaucaac uugaaaaagu ggcaccgagu cggugcuuuu 100

<210> SEQ ID NO 57
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 57
aucauccuga guuuuucugu guuuuagagc uagaaauagc aaguuaaaau aaggcuaguc 60
cguuaucaac uugaaaaagu ggcaccgagu cggugcuuuu 100

<210> SEQ ID NO 58
<211> LENGTH: 100
<212> TYPE: RNA
<213> ORGANISM: Artificial Sequence
<220> FEATURE:
<223> OTHER INFORMATION: Description of Artificial Sequence: Synthetic -continued polynucleotide

<400> SEQUENCE: 58
uuacuaaaac uuuauuuuac guuuuagagc uagaaauagc aaguuaaaau aaggcuaguc 60
cguuaucaac uugaaaaagu ggcaccgagu cggugcuuuu 100

<210> SEQ ID NO 59
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 59
accuuuuuuu uuuuuuaccu guuuuagagc uagaaauagc aaguuaaaau aaggcuaguc 60
cguuaucaac uugaaaaagu ggcaccgagu cggugcuuuu 100

<210> SEQ ID NO 60
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 60
agugcaaugg auaggucuuu guuuuagagc uagaaauagc aaguuaaaau aaggcuaguc 60
cguuaucaac uugaaaaagu ggcaccgagu cggugcuuuu 100

<210> SEQ ID NO 61
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 61
ugauuccuac agaaaaacuc guuuuagagc uagaaauagc aaguuaaaau aaggcuaguc 60
cguuaucaac uugaaaaagu ggcaccgagu cggugcuuuu 100

<210> SEQ ID NO 62
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 62
ugggcaaggg aagaaaaaaa guuuuagagc uagaaauagc aaguuaaaau aaggcuaguc 60
cguuaucaac uugaaaaagu ggcaccgagu cggugcuuuu 100

<210> SEQ ID NO 63
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 63
ccucacucuu gucugggcaa guuuuagagc uagaaauagc aaguuaaaau aaggcuaguc 60
cguuaucaac uugaaaaagu ggcaccgagu cggugcuuuu 100

<210> SEQ ID NO 64
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 64
accucacucu ugucugggca guuuuagagc uagaaauagc aaguuaaaau aaggcuaguc 60
cguuaucaac uugaaaaagu ggcaccgagu cggugcuuuu 100

<210> SEQ ID NO 65
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 65
ugagcaaccu cacucuuguc guuuuagagc uagaaauagc aaguuaaaau aaggcuaguc 60
cguuaucaac uugaaaaagu ggcaccgagu cggugcuuuu 100

<210> SEQ ID NO 66
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 66
gagcaaccuc acucuugucu guuuuagagc uagaaauagc aaguuaaaau aaggcuaguc 60
cguuaucaac uugaaaaagu ggcaccgagu cggugcuuuu 100

<210> SEQ ID NO 67
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 67
augcauuugu uucaaaauau guuuuagagc uagaaauagc aaguuaaaau aaggcuaguc 60
cguuaucaac uugaaaaagu ggcaccgagu cggugcuuuu 100

<210> SEQ ID NO 68
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 68
ugcauuuguu ucaaaauauu guuuuagagc uagaaauagc aaguuaaaau aaggcuaguc 60
cguuaucaac uugaaaaagu ggcaccgagu cggugcuuuu 100

<210> SEQ ID NO 69
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 69
auuuaugaga ucaacagcac guuuuagagc uagaaauagc aaguuaaaau aaggcuaguc 60
cguuaucaac uugaaaaagu ggcaccgagu cggugcuuuu 100

<210> SEQ ID NO 70
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 70
gaucaacagc acagguuuug guuuuagagc uagaaauagc aaguuaaaau aaggcuaguc 60
cguuaucaac uugaaaaagu ggcaccgagu cggugcuuuu 100

<210> SEQ ID NO 71
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 71
uuaaauaaag cauagugcaa guuuuagagc uagaaauagc aaguuaaaau aaggcuaguc 60
cguuaucaac uugaaaaagu ggcaccgagu cggugcuuuu 100

<210> SEQ ID NO 72
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 72
uaaagcauag ugcaauggau guuuuagagc uagaaauagc aaguuaaaau aaggcuaguc 60
cguuaucaac uugaaaaagu ggcaccgagu cggugcuuuu 100

<210> SEQ ID NO 73
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 73
uagugcaaug gauaggucuu guuuuagagc uagaaauagc aaguuaaaau aaggcuaguc 60
cguuaucaac uugaaaaagu ggcaccgagu cggugcuuuu 100

<210> SEQ ID NO 74
<211> LENGTH: 100
<212> TYPE: RNA

<213> ORGANISM: Artificial Sequence
<220> FEATURE:
<223> OTHER INFORMATION: Description of Artificial Sequence: Synthetic
polynucleotide

<400> SEQUENCE: 74
uacuaaaacu uuauuuuacu guuuuagagc uagaaauagc aaguuaaaau aaggcuaguc 60
cguuaucaac uugaaaaagu ggcaccgagu cggugcuuuu 100

<210> SEQ ID NO 75
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 75
aaaguugaac aauagaaaaa guuuuagagc uagaaauagc aaguuaaaau aaggcuaguc 60
cguuaucaac uugaaaaagu ggcaccgagu cggugcuuuu 100

<210> SEQ ID NO 76
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 76
aaugcauaau cuaagucaaa guuuuagagc uagaaauagc aaguuaaaau aaggcuaguc 60
cguuaucaac uugaaaaagu ggcaccgagu cggugcuuuu 100

<210> SEQ ID NO 77
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 77
uaauaaaauu caaacauccu guuuuagagc uagaaauagc aaguuaaaau aaggcuaguc 60
cguuaucaac uugaaaaagu ggcaccgagu cggugcuuuu 100

<210> SEQ ID NO 78
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 78
gcaucuuuaa agaauuauuu guuuuagagc uagaaauagc aaguuaaaau aaggcuaguc 60
cguuaucaac uugaaaaagu ggcaccgagu cggugcuuuu 100

<210> SEQ ID NO 79
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 79
uuuggcauuu auuucuaaaa guuuuagagc uagaaauagc aaguuaaaau aaggcuaguc 60
cguuaucaac uugaaaaagu ggcaccgagu cggugcuuuu 100

<210> SEQ ID NO 80
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 80
uguauuugug aagucuuaca guuuuagagc uagaaauagc aaguuaaaau aaggcuaguc 60
cguuaucaac uugaaaaagu ggcaccgagu cggugcuuuu 100

<210> SEQ ID NO 81
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 81
uccuagguaa aaaaaaaaaa guuuuagagc uagaaauagc aaguuaaaau aaggcuaguc 60
cguuaucaac uugaaaaagu ggcaccgagu cggugcuuuu 100

<210> SEQ ID NO 82
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 82
uaauuuucuu uugcgcacua guuuuagagc uagaaauagc aaguuaaaau aaggcuaguc 60
cguuaucaac uugaaaaagu ggcaccgagu cggugcuuuu 100

<210> SEQ ID NO 83
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 83
ugacugaaac uucacagaau guuuuagagc uagaaauagc aaguuaaaau aaggcuaguc 60
cguuaucaac uugaaaaagu ggcaccgagu cggugcuuuu 100

<210> SEQ ID NO 84
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 84
gacugaaacu ucacagaaua guuuuagagc uagaaauagc aaguuaaaau aaggcuaguc 60
cguuaucaac uugaaaaagu ggcaccgagu cggugcuuuu 100

<210> SEQ ID NO 85
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 85
uucauuuuag ucugucuucu guuuuagagc uagaaauagc aaguuaaaau aaggcuaguc 60
cguuaucaac uugaaaaagu ggcaccgagu cggugcuuuu 100

<210> SEQ ID NO 86
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 86
auuaucuaag uuugaauaua guuuuagagc uagaaauagc aaguuaaaau aaggcuaguc 60
cguuaucaac uugaaaaagu ggcaccgagu cggugcuuuu 100

<210> SEQ ID NO 87
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 87
aauuuuuaaa auaguauucu guuuuagagc uagaaauagc aaguuaaaau aaggcuaguc 60
cguuaucaac uugaaaaagu ggcaccgagu cggugcuuuu 100

<210> SEQ ID NO 88
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 88
ugaauuauuc uucuguuuaa guuuuagagc uagaaauagc aaguuaaaau aaggcuaguc 60
cguuaucaac uugaaaaagu ggcaccgagu cggugcuuuu 100

<210> SEQ ID NO 89
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 89
aucauccuga guuuuucugu guuuuagagc uagaaauagc aaguuaaaau aaggcuaguc 60
cguuaucaac uugaaaaagu ggcaccgagu cggugcuuuu 100

<210> SEQ ID NO 90
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 90
uuacuaaaac uuuauuuuac guuuuagagc uagaaauagc aaguuaaaau aaggcuaguc 60
cguuaucaac uugaaaaagu ggcaccgagu cggugcuuuu 100

<210> SEQ ID NO 91
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 91
accuuuuuuu uuuuuuaccu guuuuagagc uagaaauagc aaguuaaaau aaggcuaguc 60
cguuaucaac uugaaaaagu ggcaccgagu cggugcuuuu 100

<210> SEQ ID NO 92
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 92
agugcaaugg auaggucuuu guuuuagagc uagaaauagc aaguuaaaau aaggcuaguc 60
cguuaucaac uugaaaaagu ggcaccgagu cggugcuuuu 100

<210> SEQ ID NO 93
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 93
ugauuccuac agaaaaacuc guuuuagagc uagaaauagc aaguuaaaau aaggcuaguc 60
cguuaucaac uugaaaaagu ggcaccgagu cggugcuuuu 100

<210> SEQ ID NO 94
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 94
ugggcaaggg aagaaaaaaa guuuuagagc uagaaauagc aaguuaaaau aaggcuaguc 60
cguuaucaac uugaaaaagu ggcaccgagu cggugcuuuu 100

<210> SEQ ID NO 95
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 95
ccucacucuu gucugggcaa guuuuagagc uagaaauagc aaguuaaaau aaggcuaguc 60
cguuaucaac uugaaaaagu ggcaccgagu cggugcuuuu 100

<210> SEQ ID NO 96
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 96
accucacucu ugucugggca guuuuagagc uagaaauagc aaguuaaaau aaggcuaguc 60
cguuaucaac uugaaaaagu ggcaccgagu cggugcuuuu 100

<210> SEQ ID NO 97
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 97
ugagcaaccu cacucuuguc guuuuagagc uagaaauagc aaguuaaaau aaggcuaguc 60
cguuaucaac uugaaaaagu ggcaccgagu cggugcuuuu 100

<210> SEQ ID NO 98
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 98
auuugcaucu gagaacccuu 20

<210> SEQ ID NO 99
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 99
aucgggaacu ggcaucuuca 20

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 100
guuacaggaa aaucugaagg 20

<210> SEQ ID NO 101
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 101
gaucgggaac uggcaucuuc 20

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 102
ugcaucugag aacccuuagg 20

<210> SEQ ID NO 103
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 103
cacucuuguc uguggaaaca 20

<210> SEQ ID NO 104
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 104
aucguuacag gaaaaucuga 20

<210> SEQ ID NO 105
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 105
gcaucuucag ggaguagcuu 20

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 106
caaucuuuaa auauguugug 20

-continued

<210> SEQ ID NO 107
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 107
ucacucuugu cuguggaaac 20

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 108
ugcuuguauu uuucuaguaa 20

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 109
guaaauaucu acuaagacaa 20

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 110
uuuuucuagu aauggaagcc 20

<210> SEQ ID NO 111
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 111
uuauauuauu gauauauuuu 20

<210> SEQ ID NO 112
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 112
gcacagauau aaacacuuaa 20

<210> SEQ ID NO 113

<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 113
cacagauaua aacacuuaac 20

<210> SEQ ID NO 114
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 114
gguuuuaaaa auaauaaugu 20

<210> SEQ ID NO 115
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115
ucagauuuuc cuguaacgau 20

<210> SEQ ID NO 116
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
cagauuuucc uguaacgauc 20

<210> SEQ ID NO 117
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
caaugguaaa uaagaaauaa 20

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
ggaaaaucug aagguggcaa 20

<210> SEQ ID NO 119
<211> LENGTH: 20

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 119
ggcgaucuca cucuugucug 20

<210> SEQ ID NO 120
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 120
auuugcaucu gagaacccuu guuuuagagc uagaaauagc aaguuaaaau aaggcuaguc 60
cguuaucaac uugaaaaagu ggcaccgagu cggugcuuuu 100

<210> SEQ ID NO 121
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 121
aucgggaacu ggcaucuuca guuuuagagc uagaaauagc aaguuaaaau aaggcuaguc 60
cguuaucaac uugaaaaagu ggcaccgagu cggugcuuuu 100

<210> SEQ ID NO 122
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 122
guuacaggaa aaucugaagg guuuuagagc uagaaauagc aaguuaaaau aaggcuaguc 60
cguuaucaac uugaaaaagu ggcaccgagu cggugcuuuu 100

<210> SEQ ID NO 123
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 123
gaucgggaac uggcaucuuc guuuuagagc uagaaauagc aaguuaaaau aaggcuaguc 60
cguuaucaac uugaaaaagu ggcaccgagu cggugcuuuu 100

<210> SEQ ID NO 124
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 124
ugcaucugag aacccuuagg guuuuagagc uagaaauagc aaguuaaaau aaggcuaguc 60
cguuaucaac uugaaaaagu ggcaccgagu cggugcuuuu 100

<210> SEQ ID NO 125
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 125
cacucuuguc uguggaaaca guuuuagagc uagaaauagc aaguuaaaau aaggcuaguc 60
cguuaucaac uugaaaaagu ggcaccgagu cggugcuuuu 100

<210> SEQ ID NO 126
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 126
aucguuacag gaaaaucuga guuuuagagc uagaaauagc aaguuaaaau aaggcuaguc 60
cguuaucaac uugaaaaagu ggcaccgagu cggugcuuuu 100

<210> SEQ ID NO 127
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 127
gcaucuucag ggaguagcuu guuuuagagc uagaaauagc aaguuaaaau aaggcuaguc 60
cguuaucaac uugaaaaagu ggcaccgagu cggugcuuuu 100

<210> SEQ ID NO 128
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 128
caaucuuuaa auauguugug guuuuagagc uagaaauagc aaguuaaaau aaggcuaguc 60
cguuaucaac uugaaaaagu ggcaccgagu cggugcuuuu 100

<210> SEQ ID NO 129
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 129
ucacucuugu cuguggaaac guuuuagagc uagaaauagc aaguuaaaau aaggcuaguc 60
cguuaucaac uugaaaaagu ggcaccgagu cggugcuuuu 100

<210> SEQ ID NO 130
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 130
ugcuuguauu uuucuaguaa guuuuagagc uagaaauagc aaguuaaaau aaggcuaguc 60
cguuaucaac uugaaaaagu ggcaccgagu cggugcuuuu 100

<210> SEQ ID NO 131
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 131
guaaauaucu acuaagacaa guuuuagagc uagaaauagc aaguuaaaau aaggcuaguc 60
cguuaucaac uugaaaaagu ggcaccgagu cggugcuuuu 100

<210> SEQ ID NO 132
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 132
uuuuucuagu aauggaagcc guuuuagagc uagaaauagc aaguuaaaau aaggcuaguc 60
cguuaucaac uugaaaaagu ggcaccgagu cggugcuuuu 100

<210> SEQ ID NO 133
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 133
uuauauuauu gauauauuuu guuuuagagc uagaaauagc aaguuaaaau aaggcuaguc 60
cguuaucaac uugaaaaagu ggcaccgagu cggugcuuuu 100

<210> SEQ ID NO 134
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 134
gcacagauau aaacacuuaa guuuuagagc uagaaauagc aaguuaaaau aaggcuaguc 60
cguuaucaac uugaaaaagu ggcaccgagu cggugcuuuu 100

<210> SEQ ID NO 135

<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 135
cacagauaua aacacuuaac guuuuagagc uagaaauagc aaguuaaaau aaggcuaguc 60
cguuaucaac uugaaaaagu ggcaccgagu cggugcuuuu 100

<210> SEQ ID NO 136
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 136
gguuuuaaaa auaauaaugu guuuuagagc uagaaauagc aaguuaaaau aaggcuaguc 60
cguuaucaac uugaaaaagu ggcaccgagu cggugcuuuu 100

<210> SEQ ID NO 137
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 137
ucagauuuuc cuguaacgau guuuuagagc uagaaauagc aaguuaaaau aaggcuaguc 60
cguuaucaac uugaaaaagu ggcaccgagu cggugcuuuu 100

<210> SEQ ID NO 138
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 138
cagauuuucc uguaacgauc guuuuagagc uagaaauagc aaguuaaaau aaggcuaguc 60
cguuaucaac uugaaaaagu ggcaccgagu cggugcuuuu 100

<210> SEQ ID NO 139
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 139
caaugguaaa uaagaaauaa guuuuagagc uagaaauagc aaguuaaaau aaggcuaguc 60
cguuaucaac uugaaaaagu ggcaccgagu cggugcuuuu 100

<210> SEQ ID NO 140
<211> LENGTH: 100
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 140
ggaaaaucug aagguggcaa guuuuagagc uagaaauagc aaguuaaaau aaggcuaguc     60
cguuaucaac uugaaaaagu ggcaccgagu cggugcuuuu                           100

<210> SEQ ID NO 141
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 141
ggcgaucuca cucuugucug guuuuagagc uagaaauagc aaguuaaaau aaggcuaguc     60
cguuaucaac uugaaaaagu ggcaccgagu cggugcuuuu                           100

<210> SEQ ID NO 142
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 142
auuugcaucu gagaacccuu guuuuagagc uagaaauagc aaguuaaaau aaggcuaguc     60
cguuaucaac uugaaaaagu ggcaccgagu cggugcuuuu                           100

<210> SEQ ID NO 143
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 143
aucgggaacu ggcaucuuca guuuuagagc uagaaauagc aaguuaaaau aaggcuaguc     60
cguuaucaac uugaaaaagu ggcaccgagu cggugcuuuu                           100

<210> SEQ ID NO 144
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 144
guuacaggaa aaucugaagg guuuuagagc uagaaauagc aaguuaaaau aaggcuaguc     60
cguuaucaac uugaaaaagu ggcaccgagu cggugcuuuu                           100

<210> SEQ ID NO 145
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 145
gaucgggaac uggcaucuuc guuuuagagc uagaaauagc aaguuaaaau aaggcuaguc 60
cguuaucaac uugaaaaagu ggcaccgagu cggugcuuuu 100

<210> SEQ ID NO 146
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 146
ugcaucugag aacccuuagg guuuuagagc uagaaauagc aaguuaaaau aaggcuaguc 60
cguuaucaac uugaaaaagu ggcaccgagu cggugcuuuu 100

<210> SEQ ID NO 147
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 147
cacucuuguc uguggaaaca guuuuagagc uagaaauagc aaguuaaaau aaggcuaguc 60
cguuaucaac uugaaaaagu ggcaccgagu cggugcuuuu 100

<210> SEQ ID NO 148
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 148
aucguuacag gaaaaucuga guuuuagagc uagaaauagc aaguuaaaau aaggcuaguc 60
cguuaucaac uugaaaaagu ggcaccgagu cggugcuuuu 100

<210> SEQ ID NO 149
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 149
gcaucuucag ggaguagcuu guuuuagagc uagaaauagc aaguuaaaau aaggcuaguc 60
cguuaucaac uugaaaaagu ggcaccgagu cggugcuuuu 100

<210> SEQ ID NO 150
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 150
caaucuuuaa auauguugug guuuuagagc uagaaauagc aaguuaaaau aaggcuaguc 60
cguuaucaac uugaaaaagu ggcaccgagu cggugcuuuu 100

<210> SEQ ID NO 151
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 151
ucacucuugu cuguggaaac guuuuagagc uagaaauagc aaguuaaaau aaggcuaguc 60
cguuaucaac uugaaaaagu ggcaccgagu cggugcuuuu 100

<210> SEQ ID NO 152
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 152
ugcuuguauu uuucuaguaa guuuuagagc uagaaauagc aaguuaaaau aaggcuaguc 60
cguuaucaac uugaaaaagu ggcaccgagu cggugcuuuu 100

<210> SEQ ID NO 153
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 153
guaaauaucu acuaagacaa guuuuagagc uagaaauagc aaguuaaaau aaggcuaguc 60
cguuaucaac uugaaaaagu ggcaccgagu cggugcuuuu 100

<210> SEQ ID NO 154
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 154
uuuuucuagu aauggaagcc guuuuagagc uagaaauagc aaguuaaaau aaggcuaguc 60
cguuaucaac uugaaaaagu ggcaccgagu cggugcuuuu 100

<210> SEQ ID NO 155
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 155
uuauauuauu gauauauuuu guuuuagagc uagaaauagc aaguuaaaau aaggcuaguc 60
cguuaucaac uugaaaaagu ggcaccgagu cggugcuuuu 100

<210> SEQ ID NO 156
<211> LENGTH: 100

<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 156
gcacagauau aaacacuuaa guuuuagagc uagaaauagc aaguuaaaau aaggcuaguc 60
cguuaucaac uugaaaaagu ggcaccgagu cggugcuuuu 100

<210> SEQ ID NO 157
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 157
cacagauaua aacacuuaac guuuuagagc uagaaauagc aaguuaaaau aaggcuaguc 60
cguuaucaac uugaaaaagu ggcaccgagu cggugcuuuu 100

<210> SEQ ID NO 158
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 158
gguuuuaaaa auaauaaugu guuuuagagc uagaaauagc aaguuaaaau aaggcuaguc 60
cguuaucaac uugaaaaagu ggcaccgagu cggugcuuuu 100

<210> SEQ ID NO 159
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 159
ucagauuuuc cuguaacgau guuuuagagc uagaaauagc aaguuaaaau aaggcuaguc 60
cguuaucaac uugaaaaagu ggcaccgagu cggugcuuuu 100

<210> SEQ ID NO 160
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 160
cagauuuucc uguaacgauc guuuuagagc uagaaauagc aaguuaaaau aaggcuaguc 60
cguuaucaac uugaaaaagu ggcaccgagu cggugcuuuu 100

<210> SEQ ID NO 161
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 161
caaugguaaa uaagaaauaa guuuuagagc uagaaauagc aaguuaaaau aaggcuaguc 60
cguuaucaac uugaaaaagu ggcaccgagu cggugcuuuu 100

<210> SEQ ID NO 162
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 162
ggaaaaucug aagguggcaa guuuuagagc uagaaauagc aaguuaaaau aaggcuaguc 60
cguuaucaac uugaaaaagu ggcaccgagu cggugcuuuu 100

<210> SEQ ID NO 163
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 163
ggcgaucuca cucuugucug guuuuagagc uagaaauagc aaguuaaaau aaggcuaguc 60
cguuaucaac uugaaaaagu ggcaccgagu cggugcuuuu 100

<210> SEQ ID NO 164

<400> SEQUENCE: 164

000

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 165
agcaaccuca cucuugucug 20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 166
accucacucu ugucugggga 20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 167
ccucacucuu gucuggggaa 20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 168
cucacucuug ucuggggaag 20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 169
ggggaagggg agaaaaaaaa 20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 170
gggaagggga gaaaaaaaaa 20

<210> SEQ ID NO 171

<400> SEQUENCE: 171

000

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 172
ugcauuuguu ucaaaauauu 20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 173
ugauuccuac agaaaaaguc 20

<210> SEQ ID NO 174

<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uacagaaaaa gucaggauaa 20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uuucuucugc cuuuaaacag 20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uuauaguuuu auauucaaac 20

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 182
agugcaaugg auaggucuua 20

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 183
uuacuuugca cuuuccuuag 20

<210> SEQ ID NO 184
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 184
uacuuugcac uuuccuuagu 20

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 185
ucugaccuuu uauuuuaccu 20

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 189
auuauccuga cuuuuucugu 20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 190
ugaauuauuc cucuguuuaa 20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 191
uaauuuucuu uugcccacua 20

<210> SEQ ID NO 192
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 192
aaaaggucag aauuguuuag 20

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 193
aacauccuag guaaaauaaa 20

<210> SEQ ID NO 194

<400> SEQUENCE: 194

000

<210> SEQ ID NO 195
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 195
uugucaugua uuucuaaaau 20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 196
uuugucaugu auuucuaaaa 20

<210> SEQ ID NO 197

<400> SEQUENCE: 197

000

<210> SEQ ID NO 198
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 198
agcaaccuca cucuugucug guuuuagagc uagaaauagc aaguuaaaau aaggcuaguc 60
cguuaucaac uugaaaaagu ggcaccgagu cggugcuuuu 100

<210> SEQ ID NO 199
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 199
accucacucu ugucugggga guuuuagagc uagaaauagc aaguuaaaau aaggcuaguc 60
cguuaucaac uugaaaaagu ggcaccgagu cggugcuuuu 100

<210> SEQ ID NO 200
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 200
ccucacucuu gucuggggaa guuuuagagc uagaaauagc aaguuaaaau aaggcuaguc 60
cguuaucaac uugaaaaagu ggcaccgagu cggugcuuuu 100

<210> SEQ ID NO 201
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 201
cucacucuug ucuggggaag guuuuagagc uagaaauagc aaguuaaaau aaggcuaguc 60
cguuaucaac uugaaaaagu ggcaccgagu cggugcuuuu 100

<210> SEQ ID NO 202
<211> LENGTH: 100
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 202
ggggaagggg agaaaaaaaa guuuuagagc uagaaauagc aaguuaaaau aaggcuaguc     60
cguuaucaac uugaaaaagu ggcaccgagu cggugcuuuu                          100

<210> SEQ ID NO 203
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 203
gggaagggga gaaaaaaaaa guuuuagagc uagaaauagc aaguuaaaau aaggcuaguc     60
cguuaucaac uugaaaaagu ggcaccgagu cggugcuuuu                          100

<210> SEQ ID NO 204

<400> SEQUENCE: 204

000

<210> SEQ ID NO 205

<400> SEQUENCE: 205

000

<210> SEQ ID NO 206
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 206
ugauuccuac agaaaaaguc guuuuagagc uagaaauagc aaguuaaaau aaggcuaguc     60
cguuaucaac uugaaaaagu ggcaccgagu cggugcuuuu                          100

<210> SEQ ID NO 207
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 207
uacagaaaaa gucaggauaa guuuuagagc uagaaauagc aaguuaaaau aaggcuaguc     60
cguuaucaac uugaaaaagu ggcaccgagu cggugcuuuu                          100

<210> SEQ ID NO 208
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 208
uuucuucugc cuuuaaacag guuuuagagc uagaaauagc aaguuaaaau aaggcuaguc 60
cguuaucaac uugaaaaagu ggcaccgagu cggugcuuuu 100

<210> SEQ ID NO 209
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 209
uuauaguuuu auauucaaac guuuuagagc uagaaauagc aaguuaaaau aaggcuaguc 60
cguuaucaac uugaaaaagu ggcaccgagu cggugcuuuu 100

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 215
agugcaaugg auaggucuua guuuuagagc uagaaauagc aaguuaaaau aaggcuaguc 60
cguuaucaac uugaaaaagu ggcaccgagu cggugcuuuu 100

<210> SEQ ID NO 216
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 216
uuacuuugca cuuuccuuag guuuuagagc uagaaauagc aaguuaaaau aaggcuaguc 60
cguuaucaac uugaaaaagu ggcaccgagu cggugcuuuu 100

<210> SEQ ID NO 217
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 217
uacuuugcac uuuccuuagu guuuuagagc uagaaauagc aaguuaaaau aaggcuaguc 60
cguuaucaac uugaaaaagu ggcaccgagu cggugcuuuu 100

<210> SEQ ID NO 218
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 218
ucugaccuuu uauuuuaccu guuuuagagc uagaaauagc aaguuaaaau aaggcuaguc 60
cguuaucaac uugaaaaagu ggcaccgagu cggugcuuuu 100

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 222
auuauccuga cuuuuucugu guuuuagagc uagaaauagc aaguuaaaau aaggcuaguc 60
cguuaucaac uugaaaaagu ggcaccgagu cggugcuuuu 100

<210> SEQ ID NO 223
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 223
ugaauuauuc cucuguuuaa guuuuagagc uagaaauagc aaguuaaaau aaggcuaguc 60
cguuaucaac uugaaaaagu ggcaccgagu cggugcuuuu 100

<210> SEQ ID NO 224
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 224
uaauuuucuu uugcccacua guuuuagagc uagaaauagc aaguuaaaau aaggcuaguc 60
cguuaucaac uugaaaaagu ggcaccgagu cggugcuuuu 100

<210> SEQ ID NO 225
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 225
aaaaggucag aauuguuuag guuuuagagc uagaaauagc aaguuaaaau aaggcuaguc 60
cguuaucaac uugaaaaagu ggcaccgagu cggugcuuuu 100

<210> SEQ ID NO 226
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 226
aacauccuag guaaaauaaa guuuuagagc uagaaauagc aaguuaaaau aaggcuaguc 60
cguuaucaac uugaaaaagu ggcaccgagu cggugcuuuu 100

<210> SEQ ID NO 227

<400> SEQUENCE: 227

000

<210> SEQ ID NO 228
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 228
uugucaugua uuucuaaaau guuuuagagc uagaaauagc aaguuaaaau aaggcuaguc 60
cguuaucaac uugaaaaagu ggcaccgagu cggugcuuuu 100

<210> SEQ ID NO 229
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 229
uuugucaugu auuucuaaaa guuuuagagc uagaaauagc aaguuaaaau aaggcuaguc 60
cguuaucaac uugaaaaagu ggcaccgagu cggugcuuuu 100

<210> SEQ ID NO 230

<400> SEQUENCE: 230

000

<210> SEQ ID NO 231
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 231
agcaaccuca cucuugucug guuuuagagc uagaaauagc aaguuaaaau aaggcuaguc 60
cguuaucaac uugaaaaagu ggcaccgagu cggugcuuuu 100

<210> SEQ ID NO 232
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 232
accucacucu ugucugggga guuuuagagc uagaaauagc aaguuaaaau aaggcuaguc 60
cguuaucaac uugaaaaagu ggcaccgagu cggugcuuuu 100

<210> SEQ ID NO 233
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 233
ccucacucuu gucuggggaa guuuuagagc uagaaauagc aaguuaaaau aaggcuaguc 60
cguuaucaac uugaaaaagu ggcaccgagu cggugcuuuu 100

<210> SEQ ID NO 234
<211> LENGTH: 100
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 234
cucacucuug ucuggggaag guuuuagagc uagaaauagc aaguuaaaau aaggcuaguc 60
cguuaucaac uugaaaaagu ggcaccgagu cggugcuuuu 100

<210> SEQ ID NO 235

<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 235
ggggaagggg agaaaaaaaa guuuuagagc uagaaauagc aaguuaaaau aaggcuaguc     60
cguuaucaac uugaaaaagu ggcaccgagu cggugcuuuu                          100

<210> SEQ ID NO 236
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 236
gggaagggga gaaaaaaaaa guuuuagagc uagaaauagc aaguuaaaau aaggcuaguc     60
cguuaucaac uugaaaaagu ggcaccgagu cggugcuuuu                          100

<210> SEQ ID NO 237

<400> SEQUENCE: 237

000

<210> SEQ ID NO 238

<400> SEQUENCE: 238

000

<210> SEQ ID NO 239
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 239
ugauuccuac agaaaaaguc guuuuagagc uagaaauagc aaguuaaaau aaggcuaguc     60
cguuaucaac uugaaaaagu ggcaccgagu cggugcuuuu                          100

<210> SEQ ID NO 240
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 240
uacagaaaaa gucaggauaa guuuuagagc uagaaauagc aaguuaaaau aaggcuaguc     60
cguuaucaac uugaaaaagu ggcaccgagu cggugcuuuu                          100

<210> SEQ ID NO 241
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 241
uuucuucugc cuuuaaacag guuuuagagc uagaaauagc aaguuaaaau aaggcuaguc 60
cguuaucaac uugaaaaagu ggcaccgagu cggugcuuuu 100

<210> SEQ ID NO 242
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 242
uuauaguuuu auauucaaac guuuuagagc uagaaauagc aaguuaaaau aaggcuaguc 60
cguuaucaac uugaaaaagu ggcaccgagu cggugcuuuu 100

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 248
agugcaaugg auaggucuua guuuuagagc uagaaauagc aaguuaaaau aaggcuaguc 60
cguuaucaac uugaaaaagu ggcaccgagu cggugcuuuu 100

<210> SEQ ID NO 249
<211> LENGTH: 100
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 249
uuacuuugca cuuuccuuag guuuuagagc uagaaauagc aaguuaaaau aaggcuaguc     60
cguuaucaac uugaaaaagu ggcaccgagu cggugcuuuu                           100

<210> SEQ ID NO 250
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 250
uacuuugcac uuuccuuagu guuuuagagc uagaaauagc aaguuaaaau aaggcuaguc     60
cguuaucaac uugaaaaagu ggcaccgagu cggugcuuuu                           100

<210> SEQ ID NO 251
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 251
ucugaccuuu uauuuuaccu guuuuagagc uagaaauagc aaguuaaaau aaggcuaguc     60
cguuaucaac uugaaaaagu ggcaccgagu cggugcuuuu                           100

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 255
auuauccuga cuuuuucugu guuuuagagc uagaaauagc aaguuaaaau aaggcuaguc     60
cguuaucaac uugaaaaagu ggcaccgagu cggugcuuuu                           100

<210> SEQ ID NO 256
<211> LENGTH: 100
<212> TYPE: RNA

<213> ORGANISM: Artificial Sequence
<220> FEATURE:
<223> OTHER INFORMATION: Description of Artificial Sequence: Synthetic polynucleotide

<400> SEQUENCE: 256
ugaauuauuc cucuguuuaa guuuuagagc uagaaauagc aaguuaaaau aaggcuaguc 60
cguuaucaac uugaaaaagu ggcaccgagu cggugcuuuu 100

<210> SEQ ID NO 257
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 257
uaauuuucuu uugcccacua guuuuagagc uagaaauagc aaguuaaaau aaggcuaguc 60
cguuaucaac uugaaaaagu ggcaccgagu cggugcuuuu 100

<210> SEQ ID NO 258
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 258
aaaaggucag aauuguuuag guuuuagagc uagaaauagc aaguuaaaau aaggcuaguc 60
cguuaucaac uugaaaaagu ggcaccgagu cggugcuuuu 100

<210> SEQ ID NO 259
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 259
aacauccuag guaaaauaaa guuuuagagc uagaaauagc aaguuaaaau aaggcuaguc 60
cguuaucaac uugaaaaagu ggcaccgagu cggugcuuuu 100

<210> SEQ ID NO 260

<400> SEQUENCE: 260

000

<210> SEQ ID NO 261
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 261
uugucaugua uuucuaaaau guuuuagagc uagaaauagc aaguuaaaau aaggcuaguc 60
cguuaucaac uugaaaaagu ggcaccgagu cggugcuuuu 100

<210> SEQ ID NO 262
<211> LENGTH: 100
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 262
uuugucaugu auuucuaaaa guuuuagagc uagaaauagc aaguuaaaau aaggcuaguc 60
cguuaucaac uugaaaaagu ggcaccgagu cggugcuuuu 100

<210> SEQ ID NO 263
<211> LENGTH: 145
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 263
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcct 145

<210> SEQ ID NO 264
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 264
taggtcagtg aagagaagaa caaaaagcag catattacag ttagttgtct tcatcaatct 60
ttaaatatgt tgtgtggttt ttctctccct gtttccacag 100

<210> SEQ ID NO 265
<211> LENGTH: 1296
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 265
tttcttgatc atgaaaacgc caacaaaatt ctgaatcggc caaagaggta taattcaggt 60
aaattggaag agtttgttca agggaacctt gagagagaat gtatggaaga aaagtgtagt 120
tttgaagaag cacgagaagt ttttgaaaac actgaaagaa caactgaatt ttggaagcag 180
tatgttgatg gagatcagtg tgagtccaat ccatgtttaa atggcggcag ttgcaaggat 240
gacattaatt cctatgaatg ttggtgtccc tttggatttg aaggaaagaa ctgtgaatta 300
gatgtaacat gtaacattaa gaatggcaga tgcgagcagt tttgtaaaaa tagtgctgat 360
aacaaggtgg tttgctcctg tactgaggga tatcgacttg cagaaaacca gaagtcctgt 420
gaaccagcag tgccatttcc atgtggaaga gtttctgttt cacaaacttc taagctcacc 480
cgtgctgaga ctgtttttcc tgatgtggac tatgtaaatt ctactgaagc tgaaaccatt 540
ttggataaca tcactcaaag cacccaatca tttaatgact tcactcgggt tgttggtgga 600
gaagatgcca aaccaggtca attcccttgg caggttgttt tgaatggtaa agttgatgca 660
ttctgtggag gctctatcgt taatgaaaaa tggattgtaa ctgctgccca ctgtgttgaa 720
actggtgtta aaattacagt tgtcgcaggt gaacataata ttgaggagac agaacataca 780
gagcaaaagc gaaatgtgat tcgaattatt cctcaccaca actacaatgc agctattaat 840
aagtacaacc atgacattgc ccttctggaa ctggacgaac ccttagtgct aaacagctac 900
gttacaccta tttgcattgc tgacaaggaa tacacgaaca tcttcctcaa atttggatct 960
ggctatgtaa gtggctgggg aagagtcttc cacaaaggga gatcagcttt agttcttcag 1020
taccttagag ttccacttgt tgaccgagcc acatgtcttc tatctacaaa gttcaccatc 1080
tataacaaca tgttctgtgc tggcttccat gaaggaggta gagattcatg tcaaggagat 1140
agtgggggac cccatgttac tgaagtggaa gggaccagtt tcttaactgg aattattagc 1200
tggggtgaag agtgtgcaat gaaaggcaaa tatggaatat ataccaaggt atcccggtat 1260
gtcaactgga ttaaggaaaa aacaaagctc acttaa 1296

<210> SEQ ID NO 266
<211> LENGTH: 276
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 266
cctcgactgt gccttctagt tgccagccat ctgttgtttg cccctccccc gtgccttcct 60
tgaccctgga aggtgccact cccactgtcc tttcctaata aaatgaggaa attgcatcgc 120
attgtctgag taggtgtcat tctattctgg ggggtggggt ggggcaggac agcaaggggg 180
aggattggga agacaatagc aggcatgctg gggatgcggt gggctctatg gcttctgagg 240
cggaaagaac cagctggggc tctagggggt atcccc 276

<210> SEQ ID NO 267
<211> LENGTH: 192
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 267
aaaaaacctc ccacacctcc ccctgaacct gaaacataaa atgaatgcaa ttgttgttgt 60
taacttgttt attgcagctt ataatggtta caaataaagc aatagcatca caaatttcac 120
aaataaagca tttttttcac tgcattctag ttgtggtttg tccaaactca tcaatgtatc 180
ttatcatgtc tg 192

<210> SEQ ID NO 268
<211> LENGTH: 1296
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 268
ttaggtgagc ttagtctttt cttttatcca attcacgtag cgagagacct tcgtatagat 60
gccatatttc cccttcatcg cacattcctc cccccaactt attatcccgg tcaagaaact 120
tgttccttcg acttcagtga cgtgtggtcc acctgaatca ccttggcatg agtcgcgacc 180

```
gccctcgtga aacccagcac aaaacatgtt attgtaaatc gtaaatttcg tggacagaag    240

acaggtcgct ctatcgacca acgggacgcg caaatattgc agaacgaggg ctgatcgacc    300

tttgtggaag acccgccccc acccactcac atatccgctc ccaaatttca agaagatatt    360

tgtatattct ttatcggcta tacaaatcgg ggtaacatag gagttaagta cgagtggctc    420

gtccagctcc aggagggcta tatcatggtt gtacttgttt atagcggcat tataattgtg    480

atggggtatg atcctgataa cattcctttt ctgttcagta tgctcagttt cttcaatgtt    540

gtgttcgcca gccacgaccg taatcttaac ccccgtctcg acacagtgtg cggccgttac    600

aatccacttt tcattgacta tggagccccc acaaaacgcg tcgacttttc cgttgagcac    660

cacctgccat ggaaattggc caggtttagc gtcctcgccc ccgacaaccc tagtaaagtc    720

attaaatgac tgtgtggatt gtgttatatt atcaagaatc gtttcggctt cagtagagtt    780

aacgtagtcc acatcgggaa aaactgtctc ggcccttgtc aactttgatg tctgggacac    840

acttacccga ccgcacggga agggcaccgc cggttcacag ctcttttgat tctcagcgag    900

ccggtagccc tcagtgcaac tacacacaac tttgttgtcg gcggaatttt tacagaattg    960

ctcgcatcgt ccatttttaa tgttgcaggt gacgtccaac tcgcagtttt ttccttcaaa   1020

accaaaaggg caccaacact cgtaggaatt tatatcgtct ttacaactcc ccccattcag   1080

acatggatta gattcgcatt ggtccccatc gacatattgc ttccagaact cagtggtccg   1140

ttctgtattc tcaaacacct cgcgcgcttc ttcaaaactg cattttttcct ccatacactc   1200

tcgctccaag ttcccttgca cgaattcttc aagctttcct gagttatacc ttttaggccg   1260

gttaagtatc ttattcgcgt tttcgtggtc cagaaa                             1296
```

<210> SEQ ID NO 269
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 269

```
ctgtggaaac agggagagaa aaaccacaca acatatttaa agattgatga agacaactaa     60

ctgtaatatg ctgctttttg ttcttctctt cactgaccta                          100
```

<210> SEQ ID NO 270
<211> LENGTH: 145
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 270

```
aggaacccct agtgatggag ttggccactc cctctctgcg cgctcgctcg ctcactgagg     60

ccgcccgggc aaagcccggg cgtcgggcga cctttggtcg cccggcctca gtgagcgagc    120

gagcgcgcag agagggagtg gccaa                                          145
```

<210> SEQ ID NO 271
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 271
gattatttgg attaaaaaca aagactttct taagagatgt aaaattttca tgatgttttc 60
ttttttgcta aaactaaaga attattcttt tacatttcag 100

<210> SEQ ID NO 272
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 272
tttcttgatc atgaaaacgc caacaaaatt ctgaatcggc caaagaggta taattcaggt 60
aaattggaag agtttgttca agggaacctt gagagagaat gtatggaaga aaagtgtagt 120
tttgaagaag cacgagaagt tttgaaaac actgaaagaa caactgaatt ttggaagcag 180
tatgttgatg gagatcagtg tgagtccaat ccatgtttaa atggcggcag ttgcaaggat 240
gacattaatt cctatgaatg ttggtgtccc tttggatttg aaggaaagaa ctgtgaatta 300
gatgtaacat gtaacattaa gaatggcaga tgcgagcagt tttgtaaaaa tagtgctgat 360
aacaaggtgg tttgctcctg tactgaggga tatcgacttg cagaaaacca gaagtcctgt 420
gaaccagcag tgccatttcc atgtggaaga gtttctgttt cacaaacttc taagctcacc 480
cgtgctgaga ctgtttttcc tgatgtggac tatgtaaatt ctactgaagc tgaaaccatt 540
ttggataaca tcactcaaag cacccaatca tttaatgact tcactcgggt tgttggtgga 600
gaagatgcca aaccaggtca attcccttgg caggttgttt tgaatggtaa agttgatgca 660
ttctgtggag gctctatcgt taatgaaaaa tggattgtaa ctgctgccca ctgtgttgaa 720
actggtgtta aaattacagt tgtcgcaggt gaacataata ttgaggagac agaacataca 780
gagcaaaagc gaaatgtgat tcgaattatt cctcaccaca actacaatgc agctattaat 840
aagtacaacc atgacattgc ccttctggaa ctggacgaac ccttagtgct aaacagctac 900
gttacaccta tttgcattgc tgacaaggaa tacacgaaca tcttcctcaa atttggatct 960
ggctatgtaa gtggctgggg aagagtcttc cacaaaggga gatcagcttt agttcttcag 1020
taccttagag ttccacttgt tgaccgagcc acatgtcttc tatctacaaa gttcaccatc 1080
tataacaaca tgttctgtgc tggcttccat gaaggaggta gagattcatg tcaaggagat 1140
agtgggggac cccatgttac tgaagtggaa gggaccagtt tcttaactgg aattattagc 1200
tggggtgaag agtgtgcaat gaaaggcaaa tatggaatat ataccaaggt ctcccggtat 1260
gtcaactgga ttaaggaaaa aacaaagctc actgtcagcg gatggagact gttcaagaag 1320
atcagctaa 1329

<210> SEQ ID NO 273
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 273
ttaggaaatc ttcttaaaca gccgccagcc gctcacggtg agcttagtct tttcttttat 60
ccaattcacg tagcgagaga ccttcgtata gatgccatat ttccccttca tcgcacattc 120
ctccccccaa cttattatcc cggtcaagaa acttgttcct tcgacttcag tgacgtgtgg 180
tccacctgaa tcaccttggc atgagtcgcg accgccctcg tgaaacccag cacaaaacat 240
gttattgtaa atcgtaaatt tcgtggacag aagacaggtc gctctatcga ccaacgggac 300
gcgcaaatat tgcagaacga gggctgatcg acctttgtgg aagacccgcc cccacccact 360
cacatatccg ctcccaaatt tcaagaagat atttgtatat tctttatcgg ctatacaaat 420
cggggtaaca taggagttaa gtacgagtgg ctcgtccagc tccaggaggg ctatatcatg 480
gttgtacttg tttatagcgg cattataatt gtgatggggt atgatcctga taacattcct 540
tttctgttca gtatgctcag tttcttcaat gttgtgttcg ccagccacga ccgtaatctt 600
aacccccgtc tcgacacagt gtgcggccgt tacaatccac ttttcattga ctatggagcc 660
cccacaaaac gcgtcgactt ttccgttgag caccacctgc catggaaatt ggccaggttt 720
agcgtcctcg cccccgacaa ccctagtaaa gtcattaaat gactgtgtgg attgtgttat 780
attatcaaga atcgtttcgg cttcagtaga gttaacgtag tccacatcgg gaaaaactgt 840
ctcggccctt gtcaactttg atgtctggga cacacttacc cgaccgcacg ggaagggcac 900
cgccggttca cagctctttt gattctcagc gagccggtag ccctcagtgc aactacacac 960
aactttgttg tcggcggaat ttttacagaa ttgctcgcat cgtccatttt taatgttgca 1020
ggtgacgtcc aactcgcagt tttttccttc aaaaccaaaa gggcaccaac actcgtagga 1080
atttatatcg tctttacaac tccccccatt cagacatgga ttagattcgc attggtcccc 1140
atcgacatat tgcttccaga actcagtggt ccgttctgta ttctcaaaca cctcgcgcgc 1200
ttcttcaaaa ctgcattttt cctccataca ctctcgctcc aagttccctt gcacgaattc 1260
ttcaagcttt cctgagttat accttttagg ccggttaagt atcttattcg cgttttcgtg 1320
gtccagaaa 1329

<210> SEQ ID NO 274
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 274
ctgaaatgta aaagaataat tctttagttt tagcaaaaaa gaaaacatca tgaaaatttt 60
acatctctta agaaagtctt tgtttttaat ccaaataatc 100

<210> SEQ ID NO 275
<211> LENGTH: 1446
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 275
tttcttgatc atgaaaacgc caacaaaatt ctgaatcggc caaagaggta taattcaggt 60
aaattggaag agtttgttca agggaacctt gagagagaat gtatggaaga aaagtgtagt 120
tttgaagaag cagtattcac tttggaggac tttgtcggtg actggaggca aaccgctggt 180
tataatctcg accaagtact ggaacagggc ggggtaagtt ccctctttca gaatttgggt 240
gtaagcgtca caccaatcca gcggattgtg ttgtctggag agaacggact caaaattgac 300
atccatgtta tcattccata tgaaggtctc agtggagacc aaatggggca gatcgagaag 360

-continued

```
atttttcaagg tagtttaccc agtcgacgat caccacttca aagtcattct ccactatggc    420

acacttgtta tcgacggagt aactcctaat atgattgatt actttggtcg cccgtatgag    480

ggcatcgcag tgtttgatgg caaaaagatc accgtaacag gaacgttgtg gaatgggaac    540

aagataatcg acgagagatt gataaatcca gacgggtcac tcctgttcag ggttacaatt    600

aacggcgtca caggatggag actctgtgaa cgaatactgg ccacaaattt ttcactcctg    660

aagcaggccg gagacgtgga ggaaaaccca gggcccgtga gcaagggcga ggagctgttc    720

accggggtgg tgcccatcct ggtcgagctg gacggcgacg taaacggcca caagttcagc    780

gtgtccggcg agggcgaggg cgatgccacc tacggcaagc tgaccctgaa gttcatctgc    840

accaccggca agctgcccgt gccctggccc accctcgtga ccaccctgac ctacggcgtg    900

cagtgcttca gccgctaccc cgaccacatg aagcagcacg acttcttcaa gtccgccatg    960

cccgaaggct acgtccagga gcgcaccatc ttcttcaagg acgacggcaa ctacaagacc   1020

cgcgccgagg tgaagttcga gggcgacacc ctggtgaacc gcatcgagct gaagggcatc   1080

gacttcaagg aggacggcaa catcctgggg cacaagctgg agtacaacta caacagccac   1140

aacgtctata tcatggccga caagcagaag aacggcatca aggtgaactt caagatccgc   1200

cacaacatcg aggacggcag cgtgcagctc gccgaccact accagcagaa cacccccatc   1260

ggcgacggcc ccgtgctgct gcccgacaac cactacctga gcacccagtc cgccctgagc   1320

aaagacccca acgagaagcg cgatcacatg gtcctgctgg agttcgtgac cgccgccggg   1380

atcactctcg gcatggacga gctgtacaag ggaggaggaa gcccgaagaa gaagagaaag   1440

gtctaa                                                                1446
```

```
<210> SEQ ID NO 276
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
```

```
ttacaccttc ctcttcttct tggggctgcc gccgcccttg tacagctcgt ccatgcccag     60

ggtgatgccg gcggcggtca cgaactccag cagcaccatg tggtccctct tctcgttggg    120

gtccttgctc agggcgctct gggtgctcag gtagtggttg tcgggcagca gcacggggcc    180

gtcgccgatg gggtgttct gctggtagtg gtcggccagc tgcacgctgc cgtcctcgat     240

gttgtgcctg atcttgaagt tcaccttgat gccgttcttc tgcttgtcgg ccatgatgta    300

cacgttgtgg ctgttgtagt tgtactccag cttgtggccc aggatgttgc cgtcctcctt    360

gaagtcgatg cccttcagct cgatcctgtt caccagggtg tcgccctcga acttcacctc    420

ggccctggtc ttgtagttgc cgtcgtcctt gaagaagatg gtcctctcct gcacgtagcc    480

ctcgggcatg gcgctcttga agaagtcgtg ctgcttcatg tggtcggggt acctgctgaa    540

gcactgcacg ccgtaggtca gggtggtcac cagggtgggc cagggcacgg gcagcttgcc    600

ggtggtgcag atgaacttca gggtcagctt gccgtaggtg gcgtcgccct cgccctcgcc    660

gctcacgctg aacttgtggc cgttcacgtc gccgtccagc tccaccagga tgggcaccac    720

gccggtgaac agctcctcgc ccttgctcac ggggccgggg ttctcctcca cgtcgccggc    780

ctgcttcagc aggctgaagt tggtggccag gatcctctcg cacagcctcc agccggtcac    840

gccgttgatg gtcaccctga acagcaggct gccgtcgggg ttgatcagcc tctcgtcgat    900
```

gatcttgttg ccgttccaca gggtgccggt cacggtgatc ttcttgccgt cgaacacggc 960
gatgccctcg tagggcctgc cgaagtagtc gatcatgttg gggtcacgc cgtcgatcac 1020 cagggtgccg tagtgcagga tcaccttgaa gtggtggtcg tccacggggt acaccacctt 1080
gaaaatcttc tcgatctggc ccatctggtc gccgctcagg ccctcgtagg ggatgatcac 1140
gtggatgtcg atcttcaggc cgttctcgcc gctcagcacg atcctctgga tgggggtcac 1200
gctcacgccc aggttctgga acaggctgct cacgccgccc tgctccagca cctggtccag 1260
gttgtagccg gcggtctgcc tccagtcgcc cacgaagtcc tccagggtga acacggcctc 1320
ctcgaagctg cacttctcct ccatgcactc cctctccagg ttgccctgca cgaactcctc 1380
cagcttgccg ctgttgtacc tcttgggcct gttcaggatc ttgttggcgt tctcgtggtc 1440
caggaa 1446

<210> SEQ ID NO 277
<211> LENGTH: 3570
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 277
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tcttaggtca gtgaagagaa gaacaaaaag 180
cagcatatta cagttagttg tcttcatcaa tctttaaata tgttgtgtgg tttttctctc 240
cctgtttcca cagtttttct tgatcatgaa aacgccaaca aaattctgaa tcggccaaag 300
aggtataatt caggtaaatt ggaagagttt gttcaaggga accttgagag agaatgtatg 360
gaagaaaagt gtagttttga agaagcacga gaagtttttg aaaacactga aagaacaact 420
gaattttgga agcagtatgt tgatggagat cagtgtgagt ccaatccatg tttaaatggc 480
ggcagttgca aggatgacat taattcctat gaatgttggt gtccctttgg atttgaagga 540
aagaactgtg aattagatgt aacatgtaac attaagaatg gcagatgcga gcagttttgt 600
aaaaatagtg ctgataacaa ggtggtttgc tcctgtactg agggatatcg acttgcagaa 660
aaccagaagt cctgtgaacc agcagtgcca tttccatgtg gaagagtttc tgtttcacaa 720
acttctaagc tcacccgtgc tgagactgtt tttcctgatg tggactatgt aaattctact 780
gaagctgaaa ccattttgga taacatcact caaagcaccc aatcatttaa tgacttcact 840
cgggttgttg gtggagaaga tgccaaacca ggtcaattcc cttggcaggt tgttttgaat 900
ggtaaagttg atgcattctg tggaggctct atcgttaatg aaaaatggat tgtaactgct 960
gcccactgtg ttgaaactgg tgttaaaatt acagttgtcg caggtgaaca taatattgag 1020
gagacagaac atacagagca aaagcgaaat gtgattcgaa ttattcctca ccacaactac 1080
aatgcagcta ttaataagta caaccatgac attgcccttc tggaactgga cgaaccctta 1140
gtgctaaaca gctacgttac acctatttgc attgctgaca aggaatacac gaacatcttc 1200
ctcaaatttg gatctggcta tgtaagtggc tggggaagag tcttccacaa agggagatca 1260
gctttagttc ttcagtacct tagagttcca cttgttgacc gagccacatg tcttctatct 1320
acaaagttca ccatctataa caacatgttc tgtgctggct tccatgaagg aggtagagat 1380
tcatgtcaag gagatagtgg gggaccccat gttactgaag tggaagggac cagtttctta 1440

-continued

```
actggaatta ttagctgggg tgaagagtgt gcaatgaaag gcaaatatgg aatatatacc   1500
aaggtatccc ggtatgtcaa ctggattaag gaaaaaacaa agctcactta acctcgactg   1560
tgccttctag ttgccagcca tctgttgttt gcccctcccc cgtgccttcc ttgaccctgg   1620
aaggtgccac tcccactgtc ctttcctaat aaaatgagga aattgcatcg cattgtctga   1680
gtaggtgtca ttctattctg gggggtgggg tggggcagga cagcaagggg gaggattggg   1740
aagacaatag caggcatgct ggggatgcgg tgggctctat ggcttctgag gcggaaagaa   1800
ccagctgggg ctctaggggg tatccccaaa aaacctccca cacctccccc tgaacctgaa   1860
acataaaatg aatgcaattg ttgttgttaa cttgtttatt gcagcttata atggttacaa   1920
ataaagcaat agcatcacaa atttcacaaa taaagcattt ttttcactgc attctagttg   1980
tggtttgtcc aaactcatca atgtatctta tcatgtctgt taggtgagct tagtcttttc   2040
ttttatccaa ttcacgtagc gagagacctt cgtatagatg ccatatttcc ccttcatcgc   2100
acattcctcc ccccaactta ttatcccggt caagaaactt gttccttcga cttcagtgac   2160
gtgtggtcca cctgaatcac cttggcatga gtcgcgaccg ccctcgtgaa acccagcaca   2220
aaacatgtta ttgtaaatcg taaatttcgt ggacagaaga caggtcgctc tatcgaccaa   2280
cgggacgcgc aaatattgca gaacgagggc tgatcgacct ttgtggaaga cccgcccccca   2340
cccactcaca tatccgctcc caaatttcaa gaagatattt gtatattctt tatcggctat   2400
acaaatcggg gtaacatagg agttaagtac gagtggctcg tccagctcca ggagggctat   2460
atcatggttg tacttgttta tagcggcatt ataattgtga tggggtatga tcctgataac   2520
attccttttc tgttcagtat gctcagtttc ttcaatgttg tgttcgccag ccacgaccgt   2580
aatcttaacc cccgtctcga cacagtgtgc ggccgttaca atccactttt cattgactat   2640
ggagccccca caaaacgcgt cgacttttcc gttgagcacc acctgccatg gaaattggcc   2700
aggtttagcg tcctcgcccc cgacaaccct agtaaagtca ttaaatgact gtgtggattg   2760
tgttatatta tcaagaatcg tttcggcttc agtagagtta acgtagtcca catcgggaaa   2820
aactgtctcg gcccttgtca actttgatgt ctgggacaca cttacccgac cgcacgggaa   2880
gggcaccgcc ggttcacagc tcttttgatt ctcagcgagc cggtagccct cagtgcaact   2940
acacacaact ttgttgtcgg cggaattttt acagaattgc tcgcatcgtc catttttaat   3000
gttgcaggtg acgtccaact cgcagttttt tccttcaaaa ccaaaagggc accaacactc   3060
gtaggaattt atatcgtctt tacaactccc cccattcaga catggattag attcgcattg   3120
gtccccatcg acatattgct tccagaactc agtggtccgt tctgtattct caaacacctc   3180
gcgcgcttct tcaaaactgc atttttcctc catacactct cgctccaagt tcccttgcac   3240
gaattcttca agctttcctg agttatacct tttaggccgg ttaagtatct tattcgcgtt   3300
ttcgtggtcc agaaaaactg tggaaacagg gagagaaaaa ccacacaaca tatttaaaga   3360
ttgatgaaga caactaactg taatatgctg ctttttgttc ttctcttcac tgacctaaga   3420
gatctaggaa cccctagtga tggagttggc cactccctct ctgcgcgctc gctcgctcac   3480
tgaggccgcc cgggcaaagc ccgggcgtcg ggcgaccttt ggtcgcccgg cctcagtgag   3540
cgagcgagcg cgcagagagg gagtggccaa                                    3570
```

<210> SEQ ID NO 278
<211> LENGTH: 3636
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 278

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctagatc tctgattatt tggattaaaa acaaagactt    180
tcttaagaga tgtaaaattt tcatgatgtt ttcttttttg ctaaaactaa agaattattc    240
ttttacattt cagtttttct tgatcatgaa aacgccaaca aaattctgaa tcggccaaag    300
aggtataatt caggtaaatt ggaagagttt gttcaaggga accttgagag agaatgtatg    360
gaagaaaagt gtagttttga agaagcacga gaagtttttg aaaacactga aagaacaact    420
gaattttgga agcagtatgt tgatggagat cagtgtgagt ccaatccatg tttaaatggc    480
ggcagttgca aggatgacat taattcctat gaatgttggt gtccctttgg atttgaagga    540
aagaactgtg aattagatgt aacatgtaac attaagaatg gcagatgcga gcagttttgt    600
aaaaatagtg ctgataacaa ggtggtttgc tcctgtactg agggatatcg acttgcagaa    660
aaccagaagt cctgtgaacc agcagtgcca tttccatgtg gaagagtttc tgtttcacaa    720
acttctaagc tcacccgtgc tgagactgtt tttcctgatg tggactatgt aaattctact    780
gaagctgaaa ccattttgga taacatcact caaagcaccc aatcatttaa tgacttcact    840
cgggttgttg gtggagaaga tgccaaacca ggtcaattcc cttggcaggt tgttttgaat    900
ggtaaagttg atgcattctg tggaggctct atcgttaatg aaaaatggat tgtaactgct    960
gcccactgtg ttgaaactgg tgttaaaatt acagttgtcg caggtgaaca taatattgag   1020
gagacagaac atacagagca aaagcgaaat gtgattcgaa ttattcctca ccacaactac   1080
aatgcagcta ttaataagta caaccatgac attgcccttc tggaactgga cgaaccctta   1140
gtgctaaaca gctacgttac acctatttgc attgctgaca aggaatacac gaacatcttc   1200
ctcaaatttg gatctggcta tgtaagtggc tggggaagag tcttccacaa agggagatca   1260
gctttagttc ttcagtacct tagagttcca cttgttgacc gagccacatg tcttctatct   1320
acaaagttca ccatctataa caacatgttc tgtgctggct tccatgaagg aggtagagat   1380
tcatgtcaag gagatagtgg gggaccccat gttactgaag tggaagggac cagtttctta   1440
actggaatta ttagctgggg tgaagagtgt gcaatgaaag gcaaatatgg aatatatacc   1500
aaggtctccc ggtatgtcaa ctggattaag gaaaaaacaa agctcactgt cagcggatgg   1560
agactgttca agaagatcag ctaacctcga ctgtgccttc tagttgccag ccatctgttg   1620
tttgcccctc ccccgtgcct tccttgaccc tggaaggtgc cactcccact gtcctttcct   1680
aataaaatga ggaaattgca tcgcattgtc tgagtaggtg tcattctatt ctggggggtg   1740
gggtggggca ggacagcaag ggggaggatt gggaagacaa tagcaggcat gctggggatg   1800
cggtgggctc tatggcttct gaggcggaaa gaaccagctg gggctctagg gggtatcccc   1860
aaaaaacctc ccacacctcc ccctgaacct gaaacataaa atgaatgcaa ttgttgttgt   1920
taacttgttt attgcagctt ataatggtta caaataaagc aatagcatca caaatttcac   1980
aaataaagca tttttttcac tgcattctag ttgtggtttg tccaaactca tcaatgtatc   2040
ttatcatgtc tgttaggaaa tcttcttaaa cagccgccag ccgctcacgg tgagcttagt   2100
cttttctttt atccaattca cgtagcgaga gaccttcgta tagatgccat atttcccctt   2160
catcgcacat tcctcccccc aacttattat cccggtcaag aaacttgttc cttcgacttc   2220
agtgacgtgt ggtccacctg aatcaccttg gcatgagtcg cgaccgccct cgtgaaaccc   2280
```

```
agcacaaaac atgttattgt aaatcgtaaa tttcgtggac agaagacagg tcgctctatc   2340

gaccaacggg acgcgcaaat attgcagaac gagggctgat cgacctttgt ggaagacccg   2400

cccccaccca ctcacatatc cgctcccaaa tttcaagaag atatttgtat attctttatc   2460

ggctatacaa atcggggtaa cataggagtt aagtacgagt ggctcgtcca gctccaggag   2520

ggctatatca tggttgtact tgtttatagc ggcattataa ttgtgatggg gtatgatcct   2580

gataacattc cttttctgtt cagtatgctc agtttcttca atgttgtgtt cgccagccac   2640

gaccgtaatc ttaacccccg tctcgacaca gtgtgcggcc gttacaatcc acttttcatt   2700

gactatggag cccccacaaa acgcgtcgac ttttccgttg agcaccacct gccatggaaa   2760

ttggccaggt ttagcgtcct cgcccccgac aaccctagta aagtcattaa atgactgtgt   2820

ggattgtgtt atattatcaa gaatcgtttc ggcttcagta gagttaacgt agtccacatc   2880

gggaaaaact gtctcggccc ttgtcaactt tgatgtctgg gacacactta cccgaccgca   2940

cgggaagggc accgccggtt cacagctctt ttgattctca gcgagccggt agccctcagt   3000

gcaactacac acaactttgt tgtcggcgga atttttacag aattgctcgc atcgtccatt   3060

tttaatgttg caggtgacgt ccaactcgca gtttttttcct tcaaaaccaa aagggcacca   3120

acactcgtag gaatttatat cgtctttaca actcccccca ttcagacatg gattagattc   3180

gcattggtcc ccatcgacat attgcttcca gaactcagtg gtccgttctg tattctcaaa   3240

cacctcgcgc gcttcttcaa aactgcattt ttcctccata cactctcgct ccaagttccc   3300

ttgcacgaat tcttcaagct ttcctgagtt ataccttttta ggccggttaa gtatcttatt   3360

cgcgttttcg tggtccagaa aaactgaaat gtaaaagaat aattctttag ttttagcaaa   3420

aaagaaaaca tcatgaaaat tttacatctc ttaagaaagt ctttgttttt aatccaaata   3480

atcagagatc taggaacccc tagtgatgga gttggccact ccctctctgc gcgctcgctc   3540

gctcactgag gccgcccggg caaagcccgg gcgtcgggcg acctttggtc gcccggcctc   3600

agtgagcgag cgagcgcgca gagagggagt ggccaa                             3636
```

<210> SEQ ID NO 279
<211> LENGTH: 3615
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctagatc tcttaggtca gtgaagagaa gaacaaaaag    180

cagcatatta cagttagttg tcttcatcaa tctttaaata tgttgtgtgg tttttctctc    240

cctgtttcca cagtttttct tgatcatgaa aacgccaaca aaattctgaa tcggccaaag    300

aggtataatt caggtaaatt ggaagagttt gttcaaggga accttgagag agaatgtatg    360

gaagaaaagt gtagttttga agaagcagta ttcactttgg aggactttgt cggtgactgg    420

aggcaaaccg ctggttataa tctcgaccaa gtactggaac agggcggggt aagttccctc    480

tttcagaatt tgggtgtaag cgtcacacca atccagcgga ttgtgttgtc tggagagaac    540

ggactcaaaa ttgacatcca tgttatcatt ccatatgaag gtctcagtgg agaccaaatg    600

gggcagatcg agaagatttt caaggtagtt tacccagtcg acgatcacca cttcaaagtc    660
```

-continued

```
attctccact atggcacact tgttatcgac ggagtaactc ctaatatgat tgattacttt    720
ggtcgcccgt atgagggcat cgcagtgttt gatggcaaaa agatcaccgt aacaggaacg    780
ttgtggaatg ggaacaagat aatcgacgag agattgataa atccagacgg gtcactcctg    840
ttcagggtta caattaacgg cgtcacagga tggagactct gtgaacgaat actggccaca    900
aatttttcac tcctgaagca ggccggagac gtggaggaaa acccagggcc cgtgagcaag    960
ggcgaggagc tgttcaccgg ggtggtgccc atcctggtcg agctggacgg cgacgtaaac   1020
ggccacaagt tcagcgtgtc cggcgagggc gagggcgatg ccacctacgg caagctgacc   1080
ctgaagttca tctgcaccac cggcaagctg cccgtgccct ggcccaccct cgtgaccacc   1140
ctgacctacg gcgtgcagtg cttcagccgc taccccgacc acatgaagca gcacgacttc   1200
ttcaagtccg ccatgcccga aggctacgtc caggagcgca ccatcttctt caaggacgac   1260
ggcaactaca agacccgcgc cgaggtgaag ttcgagggcg acaccctggt gaaccgcatc   1320
gagctgaagg gcatcgactt caaggaggac ggcaacatcc tggggcacaa gctggagtac   1380
aactacaaca gccacaacgt ctatatcatg gccgacaagc agaagaacgg catcaaggtg   1440
aacttcaaga tccgccacaa catcgaggac ggcagcgtgc agctcgccga ccactaccag   1500
cagaacaccc ccatcggcga cggccccgtg ctgctgcccg acaaccacta cctgagcacc   1560
cagtccgccc tgagcaaaga ccccaacgag aagcgcgatc acatggtcct gctggagttc   1620
gtgaccgccg ccgggatcac tctcggcatg gacgagctgt acaagggagg aggaagcccg   1680
aagaagaaga gaaaggtcta acctcgactg tgccttctag ttgccagcca tctgttgttt   1740
gcccctcccc cgtgccttcc ttgaccctgg aaggtgccac tcccactgtc ctttcctaat   1800
aaaatgagga aattgcatcg cattgtctga gtaggtgtca ttctattctg gggggtgggg   1860
tggggcagga cagcaagggg gaggattggg aagacaatag caggcatgct ggggatgcgg   1920
tgggctctat ggcttctgag gcggaaagaa ccagctgggg ctctaggggg tatccccaaa   1980
aaacctccca cacctccccc tgaacctgaa acataaaatg aatgcaattg ttgttgttaa   2040
cttgtttatt gcagcttata atggttacaa ataaagcaat agcatcacaa atttcacaaa   2100
taaagcattt ttttcactgc attctagttg tggtttgtcc aaactcatca atgtatctta   2160
tcatgtctgt tacaccttcc tcttcttctt ggggctgccg ccgcccttgt acagctcgtc   2220
catgcccagg gtgatgccgg cggcggtcac gaactccagc agcaccatgt ggtccctctt   2280
ctcgttgggg tccttgctca gggcgctctg ggtgctcagg tagtggttgt cgggcagcag   2340
cacggggccg tcgccgatgg gggtgttctg ctggtagtgg tcggccagct gcacgctgcc   2400
gtcctcgatg ttgtgcctga tcttgaagtt caccttgatg ccgttcttct gcttgtcggc   2460
catgatgtac acgttgtggc tgttgtagtt gtactccagc ttgtggccca ggatgttgcc   2520
gtcctccttg aagtcgatgc ccttcagctc gatcctgttc accagggtgt cgccctcgaa   2580
cttcacctcg gccctggtct tgtagttgcc gtcgtccttg aagaagatgg tcctctcctg   2640
cacgtagccc tcgggcatgg cgctcttgaa gaagtcgtgc tgcttcatgt ggtcggggta   2700
cctgctgaag cactgcacgc cgtaggtcag ggtggtcacc agggtgggcc agggcacggg   2760
cagcttgccg gtggtgcaga tgaacttcag ggtcagcttg ccgtaggtgg cgtcgccctc   2820
gccctcgccg ctcacgctga acttgtggcc gttcacgtcg ccgtccagct ccaccaggat   2880
gggcaccacg ccggtgaaca gctcctcgcc cttgctcacg ggccggggt tctcctccac   2940
gtcgccggcc tgcttcagca ggctgaagtt ggtggccagg atcctctcgc acagcctcca   3000
```

gccggtcacg ccgttgatgg tcaccctgaa cagcaggctg ccgtcggggt tgatcagcct 3060
ctcgtcgatg atcttgttgc cgttccacag ggtgccggtc acggtgatct tcttgccgtc 3120
gaacacggcg atgccctcgt agggcctgcc gaagtagtcg atcatgttgg gggtcacgcc 3180
gtcgatcacc agggtgccgt agtgcaggat caccttgaag tggtggtcgt ccacggggta 3240
caccaccttg aaaatcttct cgatctggcc catctggtcg ccgctcaggc cctcgtaggg 3300
gatgatcacg tggatgtcga tcttcaggcc gttctcgccg ctcagcacga tcctctggat 3360
gggggtcacg ctcacgccca ggttctggaa caggctgctc acgccgccct gctccagcac 3420
ctggtccagg ttgtagccgg cggtctgcct ccagtcgccc acgaagtcct ccagggtgaa 3480
cacggcctcc tcgaagctgc acttctcctc catgcactcc ctctccaggt tgccctgcac 3540
gaactcctcc agcttgccgc tgttgtacct cttgggcctg ttcaggatct tgttggcgtt 3600
ctcgtggtcc aggaa 3615

<210> SEQ ID NO 280
<211> LENGTH: 3636
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 280
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tcttaggtca gtgaagagaa gaacaaaaag 180
cagcatatta cagttagttg tcttcatcaa tctttaaata tgttgtgtgg tttttctctc 240
cctgtttcca cagtttttct tgatcatgaa aacgccaaca aaattctgaa tcggccaaag 300
aggtataatt caggtaaatt ggaagagttt gttcaaggga accttgagag agaatgtatg 360
gaagaaaagt gtagttttga agaagcacga gaagtttttg aaaacactga aagaacaact 420
gaattttgga agcagtatgt tgatggagat cagtgtgagt ccaatccatg tttaaatggc 480
ggcagttgca aggatgacat taattcctat gaatgttggt gtccctttgg atttgaagga 540
aagaactgtg aattagatgt aacatgtaac attaagaatg gcagatgcga gcagttttgt 600
aaaaatagtg ctgataacaa ggtggtttgc tcctgtactg agggatatcg acttgcagaa 660
aaccagaagt cctgtgaacc agcagtgcca tttccatgtg gaagagtttc tgtttcacaa 720
acttctaagc tcacccgtgc tgagactgtt tttcctgatg tggactatgt aaattctact 780
gaagctgaaa ccattttgga taacatcact caaagcaccc aatcatttaa tgacttcact 840
cgggttgttg gtggagaaga tgccaaacca ggtcaattcc cttggcaggt tgttttgaat 900
ggtaaagttg atgcattctg tggaggctct atcgttaatg aaaaatggat tgtaactgct 960
gcccactgtg ttgaaactgg tgttaaaatt acagttgtcg caggtgaaca taatattgag 1020
gagacagaac atacagagca aaagcgaaat gtgattcgaa ttattcctca ccacaactac 1080
aatgcagcta ttaataagta caaccatgac attgcccttc tggaactgga cgaaccctta 1140
gtgctaaaca gctacgttac acctatttgc attgctgaca aggaatacac gaacatcttc 1200
ctcaaatttg gatctggcta tgtaagtggc tggggaagag tcttccacaa agggagatca 1260
gctttagttc ttcagtacct tagagttcca cttgttgacc gagccacatg tcttctatct 1320
acaaagttca ccatctataa caacatgttc tgtgctggct tccatgaagg aggtagagat 1380

-continued

```
tcatgtcaag gagatagtgg gggaccccat gttactgaag tggaagggac cagtttctta   1440
actggaatta ttagctgggg tgaagagtgt gcaatgaaag gcaaatatgg aatatatacc   1500
aaggtctccc ggtatgtcaa ctggattaag gaaaaaacaa agctcactgt cagcggatgg   1560
agactgttca agaagatcag ctaacctcga ctgtgccttc tagttgccag ccatctgttg   1620
tttgcccctc ccccgtgcct tccttgaccc tggaaggtgc cactcccact gtcctttcct   1680
aataaaatga ggaaattgca tcgcattgtc tgagtaggtg tcattctatt ctggggggtg   1740
gggtggggca ggacagcaag ggggaggatt gggaagacaa tagcaggcat gctggggatg   1800
cggtgggctc tatggcttct gaggcggaaa gaaccagctg gggctctagg gggtatcccc   1860
aaaaaacctc ccacacctcc ccctgaacct gaaacataaa atgaatgcaa ttgttgttgt   1920
taacttgttt attgcagctt ataatggtta caaataaagc aatagcatca caaatttcac   1980
aaataaagca ttttttcac tgcattctag ttgtggtttg tccaaactca tcaatgtatc   2040
ttatcatgtc tgttaggaaa tcttcttaaa cagccgccag ccgctcacgg tgagcttagt   2100
cttttctttt atccaattca cgtagcgaga gaccttcgta tagatgccat atttcccctt   2160
catcgcacat tcctcccccc aacttattat cccggtcaag aaacttgttc cttcgacttc   2220
agtgacgtgt ggtccacctg aatcaccttg gcatgagtcg cgaccgccct cgtgaaaccc   2280
agcacaaaac atgttattgt aaatcgtaaa tttcgtggac agaagacagg tcgctctatc   2340
gaccaacggg acgcgcaaat attgcagaac gagggctgat cgacctttgt ggaagacccg   2400
cccccaccca ctcacatatc cgctcccaaa tttcaagaag atatttgtat attctttatc   2460
ggctatacaa atcggggtaa cataggagtt aagtacgagt ggctcgtcca gctccaggag   2520
ggctatatca tggttgtact tgtttatagc ggcattataa ttgtgatggg gtatgatcct   2580
gataacattc cttttctgtt cagtatgctc agtttcttca atgttgtgtt cgccagccac   2640
gaccgtaatc ttaacccccg tctcgacaca gtgtgcggcc gttacaatcc acttttcatt   2700
gactatggag cccccacaaa acgcgtcgac ttttccgttg agcaccacct gccatggaaa   2760
ttggccaggt ttagcgtcct cgcccccgac aaccctagta aagtcattaa atgactgtgt   2820
ggattgtgtt atattatcaa gaatcgtttc ggcttcagta gagttaacgt agtccacatc   2880
gggaaaaact gtctcggccc ttgtcaactt tgatgtctgg gacacactta cccgaccgca   2940
cgggaagggc accgccggtt cacagctctt ttgattctca gcgagccggt agccctcagt   3000
gcaactacac acaactttgt tgtcggcgga atttttacag aattgctcgc atcgtccatt   3060
tttaatgttg caggtgacgt ccaactcgca gtttttttcct tcaaaaccaa aagggcacca   3120
acactcgtag gaatttatat cgtctttaca actcccccca ttcagacatg gattagattc   3180
gcattggtcc ccatcgacat attgcttcca gaactcagtg gtccgttctg tattctcaaa   3240
cacctcgcgc gcttcttcaa aactgcattt ttcctccata cactctcgct ccaagttccc   3300
ttgcacgaat tcttcaagct ttcctgagtt ataccttta ggccggttaa gtatcttatt   3360
cgcgttttcg tggtccagaa aaactgtgga aacagggaga gaaaaaccac acaacatatt   3420
taaagattga tgaagacaac taactgtaat atgctgcttt ttgttcttct cttcactgac   3480
ctaagagatc taggaacccc tagtgatgga gttggccact ccctctctgc gcgctcgctc   3540
gctcactgag gccgcccggg caaagcccgg gcgtcgggcg acctttggtc gcccggcctc   3600
agtgagcgag cgagcgcgca gagagggagt ggccaa                             3636
```

<210> SEQ ID NO 281
<211> LENGTH: 1954

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281
ggccactccc tctctgcgcg ctcgctcgct cactgaggcc gggcgaccaa aggtcgcccg 60
acgcccgggc tttgcccggg cggcctcagt gagcgagcga gcgcgcagag agggagtggc 120
caactccatc actaggggtt cctggagggg tggagtcgtg ataggtcagt gaagagaaga 180
acaaaaagca gcatattaca gttagttgtc ttcatcaatc tttaaatatg ttgtgtggtt 240
tttctctccc tgtttccaca gtttttcttg atcatgaaaa cgccaacaaa attctgaatc 300
ggccaaagag gtataattca ggtaaattgg aagagtttgt tcaagggaac cttgagagag 360
aatgtatgga agaaaagtgt agttttgaag aagcacgaga agtttttgaa aacactgaaa 420
gaacaactga attttggaag cagtatgttg atggagatca gtgtgagtcc aatccatgtt 480
taaatggcgg cagttgcaag gatgacatta attcctatga atgttggtgt ccctttggat 540
ttgaaggaaa gaactgtgaa ttagatgtaa catgtaacat taagaatggc agatgcgagc 600
agttttgtaa aaatagtgct gataacaagg tggtttgctc ctgtactgag ggatatcgac 660
ttgcagaaaa ccagaagtcc tgtgaaccag cagtgccatt tccatgtgga agagtttctg 720
tttcacaaac ttctaagctc acccgtgctg agactgtttt tcctgatgtg gactatgtaa 780
attctactga agctgaaacc attttggata acatcactca aagcacccaa tcatttaatg 840
acttcactcg ggttgttggt ggagaagatg ccaaaccagg tcaattccct tggcaggttg 900
ttttgaatgg taaagttgat gcattctgtg gaggctctat cgttaatgaa aaatggattg 960
taactgctgc ccactgtgtt gaaactggtg ttaaaattac agttgtcgca ggtgaacata 1020
atattgagga gacagaacat acagagcaaa agcgaaatgt gattcgaatt attcctcacc 1080
acaactacaa tgcagctatt aataagtaca accatgacat tgcccttctg gaactggacg 1140
aacccttagt gctaaacagc tacgttacac ctatttgcat tgctgacaag gaatacacga 1200
acatcttcct caaatttgga tctggctatg taagtggctg ggggaagagtc ttccacaaag 1260 ggagatcagc tttagttctt cagtacctta gagttccact tgttgaccga gccacatgtc 1320
ttctatctac aaagttcacc atctataaca acatgttctg tgctggcttc catgaaggag 1380
gtagagattc atgtcaagga gatagtgggg gaccccatgt tactgaagtg gaagggacca 1440
gtttcttaac tggaattatt agctggggtg aagagtgtgc aatgaaaggc aaatatggaa 1500
tatataccaa ggtatcccgg tatgtcaact ggattaagga aaaaacaaag ctcacttaac 1560
ctcgactgtg ccttctagtt gccagccatc tgttgtttgc ccctcccccg tgccttcctt 1620
gaccctggaa ggtgccactc ccactgtcct ttcctaataa aatgaggaaa ttgcatcgca 1680
ttgtctgagt aggtgtcatt ctattctggg gggtggggtg gggcaggaca gcaaggggga 1740
ggattgggaa gacaatagca ggcatgctgg ggatgcggtg ggctctatgg cttctgaggc 1800
ggaaagaacc agctggggct ctagggggta tccccactag tccactccct ctctgcgcgc 1860
tcgctcgctc actgaggccg ggcgaccaaa ggtcgcccga cgcccgggct ttgcccgggc 1920
ggcctcagtg agcgagcgag cgcgcagaga ggga 1954

<210> SEQ ID NO 282
<211> LENGTH: 2359
<212> TYPE: DNA
<213> ORGANISM: Artificial Sequence -continued
<220> FEATURE:
<223> OTHER INFORMATION: Description of Artificial Sequence: Synthetic
polynucleotide

<400> SEQUENCE: 282
ggccactccc tctctgcgcg ctcgctcgct cactgaggcc gggcgaccaa aggtcgcccg 60
acgcccgggc tttgcccggg cggcctcagt gagcgagcga gcgcgcagag agggagtggc 120
caactccatc actaggggtt cctggagggg tggagtcgtg acctaggtcg tctccggctc 180
tgctttttcc aggggtgtgt ttcgccgaga agcacgtaag agttttatgt tttttcatct 240
ctgcttgtat ttttctagta atggaagcct ggtattttaa aatagttaaa ttttccttta 300
gtgctgattt ctagattatt attactgttg ttgttgttat tattgtcatt atttgcatct 360
gagaactagg tcagtgaaga gaagaacaaa aagcagcata ttacagttag ttgtcttcat 420
caatctttaa atatgttgtg tggtttttct ctccctgttt ccacagtttt tcttgatcat 480
gaaaacgcca acaaaattct gaatcggcca aagaggtata attcaggtaa attggaagag 540
tttgttcaag ggaaccttga gagagaatgt atggaagaaa agtgtagttt tgaagaagca 600
cgagaagttt ttgaaaacac tgaaagaaca actgaatttt ggaagcagta tgttgatgga 660
gatcagtgtg agtccaatcc atgtttaaat ggcggcagtt gcaaggatga cattaattcc 720
tatgaatgtt ggtgtccctt tggatttgaa ggaaagaact gtgaattaga tgtaacatgt 780
aacattaaga atggcagatg cgagcagttt tgtaaaaata gtgctgataa caaggtggtt 840
tgctcctgta ctgagggata tcgacttgca gaaaaccaga agtcctgtga accagcagtg 900
ccatttccat gtggaagagt ttctgtttca caaacttcta agctcacccg tgctgagact 960
gtttttcctg atgtggacta tgtaaattct actgaagctg aaaccatttt ggataacatc 1020
actcaaagca cccaatcatt taatgacttc actcgggttg ttggtggaga agatgccaaa 1080
ccaggtcaat tcccttggca ggttgttttg aatggtaaag ttgatgcatt ctgtggaggc 1140
tctatcgtta atgaaaaatg gattgtaact gctgcccact gtgttgaaac tggtgttaaa 1200
attacagttg tcgcaggtga acataatatt gaggagacag aacatacaga gcaaaagcga 1260
aatgtgattc gaattattcc tcaccacaac tacaatgcag ctattaataa gtacaaccat 1320
gacattgccc ttctggaact ggacgaaccc ttagtgctaa acagctacgt tacacctatt 1380
tgcattgctg acaaggaata cacgaacatc ttcctcaaat ttggatctgg ctatgtaagt 1440
ggctggggaa gagtcttcca caaagggaga tcagctttag ttcttcagta ccttagagtt 1500
ccacttgttg accgagccac atgtcttcta tctacaaagt tcaccatcta taacaacatg 1560
ttctgtgctg gcttccatga aggaggtaga gattcatgtc aaggagatag tgggggaccc 1620
catgttactg aagtggaagg gaccagtttc ttaactggaa ttattagctg gggtgaagag 1680
tgtgcaatga aaggcaaata tggaatatat accaaggtat cccggtatgt caactggatt 1740
aaggaaaaaa caaagctcac ttaacctcga ctgtgccttc tagttgccag ccatctgttg 1800
tttgcccctc ccccgtgcct tccttgaccc tggaaggtgc cactcccact gtcctttcct 1860
aataaaatga ggaaattgca tcgcattgtc tgagtaggtg tcattctatt ctggggggtg 1920
gggtggggca ggacagcaag ggggaggatt gggaagacaa tagcaggcat gctggggatg 1980
cggtgggctc tatggcttct gaggcggaaa gaaccagctg gggctctagg gggtatcccc 2040
cttaggtggt tatattattg atatattttt ggtatctttg atgacaataa tgggggattt 2100
tgaaagctta gctttaaatt tcttttaatt aaaaaaaaat gctaggcaga atgactcaaa 2160
ttacgttgga tacagttgaa tttattacgg tctcataggg cctgcctgct cgaccatgct 2220
atactaaaaa ttaaaagtgt actagtccac tccctctctg cgcgctcgct cgctcactga 2280
ggccgggcga ccaaaggtcg cccgacgccc gggctttgcc cgggcggcct cagtgagcga 2340
gcgagcgcgc agagaggga 2359

<210> SEQ ID NO 283
<211> LENGTH: 2925
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 283
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tgattttgaa agcttagctt taaatttctt 180
ttaattaaaa aaaaatgcta ggcagaatga ctcaaattac gttggataca gttgaattta 240
ttacggtctc atagggcctg cctgctcgac catgctatac taaaaattaa aagtgtgtgt 300
tactaatttt ataaatggag tttccattta tatttacctt tatttcttat ttaccattgt 360
cttagtagat atttacaaac atgacagaaa cactaaatct tgagtttgaa tgcacagata 420
taaacactta acgggtttta aaaataataa tgttggtgaa aaaatataac tttgagtgta 480
gcagagagga accattgcca ccttcagatt ttcctgtaac gatcgggaac tggcatcttc 540
agggagtagc ttaggtcagt gaagagaaga acaaaaagca gcatattaca gttagttgtc 600
ttcatcaatc tttaaatatg ttgtgtggtt tttctctccc tgtttccaca gtttttcttg 660
atcatgaaaa cgccaacaaa attctgaatc ggccaaagag gtttcttgat catgaaaacg 720
ccaacaaaat tctgaatcgg ccaaagaggt ataattcagg taaattggaa gagtttgttc 780
aagggaacct tgagagagaa tgtatggaag aaaagtgtag ttttgaagaa gcacgagaag 840
tttttgaaaa cactgaaaga acaactgaat tttggaagca gtatgttgat ggagatcagt 900
gtgagtccaa tccatgttta aatggcggca gttgcaagga tgacattaat tcctatgaat 960
gttggtgtcc ctttggattt gaaggaaaga actgtgaatt agatgtaaca tgtaacatta 1020
agaatggcag atgcgagcag ttttgtaaaa atagtgctga taacaaggtg gtttgctcct 1080
gtactgaggg atatcgactt gcagaaaacc agaagtcctg tgaaccagca gtgccatttc 1140
catgtggaag agtttctgtt tcacaaactt ctaagctcac ccgtgctgag actgtttttc 1200
ctgatgtgga ctatgtaaat tctactgaag ctgaaaccat tttggataac atcactcaaa 1260
gcacccaatc atttaatgac ttcactcggg ttgttggtgg agaagatgcc aaaccaggtc 1320
aattcccttg gcaggttgtt ttgaatggta aagttgatgc attctgtgga ggctctatcg 1380
ttaatgaaaa atggattgta actgctgccc actgtgttga aactggtgtt aaaattacag 1440
ttgtcgcagg tgaacataat attgaggaga cagaacatac agagcaaaag cgaaatgtga 1500
ttcgaattat tcctcaccac aactacaatg cagctattaa taagtacaac catgacattg 1560
cccttctgga actggacgaa cccttagtgc taaacagcta cgttacacct atttgcattg 1620
ctgacaagga atacacgaac atcttcctca aatttggatc tggctatgta agtggctggg 1680
gaagagtctt ccacaaaggg agatcagctt tagttcttca gtaccttaga gttccacttg 1740
ttgaccgagc cacatgtctt ctatctacaa agttcaccat ctataacaac atgttctgtg 1800
ctggcttcca tgaaggaggt agagattcat gtcaaggaga tagtgggggg ccccatgtta 1860

```
ctgaagtgga agggaccagt ttcttaactg gaattattag ctggggtgaa gagtgtgcaa   1920

tgaaaggcaa atatggaata tataccaagg tatcccggta tgtcaactgg attaaggaaa   1980

aaacaaagct cacttaacct cgactgtgcc ttctagttgc cagccatctg ttgtttgccc   2040

ctcccccgtg ccttccttga ccctggaagg tgccactccc actgtccttt cctaataaaa   2100

tgaggaaatt gcatcgcatt gtctgagtag gtgtcattct attctggggg gtggggtggg   2160

gcaggacagc aagggggagg attgggaaga caatagcagg catgctgggg atgcggtggg   2220

ctctatggct tctgaggcgg aaagaaccag ctggggctct agggggtatc cccgtgagat   2280

cgcccatcgg tataatgatt tgggagaaca acatttcaaa ggcctgtaag ttataatgct   2340

gaaagcccac ttaatatttc tggtagtatt agttaaagtt ttaaaacacc tttttccacc   2400

ttgagtgtga gaattgtaga gcagtgctgt ccagtagaaa tgtgtgcatt gacagaaaga   2460

ctgtggatct gtgctgagca atgtggcagc cagagatcac aaggctatca agcactttgc   2520

acatggcaag tgtaactgag aagcacacat tcaaataata gttaatttta attgaatgta   2580

tctagccatg tgtggctagt agctcctttc ctggagagag aatctggagc ccacatctaa   2640

cttgttaagt ctggaatctt atttttttatt tctggaaagg tctatgaact atagttttgg   2700

gggcagctca cttactaact tttaatgcaa taagaatctc atggtatctt gagaacatta   2760

ttttgtctct ttgtagatct aggaacccct agtgatggag ttggccactc cctctctgcg   2820

cgctcgctcg ctcactgagg ccgcccgggc aaagcccggg cgtcgggcga cctttggtcg   2880

cccggcctca gtgagcgagc gagcgcgcag agagggagtg gccaa                   2925
```

<210> SEQ ID NO 284
<211> LENGTH: 3477
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 284

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctagatc ttagcctctg gcaaaatgaa gtgggtaacc    180

tttctcctcc tcctcttcgt ctccggctct gctttttcca ggggtgtgtt tcgccgagaa    240

gcacgtaaga gttttatgtt ttttcatctc tgcttgtatt tttctagtaa tggaagcctg    300

gtattttaaa atagttaaat tttcctttag tgctgatttc tagattatta ttactgttgt    360

tgttgttatt attgtcatta tttgcatctg agaaccctta ggtggttata ttattgatat    420

atttttggta tctttgatga caataatggg ggattttgaa agcttagctt taaatttctt    480

ttaattaaaa aaaaatgcta ggcagaatga ctcaaattac gttggataca gttgaattta    540

ttacggtctc atagggcctg cctgctcgac catgctatac taaaaattaa aagtgtgtgt    600

tactaatttt ataaatggag tttccattta tatttacctt tatttcttat ttaccattgt    660

cttagtagat atttacaaac atgacagaaa cactaaatct tgagtttgaa tgcacagata    720

taaacactta acgggtttta aaaataataa tgttggtgaa aaaatataac tttgagtgta    780

gcagagagga accattgcca ccttcagatt ttcctgtaac gatcgggaac tggcatcttc    840

agggagtagc ttaggtcagt gaagagaaga acaaaaagca gcatattaca gttagttgtc    900

ttcatcaatc tttaaatatg ttgtgtggtt tttctctccc tgtttccaca gtttttcttg    960
```

-continued

```
atcatgaaaa cgccaacaaa attctgaatc ggccaaagag gtataattca ggtaaattgg   1020
aagagtttgt tcaagggaac cttgagagag aatgtatgga agaaaagtgt agttttgaag   1080
aagcacgaga agtttttgaa aacactgaaa gaacaactga attttggaag cagtatgttg   1140
atggagatca gtgtgagtcc aatccatgtt taaatggcgg cagttgcaag gatgacatta   1200
attcctatga atgttggtgt ccctttggat ttgaaggaaa gaactgtgaa ttagatgtaa   1260
catgtaacat taagaatggc agatgcgagc agttttgtaa aaatagtgct gataacaagg   1320
tggtttgctc ctgtactgag ggatatcgac ttgcagaaaa ccagaagtcc tgtgaaccag   1380
cagtgccatt tccatgtgga agagtttctg tttcacaaac ttctaagctc acccgtgctg   1440
agactgtttt tcctgatgtg gactatgtaa attctactga agctgaaacc attttggata   1500
acatcactca aagcacccaa tcatttaatg acttcactcg ggttgttggt ggagaagatg   1560
ccaaaccagg tcaattccct tggcaggttg ttttgaatgg taaagttgat gcattctgtg   1620
gaggctctat cgttaatgaa aaatggattg taactgctgc ccactgtgtt gaaactggtg   1680
ttaaaattac agttgtcgca ggtgaacata atattgagga gacagaacat acagagcaaa   1740
agcgaaatgt gattcgaatt attcctcacc acaactacaa tgcagctatt aataagtaca   1800
accatgacat tgcccttctg gaactggacg aacccttagt gctaaacagc tacgttacac   1860
ctatttgcat tgctgacaag gaatacacga acatcttcct caaatttgga tctggctatg   1920
taagtggctg ggaagagtc ttccacaaag ggagatcagc tttagttctt cagtacctta   1980
gagttccact tgttgaccga gccacatgtc ttctatctac aaagttcacc atctataaca   2040
acatgttctg tgctggcttc catgaaggag gtagagattc atgtcaagga gatagtgggg   2100
gaccccatgt tactgaagtg gaagggacca gtttcttaac tggaattatt agctggggtg   2160
aagagtgtgc aatgaaaggc aaatatggaa tatataccaa ggtatcccgg tatgtcaact   2220
ggattaagga aaaaacaaag ctcacttaac ctcgactgtg ccttctagtt gccagccatc   2280
tgttgtttgc ccctcccccg tgccttcctt gaccctggaa ggtgccactc ccactgtcct   2340
ttcctaataa aatgaggaaa ttgcatcgca ttgtctgagt aggtgtcatt ctattctggg   2400
gggtggggtg gggcaggaca gcaaggggga ggattgggaa gacaatagca ggcatgctgg   2460
ggatgcggtg ggctctatgg cttctgaggc ggaaagaacc agctggggct ctagggggta   2520
tccccgtgag atcgcccatc ggtataatga tttgggagaa caacatttca aaggcctgta   2580
agttataatg ctgaaagccc acttaatatt tctggtagta ttagttaaag ttttaaaaca   2640
cctttttcca ccttgagtgt gagaattgta gagcagtgct gtccagtaga aatgtgtgca   2700
ttgacagaaa gactgtggat ctgtgctgag caatgtggca gccagagatc acaaggctat   2760
caagcacttt gcacatggca agtgtaactg agaagcacac attcaaataa tagttaattt   2820
taattgaatg tatctagcca tgtgtggcta gtagctcctt tcctggagag agaatctgga   2880
gcccacatct aacttgttaa gtctggaatc ttattttttta tttctggaaa ggtctatgaa   2940
ctatagtttt gggggcagct cacttactaa cttttaatgc aataagaatc tcatggtatc   3000
ttgagaacat tattttgtct ctttgtagta ctgaaacctt atacatgtga agtaaggggt   3060
ctatacttaa gtcacatctc caaccttagt aatgttttaa tgtagtaaaa aaatgagtaa   3120
ttaatttatt tttagaaggt caatagtatc atgtattcca aataacagag gtatatggtt   3180
agaaaagaaa caattcaaag gacttatata atatctagcc ttgacaatga ataaatttag   3240
agagtagttt gcctgtttgc ctcatgttca taaatctatt gacacatatg tgcatctgca   3300
```

cttcagcatg gtagaagtcc atattcagat ctaggaaccc ctagtgatgg agttggccac 3360
tccctctctg cgcgctcgct cgctcactga ggccgcccgg gcaaagcccg ggcgtcgggc 3420
gacctttggt cgcccggcct cagtgagcga gcgagcgcgc agagagggag tggccaa 3477

<210> SEQ ID NO 285
<211> LENGTH: 2476
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 285
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc taagtatatt agagcgagtc tttctgcaca 180
cagatcacct ttcctatcaa ccccactagc ctctggcaaa atgaagtggg taacctttct 240
cctcctcctc ttcgtctccg gctctgcttt ttccaggggt gtgtttcgcc gagaagcacg 300
taagagtttt atgtttttttc atctctgctt gtatttttct agtaatggaa gcctggtatt 360
ttaaaatagt taaattttcc tttagtgctg atttctagat tattattact gttgttgttg 420
ttattattgt cattatttgc atctgagaac ctttttcttg atcatgaaaa cgccaacaaa 480
attctgaatc ggccaaagag gtataattca ggtaaattgg aagagtttgt tcaagggaac 540
cttgagagag aatgtatgga agaaaagtgt agttttgaag aagcacgaga agtttttgaa 600
aacactgaaa gaacaactga attttggaag cagtatgttg atggagatca gtgtgagtcc 660
aatccatgtt taaatggcgg cagttgcaag gatgacatta attcctatga atgttggtgt 720
ccctttggat ttgaaggaaa gaactgtgaa ttagatgtaa catgtaacat taagaatggc 780
agatgcgagc agttttgtaa aaatagtgct gataacaagg tggtttgctc ctgtactgag 840
ggatatcgac ttgcagaaaa ccagaagtcc tgtgaaccag cagtgccatt tccatgtgga 900
agagtttctg tttcacaaac ttctaagctc acccgtgctg agactgtttt tcctgatgtg 960
gactatgtaa attctactga agctgaaacc attttggata acatcactca aagcacccaa 1020
tcatttaatg acttcactcg ggttgttggt ggagaagatg ccaaaccagg tcaattccct 1080
tggcaggttg ttttgaatgg taaagttgat gcattctgtg gaggctctat cgttaatgaa 1140
aaatggattg taactgctgc ccactgtgtt gaaactggtg ttaaaattac agttgtcgca 1200
ggtgaacata atattgagga gacagaacat acagagcaaa agcgaaatgt gattcgaatt 1260
attcctcacc acaactacaa tgcagctatt aataagtaca accatgacat tgcccttctg 1320
gaactggacg aaccccttagt gctaaacagc tacgttacac ctatttgcat tgctgacaag 1380
gaatacacga acatcttcct caaatttgga tctggctatg taagtggctg gggaagagtc 1440
ttccacaaag ggagatcagc tttagttctt cagtacctta gagttccact tgttgaccga 1500
gccacatgtc ttctatctac aaagttcacc atctataaca acatgttctg tgctggcttc 1560
catgaaggag gtagagattc atgtcaagga gatagtgggg gaccccatgt tactgaagtg 1620
gaagggacca gtttcttaac tggaattatt agctggggtg aagagtgtgc aatgaaaggc 1680
aaatatggaa tatataccaa ggtatcccgg tatgtcaact ggattaagga aaaaacaaag 1740
ctcacttaac ctcgactgtg ccttctagtt gccagccatc tgttgtttgc ccctcccccg 1800
tgccttcctt gaccctggaa ggtgccactc ccactgtcct ttcctaataa aatgaggaaa 1860
ttgcatcgca ttgtctgagt aggtgtcatt ctattctggg gggtggggtg gggcaggaca 1920
gcaaggggga ggattgggaa gacaatagca ggcatgctgg ggatgcggtg ggctctatgg 1980
cttctgaggc ggaaagaacc agctggggct ctagggggta tccccccttag gtggttatat 2040 tattgatata tttttggtat ctttgatgac aataatgggg gattttgaaa gcttagcttt 2100
aaatttcttt taattaaaaa aaaatgctag gcagaatgac tcaaattacg ttggatacag 2160
ttgaatttat tacggtctca tagggcctgc ctgctcgacc atgctatact aaaaattaaa 2220
agtgtgtgtt actaatttta taaatggagt ttccatttat atttaccttt atttcttatt 2280
taccattgtc ttagtagata tttacaaaca tgacagaaac actaaagatc taggaacccc 2340
tagtgatgga gttggccact ccctctctgc gcgctcgctc gctcactgag gccgcccggg 2400
caaagcccgg gcgtcgggcg acctttggtc gcccggcctc agtgagcgag cgagcgcgca 2460
gagagggagt ggccaa 2476

<210> SEQ ID NO 286
<211> LENGTH: 4175
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 286
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc taagtatatt agagcgagtc tttctgcaca 180
cagatcacct ttcctatcaa ccccactagc ctctggcaaa atgaagtggg taacctttct 240
cctcctcctc ttcgtctccg gctctgcttt ttccaggggt gtgtttcgcc gagaagcacg 300
taagagtttt atgtttttc atctctgctt gtatttttct agtaatggaa gcctggtatt 360
ttaaaatagt taaattttcc tttagtgctg atttctagat tattattact gttgttgttg 420
ttattattgt cattatttgc atctgagaac ctttttcttg atcatgaaaa cgccaacaaa 480
attctgaatc ggccaaagag gtataattca ggtaaattgg aagagtttgt tcaagggaac 540
cttgagagag aatgtatgga agaaaagtgt agttttgaag aagcacgaga agtttttgaa 600
aacactgaaa gaacaactga attttggaag cagtatgttg atggagatca gtgtgagtcc 660
aatccatgtt taaatggcgg cagttgcaag gatgacatta attcctatga atgttggtgt 720
ccctttggat ttgaaggaaa gaactgtgaa ttagatgtaa catgtaacat taagaatggc 780
agatgcgagc agttttgtaa aaatagtgct gataacaagg tggtttgctc ctgtactgag 840
ggatatcgac ttgcagaaaa ccagaagtcc tgtgaaccag cagtgccatt tccatgtgga 900
agagtttctg tttcacaaac ttctaagctc acccgtgctg agactgtttt tcctgatgtg 960
gactatgtaa attctactga agctgaaacc attttggata acatcactca aagcacccaa 1020
tcatttaatg acttcactcg ggttgttggt ggagaagatg ccaaaccagg tcaattccct 1080
tggcaggttg ttttgaatgg taaagttgat gcattctgtg gaggctctat cgttaatgaa 1140
aaatggattg taactgctgc ccactgtgtt gaaactggtg ttaaaattac agttgtcgca 1200
ggtgaacata atattgagga gacagaacat acagagcaaa agcgaaatgt gattcgaatt 1260
attcctcacc acaactacaa tgcagctatt aataagtaca accatgacat tgcccttctg 1320
gaactggacg aacccttagt gctaaacagc tacgttacac ctatttgcat tgctgacaag 1380

-continued

```
gaatacacga acatcttcct caaatttgga tctggctatg taagtggctg gggaagagtc   1440
ttccacaaag ggagatcagc tttagttctt cagtacctta gagttccact tgttgaccga   1500
gccacatgtc ttctatctac aaagttcacc atctataaca acatgttctg tgctggcttc   1560
catgaaggag gtagagattc atgtcaagga gatagtgggg gaccccatgt tactgaagtg   1620
gaagggacca gtttcttaac tggaattatt agctggggtg aagagtgtgc aatgaaaggc   1680
aaatatggaa tatataccaa ggtatcccgg tatgtcaact ggattaagga aaaaacaaag   1740
ctcacttaac ctcgactgtg ccttctagtt gccagccatc tgttgtttgc ccctcccccg   1800
tgccttcctt gaccctggaa ggtgccactc ccactgtcct ttcctaataa aatgaggaaa   1860
ttgcatcgca ttgtctgagt aggtgtcatt ctattctggg gggtggggtg gggcaggaca   1920
gcaaggggga ggattgggaa gacaatagca ggcatgctgg ggatgcggtg ggctctatgg   1980
cttctgaggc ggaaagaacc agctggggct ctagggggta tccccccttag gtggttatat  2040
tattgatata tttttggtat ctttgatgac aataatgggg gattttgaaa gcttagcttt   2100
aaatttcttt taattaaaaa aaaatgctag gcagaatgac tcaaattacg ttggatacag   2160
ttgaatttat tacggtctca tagggcctgc ctgctcgacc atgctatact aaaaattaaa   2220
agtgtgtgtt actaatttta taaatggagt ttccatttat atttaccttt atttcttatt   2280
taccattgtc ttagtagata tttacaaaca tgacagaaac actaaatctt gagtttgaat   2340
gcacagatat aaacacttaa cgggttttaa aaataataat gttggtgaaa aaatataact   2400
ttgagtgtag cagagaggaa ccattgccac cttcagattt tcctgtaacg atcgggaact   2460
ggcatcttca gggagtagct taggtcagtg aagagaagaa caaaaagcag catattacag   2520
ttagttgtct tcatcaatct ttaaatatgt tgtgtggttt ttctctccct gtttccacag   2580
acaagagtga gatcgcccat cggtataatg atttgggaga acaacatttc aaaggcctgt   2640
aagttataat gctgaaagcc cacttaatat ttctggtagt attagttaaa gttttaaaac   2700
acctttttcc accttgagtg tgagaattgt agagcagtgc tgtccagtag aaatgtgtgc   2760
attgacagaa agactgtgga tctgtgctga gcaatgtggc agccagagat cacaaggcta   2820
tcaagcactt tgcacatggc aagtgtaact gagaagcaca cattcaaata atagttaatt   2880
ttaattgaat gtatctagcc atgtgtggct agtagctcct ttcctggaga gagaatctgg   2940
agcccacatc taacttgtta agtctggaat cttatttttt atttctggaa aggtctatga   3000
actatagttt tgggggcagc tcacttacta acttttaatg caataagatc catggtatct   3060
tgagaacatt attttgtctc tttgtagtac tgaaacctta tacatgtgaa gtaaggggtc   3120
tatacttaag tcacatctcc aaccttagta atgttttaat gtagtaaaaa aatgagtaat   3180
taatttattt ttagaaggtc aatagtatca tgtattccaa ataacagagg tatatggtta   3240
gaaaagaaac aattcaaagg acttatataa tatctagcct tgacaatgaa taaatttaga   3300
gagtagtttg cctgtttgcc tcatgttcat aaatctattg acacatatgt gcatctgcac   3360
ttcagcatgg tagaagtcca tattcctttg cttggaaagg caggtgttcc cattacgcct   3420
cagagaatag ctgacgggaa gaggctttct agatagttgt atgaaagata tacaaaatct   3480
cgcaggtata cacaggcatg atttgctggt tgggagagcc acttgcctca tactgaggtt   3540
tttgtgtctg cttttcagag tcctgattgc cttttcccag tatctccaga aatgctcata   3600
cgatgagcat gccaaattag tgcaggaagt aacagacttt gcaaagacgt gtgttgccga   3660
tgagtctgcc gccaactgtg acaaatccct tgtgagtacc ttctgatttt gtggatctac   3720
tttcctgctt tctggaactc tgtttcaaag ccaatcatga ctccatcact taaggccccg   3780
```

ggaacactgt ggcagagggc agcagagaga ttgataaagc cagggtgatg ggaattttct 3840
gtgggactcc atttcatagt aattgcagaa gctacaatac actcaaaaag tctcaccaca 3900
tgactgccca aatgggagct tgacagtgac agtgacagta gatatgccaa agtggatgag 3960
ggaaagacca caagagctaa accctgtaaa aagaactgta ggcaactaag gaatgcagag 4020
agaaagatct aggaacccct agtgatggag ttggccactc cctctctgcg cgctcgctcg 4080
ctcactgagg ccgcccgggc aaagcccggg cgtcgggcga cctttggtcg cccggcctca 4140
gtgagcgagc gagcgcgcag agagggagtg gccaa 4175

<210> SEQ ID NO 287
<211> LENGTH: 3675
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 287
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc taagtatatt agagcgagtc tttctgcaca 180
cagatcacct ttcctatcaa ccccactagc ctctggcaaa atgaagtggg taacctttct 240
cctcctcctc ttcgtctccg gctctgcttt ttccaggggt gtgtttcgcc gagaagcacg 300
taagagtttt atgtttttc atctctgctt gtatttttct agtaatggaa gcctggtatt 360
ttaaaatagt taaattttcc tttagtgctg atttctagat tattattact gttgttgttg 420
ttattattgt cattatttgc atctgagaac ctttttcttg atcatgaaaa cgccaacaaa 480
attctgaatc ggccaaagag gtataattca ggtaaattgg aagagtttgt tcaagggaac 540
cttgagagag aatgtatgga agaaaagtgt agttttgaag aagcacgaga agtttttgaa 600
aacactgaaa gaacaactga attttggaag cagtatgttg atggagatca gtgtgagtcc 660
aatccatgtt taaatggcgg cagttgcaag gatgacatta attcctatga atgttggtgt 720
ccctttggat ttgaaggaaa gaactgtgaa ttagatgtaa catgtaacat taagaatggc 780
agatgcgagc agttttgtaa aaatagtgct gataacaagg tggtttgctc ctgtactgag 840
ggatatcgac ttgcagaaaa ccagaagtcc tgtgaaccag cagtgccatt tccatgtgga 900
agagtttctg tttcacaaac ttctaagctc acccgtgctg agactgtttt tcctgatgtg 960
gactatgtaa attctactga agctgaaacc attttggata acatcactca aagcacccaa 1020
tcatttaatg acttcactcg ggttgttggt ggagaagatg ccaaaccagg tcaattccct 1080
tggcaggttg ttttgaatgg taaagttgat gcattctgtg gaggctctat cgttaatgaa 1140
aaatggattg taactgctgc ccactgtgtt gaaactggtg ttaaaattac agttgtcgca 1200
ggtgaacata atattgagga gacagaacat acagagcaaa agcgaaatgt gattcgaatt 1260
attcctcacc acaactacaa tgcagctatt aataagtaca accatgacat tgcccttctg 1320
gaactggacg aacccttagt gctaaacagc tacgttacac ctatttgcat tgctgacaag 1380
gaatacacga acatcttcct caaatttgga tctggctatg taagtggctg ggaagagtc 1440 ttccacaaag ggagatcagc tttagttctt cagtacctta gagttccact tgttgaccga 1500
gccacatgtc ttctatctac aaagttcacc atctataaca acatgttctg tgctggcttc 1560
catgaaggag gtagagattc atgtcaagga gatagtgggg gaccccatgt tactgaagtg 1620

-continued

```
gaagggacca gtttcttaac tggaattatt agctggggtg aagagtgtgc aatgaaaggc   1680
aaatatggaa tatataccaa ggtatcccgg tatgtcaact ggattaagga aaaaacaaag   1740
ctcacttaac ctcgactgtg ccttctagtt gccagccatc tgttgtttgc ccctcccccg   1800
tgccttcctt gaccctggaa ggtgccactc ccactgtcct ttcctaataa aatgaggaaa   1860
ttgcatcgca ttgtctgagt aggtgtcatt ctattctggg gggtggggtg gggcaggaca   1920
gcaaggggga ggattgggaa gacaatagca ggcatgctgg ggatgcggtg ggctctatgg   1980
cttctgaggc ggaaagaacc agctggggct ctagggggta tccccccttag gtggttatat   2040
tattgatata tttttggtat ctttgatgac aataatgggg gattttgaaa gcttagcttt   2100
aaatttcttt taattaaaaa aaaatgctag gcagaatgac tcaaattacg ttggatacag   2160
ttgaatttat tacggtctca tagggcctgc ctgctcgacc atgctatact aaaaattaaa   2220
agtgtgtgtt actaatttta taaatggagt ttccatttat atttaccttt atttcttatt   2280
taccattgtc ttagtagata tttacaaaca tgacagaaac actaaatctt gagtttgaat   2340
gcacagatat aaacacttaa cgggttttaa aaataataat gttggtgaaa aaatataact   2400
ttgagtgtag cagagaggaa ccattgccac cttcagattt tcctgtaacg atcgggaact   2460
ggcatcttca gggagtagct taggtcagtg aagagaagaa caaaaagcag catattacag   2520
ttagttgtct tcatcaatct ttaaatatgt tgtgtggttt ttctctccct gtttccacag   2580
acaagagtga gatcgcccat cggtataatg atttgggaga acaacatttc aaaggcctgt   2640
aagttataat gctgaaagcc cacttaatat ttctggtagt attagttaaa gttttaaaac   2700
acctttttcc accttgagtg tgagaattgt agagcagtgc tgtccagtag aaatgtgtgc   2760
attgacagaa agactgtgga tctgtgctga gcaatgtggc agccagagat cacaaggcta   2820
tcaagcactt tgcacatggc aagtgtaact gagaagcaca cattcaaata atagttaatt   2880
ttaattgaat gtatctagcc atgtgtggct agtagctcct ttcctggaga gagaatctgg   2940
agcccacatc taacttgtta agtctggaat cttatttttt atttctggaa aggtctatga   3000
actatagttt tgggggcagc tcacttacta acttttaatg caataagatc catggtatct   3060
tgagaacatt attttgtctc tttgtagtac tgaaacctta tacatgtgaa gtaaggggtc   3120
tatacttaag tcacatctcc aaccttagta atgttttaat gtagtaaaaa aatgagtaat   3180
taatttattt ttagaaggtc aatagtatca tgtattccaa ataacagagg tatatggtta   3240
gaaaagaaac aattcaaagg acttatataa tatctagcct tgacaatgaa taaatttaga   3300
gagtagtttg cctgtttgcc tcatgttcat aaatctattg acacatatgt gcatctgcac   3360
ttcagcatgg tagaagtcca tattcctttg cttggaaagg caggtgttcc cattacgcct   3420
cagagaatag ctgacgggaa gaggctttct agatagttgt atgaaagata tacaaaatct   3480
cgcaggtata cacaggcatg atttgctggt tgggagagcc acttagatct aggaacccct   3540
agtgatggag ttggccactc cctctctgcg cgctcgctcg ctcactgagg ccgcccgggc   3600
aaagcccggg cgtcgggcga cctttggtcg cccggcctca gtgagcgagc gagcgcgcag   3660
agagggagtg gccaa                                                    3675
```

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 100

<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 300
nnnnnnnnnn nnnnnnnnnn guuuuagagc uagaaauagc aaguuaaaau aaggcuaguc 60
cguuaucaac uugaaaaagu ggcaccgagu cggugcuuuu 100

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

-continued

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

-continued

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 400
guuuuagagc uaugcuguuu ug 22

<210> SEQ ID NO 401
<211> LENGTH: 80
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 401
guuuuagagc uagaaauagc aaguuaaaau aaggcuaguc cguuaucaac uugaaaaagu 60
ggcaccgagu cggugcuuuu 80

<210> SEQ ID NO 402
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 402
guuuuagagc uagaaauagc aaguuaaaau aaggcuaguc cguuaucaac uugaaaaagu 60
ggcaccgagu cggugc 76

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

-continued

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

-continued

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 500 ctggaccga 9

<210> SEQ ID NO 501
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 501 tcggtccag 9

<210> SEQ ID NO 502
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 502 tcggtccag 9

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

-continued

000

<210> SEQ ID NO 553
<400> SEQUENCE: 553
000

<210> SEQ ID NO 554
<400> SEQUENCE: 554
000

<210> SEQ ID NO 555
<400> SEQUENCE: 555
000

<210> SEQ ID NO 556
<400> SEQUENCE: 556
000

<210> SEQ ID NO 557
<400> SEQUENCE: 557
000

<210> SEQ ID NO 558
<400> SEQUENCE: 558
000

<210> SEQ ID NO 559
<400> SEQUENCE: 559
000

<210> SEQ ID NO 560
<400> SEQUENCE: 560
000

<210> SEQ ID NO 561
<400> SEQUENCE: 561
000

<210> SEQ ID NO 562
<400> SEQUENCE: 562
000

<210> SEQ ID NO 563
<400> SEQUENCE: 563
000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600
<211> LENGTH: 7
<212> TYPE: PRT
<213> ORGANISM: Simian virus 40

<400> SEQUENCE: 600

Pro Lys Lys Lys Arg Lys Val
1               5

<210> SEQ ID NO 601
<211> LENGTH: 7
<212> TYPE: PRT
<213> ORGANISM: Simian virus 40

<400> SEQUENCE: 601

Pro Lys Lys Lys Arg Arg Val
1               5

<210> SEQ ID NO 602
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 602

Lys Arg Pro Ala Ala Thr Lys Lys Ala Gly Gln Ala Lys Lys Lys Lys
1               5                   10                  15

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

-continued

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

-continued

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700
<211> LENGTH: 461
<212> TYPE: PRT
<213> ORGANISM: Homo sapiens

<400> SEQUENCE: 700

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270
```

-continued

Val Lys Ile Thr Val Val Ala Gly Glu His Asn Ile Glu Glu Thr Glu
275 280 285

His Thr Glu Gln Lys Arg Asn Val Ile Arg Ile Ile Pro His His Asn
290 295 300

Tyr Asn Ala Ala Ile Asn Lys Tyr Asn His Asp Ile Ala Leu Leu Glu
305 310 315 320

Leu Asp Glu Pro Leu Val Leu Asn Ser Tyr Val Thr Pro Ile Cys Ile
325 330 335

Ala Asp Lys Glu Tyr Thr Asn Ile Phe Leu Lys Phe Gly Ser Gly Tyr
340 345 350

Val Ser Gly Trp Gly Arg Val Phe His Lys Gly Arg Ser Ala Leu Val
355 360 365

Leu Gln Tyr Leu Arg Val Pro Leu Val Asp Arg Ala Thr Cys Leu Arg
370 375 380

Ser Thr Lys Phe Thr Ile Tyr Asn Asn Met Phe Cys Ala Gly Phe His
385 390 395 400

Glu Gly Gly Arg Asp Ser Cys Gln Gly Asp Ser Gly Gly Pro His Val
405 410 415

Thr Glu Val Glu Gly Thr Ser Phe Leu Thr Gly Ile Ile Ser Trp Gly
420 425 430

Glu Glu Cys Ala Met Lys Gly Lys Tyr Gly Ile Tyr Thr Lys Val Ser
435 440 445

Arg Tyr Val Asn Trp Ile Lys Glu Lys Thr Lys Leu Thr
450 455 460

<210> SEQ ID NO 701
<211> LENGTH: 415
<212> TYPE: PRT
<213> ORGANISM: Homo sapiens

<400> SEQUENCE: 701

Tyr Asn Ser Gly Lys Leu Glu Glu Phe Val Gln Gly Asn Leu Glu Arg
1 5 10 15

Glu Cys Met Glu Glu Lys Cys Ser Phe Glu Glu Ala Arg Glu Val Phe
20 25 30

Glu Asn Thr Glu Arg Thr Thr Glu Phe Trp Lys Gln Tyr Val Asp Gly
35 40 45

Asp Gln Cys Glu Ser Asn Pro Cys Leu Asn Gly Gly Ser Cys Lys Asp
50 55 60

Asp Ile Asn Ser Tyr Glu Cys Trp Cys Pro Phe Gly Phe Glu Gly Lys
65 70 75 80

Asn Cys Glu Leu Asp Val Thr Cys Asn Ile Lys Asn Gly Arg Cys Glu
85 90 95

Gln Phe Cys Lys Asn Ser Ala Asp Asn Lys Val Val Cys Ser Cys Thr
100 105 110

Glu Gly Tyr Arg Leu Ala Glu Asn Gln Lys Ser Cys Glu Pro Ala Val
115 120 125

Pro Phe Pro Cys Gly Arg Val Ser Val Ser Gln Thr Ser Lys Leu Thr
130 135 140

Arg Ala Glu Thr Val Phe Pro Asp Val Asp Tyr Val Asn Ser Thr Glu
145 150 155 160

Ala Glu Thr Ile Leu Asp Asn Ile Thr Gln Ser Thr Gln Ser Phe Asn
165 170 175

Asp Phe Thr Arg Val Val Gly Gly Glu Asp Ala Lys Pro Gly Gln Phe
180 185 190

```
Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415


<210> SEQ ID NO 702
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
```

```
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Leu Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415
```

<210> SEQ ID NO 703
<211> LENGTH: 4104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 703

```
atggataaga agtactcaat cgggctggat atcggaacta attccgtggg ttgggcagtg     60

atcacggatg aatacaaagt gccgtccaag aagttcaagg tcctggggaa caccgataga    120

cacagcatca agaaaaatct catcggagcc ctgctgtttg actccggcga aaccgcagaa    180

gcgacccggc tcaaacgtac cgcgaggcga cgctacaccc ggcggaagaa tcgcatctgc    240

tatctgcaag agatcttttc gaacgaaatg gcaaaggtcg acgacagctt cttccaccgc    300

ctggaagaat ctttcctggt ggaggaggac aagaagcatg aacggcatcc tatctttgga    360

aacatcgtcg acgaagtggc gtaccacgaa aagtacccga ccatctacca tctgcggaag    420

aagttggttg actcaactga caaggccgac ctcagattga tctacttggc cctcgcccat    480
```

-continued

```
atgatcaaat tccgcggaca cttcctgatc gaaggcgatc tgaaccctga taactccgac    540
gtggataagc ttttcattca actggtgcag acctacaacc aactgttcga agaaaaccca    600
atcaatgcta gcggcgtcga tgccaaggcc atcctgtccg cccggctgtc gaagtcgcgg    660
cgcctcgaaa acctgatcgc acagctgccg ggagagaaaa agaacggact tttcggcaac    720
ttgatcgctc tctcactggg actcactccc aatttcaagt ccaattttga cctggccgag    780
gacgcgaagc tgcaactctc aaaggacacc tacgacgacg acttggacaa tttgctggca    840
caaattggcg atcagtacgc ggatctgttc cttgccgcta agaacctttc ggacgcaatc    900
ttgctgtccg atatcctgcg cgtgaacacc gaaataacca aagcgccgct tagcgcctcg    960
atgattaagc ggtacgacga gcatcaccag gatctcacgc tgctcaaagc gctcgtgaga   1020
cagcaactgc ctgaaaagta caaggagatc ttcttcgacc agtccaagaa tgggtacgca   1080
gggtacatcg atggaggcgc tagccaggaa gagttctata agttcatcaa gccaatcctg   1140
gaaaagatgg acggaaccga agaactgctg gtcaagctga acagggagga tctgctccgg   1200
aaacagagaa cctttgacaa cggatccatt ccccaccaga tccatctggg tgagctgcac   1260
gccatcttgc ggcgccagga ggacttttac ccattcctca aggacaaccg ggaaaagatc   1320
gagaaaattc tgacgttccg catcccgtat tacgtgggcc cactggcgcg cggcaattcg   1380
cgcttcgcgt ggatgactag aaaatcagag gaaaccatca ctccttggaa tttcgaggaa   1440
gttgtggata agggagcttc ggcacaaagc ttcatcgaac gaatgaccaa cttcgacaag   1500
aatctcccaa acgagaaggt gcttcctaag cacagcctcc tttacgaata cttcactgtc   1560
tacaacgaac tgactaaagt gaaatacgtt actgaaggaa tgaggaagcc ggcctttctg   1620
tccggagaac agaagaaagc aattgtcgat ctgctgttca agaccaaccg caaggtgacc   1680
gtcaagcagc ttaaagagga ctacttcaag aagatcgagt gtttcgactc agtggaaatc   1740
agcggggtgg aggacagatt caacgcttcg ctgggaacct atcatgatct cctgaagatc   1800
atcaaggaca aggacttcct tgacaacgag gagaacgagg acatcctgga agatatcgtc   1860
ctgaccttga cccttttcga ggatcgcgag atgatcgagg agaggcttaa gacctacgct   1920
catctcttcg acgataaggt catgaaacaa ctcaagcgcc gccggtacac tggttggggc   1980
cgcctctccc gcaagctgat caacggtatt cgcgataaac agagcggtaa aactatcctg   2040
gatttcctca aatcggatgg cttcgctaat cgtaacttca tgcaattgat ccacgacgac   2100
agcctgacct ttaaggagga catccaaaaa gcacaagtgt ccggacaggg agactcactc   2160
catgaacaca tcgcgaatct ggccggttcg ccggcgatta agaagggaat tctgcaaact   2220
gtgaaggtgg tcgacgagct ggtgaaggtc atgggacggc acaaaccgga gaatatcgtg   2280
attgaaatgg cccgagaaaa ccagactacc cagaagggcc agaaaaactc ccgcgaaagg   2340
atgaagcgga tcgaagaagg aatcaaggag ctgggcagcc agatcctgaa agagcacccg   2400
gtggaaaaca cgcagctgca gaacgagaag ctctacctgt actatttgca aaatggacgg   2460
gacatgtacg tggaccaaga gctggacatc aatcggttgt ctgattacga cgtggaccac   2520
atcgttccac agtcctttct gaaggatgac tcgatcgata acaaggtgtt gactcgcagc   2580
gacaagaaca gagggaagtc agataatgtg ccatcggagg aggtcgtgaa gaagatgaag   2640
aattactggc ggcagctcct gaatgcgaag ctgattaccc agagaaagtt tgacaatctc   2700
actaaagccg agcgcggcgg actctcagag ctggataagg ctggattcat caaacggcag   2760
ctggtcgaga ctcggcagat taccaagcac gtggcgcaga tcttggactc ccgcatgaac   2820
```

```
actaaatacg acgagaacga taagctcatc cgggaagtga aggtgattac cctgaaaagc   2880
aaacttgtgt cggactttcg gaaggacttt cagttttaca aagtgagaga aatcaacaac   2940
taccatcacg cgcatgacgc atacctcaac gctgtggtcg gtaccgccct gatcaaaaag   3000
taccctaaac ttgaatcgga gtttgtgtac ggagactaca aggtctacga cgtgaggaag   3060
atgatagcca agtccgaaca ggaaatcggg aaagcaactg cgaaatactt cttttactca   3120
aacatcatga actttttcaa gactgaaatt acgctggcca atggagaaat caggaagagg   3180
ccactgatcg aaactaacgg agaaacgggc gaaatcgtgt gggacaaggg cagggacttc   3240
gcaactgttc gcaaagtgct ctctatgccg caagtcaata ttgtgaagaa aaccgaagtg   3300
caaaccggcg gattttcaaa ggaatcgatc ctcccaaaga gaaatagcga caagctcatt   3360
gcacgcaaga aagactggga cccgaagaag tacggaggat tcgattcgcc gactgtcgca   3420
tactccgtcc tcgtggtggc caaggtggag aagggaaaga gcaaaaagct caaatccgtc   3480
aaagagctgc tggggattac catcatggaa cgatcctcgt tcgagaagaa cccgattgat   3540
ttcctcgagg cgaagggtta caaggaggtg aagaaggatc tgatcatcaa actccccaag   3600
tactcactgt tcgaactgga aaatggtcgg aagcgcatgc tggcttcggc cggagaactc   3660
caaaaaggaa atgagctggc cttgcctagc aagtacgtca acttcctcta tcttgcttcg   3720
cactacgaaa aactcaaagg gtcaccggaa gataacgaac agaagcagct tttcgtggag   3780
cagcacaagc attatctgga tgaaatcatc gaacaaatct ccgagttttc aaagcgcgtg   3840
atcctcgccg acgccaacct cgacaaagtc ctgtcggcct acaataagca tagagataag   3900
ccgatcagag aacaggccga gaacattatc cacttgttca ccctgactaa cctgggagcc   3960
ccagccgcct tcaagtactt cgatactact atcgatcgca aaagatacac gtccaccaag   4020
gaagttctgg acgcgaccct gatccaccaa agcatcactg gactctacga aactaggatc   4080
gatctgtcgc agctgggtgg cgat                                          4104
```

<210> SEQ ID NO 704
<211> LENGTH: 4140
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 704

```
atggacaaga agtacagcat cggactggac atcggaacaa acagcgtcgg atgggcagtc     60
atcacagacg aatacaaggt cccgagcaag aagttcaagg tcctgggaaa cacagacaga    120
cacagcatca agaagaacct gatcggagca ctgctgttcg acagcggaga aacagcagaa    180
gcaacaagac tgaagagaac agcaagaaga agatacacaa gaagaaagaa cagaatctgc    240
tacctgcagg aaatcttcag caacgaaatg gcaaaggtcg acgacagctt cttccacaga    300
ctggaagaaa gcttcctggt cgaagaagac aagaagcacg aaagacaccc gatcttcgga    360
aacatcgtcg acgaagtcgc ataccacgaa aagtacccga caatctacca cctgagaaag    420
aagctggtcg acagcacaga caaggcagac ctgagactga tctacctggc actggcacac    480
atgatcaagt tcagaggaca cttcctgatc gaaggagacc tgaacccgga caacagcgac    540
gtcgacaagc tgttcatcca gctggtccag acatacaacc agctgttcga agaaaacccg    600
atcaacgcaa gcggagtcga cgcaaaggca atcctgagcg caagactgag caagagcaga    660
agactggaaa acctgatcgc acagctgccg ggagaaaaga agaacggact gttcggaaac    720
```

-continued

```
ctgatcgcac tgagcctggg actgacaccg aacttcaaga gcaacttcga cctggcagaa    780
gacgcaaagc tgcagctgag caaggacaca tacgacgacg acctggacaa cctgctggca    840
cagatcggag accagtacgc agacctgttc ctggcagcaa agaacctgag cgacgcaatc    900
ctgctgagcg acatcctgag agtcaacaca gaaatcacaa aggcaccgct gagcgcaagc    960
atgatcaaga gatacgacga acaccaccag gacctgacac tgctgaaggc actggtcaga   1020
cagcagctgc cggaaaagta caaggaaatc ttcttcgacc agagcaagaa cggatacgca   1080
ggatacatcg acggaggagc aagccaggaa gaattctaca agttcatcaa gccgatcctg   1140
gaaaagatgg acggaacaga agaactgctg gtcaagctga acagagaaga cctgctgaga   1200
aagcagagaa cattcgacaa cggaagcatc ccgcaccaga tccacctggg agaactgcac   1260
gcaatcctga gaagacagga agacttctac ccgttcctga aggacaacag agaaaagatc   1320
gaaaagatcc tgacattcag aatcccgtac tacgtcggac cgctggcaag aggaaacagc   1380
agattcgcat ggatgacaag aaagagcgaa gaaacaatca caccgtggaa cttcgaagaa   1440
gtcgtcgaca agggagcaag cgcacagagc ttcatcgaaa gaatgacaaa cttcgacaag   1500
aacctgccga acgaaaaggt cctgccgaag cacagcctgc tgtacgaata cttcacagtc   1560
tacaacgaac tgacaaaggt caagtacgtc acagaaggaa tgagaaagcc ggcattcctg   1620
agcggagaac agaagaaggc aatcgtcgac ctgctgttca agacaaacag aaaggtcaca   1680
gtcaagcagc tgaaggaaga ctacttcaag aagatcgaat gcttcgacag cgtcgaaatc   1740
agcggagtcg aagacagatt caacgcaagc ctgggaacat accacgacct gctgaagatc   1800
atcaaggaca aggacttcct ggacaacgaa gaaaacgaag acatcctgga agacatcgtc   1860
ctgacactga cactgttcga agacagagaa atgatcgaag aaagactgaa gacatacgca   1920
cacctgttcg acgacaaggt catgaagcag ctgaagagaa gaagatacac aggatgggga   1980
agactgagca gaaagctgat caacggaatc agagacaagc agagcggaaa gacaatcctg   2040
gacttcctga agagcgacgg attcgcaaac agaaacttca tgcagctgat ccacgacgac   2100
agcctgacat tcaaggaaga catccagaag gcacaggtca gcggacaggg agacagcctg   2160
cacgaacaca tcgcaaacct ggcaggaagc ccggcaatca agaagggaat cctgcagaca   2220
gtcaaggtcg tcgacgaact ggtcaaggtc atgggaagac acaagccgga aaacatcgtc   2280
atcgaaatgg caagagaaaa ccagacaaca cagaagggac agaagaacag cagagaaaga   2340
atgaagagaa tcgaagaagg aatcaaggaa ctgggaagcc agatcctgaa ggaacacccg   2400
gtcgaaaaca cacagctgca gaacgaaaag ctgtacctgt actacctgca gaacggaaga   2460
gacatgtacg tcgaccagga actggacatc aacagactga gcgactacga cgtcgaccac   2520
atcgtcccgc agagcttcct gaaggacgac agcatcgaca acaaggtcct gacaagaagc   2580
gacaagaaca gaggaaagag cgacaacgtc ccgagcgaag aagtcgtcaa gaagatgaag   2640
aactactgga gacagctgct gaacgcaaag ctgatcacac agagaaagtt cgacaacctg   2700
acaaaggcag agagaggagg actgagcgaa ctggacaagg caggattcat caagagacag   2760
ctggtcgaaa caagacagat cacaaagcac gtcgcacaga tcctggacag cagaatgaac   2820
acaaagtacg acgaaaacga caagctgatc agagaagtca aggtcatcac actgaagagc   2880
aagctggtca gcgacttcag aaaggacttc cagttctaca aggtcagaga aatcaacaac   2940
taccaccacg cacacgacgc atacctgaac gcagtcgtcg gaacagcact gatcaagaag   3000
tacccgaagc tggaaagcga attcgtctac ggagactaca aggtctacga cgtcagaaag   3060
atgatcgcaa agagcgaaca ggaaatcgga aaggcaacag caaagtactt cttctacagc   3120
```

aacatcatga acttcttcaa gacagaaatc acactggcaa acggagaaat cagaaagaga 3180
ccgctgatcg aaacaaacgg agaaacagga gaaatcgtct gggacaaggg aagagacttc 3240
gcaacagtca gaaaggtcct gagcatgccg caggtcaaca tcgtcaagaa gacagaagtc 3300
cagacaggag gattcagcaa ggaaagcatc ctgccgaaga gaaacagcga caagctgatc 3360
gcaagaaaga aggactggga cccgaagaag tacggaggat tcgacagccc gacagtcgca 3420
tacagcgtcc tggtcgtcgc aaaggtcgaa aagggaaaga gcaagaagct gaagagcgtc 3480
aaggaactgc tgggaatcac aatcatggaa agaagcagct tcgaaaagaa cccgatcgac 3540
ttcctggaag caaagggata caaggaagtc aagaaggacc tgatcatcaa gctgccgaag 3600
tacagcctgt tcgaactgga aaacggaaga aagagaatgc tggcaagcgc aggagaactg 3660
cagaagggaa acgaactggc actgccgagc aagtacgtca acttcctgta cctggcaagc 3720
cactacgaaa agctgaaggg aagcccggaa gacaacgaac agaagcagct gttcgtcgaa 3780
cagcacaagc actacctgga cgaaatcatc gaacagatca gcgaattcag caagagagtc 3840
atcctggcag acgcaaacct ggacaaggtc ctgagcgcat acaacaagca cagagacaag 3900
ccgatcagag aacaggcaga aaacatcatc cacctgttca cactgacaaa cctgggagca 3960
ccggcagcat tcaagtactt cgacacaaca atcgacagaa agagatacac aagcacaaag 4020
gaagtcctgg acgcaacact gatccaccag agcatcacag gactgtacga aacaagaatc 4080
gacctgagcc agctgggagg agacggagga ggaagcccga agaagaagag aaaggtctag 4140

<210> SEQ ID NO 705
<211> LENGTH: 4501
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 705
gggucccgca gucggcgucc agcggcucug cuuguucgug ugugugucgu ugcaggccuu 60
auucggaucc gccaccaugg acaagaagua cagcaucgga cuggacaucg gaacaaacag 120
cgucggaugg gcagucauca cagacgaaua caaggucccg agcaagaagu ucaagguccu 180
gggaaacaca gacagacaca gcaucaagaa gaaccugauc ggagcacugc uguucgacag 240
cggagaaaca gcagaagcaa caagacugaa gagaacagca agaagaagau acacaagaag 300
aaagaacaga aucugcuacc ugcaggaaau cuucagcaac gaaauggcaa aggucgacga 360
cagcuucuuc cacagacugg aagaaagcuu ccuggucgaa gaagacaaga agcacgaaag 420
acacccgauc uucggaaaca ucgucgacga agucgcauac cacgaaaagu acccgacaau 480
cuaccaccug agaaagaagc uggucgacag cacagacaag gcagaccuga gacugaucua 540
ccuggcacug gcacacauga ucaaguucag aggacacuuc cugaucgaag gagaccugaa 600
cccggacaac agcgacgucg acaagcuguu cauccagcug guccagacau acaaccagcu 660
guucgaagaa aacccgauca acgcaagcgg agucgacgca aaggcaaucc ugagcgcaag 720
acugagcaag agcagaagac uggaaaaccu gaucgcacag cugccgggag aaaagaagaa 780
cggacuguuc ggaaaccuga ucgcacugag ccugggacug acaccgaacu ucaagagcaa 840
cuucgaccug gcagaagacg caaagcugca gcugagcaag gacacauacg acgacgaccu 900
ggacaaccug cuggcacaga ucggagacca guacgcagac cuguuccugg cagcaaagaa 960
ccugagcgac gcaauccugc ugagcgacau ccugagaguc aacacagaaa ucacaaaggc 1020
accgcugagc gcaagcauga ucaagagaua cgacgaacac caccaggacc ugacacugcu 1080
gaaggcacug gucagacagc agcugccgga aaaguacaag gaaaucuucu ucgaccagag 1140
caagaacgga uacgcaggau acaucgacgg aggagcaagc caggaagaau ucuacaaguu 1200
caucaagccg auccuggaaa agauggacgg aacagaagaa cugcugguca agcugaacag 1260
agaagaccug cugagaaagc agagaacauu cgacaacgga agcaucccgc accagaucca 1320
ccugggagaa cugcacgcaa uccugagaag acaggaagac uucuacccgu uccugaagga 1380
caacagagaa aagaucgaaa agauccugac auucagaauc ccguacuacg ucggaccgcu 1440
ggcaagagga aacagcagau ucgcauggau gacaagaaag agcgaagaaa caaucacacc 1500
guggaacuuc gaagaagucg ucgacaaggg agcaagcgca cagagcuuca ucgaaagaau 1560
gacaaacuuc gacaagaacc ugccgaacga aaagguccug ccgaagcaca gccugcugua 1620
cgaauacuuc acagucuaca acgaacugac aaaggucaag uacgucacag aaggaaugag 1680
aaagccggca uuccugagcg gagaacagaa gaaggcaauc gucgaccugc uguucaagac 1740
aaacagaaag gucacaguca agcagcugaa ggaagacuac uucaagaaga ucgaaugcuu 1800
cgacagcguc gaaaucagcg gagucgaaga cagauucaac gcaagccugg gaacauacca 1860
cgaccugcug aagaucauca aggacaagga cuuccuggac aacgaagaaa acgaagacau 1920
ccuggaagac aucguccuga cacugacacu guucgaagac agagaaauga ucgaagaaag 1980
acugaagaca uacgcacacc uguucgacga caaggucaug aagcagcuga agagaagaag 2040
auacacagga uggggaagac ugagcagaaa gcugaucaac ggaaucagag acaagcagag 2100
cggaaagaca auccuggacu uccugaagag cgacggauuc gcaaacagaa acuucaugca 2160
gcugauccac gacgacagcc ugacauucaa ggaagacauc cagaaggcac aggucagcgg 2220
acagggagac agccugcacg aacacaucgc aaaccuggca ggaagcccgg caaucaagaa 2280
gggaauccug cagacaguca aggucgucga cgaacugguc aaggucaugg gaagacacaa 2340
gccggaaaac aucgucaucg aaauggcaag agaaaaccag acaacacaga agggacagaa 2400
gaacagcaga gaaagaauga agagaaucga agaaggaauc aaggaacugg gaagccagau 2460
ccugaaggaa cacccggucg aaaacacaca gcugcagaac gaaaagcugu accuguacua 2520
ccugcagaac ggaagagaca uguacgucga ccaggaacug gacaucaaca gacugagcga 2580
cuacgacguc gaccacaucg ucccgcagag cuuccugaag gacgacagca ucgacaacaa 2640
gguccugaca agaagcgaca agaacagagg aaagagcgac aacgucccga gcgaagaagu 2700
cgucaagaag augaagaacu acuggagaca gcugcugaac gcaaagcuga ucacacagag 2760
aaaguucgac aaccugacaa aggcagagag aggaggacug agcgaacugg acaaggcagg 2820
auucaucaag agacagcugg ucgaaacaag acagaucaca aagcacgucg cacagauccu 2880
ggacagcaga augaacacaa aguacgacga aaacgacaag cugaucagag aagucaaggu 2940
caucacacug aagagcaagc uggucagcga cuucagaaag gacuuccagu ucuacaaggu 3000
cagagaaauc aacaacuacc accacgcaca cgacgcauac cugaacgcag ucgucggaac 3060
agcacugauc aagaaguacc cgaagcugga aagcgaauuc gucuacggag acuacaaggu 3120
cuacgacguc agaaagauga ucgcaaagag cgaacaggaa aucggaaagg caacagcaaa 3180
guacuucuuc uacagcaaca ucaugaacuu cuucaagaca gaaaucacac uggcaaacgg 3240
agaaaucaga aagagaccgc ugaucgaaac aaacggagaa acaggagaaa ucgucuggga 3300
caagggaaga gacuucgcaa cagucagaaa gguccugagc augccgcagg ucaacaucgu 3360

```
caagaagaca gaaguccaga caggaggauu cagcaaggaa agcauccugc cgaagagaaa   3420
cagcgacaag cugaucgcaa gaaagaagga cugggacccg aagaaguacg gaggauucga   3480
cagcccgaca gucgcauaca gcguccuggu cgucgcaaag gucgaaaagg gaaagagcaa   3540
gaagcugaag agcgucaagg aacugcuggg aaucacaauc auggaaagaa gcagcuucga   3600
aaagaacccg aucgacuucc uggaagcaaa gggauacaag gaagucaaga aggaccugau   3660
caucaagcug ccgaaguaca gccuguucga acuggaaaac ggaagaaaga gaaugcuggc   3720
aagcgcagga gaacugcaga agggaaacga acuggcacug ccgagcaagu acgucaacuu   3780
ccuguaccug gcaagccacu acgaaaagcu gaagggaagc ccggaagaca acgaacagaa   3840
gcagcuguuc gucgaacagc acaagcacua ccuggacgaa aucaucgaac agaucagcga   3900
auucagcaag agagucaucc uggcagacgc aaaccuggac aagguccuga gcgcauacaa   3960
caagcacaga gacaagccga ucagagaaca ggcagaaaac aucauccacc uguucacacu   4020
gacaaaccug ggagcaccgg cagcauucaa guacuucgac acaacaaucg acagaaagag   4080
auacacaagc acaaaggaag uccuggacgc aacacugauc caccagagca ucacaggacu   4140
guacgaaaca agaaucgacc ugagccagcu gggaggagac ggaggaggaa gcccgaagaa   4200
gaagagaaag gucuagcuag ccaucacauu uaaaagcauc ucagccuacc augagaauaa   4260
gagaaagaaa augaagauca auagcuuauu caucucuuuu ucuuuuucgu ugguguaaag   4320
ccaacacccu gucuaaaaaa cauaaauuuc uuuaaucauu uugccucuuu ucucugugcu   4380
ucaauuaaua aaaaauggaa agaaccucga gaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
a                                                                   4501
```

<210> SEQ ID NO 706
<211> LENGTH: 2802
<212> TYPE: DNA
<213> ORGANISM: Homo sapiens

<400> SEQUENCE: 706

```
accactttca caatctgcta gcaaaggtta tgcagcgcgt gaacatgatc atggcagaat     60
caccaggcct catcaccatc tgccttttag gatatctact cagtgctgaa tgtacagttt    120
ttcttgatca tgaaaacgcc aacaaaattc tgaatcggcc aaagaggtat aattcaggta    180
aattggaaga gtttgttcaa gggaaccttg agagagaatg tatggaagaa aagtgtagtt    240
ttgaagaagc acgagaagtt tttgaaaaca ctgaaagaac aactgaattt tggaagcagt    300
atgttgatgg agatcagtgt gagtccaatc catgtttaaa tggcggcagt tgcaaggatg    360
acattaattc ctatgaatgt tggtgtccct ttggatttga aggaaagaac tgtgaattag    420
atgtaacatg taacattaag aatggcagat gcgagcagtt ttgtaaaaat agtgctgata    480
acaaggtggt ttgctcctgt actgagggat atcgacttgc agaaaaccag aagtcctgtg    540
aaccagcagt gccatttcca tgtggaagag tttctgtttc acaaacttct aagctcaccc    600
gtgctgagac tgtttttcct gatgtggact atgtaaattc tactgaagct gaaaccattt    660
tggataacat cactcaaagc acccaatcat ttaatgactt cactcgggtt gttggtggag    720
aagatgccaa accaggtcaa ttcccttggc aggttgtttt gaatggtaaa gttgatgcat    780
tctgtggagg ctctatcgtt aatgaaaaat ggattgtaac tgctgcccac tgtgttgaaa    840
ctggtgttaa aattacagtt gtcgcaggtg aacataatat tgaggagaca gaacatacag    900
agcaaaagcg aaatgtgatt cgaattattc ctcaccacaa ctacaatgca gctattaata    960
```

agtacaacca tgacattgcc cttctggaac tggacgaacc cttagtgcta aacagctacg 1020
ttacacctat ttgcattgct gacaaggaat acacgaacat cttcctcaaa tttggatctg 1080
gctatgtaag tggctgggga agagtcttcc acaaagggag atcagcttta gttcttcagt 1140
accttagagt tccacttgtt gaccgagcca catgtcttcg atctacaaag ttcaccatct 1200
ataacaacat gttctgtgct ggcttccatg aaggaggtag agattcatgt caaggagata 1260
gtgggggacc ccatgttact gaagtggaag ggaccagttt cttaactgga attattagct 1320
ggggtgaaga gtgtgcaatg aaaggcaaat atggaatata taccaaggta tcccggtatg 1380
tcaactggat taaggaaaaa acaaagctca cttaatgaaa gatggatttc caaggttaat 1440
tcattggaat tgaaaattaa cagggcctct cactaactaa tcactttccc atcttttgtt 1500
agatttgaat atatacattc tatgatcatt gctttttctc tttacagggg agaatttcat 1560
attttacctg agcaaattga ttagaaaatg gaaccactag aggaatataa tgtgttagga 1620
aattacagtc atttctaagg gcccagccct tgacaaaatt gtgaagttaa attctccact 1680
ctgtccatca gatactatgg ttctccacta tggcaactaa ctcactcaat tttccctcct 1740
tagcagcatt ccatcttccc gatcttcttt gcttctccaa ccaaaacatc aatgtttatt 1800
agttctgtat acagtacagg atctttggtc tactctatca caaggccagt accacactca 1860
tgaagaaaga acacaggagt agctgagagg ctaaaactca tcaaaaacac tactcctttt 1920
cctctaccct attcctcaat cttttacctt ttccaaatcc caatccccaa atcagttttt 1980
ctctttctta ctccctctct cccttttacc ctccatggtc gttaaaggag agatggggag 2040
catcattctg ttatacttct gtacacagtt atacatgtct atcaaaccca gacttgcttc 2100
cgtagtggag acttgctttt cagaacatag ggatgaagta aggtgcctga aaagtttggg 2160
ggaaaagttt ctttcagaga gttaagttat tttatatata taatatatat ataaaatata 2220
taatatacaa tataaatata tagtgtgtgt gtatgcgtgt gtgtagacac acacgcatac 2280
acacatataa tggaagcaat aagccattct aagagcttgt atggttatgg aggtctgact 2340
aggcatgatt tcacgaaggc aagattggca tatcattgta actaaaaaag ctgacattga 2400
cccagacata ttgtactctt tctaaaaata ataataataa tgctaacaga aagaagagaa 2460
ccgttcgttt gcaatctaca gctagtagag actttgagga agaattcaac agtgtgtctt 2520
cagcagtgtt cagagccaag caagaagttg aagttgccta gaccagagga cataagtatc 2580
atgtctcctt taactagcat accccgaagt ggagaagggt gcagcaggct caaaggcata 2640
agtcattcca atcagccaac taagttgtcc ttttctggtt tcgtgttcac catggaacat 2700
tttgattata gttaatcctt ctatcttgaa tcttctagag agttgctgac caactgacgt 2760
atgtttccct ttgtgaatta ataaactggt gttctggttc at 2802

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

-continued

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

-continued

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761

<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765

<400> SEQUENCE: 765

-continued

000

<210> SEQ ID NO 766

<400> SEQUENCE: 766

000

<210> SEQ ID NO 767

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800
<211> LENGTH: 6
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 800 aauaaa 6

<210> SEQ ID NO 801
<211> LENGTH: 6
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 801 uauaaa 6

<210> SEQ ID NO 802
<211> LENGTH: 6
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 802 akuaaa 6

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820
<400> SEQUENCE: 820
000

<210> SEQ ID NO 821
<400> SEQUENCE: 821
000

<210> SEQ ID NO 822
<400> SEQUENCE: 822
000

<210> SEQ ID NO 823
<400> SEQUENCE: 823
000

<210> SEQ ID NO 824
<400> SEQUENCE: 824
000

<210> SEQ ID NO 825
<400> SEQUENCE: 825
000

<210> SEQ ID NO 826
<400> SEQUENCE: 826
000

<210> SEQ ID NO 827
<400> SEQUENCE: 827
000

<210> SEQ ID NO 828
<400> SEQUENCE: 828
000

<210> SEQ ID NO 829
<400> SEQUENCE: 829
000

<210> SEQ ID NO 830
<400> SEQUENCE: 830
000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

-continued

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

-continued

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

-continued

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

<400> SEQUENCE: 913

000

<210> SEQ ID NO 914

<400> SEQUENCE: 914

000

<210> SEQ ID NO 915

<400> SEQUENCE: 915

000

<210> SEQ ID NO 916

<400> SEQUENCE: 916

000

<210> SEQ ID NO 917

<400> SEQUENCE: 917

000

<210> SEQ ID NO 918

<400> SEQUENCE: 918

000

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

<210> SEQ ID NO 925

<400> SEQUENCE: 925

000

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

-continued

<210> SEQ ID NO 1000

<400> SEQUENCE: 1000

000

<210> SEQ ID NO 1001

<400> SEQUENCE: 1001

000

<210> SEQ ID NO 1002

<400> SEQUENCE: 1002

000

<210> SEQ ID NO 1003

<400> SEQUENCE: 1003

000

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057
<400> SEQUENCE: 1057
000

<210> SEQ ID NO 1058
<400> SEQUENCE: 1058
000

<210> SEQ ID NO 1059
<400> SEQUENCE: 1059
000

<210> SEQ ID NO 1060
<400> SEQUENCE: 1060
000

<210> SEQ ID NO 1061
<400> SEQUENCE: 1061
000

<210> SEQ ID NO 1062
<400> SEQUENCE: 1062
000

<210> SEQ ID NO 1063
<400> SEQUENCE: 1063
000

<210> SEQ ID NO 1064
<400> SEQUENCE: 1064
000

<210> SEQ ID NO 1065
<400> SEQUENCE: 1065
000

<210> SEQ ID NO 1066
<400> SEQUENCE: 1066
000

<210> SEQ ID NO 1067
<400> SEQUENCE: 1067
000

<210> SEQ ID NO 1068
<400> SEQUENCE: 1068
000

<210> SEQ ID NO 1069
<400> SEQUENCE: 1069
000

<210> SEQ ID NO 1070
<400> SEQUENCE: 1070
000

<210> SEQ ID NO 1071
<400> SEQUENCE: 1071
000

<210> SEQ ID NO 1072
<400> SEQUENCE: 1072
000

<210> SEQ ID NO 1073
<400> SEQUENCE: 1073
000

<210> SEQ ID NO 1074
<400> SEQUENCE: 1074
000

<210> SEQ ID NO 1075
<400> SEQUENCE: 1075
000

<210> SEQ ID NO 1076
<400> SEQUENCE: 1076
000

<210> SEQ ID NO 1077
<400> SEQUENCE: 1077
000

<210> SEQ ID NO 1078
<400> SEQUENCE: 1078
000

-continued

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

<400> SEQUENCE: 1106

000

<210> SEQ ID NO 1107

<400> SEQUENCE: 1107

000

<210> SEQ ID NO 1108

<400> SEQUENCE: 1108

000

<210> SEQ ID NO 1109

<400> SEQUENCE: 1109

000

<210> SEQ ID NO 1110

<400> SEQUENCE: 1110

000

<210> SEQ ID NO 1111

<400> SEQUENCE: 1111

000

<210> SEQ ID NO 1112

<400> SEQUENCE: 1112

000

<210> SEQ ID NO 1113

<400> SEQUENCE: 1113

000

<210> SEQ ID NO 1114

<400> SEQUENCE: 1114

000

<210> SEQ ID NO 1115

<400> SEQUENCE: 1115

000

<210> SEQ ID NO 1116

<400> SEQUENCE: 1116

000

<210> SEQ ID NO 1117

<400> SEQUENCE: 1117

000

<210> SEQ ID NO 1118

<400> SEQUENCE: 1118

000

<210> SEQ ID NO 1119

<400> SEQUENCE: 1119

000

<210> SEQ ID NO 1120

<400> SEQUENCE: 1120

000

<210> SEQ ID NO 1121

<400> SEQUENCE: 1121

000

<210> SEQ ID NO 1122

<400> SEQUENCE: 1122

000

<210> SEQ ID NO 1123

<400> SEQUENCE: 1123

000

<210> SEQ ID NO 1124

-continued

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

<400> SEQUENCE: 1128

000

<210> SEQ ID NO 1129
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1129
gaguccgagc agaagaagaa 20

<210> SEQ ID NO 1130
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1130
gacccccucc accccgccuc 20